US012208140B2

(12) United States Patent
Choudhary et al.

(10) Patent No.: US 12,208,140 B2
(45) Date of Patent: Jan. 28, 2025

(54) TARGETED DELIVERY TO BETA CELLS

(71) Applicants: THE BROAD INSTITUTE, INC., Cambridge, MA (US); THE BRIGHAM AND WOMEN'S HOSPITAL, INC., Boston, MA (US)

(72) Inventors: Amit Choudhary, Boston, MA (US); Debasish Manna, Boston, MA (US); Miseon Lee, Cambridge, MA (US); Bridget Wagner, Cambridge, MA (US); Basudeb Maji, Cambridge, MA (US)

(73) Assignees: The Broad Institute, Inc., Cambridge, MA (US); The Brigham and Women's Hospital, Inc., Cambridge, MA (US)

( * ) Notice: Subject to any disclaimer, the term of this patent is extended or adjusted under 35 U.S.C. 154(b) by 386 days.

(21) Appl. No.: 16/607,089

(22) PCT Filed: Apr. 20, 2018

(86) PCT No.: PCT/US2018/028660
§ 371 (c)(1),
(2) Date: Oct. 21, 2019

(87) PCT Pub. No.: WO2018/195486
PCT Pub. Date: Oct. 25, 2018

(65) Prior Publication Data
US 2020/0384115 A1   Dec. 10, 2020

Related U.S. Application Data

(60) Provisional application No. 62/488,130, filed on Apr. 21, 2017.

(51) Int. Cl.
*A61K 31/436* (2006.01)
*A61K 31/7105* (2006.01)
*A61K 38/46* (2006.01)
*A61K 47/54* (2017.01)
*A61K 49/00* (2006.01)

(52) U.S. Cl.
CPC .......... *A61K 47/547* (2017.08); *A61K 31/436* (2013.01); *A61K 31/7105* (2013.01); *A61K 38/465* (2013.01); *A61K 49/0017* (2013.01); *A61K 49/0052* (2013.01)

(58) Field of Classification Search
CPC ............ A61K 2121/00; A61K 2123/00; A61K 47/00; A61K 47/547; A61K 31/00; A61K 31/436; A61K 31/7105; A61K 38/00; A61K 38/465; A61K 49/00; A61K 49/0017; A61K 49/0052; A61K 49/0041; C12N 15/102; C12N 15/63; C12N 15/10; C07K 14/7051
USPC .......... 424/1.11, 1.49, 1.65, 1.69, 1.81, 1.85, 424/1.89, 9.1, 9.2; 514/1, 1.1; 534/7, 534/10–16; 530/300
See application file for complete search history.

(56) References Cited

U.S. PATENT DOCUMENTS

2011/0033378 A1* 2/2011 Dimasi ................ A61P 35/02
424/1.49

FOREIGN PATENT DOCUMENTS

| WO | 2015089486 A2 | 6/2015 |
| WO | 2016106244 A1 | 6/2016 |
| WO | 2018195486 A1 | 10/2018 |

OTHER PUBLICATIONS

Aoki et al., J. Am. Chem. Soc., vol. 124, pp. 5256-5257 (Year: 2002).*
Turkyilmaz et al., Organic & Biomolecular Chemistry, vol. 12, pp. 5645-5655 (Year: 2014).*
Leriche et al., Bioorganic & Medicinal Chemistry, vol. 20, pp. 571-582 (Year: 2012).*
"Communication pursuant to Article 94(3) EPC", issued by the European Patent Office (EPO) on Feb. 3, 2021 for EP Application No. EP18726260.5.
Zastrow, et al., "Reaction-Based Probes for Imaging Mobile Zinc in Live Cells and Tissues", ACS Sensors, vol. 1, pp. 32-39, Sep. 23, 2015.
"International Search Report and Written Opinion issued in International Application No. PCT/US2018/028660", mailed on Aug. 8, 2018, 11 pages.
Annes, et al., "Adenosine Kinase Inhibition Selectively Promotes Rodent And Porcine Islet β-Cell Replication", Proceedings of the National Academy of Sciences of the United States of America, vol. 109, No. 10, Mar. 6, 2012, 3915-3920.
Banaszynski, et al., "A Rapid, Reversible, and Tunable Method to Regulate Protein Function in Living Cells Using Synthetic Small Molecules", Cell, vol. 126, No. 5, Sep. 8, 2006, 995-1004.
Banaszynski, et al., "Chemical Control of Protein Stability and Function in Living Mice", Nature Medicine, vol. 14, No. 10, Oct. 2008, 1123-1127.
Bhatt, et al., "Preserved DNA Damage Checkpoint Pathway Protects against Complications in Long-Standing Type 1 Diabetes", Cell Metabolism, vol. 22, No. 2, Aug. 4, 2015, 239-252.

(Continued)

*Primary Examiner* — Micah Paul Young
(74) *Attorney, Agent, or Firm* — F. Brent Nix, Esq.; Johnson, Marcou, Isaacs & Nix, LLC; Drew P. Harding

(57) ABSTRACT

The disclosure includes zinc prodrugs for targeted delivery of therapeutic, diagnostic or imaging agents to β-cells and methods of use therefor. The disclosure also includes targeted delivery of small molecules to β-cells that stabilize and activate CRISPR effector proteins comprising at least one destabilization domain, to enable CRISPR-based genome editing and transcriptional activation or repression in β-cells.

15 Claims, 33 Drawing Sheets

(56) References Cited

OTHER PUBLICATIONS

Blencowe, et al., "Self-Immolative Linkers in Polymeric Delivery Systems", Polymer Chemistry, Issue 4, 2011, 773-790.
Chao, et al., "Structural Basis for the Coevolution of a Viral RNA-Protein Complex", Nature Structural & Molecular Biology, vol. 15, No. 15, No. 1, Jan. 2008, 103-105.
Chou, et al., "Kinase-Independent Small-Molecule Inhibition of JAK-STAT Signaling", Journal of the American Chemical Society, vol. 137, No. 24, 2015, 7929-7934.
Chung, et al., "Tunable and Reversible Drug Control of Protein Production Via a Self-excising Degron", Nature Chemical Biology, vol. 11, No. 9, Sep. 2015, 713-720.
Cong, et al., "Multiplex Genome Engineering Using CRISPR/Cas Systems", Science, vol. 339, No. 6121, Feb. 15, 2013, 819-823.
Debdab, "Leucettines, A Class of Potent Inhibitors of CDC2-Like Kinases and Dual Specificity, Tyrosine Phosphorylation Regulated Kinases Derived From the Marine Sponge Leucettamine B: Modulation of Alternative Pre-RNA Splicing", Journal of Medicinal Chemistry, vol. 64, No. 12, May 26, 2011, 4172-4186.
Dewit, et al., "A Cascade Biodegradable Polymer Based on Alternating Cyclization and Elimination Reactions", Journal of the American Chemical Society, vol. 131, No. 51, Dec. 30, 2009, 18327-18334.
Dhawan, et al., "Inhibition of TGF-β Signaling Promotes Human Pancreatic β-Cell Replication", Diabetes, vol. 65, No. 5, May 2016, 1208-11218.
Dirice, et al., "Inhibition of DYRK1A Stimulates Human β-Cell Proliferation", Diabetes, vol. 65, No. 6, Jun. 2016, 12 pages.
Dirice, et al., "Soluble Factors Secreted by T Cells Promote B-Cell Proliferation", Diabetes, vol. 63, No. 1, Jan. 2014, 188-202.
Doench, et al., "Rational Design of Highly Active SgRNAs for CRISPR-Cas9-Mediated Gene Inactivation", Nature Biotechnology, vol. 32, No. 12, Dec. 2014, 1262-1267.
Fomina, et al., "Small-Molecule Inducers of Insulin Expression In Pancreatic Alpha Cells", Proceedings of the National Academy of Sciences of the United States of America, vol. 107, No. 34, Aug. 24, 2010, 15099-15104.
Helman, et al., "Effects of Ageing and Senescence on Pancreatic β-Cell Function", Diabetes, Obesity and Metabolism, vol. 1, Sep. 2016, 58-62.
Hsu, et al., "Development and Applications of CRISPR-Cas9 for Genome Engineering", Cell, vol. 157, No. 6, Jun. 5, 2014, 1262-1278.
Hsu, et al., "DNA Targeting Specificity of Rna-Guided Cas9 Nucleases", Nature Biotechnology, vol. 31, No. 9, Sep. 2013, 1-8.
Huang, et al., "Coupling of Insulin Secretion and Display of a Granule-resident Zinc Transporter ZnT8 on the Surface of Pancreatic Beta Cells", Journal of Biological Chemistry, vol. 292, No. 10, Mar. 10, 2017, 4034-4043.
Jiang, et al., "RNA-Guided Editing of Bacterial Genomes Using CRISPR-Cas Systems", Nature Biotechnology, vol. 31, No. 3, Mar. 2013, 233-239.
Jinek, et al., "A Programmable Dual-RNA-Guided DNA Endonuclease in Adaptive Bacterial immunity", Science, vol. 337, No. 6096, Aug. 17, 2012, 816-821.
Kim, et al., "Crystal Structure of Cas1 from Archaeoglobus Fulgidus and Characterization of its Nucleolytic Activity", Biochemical and Biophysical Research Communications, vol. 441, No. 4,, Nov. 29, 2013, 720-725.
Kleinstiver, "Engineered Crispr-Cas9 Nucleases with Altered Pam Specificities", Nature, vol. 523, Jul. 23, 2015, 481-485.
Konermann, et al., "Genome-Scale Transcriptional Activation by an Engineered CRISPR-Cas9 Complex", Nature, vol. 517, No. 7536, Jan. 29, 2015, 583-588.
Konermann, et al., "Optical Control of Mammalian Endogenous Transcription and Epigenetic States", Nature, vol. 500, No. 7463, Aug. 22, 2013, 472-476.
Krishnamurthy, et al., "P16Ink4A Induces an Age-Dependent Decline in Islet Regenerative Potential", Nature, vol. 443, No. 7110, Sep. 28, 2006.
Li, et al., "GLP-1 Receptor Mediated Targeting of a Fluorescent Zn2+ Sensor to Beta Cell Surface for Imaging Insulin/Zn2+ Release", Bioconjugate Chemistry, vol. 26, No. 8, Jun. 29, 2015, 1443-1450.
Li, et al., "Zinc And Insulin in Pancreatic Beta-Cells", Endocrine, vol. 45, No. 2, Mar. 2014, 178-189.
Lim, et al., "Altering the RNA Binding Specificity of a Translational Repressor", Journal of Biological Chemistry, vol. 269, No. 12, Mar. 25, 1994, 9006-9010.
Maeder, et al., "CRISPR RNA-Guided Activation of Endogenous Human Genes", Nature Methods, vol. 10, No. 10, Oct. 2013, 977-979.
Magalhaes, et al., "A General RNA Motif for Cellular Transfection", Molecular Therapy, vol. 20, No. 3, Mar. 2012, 616-624.
Mali, et al., "CAS9 Transcriptional Activators for Target Specificity Screening and Paired Nickases for Cooperative Genome Engineering", Nature Biotechnology, vol. 31, No. 9, Sep. 2013, 833-838.
Mali, et al., "RNA-Guided Human Genome Engineering via Cas9", Science, vol. 339, No. 6121, Feb. 15, 2013, 823-826.
Maolanon, et al., "Innovative Strategies for Selective Inhibition of Histone Deacetylases", Cell Chemical Biology, vol. 23, No. 7, Jul. 21, 2016, 759-768.
Miyazaki, et al., "Destabilizing Domains Derived from the Human Estrogen Receptor", Journal of the American Chemical Society, vol. 134, No. 9, 2012, 3942-3945.
Moscou, et al., "A Simple Cipher Governs DNA Recognition by TAL Effectors", Science, vol. 326, Issue 5959, Dec. 11, 2009, 1509-1512.
Nishimasu, et al., "Crystal Structure of Cas9 in Complex with Guide RNA and Target DNA", Cell, vol. 156, No. 5, Feb. 27, 2014, 935-949.
Ouaamari, et al., "SerpinB1 Promotes Pancreatic B Cell Proliferation", Cell Metabolism, vol. 23, No. 1, Jan. 12, 2016, 194-205.
Perez-Pinera, et al., "RNA-Guided Gene Activation by CRISPR-Cas9-Based Transcription Factors", Nature Methods, vol. 10, No. 10, Oct. 2013, 973-976.
Platt, et al., "CRISPR-Cas9 Knockin Mice for Genome Editing and Cancer Modeling", Cell, vol. 159, No. 2, Oct. 9, 2014, 440-455.
Ran, et al., "Double Nicking by RNA-Guided CRISPR Cas9 for Enhanced Genome Editing Specificity", Cell, vol. 154, No. 6, Sep. 12, 2013, 1380-1389.
Ran, et al., "Genome Engineering Using the CRISPR-Cas9 System", Nature Protocols, vol. 8, No. 11, Nov. 2013, 2281-2308.
Rodriguez, et al., "Targeted Chemical-Genetic Regulation of Protein Stability In Vivo", Chemistry & Biology, vol. 19, No. 3, Mar. 23, 2012, 391-398.
Shalem, et al., "Genome-Scale CRISPR-Cas9 Knockout Screening in Human Cells", Science, vol. 343, No. 6166, Jan. 3, 2014, 84-87.
Shen, et al., "Inhibition of Dyrk1A and Gsk3B Induces Human β-Cell Proliferation", Nature Communications, vol. 6, Oct. 2015, 11 pages.
Sheng, "Self-Immolative Chemistry: Structural Features and Applications in Designing Smart Materials", S.T.J. Journal of the American Chemical Society, vol. 132, 2010, 43 pages.
Shmakov, et al., "Discovery and Functional Characterization of Diverse Class 2 CRISPR-Cas Systems", Molecular Cell, vol. 60, No. 3, Nov. 5, 2015, 385-397.
Smith, et al., "A Directed Approach for Engineering Conditional Protein Stability Using Biologically Silent Small Molecules", The Journal Of Biological Chemistry, vol. 282, No. 34, Aug. 24, 2007, 24866-24872.
Swiech, et al., "In Vivo Interrogation of Gene Function in the Mammalian Brain Using CRISPR-Cas9", Nature Biotechnology, vol. 33, No. 1, Jan. 2015, 102-106.
Vetere, et al., "Targeting the Pancreatic β-Cell to Treat Diabetes", Nature Reviews Drug Discovery, vol. 13, No. 4, Apr. 2014, 278-289.
Wagner, et al., "An Isochemogenic Set of Inhibitors To Define the Therapeutic Potential of Histone Deacetylases in β-Cell Protection", ACS Chemical Biology, vol. 11, No. 2, Feb. 19, 2016, 363-374.

(56) References Cited

OTHER PUBLICATIONS

Walpita, et al., "A Human Islet Cell-Culture System for High-Throughput Screening", Journal of Biomolecular Screening, vol. 17, No. 4, Apr. 2012, 509-518.

Walpita, et al., "Evaluation of Compounds in Primary Human Islet Cell Culture", Current Protocols in Chemical Biology, vol. 6, pp. 157-168, Sep. 2014.

Walpita, et al., "Evaluation of Compounds in Primary Human Islet Cell Culture", Current Protocols in Chemical Biology, vol. 6, No. 3, Sep. 9, 2014, 157-168.

Wang, et al., "A High-Throughput Chemical Screen Reveals that Harmine-Mediated Inhibition of Dyrk1A Increases Human Pancreatic Beta Cell Replication", Nature Medicine, vol. 21, No. 4, Apr. 2015, 383-388.

Wang, et al., "CRISPR/Cas9 in Genome Editing and Beyond", Annual Review of Biochemistry, vol. 85, pp. 22.1-22.38, Apr. 15, 2016.

Wang, et al., "CRISPR/Cas9 in Genome Editing and Beyond", Annual Review of Biochemistry, vol. 85, Jun. 2, 2016, 227-264.

Wang, et al., "Genetic Screens in Human Cells Using the CRISPR/Cas9 System", Science, vol. 343, No. 6166, Jan. 3, 2014, 80-84.

Wang, et al., "One-Step Generation of Mice Carrying Mutations in Multiple Genes by CRISPR/Cas-Mediated Genome Engineering", Cell, vol. 153, No. 4, May 9, 2013, 910-918.

Wu, et al., "Fluorescence Fluctuation Spectroscopy Enables Quantitative Imaging of Single Mrnas in Living Cells", Biophysical Journal, vol. 102, No. 12, Jun. 20, 2012, 2936-2944.

Wu, et al., "Genome-Wide Binding of the CRISPR Endonuclease Cas9 in Mammalian Cells", Nature Biotechnology, vol. 32, No. 7, Jul. 2014, 670-676.

Yuan, et al., "A Small-Molecule Inducer of Pdx1 Expression Identified by High-Throughput Screening", Chemistry & Biology—Journal, vol. 20, No. 12, Dec. 19, 2013, 1513-1522.

Zetsche, et al., "A Split-Cas9 Architecture for Inducible Genome Editing and Transcription Modulation", Nature Biotechnology, vol. 33, No. 2, Feb. 2015, 139-142.

Zetsche, et al., "Cpf1 is a Single RNA-Guided Endonuclease of a Class 2 CRISPR-Cas System", Cell, vol. 163, No. 3, Oct. 22, 2015, 759-771.

Zhang, et al., "Efficient construction of sequence-specific TAL effectors for modulating mammalian transcription", Nature Biotechnology, vol. 29, No. 2, 2011, 149-153.

Niittymaki, et al., "Sequence-Selective Cleavage of Oligoribonucleotides by 3d Transition Metal Complexes of 1,5,9-Triazacyclododecane-Functionalized 2'-O-Methyl Oligoribonucleotides", Bioconjugate Chem., vol. 15, pp. 1275-1280, 2004.

Wong, et al., "Mechanisms of drug release in nanotherapeutic delivery systems," Chem. Rev., vol. 15, No. 9, pp. 3388-3432, May 13, 2015.

* cited by examiner

DA-ZP1

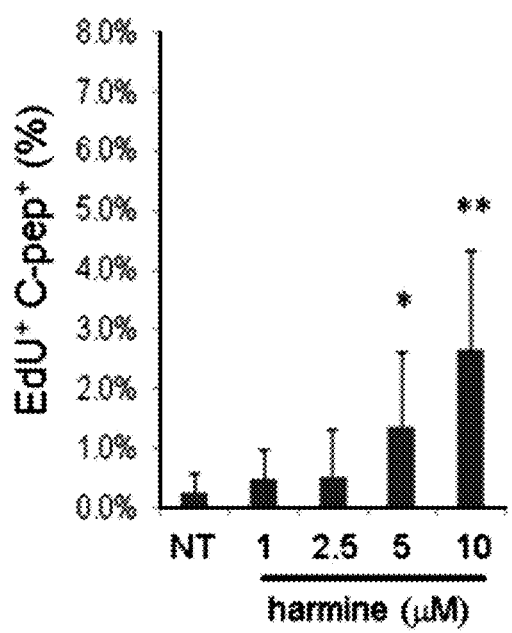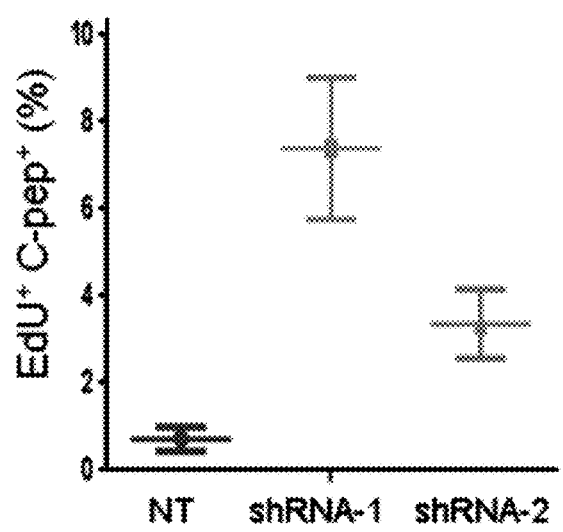
FIG. 9A                    FIG. 9B

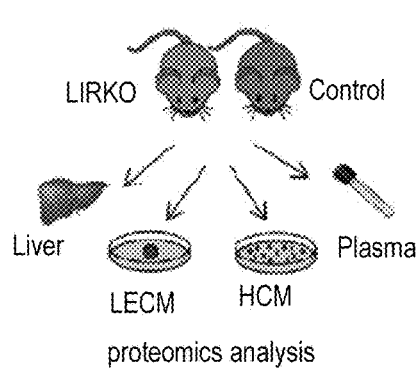
FIG. 10A
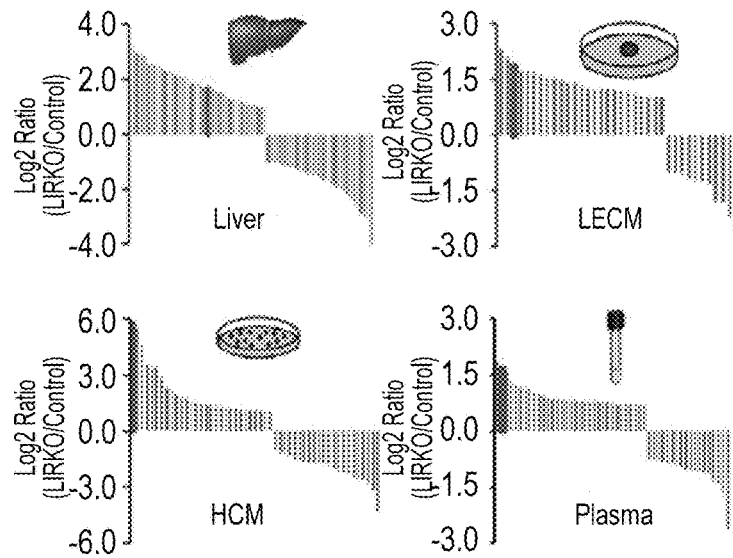
FIG. 10B
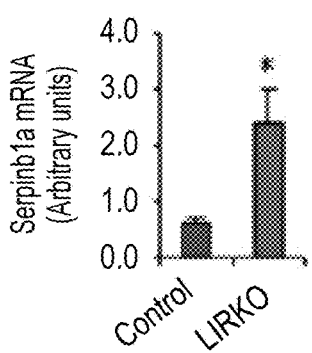 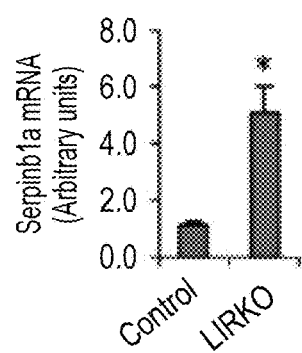
FIG. 10C   FIG. 10D
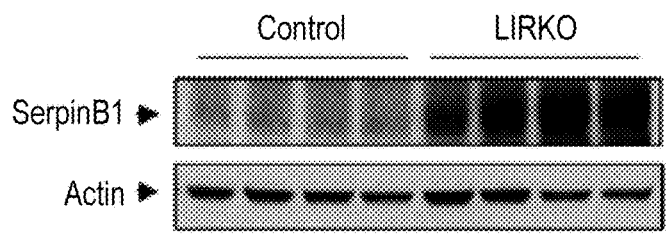
FIG. 10E

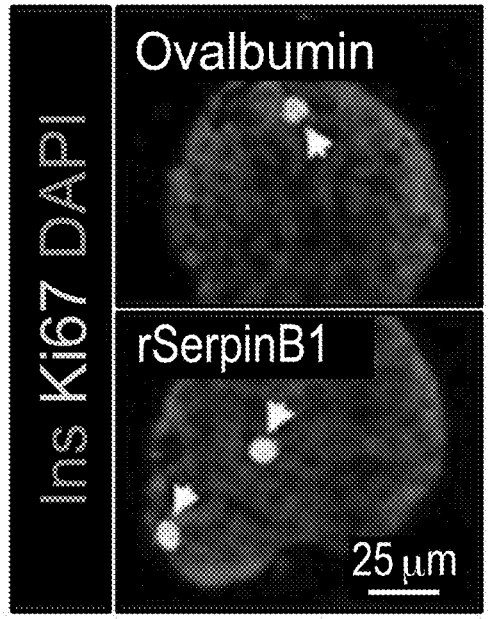
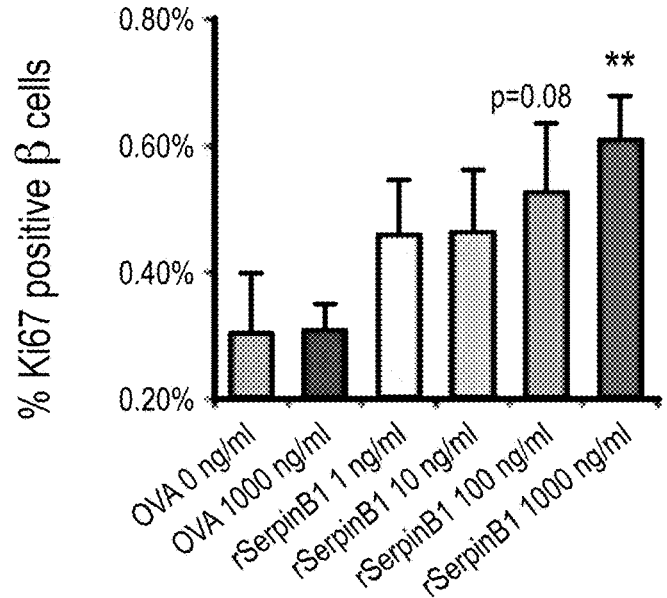
FIG. 11A
FIG. 11B
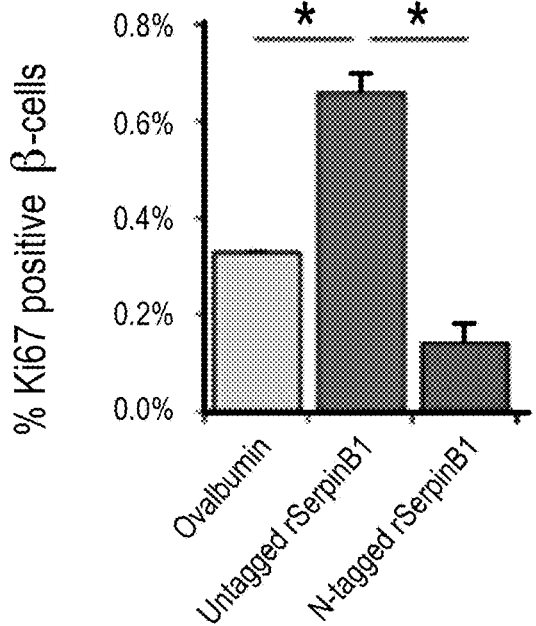
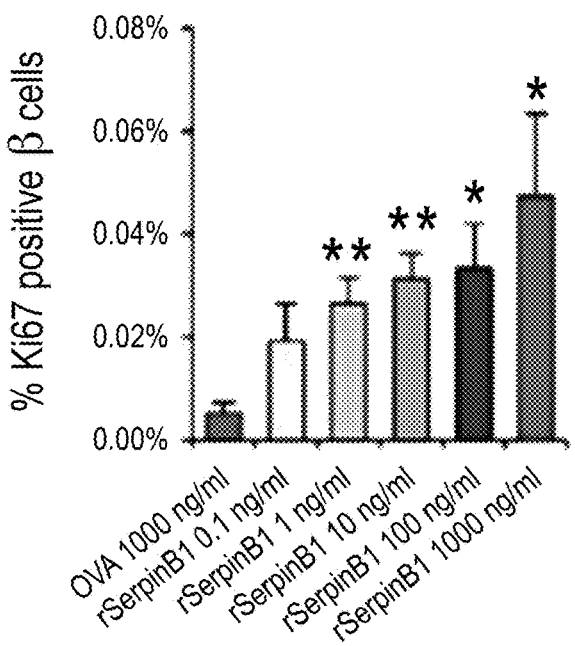
FIG. 11C
FIG. 11D

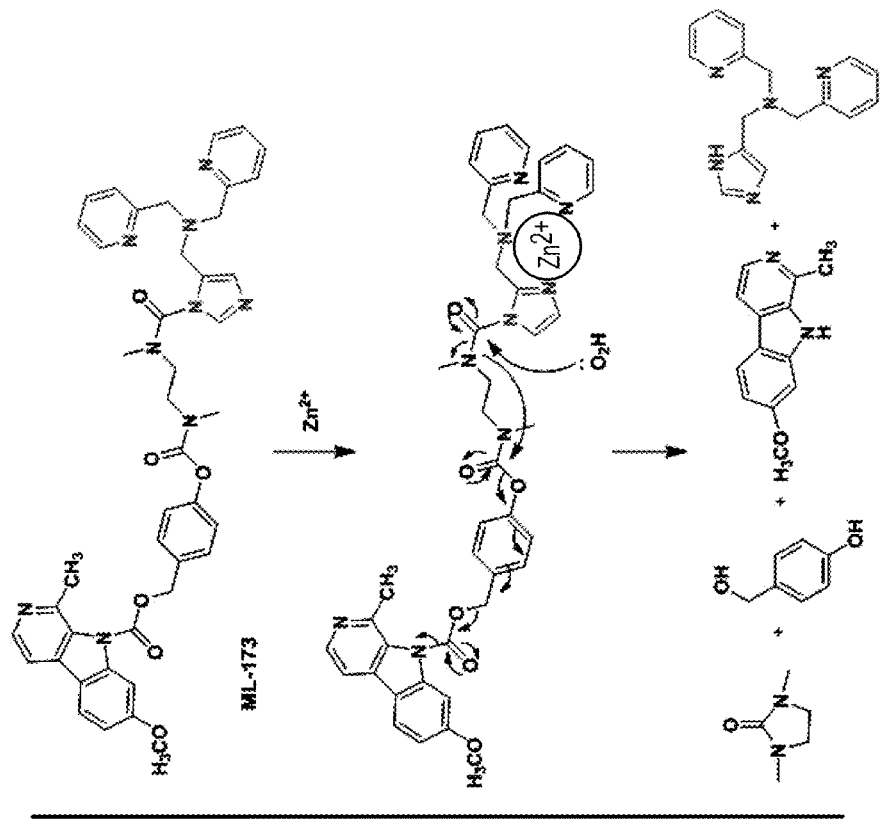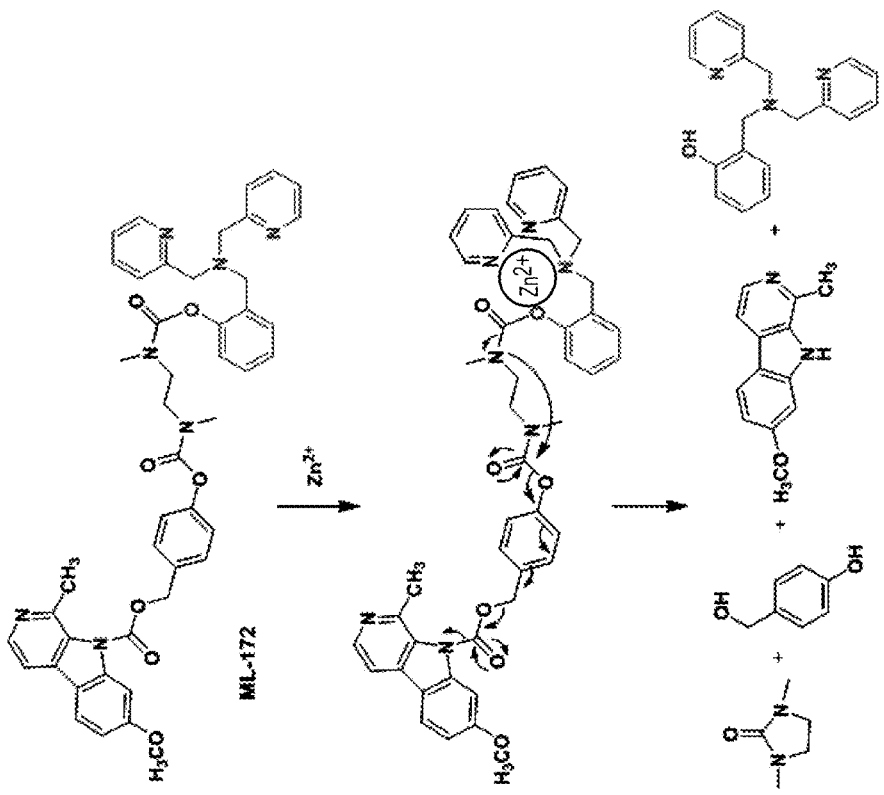
FIG. 31

TARGETED DELIVERY TO BETA CELLS

RELATED APPLICATIONS AND INCORPORATION BY REFERENCE

This application claims priority to U.S. Provisional Application No. 62/488,130 filed Apr. 21, 2017, which is incorporated herein by reference in its entirety.

STATEMENT REGARDING FEDERALLY SPONSORED RESEARCH

This invention was made with government support under Grant No. DK116255 awarded by the National Institutes of Health. The government has certain rights in the invention.

FIELD OF THE INVENTION

The present invention generally relates to selective delivery of a small molecule to β-cells. In particular, the present invention provides a zinc prodrug for selective delivery of a molecule to the β-cell. The present invention also relates to genomic editing and transcriptional control in β-cells using CRISPR system.

BACKGROUND

Nearly 350 million people worldwide currently suffer from diabetes. Of these, about 5% of patients have type-1 diabetes, which results in the absolute loss of insulin production, whereas about 95% of patients have type-2 diabetes and suffer from impaired insulin sensitivity as well as problems with insulin secretion. A third type of diabetes are monogenic diabetes caused by mutations. β-cells residing in the islets of Langerhans in the pancreas are responsible for the production of insulin. A loss of β-cell mass and biologically active insulin is one feature of both type 1 and type 2 diabetes. Therefore, ways to preserve or expand β-cell mass and function in humans could be a therapeutically important approach to treating different types of diabetes. However, most of the current therapies for diabetes focus on managing the symptoms of the disease rather than replacing or preserving β-cell mass. This is because, e.g., β-cells are not thought to regenerate in adult humans, and are considered a more quiescent cell type. Vetere, et al., *Nature Reviews Drug Discovery* (2014) 13:278-289. There exists a need in the art for effective treatments of diabetes.

SUMMARY OF THE INVENTION

There is an urgent need to selectively deliver small molecules to β-cells. Currently, no disease-modifying therapies exist for either type-1 diabetes or type-2 diabetes, and no pharmaceutical agents are in the pipeline for type-1 diabetes. The present invention clears the bottleneck in the pipeline of therapeutic development for diabetes by developing reagents for targeted cargo delivery to β-cells.

Prodrugs can be used to improve the physicochemical, biopharmaceutical, or pharmacokinetic attributes of pharmacologic agents. Targeted release of therapeutic agents (including prodrugs) offers a dual advantage: it increases the maximum tolerated dose by decreasing liabilities, while lowering the minimum efficacious dose by accumulating drug at the site of action (FIG. 1). Thus, the development of reagents for targeted release of cargo in β-cells will have great impact on therapeutic development in diabetes.

The present invention provides a composition comprising a prodrug that comprises a cargo group, a chelating ligand, and optionally a linker (such as self-immolative linker) interconnecting the cargo group and the chelating ligand, wherein binding of $Zn^{2+}$ to the chelating ligand catalyzes cleavage of the linker between the chelating ligand and the cargo group, leading to release of the cargo compound.

In some embodiments wherein the prodrug requires a self-immolative linker, the self-immolative linker can be linked to the chelating ligand via an ester, amide, or thioester group (which encompasses a carbamate, urea, carbonate, carbonothioate, or carbamothioate group linking the self-immolative linker and the chelating ligand), and the self-immolative linker can also be linked to the cargo group via an ester, amide, or thioester group (which encompasses a carbamate, urea, carbonate, carbonothioate, or carbamothioate group linking the self-immolative linker and the cargo group). In some embodiments wherein the prodrug does not comprise a self-immolative linker, the cargo group can be linked to the chelating ligand via an ester, amide, or thioester group (which encompasses a carbamate, urea, carbonate, carbonothioate, or carbamothioate group linking the cargo group and the chelating ligand). In some embodiments, the self-immolative linker comprises at least one optionally substituted aromatic or heteroaromatic ring or fused rings for improving stability. Self-immolative linkers are described in DeWit et al., J. Am. Chem. Soc. 131:18327-18334 (2009); Blencowe et al., Polym. Chem. 2:773-790 (2011); Wei Sheng, Self-Immolative Chemistry: Structural Features and Applications in Designing Smart Materials (Mich. St. Univ. 1/15/2014, available at www2.chemistry.msu.edu/courses/cem958/FS13_SS14/Wei_Sheng.pdf), each of which is incorporated by reference in its entirety.

In some embodiments, the prodrug is represented by Formula I-A: $(Car-H)_m$—S-$(L)_n$ (I-A), wherein L comprises a chelating ligand having a selective affinity for $Zn^{2+}$; S is a scaffold that comprises an optionally substituted aromatic or heteroaromatic ring or fused rings; H is a heteroatom selected from O, N, and S, which may be part of the aforementioned aromatic or heteroaromatic ring or fused rings; Car comprises (i) a cargo group and optionally (ii) a self-immolative linker interconnecting the cargo group and H, wherein (i) or (ii) comprises an acyl group covalently bound to H to form an ester, amide, or thioester group; and each of m and n is at least one (e.g., 1, 2, 3 or 4).

In some embodiments where the prodrug requires a self-immolative linker ("SIM"), the prodrug is represented by Formula I-B: $Car-H_2-SIM-H_1$—S-L (I-B), wherein L comprises a chelating ligand having a selective affinity for $Zn^{2+}$; S is a scaffold that comprises a first optionally substituted aromatic or heteroaromatic ring or fused rings; Car is a cargo group that may comprises a second optionally substituted aromatic or heteroaromatic ring or fused rings; $H_1$ and $H_2$ are each a heteroatom independently, e.g. selected from O, N, and S, wherein $H_1$ may be part of the first aromatic or heteroaromatic ring or fused rings, and $H_2$ may be part of the second aromatic or heteroaromatic ring or fused rings; wherein SIM is a self-immolative linker comprising a first acyl group covalently bound to $H_1$ to form an ester, amide, or thioester group and a second acyl group covalently bound to $H_2$ to form an ester, amide, or thioester group. In some embodiments, $H_1$ and $H_2$ are each independently selected from O and N.

In some embodiments, the immolative linker is represented by Formula II-A:

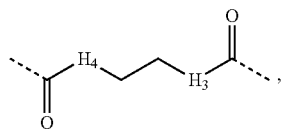

(II-A)

wherein $H_3$ and $H_4$ are each a heteroatom independently, e.g. selected from O, N, and S. In some embodiments, $H_3$ and $H_4$ are each independently selected from O and N. In some embodiments, $H_3$ and $H_4$ are each N, and $H_1$ and $H_2$ are each O.

In some embodiments, the immolative linker is represented by Formula II-B:

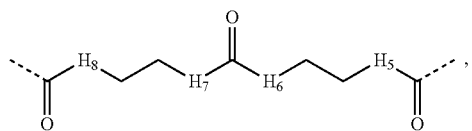

(II-B)

wherein $H_5$, $H_6$, $H_7$, and $H_8$ are each a heteroatom independently, e.g. selected from O, N, and S. In some embodiments, $H_5$, $H_6$, $H_7$, and $H_8$ are each independently selected from O and N. In some embodiments, $H_5$ and $H_6$ are each N, and $H_7$ and $H_8$ are each O or S. In some embodiments, $H_5$ and $H_6$ are each O or S, and $H_7$ and $H_8$ are each N.

In some embodiments, the immolative linker is represented by Formula II-C:

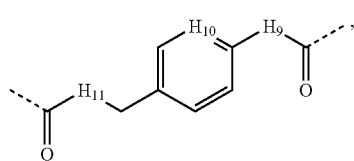

(II-C)

wherein $H_9$ and $H_{11}$ are each a heteroatom independently, e.g. selected from O, N, and S, and $H_{10}$ is C or N. In some embodiments, $H_9$ and $H_{11}$ are each independently selected from O and N. In some embodiments, $H_{11}$ is O. In some embodiments, $H_9$ and $H_{11}$ are each O, and $H_{10}$ is C.

In some embodiments, the immolative linker is represented by Formula II-D:

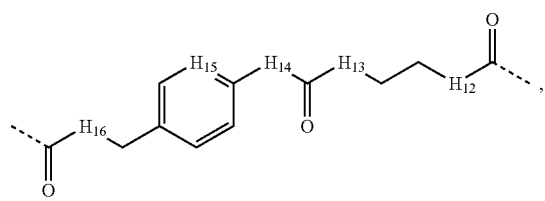

(II-D)

wherein $H_{12}$, $H_{13}$, $H_{14}$, and $H_{16}$ are each a heteroatom independently, e.g. selected from O, N, and S, and $H_{15}$ is C or N. In some embodiments, $H_{12}$, $H_{13}$, $H_{14}$, and $H_{16}$ are independently selected from O and N. In some embodiments, $H_{16}$ is O. In some embodiments, $H_{12}$ and $H_{13}$ are each N, $H_{14}$ and $H_{16}$ are each O, and $H_{15}$ is C.

In some embodiments, the immolative linker is represented by Formula II-E:

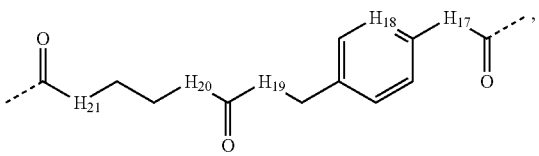

(II-E)

wherein $H_{17}$, $H_{19}$, $H_{20}$, and $H_{21}$ are each a heteroatom independently, e.g. selected from O, N, and S, and His is C or N. In some embodiments, $H_{17}$, $H_{19}$, $H_{20}$, and $H_{21}$ are each independently selected from O and N. In some embodiments, $H_{19}$ is O. In some embodiments, $H_{17}$ and $H_{19}$ are each O, $H_{20}$ and $H_21$ are each N, and His is C.

In some embodiments, S in Formula (I-A) comprises an optionally substituted phenyl ring, and H is O. In some embodiments, the prodrug is represented by Formula (III-A):

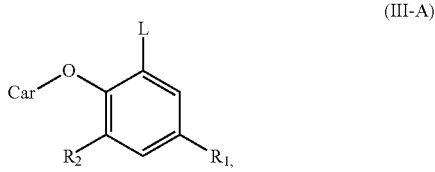

(III-A)

wherein Car and L have the same definitions as those of Formula (I-A); $R_1$ is H or comprises an electron withdrawing group or an electron donating group; and $R_2$ is H or comprises a chemical group conferring steric hindrance and/or reduction of electronic conjugation of the acyl group to the aromatic ring.

In some embodiments, S in Formula (I-A) comprises an optionally substituted imidazole ring, and H is N and forms part of the imidazole ring. In some embodiments, the prodrug is represented by Formula (III-B):

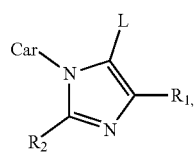

(III-B)

wherein Car and L have the same definitions as those of Formula (I-A); $R_1$ is H or comprises an electron withdrawing group or an electron donating group; and $R_2$ is H or comprises a chemical group conferring steric hindrance and/or reduction of electronic conjugation of the acyl group to the aromatic ring.

In some embodiments, S in Formula (I-B) comprises an optionally substituted phenyl ring, and $H_1$ is O. In some embodiments, the prodrug is represented by Formula (III-C):

(III-C)

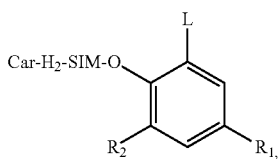

wherein Car, L, SIM, and $H_2$ have the same definitions as those in Formula (I-B); $R_1$ is H or comprises an electron withdrawing group or an electron donating group; and $R_2$ is H or comprises a chemical group conferring steric hindrance and/or reduction of electronic conjugation of the acyl group to the aromatic ring. In some embodiments, SIM is selected from Formulae II-A to II-E.

In some embodiments, S in Formula (I-B) comprises an optionally substituted imidazole ring, and $H_1$ is N and forms part of the imidazole ring. In some embodiments, the prodrug is represented by Formula (III-D):

(III-D)

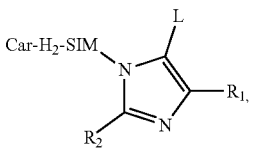

wherein Car, L, SIM, and $H_2$ have the same definitions as those in Formula (I-B); $R_1$ is H or comprises an electron withdrawing group or an electron donating group; and $R_2$ is H or comprises a chemical group conferring steric hindrance and/or reduction of electronic conjugation of the acyl group to the aromatic ring. In some embodiments, SIM is selected from Formulae II-A to II-E.

In some embodiments, Car in Formula (III-A) comprises a masked fluorophore which can be unmasked by the cleavage of the ester, amide, or thioester group to emit a fluorescent signal. In some embodiments, the prodrug is represented by Formula (IV-A):

(IV-A)

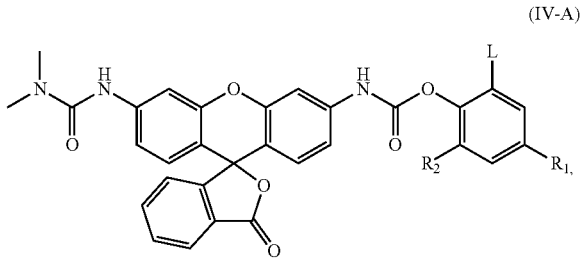

wherein R1 is H or comprises an electron withdrawing group or an electron donating group; and R2 is H or comprises a chemical group conferring steric hindrance and/or reduction of electronic conjugation of the acyl group to the aromatic ring.

In some embodiments, S in Formula (III-A) comprises a masked fluorophore which can be unmasked by the cleavage of the ester, amide, or thioester group to emit a fluorescent signal. In some embodiments, the prodrug is represented by Formula (IV-B):

(IV-B)

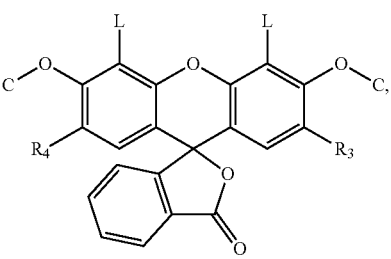

wherein each of R3 and R4 is H or comprises an electron withdrawing group, an electron donating group, or a chemical group conferring steric hindrance and/or reduction of electronic conjugation of the acyl group to the aromatic ring, and wherein C is an acyl group.

$Zn^{2+}$ is present in high concentrations in beta cells-beta cells often have over a million-fold higher $Zn^{2+}$ concentration than other cell types and plasma. Accordingly, in some embodiments, the composition is administered systematically or locally and selectively activated in beta cells. The $Zn^{2+}$ may be intracellular or extracellular $Zn^{2+}$, for example in the vicinity of the beta cells (i.e. in the islets of the pancreas). In some embodiments, the beta cells may be in vivo. In some embodiments, the beta cells may be ex vivo, for example as part of an ex vivo therapy or as part of organ-on-a-chip, such as a pancreas-on-a-chip or simply islets-on-a-chip. In some embodiments, the chelating ligand has a selective affinity for $Zn^{2+}$ over $Fe^{2+}$, $Cu^{2+}$, $Mn^{2+}$, $Co^{2+}$, and $Ni^{2+}$.

In some embodiments, the chelating ligand has a dissociation constant Kd for $Zn^{2+}$ of less than about 1 mM, less than about 100 μM, less than about 10 μM, less than about 1 μM, less than about 100 nM, less than about 10 nM, less than about 1 nM, less than about 100 pM, less than about 10 pM, less than about 1 pM, or less than about 0.1 pM. In some embodiments, the chelating ligand has a dissociation constant Kd for $Zn^{2+}$ of about 0.1 nM to about 1 mM, about 1 nM to about 100 μM, about 10 nM to about 10 μM, about 100 nM to about 1 μM, or about 1 μM to about 10 μM. In some embodiments, the chelating ligand has a dissociation constant Kd for $Zn^{2+}$ of about 0.6 pM, about 0.7 nM, about 0.7 μM, about 1.5 μM, about 33 μM, or about 0.7 mM.

In some embodiments, the chelating ligand comprises numerous chemical moieties having a variety of structural, chemical and other characteristics capable of forming coordination bonds with zinc. In some embodiments, the chelating ligand comprises at least two secondary or ternary amines. In other embodiments, the chelating ligand comprises three secondary or tertiary amines. In some embodiments, the chelating ligand comprises a tertiary alkyl amine covalently bound to at least one pyridine ring. In some embodiments, the chelating ligand comprises a tertiary alkyl amine covalently bound to at least two pyridine rings. In some embodiments, the chelating ligand comprises a tertiary alkyl amine covalently bound to at least one pyrrole ring, at least one furan ring, and/or at least one thiophene ring.

In some embodiments, the chelating ligand is selected from the group consisting of:

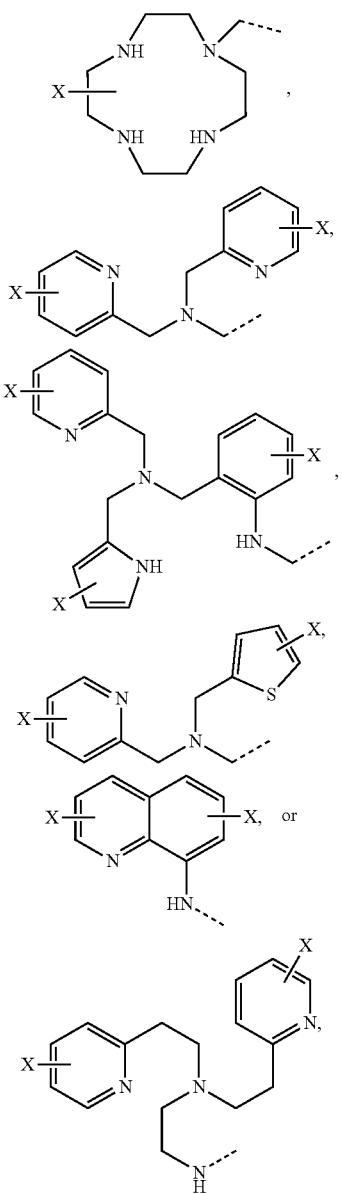

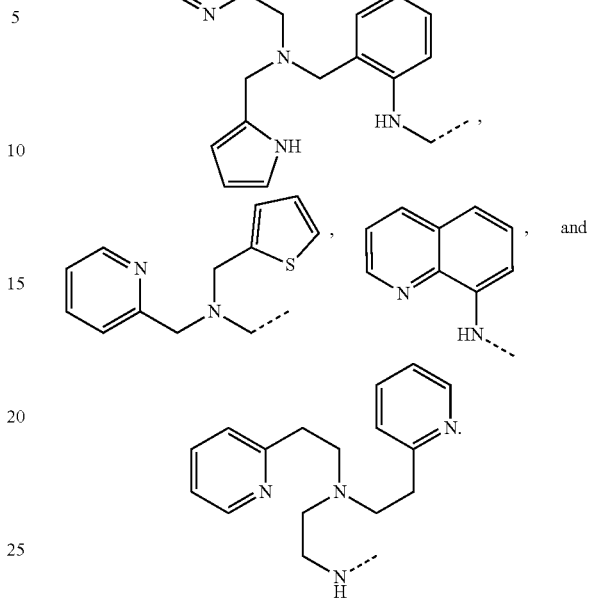

wherein X is independently H, NO₂, halogen, alkyl, alkoxy, haloalkyl, or aryl, provided that X does not interfere with the coordination between nitrogen and zinc.

In some embodiments, the chelating ligand is selected from the group consisting of:

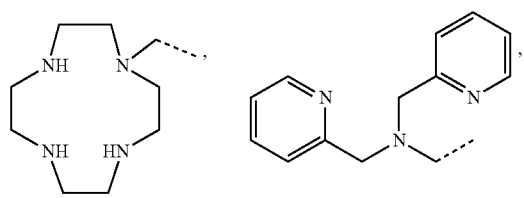

In some embodiments, the chelating ligand is

In some embodiments, the cargo compound is a therapeutic or diagnostic agent that is physiologically inactive when covalently bound to the aromatic ring or aromatic fused rings. The covalent bond is cleaved to release the therapeutic or diagnostic agent which can exhibit its known pharmacological or diagnostic effect, i.e. become active at the target delivery site. The releasing or activation of the therapeutic or diagnostic agent is achieved by a reaction mechanism that exists at the target delivery site. In some embodiments, the activation of the therapeutic or diagnostic agent is catalyzed by a zinc. In some embodiments, the covalent bond is an ester, amide, or thioester group. In some embodiments, the target delivery site is β-cell. In some embodiments, the activation of the therapeutic or diagnostic agent is catalyzed by zinc and the covalent bond is an ester, amide, or thioester group. In some embodiments, the activation of the therapeutic or diagnostic agent is catalyzed by zinc, and the target delivery site is β-cell. In some embodiments, the covalent bond is an ester, amide, or thioester group, and the target delivery site is β-cell. In some embodiments, the activation of the therapeutic or diagnostic agent is catalyzed by zinc, the covalent bond is an ester, amide, or thioester group, and the target delivery site is β-cell. Accordingly, in some embodiments, the inactive therapeutic or diagnostic agent that is covalently bound to the aromatic ring or aromatic fused rings, becomes activated upon zinc-catalyzed release at β-cell.

The key to achieve the selective release at the β-cell is to control the cleavage of the covalent bond catalyzed by $Zn^{2+}$, i.e. the cargo release process. In some embodiments, the cargo release process can be tailored by tuning the affinity of zinc chelating ligand. See FIGS. 5 and 17. A high-affinity $Zn^{2+}$ chelating ligand facilitates cargo release, but may induce a premature release of the cargo at sites with low $Zn^{2+}$ concentration. High affinity ligands can also deplete $Zn^{2+}$ and may be toxic. On the other hand, a low-affinity $Zn^{2+}$ chelating ligand reduces efficiency of cargo release. Thus, in some embodiments, the prodrug comprises a chelating ligand that confers the best β-cell selectively.

In some embodiments, the cargo release process can be tailored by controlling the stability of the covalent bond being cleaved. In some embodiments, the prodrug is represented by

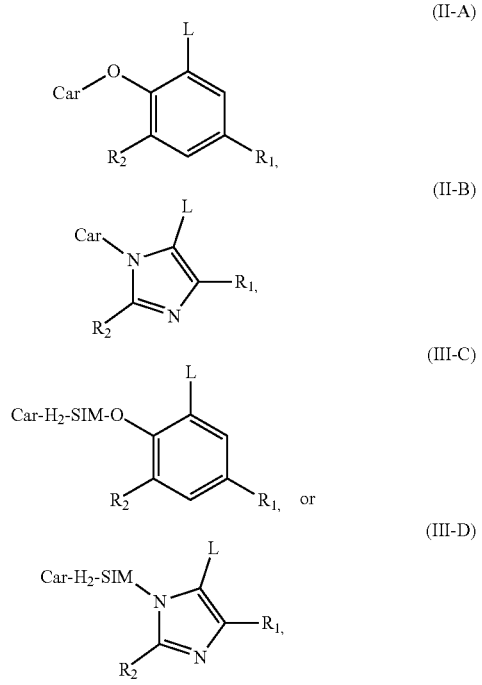

and the stability of the ester or amide group can be controlled by varying the R1 and R2 groups. In some embodiments, R1 is H. In other embodiments, R1 is an electron-withdrawing group that decreases the hydrolytic stability of the ester or amide group between the cargo (Car) and the aromatic ring.

In some embodiments, non-limiting examples of electron-withdrawing group may include NR3+, SR2+, NH3+, —NO2, —SO2R, —CN —SO2Ar, —COOH, —F, —Cl, —Br, —I, —Oar, —COOR, —OR, —COR, —SH, —SR, —OH, —CCR, —Ar and —C=CR2, wherein each R, individually, is a hydrogen, an alkyl or an aryl. In some embodiments, R1 is —CN or —NO2. In other embodiments, R1 is —Cl.

In some embodiments, R1 is an electron-donating group that increases the hydrolytic stability of the ester, amide, or thioester group between the cargo (Car) and the aromatic ring. Non-limiting examples of the electron-donating group include —NH2, —OH, —CH3, —SH, —NHCO2, —OCOH, —OCH3, —N(CH3)2, and C1-C5 saturated alkyl group.

In some embodiments, R2 is H or a halogen. In other embodiments, R2 is a chemical group conferring steric hindrance. In some embodiments, the steric hindrance group prevents the electronic conjugation of the acyl group to the aromatic ring and hinders water from approaching the reaction site. Non-limiting examples of the group conferring steric hindrance includes branched C4-C18 alkyl, C3-C8 cycloalkyl, and C6-C10 aryl, any of which may be substituted or unsubstituted, but for the most part will be unsubstituted. In some embodiments, specific examples of steric hindrance groups include iso-butyl, tert-butyl, n-pentyl, iso-pentyl, cyclopentyl, cyclohexyl, phenyl, norbornyl, cyclooctyl, (2,4,4'-trimethyl)pentyl, and heterobicycles.

In some embodiments, the prodrug is an imaging agent comprising a masked fluorophore which can be unmasked by the cleavage of the ester, amide, or thioester group to emit a fluorescent signal. In some embodiments, the imaging agent is selected from:

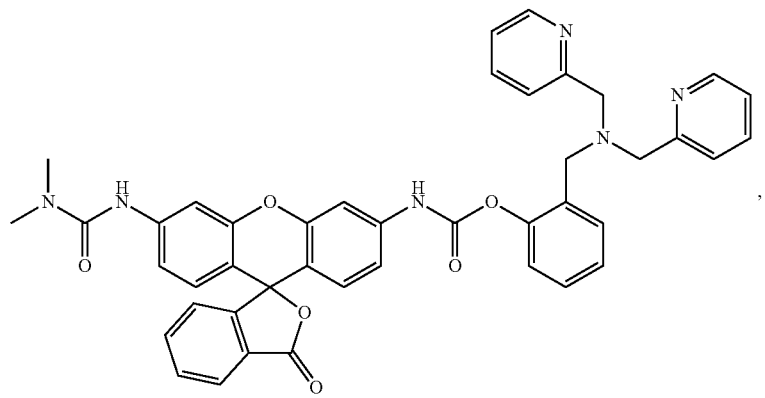

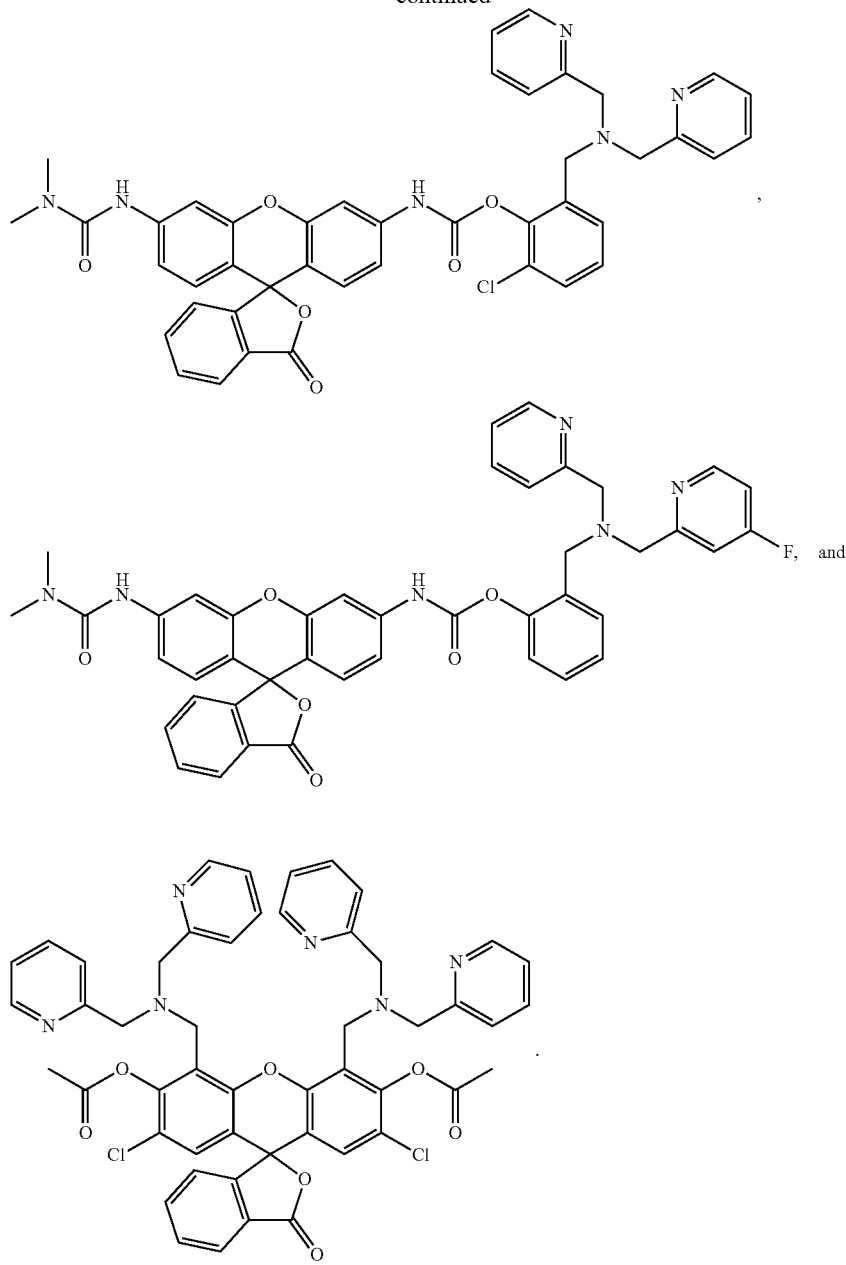

In some embodiments, the composition further comprises a pharmaceutically acceptable carrier.

In some embodiments, as the steric crowding near the $Zn^{2+}$ binding site may affect the release of the cargo, the prodrug may additionally comprise an immolative linker. Immolative linkers that undergo cascades are preferred and these may include quinone methide, intramolecular cyclization, or hemiacetal degradation.

In some embodiments, the cargo compound is a therapeutic agent for treating diabetes. In some embodiments, the therapeutic agent promotes β-cell proliferation. In other embodiments, the therapeutic agent increases insulin secretion. In some embodiments, the therapeutic agent provides protection from β-cell death. In other embodiments, the therapeutic agent is an inhibitor of cytokine-induced β-cell apoptosis. In some embodiments, the therapeutic agent prevents glucolipotoxicity-induced β-cell apoptosis.

In some embodiments, the therapeutic agent is selected from the group consisting of: insulin analogues, pramlintide, metformin, sulphonylureas, meglitinides, thiazolidinediones (TZDs), glucagon-like peptide 1 (GLP1) analogues, dipeptidyl peptidase 4 (DPP4) inhibitors, alpha-glucosidase inhibitors, sodium-dependent glucose cotransporter 2(SGLT2) inhibitors, bromocriptine, diarylamide WS6, adenosine kinase inhibitor 5-iodotubercidin (5-IT), adenosine receptor agonist 5'-N-ethylcarboxamidoadenosine (NECA), sulphonylureas, TAK-875, gliptins, TUG891, AMG-151, MBX-2982, vorinostat, IL-1 receptor agonist anakinra, and HDAC inhibitors.

In some embodiments, the therapeutic agent is selected from the group consisting of: DYRK1A inhibitors, elastase inhibitors, BRD0476, BRD3308, harmine, 5-IT, sivelestat, and GNF4877.

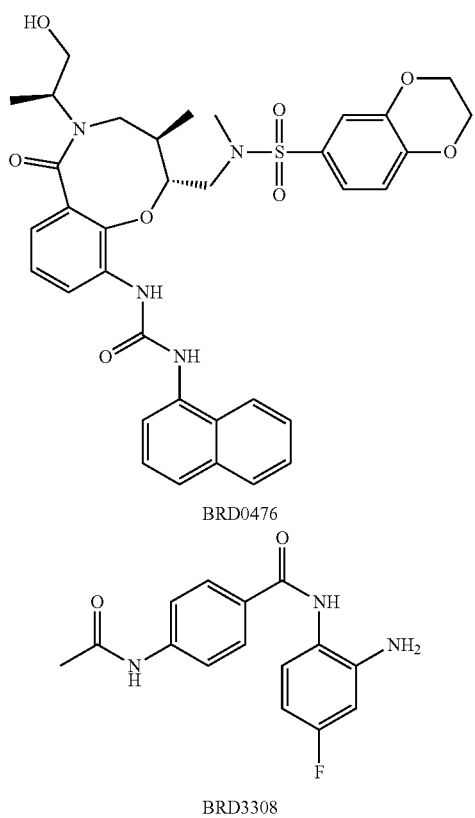

BRD0476

BRD3308

In some embodiments, the therapeutic agent is a leucettine. See Debdab et a., J. Med. Chem., 54:4172-4186 (2011), which is incorporated by reference in its entirety.

In some embodiments, the cargo compound is a diagnostic agent for diabetes. In some embodiments, the diagnostic agent binds to a protein of the β-cells, and the expression of the protein can be used to diagnose diabetes, for example by its correlation to insulin secretion. In some embodiments, the diagnostic agent binds to a pancreatic zinc transporter, for example, ZnT8. In some embodiments, the diagnostic agent comprises a detectably labeled moiety that can be used to detect the expression level of the ZnT8 protein. In some embodiments, the detectably labeled moiety is a fluorophore. Upon binding of the prodrug to β-cell, the diagnostic agent is released by zinc catalyzed ester, amide, or thioester group cleavage, and binds to ZnT8. Thus, the expression level of ZnT8 can be detected via the detection of the fluorophore, and which is known to correlate with insulin secretion and thus can be used to diagnose diabetes. See Huang et al., J. Bio. Chem. (2017) 292(10): 4034-4043.

In some embodiments, the cargo compound is an imaging agent, which can be used to detect and/or monitor β-cells. In some embodiments, the cargo compound comprises a fluorescent molecule. Upon binding of the prodrug to β-cell, the imaging agent is released by zinc catalyzed ester, amide, or thioester group cleavage, and allows imaging of the β-cell. In some embodiments, the imaging agent binds to a biomarker for islet beta cell, for example, GLP-1. In some embodiments, the imaging agent comprises a detectably labeled moiety that can be used to detect the expression level of the GLP-1 protein. In some embodiments, the detectably labeled moiety is a fluorophore. In some embodiments, upon binding of the prodrug to 3-cell, the imaging agent is released by zinc catalyzed ester, amide, or thioester group cleavage, and binds to GLP-1. Thus, the expression level of GLP-1 can be detected via the detection of the fluorophore. See Li et al., Bioconjugate Chem. (2015) 26: 1443-1450.

In one aspect, the present invention provides a method for selective delivery of a cargo compound to β-cells in vivo, comprising administering a composition of the present invention to a subject in need thereof, wherein binding of $Zn^{2+}$ to the chelating ligand of the prodrug in the β-cells catalyzes cleavage of the ester, amide, or thioester group, thereby releasing the cargo compound in the β-cells.

In another aspect, the present invention provides a method for treating diabetes, comprising administering a composition of the present invention to a subject in need thereof, wherein binding of $Zn^{2+}$ to the chelating ligand of the prodrug in the β-cells catalyzes cleavage of the ester, amide, or thioester group, thereby releasing the therapeutic agent in the β-cells.

In another aspect, the present invention provides a method for promoting β-cell proliferation and/or regeneration, comprising administering a compositions of the present invention to a subject in need thereof, wherein binding of $Zn^{2+}$ to the chelating ligand in the β-cells catalyzes cleavage of the ester, amide, or thioester group, thereby releasing the therapeutic agent in the β-cells.

In yet another aspect, the present invention provides a method for imaging β-cells in vivo, comprising administering the composition of the present invention a subject thereof, wherein binding of $Zn^{2+}$ to the chelating ligand of the prodrug in the β-cells catalyzes cleavage of the ester, amide, or thioester group, thereby allowing the cargo compound or the optionally substitute aromatic ring or aromatic fused rings to emit a fluorescent signal in the β-cells, and detecting the fluorescent signal emitted from the cargo compound or the optionally substitute aromatic ring or aromatic fused rings.

In yet another aspect, the present invention provides a method for imaging β-cells in vitro, comprising contacting a composition of the present invention with a cell culture comprising β-cells, wherein binding of $Zn^{2+}$ to the chelating ligand of the prodrug in the β-cells catalyzes cleavage of the ester, amide, or thioester group, thereby allowing the cargo compound or the optionally substituted aromatic ring or aromatic fused rings to emit a fluorescent signal in the β-cells, and detecting the fluorescent signal emitted from the cargo compound or the optionally substitute aromatic ring or aromatic fused rings.

In yet another aspect, the present invention provides a method for detecting $Zn^{2+}$ contamination or concentration, comprising contacting a composition of the present invention with a sample, wherein binding of $Zn^{2+}$ to the chelating ligand catalyzes cleavage of the ester, amide, or thioester group between the chelating ligand and the cargo compound, thereby allowing the cargo compound or the optionally substitute aromatic or heteroaromatic ring or fused rings to emit a fluorescent signal; detecting an intensity of the fluorescent signal emitted; and determining the presence or a concentration of $Zn^{2+}$ in the sample based on the detected intensity of the fluorescent signal.

The invention provides a method for determining $Zn^{2+}$ concentrations, including but not limited to, e.g. $Zn^{2+}$ availability, contamination in biological and non-biological samples. Biological samples include without limitation, serum, urine, lymph, cerebrospinal fluid (CSF), tissues extracts, foods. Non-biological samples include without limitation, soil, water, waste, industrial processes, environmental samples, plumes of polluted groundwater and the like.

In an embodiment, the invention provides a method for determining $Zn^{2+}$ concentration in a sample. In a non-limiting example, signal development is $Zn^{2+}$ concentration dependent, and $Zn^{2+}$-concentration is determined by comparison to a standard curve. The relative intensity indicates the relative quantity of Zn. In one such embodiment, the time course of signal development is observed when a reporter is brought in contact with a $Zn^{2+}$-containing composition. Signal development can be determined over a wide variety of time periods, e.g., without limitation, seconds, hours, or days.

Cargos include, e.g., small molecules, proteins, polypeptides, nucleic acids, and synthetic analogs. In preferred embodiments, the cargo moiety is linked to the chelating ligand but is not a substrate for cleavage by the chelating ligand, i.e., a bond linking the cargo to the chelating ligand is cleaved but preferably not the cargo itself.

In an embodiment, the method involves $Zn^{2+}$-dependent cleavage of a substrate accompanied by detectable signaling. For example, the cargo can be a fluorescent moiety linked to a quencher and the chelating ligand provides for release of the fluorescent moiety from the quencher such that fluorescence becomes detectable. In another embodiment, a nucleic capable of being amplified is released into solution wherein the nucleic acid is amplified and detected. In another embodiment, a protein or polypeptide, such as a fluorescent protein not limited to green fluorescent protein (GFP), red fluorescent protein (RFP), or luciferase is released and detected.

In an embodiment of the invention, the detectable moiety capable of $Zn^{2+}$-dependent cleavage and/or activation is attached to a support. In a non-limiting embodiment, the support is a test strip that can be dipped in a Zn-containing medium. In the presence of Zn, a quencher is cleaved rendering the fluorescent moiety attached to the support detectable.

In another aspect, the present invention provides compositions and methods for selective activation of a CRISPR effector protein in β-cells. In another aspect, the present invention provides compositions and methods for genome editing in β-cells. In yet another aspect, the present invention provides compositions and methods for selective transcriptional activation or repression in β-cells.

In some embodiments, the target gene in β-cells is a gene involved in β-cells proliferation. In some embodiments, the target gene is $p16^{INK4A}$, which has been reported to be involved in the senescence-mediated β-cell death. Krishnamurthy, et al., Nature (2006) 443:453-457; Helman et al., *Diabetes Obes. Metab.* (2016) 18 Suppl 1:58-62. In some embodiments, the target gene is $p19^{ARF}$. In some embodiments, the target gene comprises a mutation causing monogenic diabetes. In some embodiments, the target gene comprises a mutation in a gene or genes associated with Maturity-Onset Diabetes of the Young (MODY). In some embodiments, such target gene may include one or more of MODY 1 (HNF4A-MODY), MODY 2 (GCK-MODY), MODY 3 (HNF1A-MODY), and/or MODY 5 (HNFE1B-MODY). In some embodiments, the target gene comprises a mutation in a gene or genes associated with Neonatal Diabetes. In some embodiments, the neonatal diabetes target gene is selected from one or more of KCNJ11, ABCC8, INS or insulin gene, and/or 6q24. In some embodiments, the neonatal diabetes target gene is selected from one or more of EIF2AK3, FOXP3, GATA6, GCK, GLIS3, HNF1B, IER3IP1, NEUROD1, NEUROG3, PDX1, PTF1A, RFX6, PAX6, SLC19A2, SLC2A2, WFS1.

In some embodiments, the present invention provides a prodrug comprising a cargo compound which is a stabilizing ligand for a polypeptide comprising a destabilization domain (DD), wherein binding of the stabilizing ligand to the destabilization domain prevents proteasomal degradation of the polypeptide. In some embodiments, a method of stabilizing a CRISPR effector protein is provided, for example by retaining the activity of the CRISPR effector protein or the CRISPR effector protein in undegraded form. This may also be part of an inducible system, such as including a split CRISPR effector protein and one or more Destabilization Domains (DDs)

In some embodiments, the cargo compound is a stabilizing ligand for a destabilized dihydrofolate reductase (DHFR) or a destabilized estrogen receptor ligand binding domain (ERLBD). In some embodiments, the cargo compound is trimethoprim (TMP), 4-hydroxytamoxifen (4HT), or CMP8.

In some embodiments, where DD is DHFR, a corresponding stabilizing ligand for this DD is, in some embodiments, TMP. As such, in some embodiments, one of the at least one DDs is DHFR and a stabilizing ligand therefor is TMP.

In some embodiments, where DD is ER50, a corresponding stabilizing ligand for this DD is, in some embodiments, 4HT. As such, in some embodiments, one of the at least one DDs is ER50 and a stabilizing ligand therefor is 4HT. In some embodiments, where the DD is ER50 a corresponding stabilizing ligand for this DD is, in some embodiments, CMP8. CMP8 may therefore be an alternative stabilizing ligand to 4HT in the ER50 system.

In some embodiments, the destabilization domain is fused to a CRISPR effector protein, wherein binding of the stabilizing ligand to the destabilization domain increases activity of the CRISPR effector protein by at least one fold, at least 2 folds, at least 5 folds, at least 10 folds, at least 20 folds, at least 50 folds, or at least 100 folds.

In some embodiments, the CRISPR effector protein is Cas9, Cpf1, C2c1, C2c2, or Cas13b. In some embodiments, the CRISPR effector protein is a DNA-targeting CRISPR effector protein. In some embodiments, the CRISPR effector protein is a Type-II CRISPR effector protein such as Cas9. In some embodiments, the CRISPR effector protein is a Type-V CRISPR effector protein such as Cpf1 or C2c1. In some embodiments, the CRISPR effector protein is a RNA-targeting CRISPR effector protein. In some embodiments, the CRISPR effector protein is a Type-VI CRISPR effector protein such as C2c2 or Cas13b.

In some embodiments, the destabilization domain is fused to (i) an aptamer ligand and (ii) a functional domain, such as a transcriptional activation domain or a transcriptional repression domain, wherein binding of the stabilizing ligand to the destabilization domain increases activity of the aptamer ligand by at least one fold, at least 2 folds, at least 5 folds, at least 10 folds, at least 20 folds, at least 50 folds, or at least 100 folds.

In some embodiments, the aptamer ligand is selected from MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, or PRR1. In some embodiments, the functional domain is a transcriptional activation domain or a transcriptional repression domain. These may be selected from VP64, P65, MyoD1, HSF1, RTA, SET7/9, KRAB, NuE, NcoR, SID, or SID4X.

In one aspect, the present invention provides a method for selective activation of a CRISPR effector protein in β-cells, comprising administering the composition of the present invention to a subject in need thereof, simultaneously or sequentially with a fusion protein of a CRISPR effector protein and at least one destabilization domain, or a polynucleotide encoding the fusion protein, wherein binding of $Zn^{2+}$ to the chelating ligand in the β-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the CRISPR effector protein to function in the β-cells. In some embodiments, the target sequence is a gene involved in β-cell proliferation. In some embodiments, the target sequence is $p16^{INK4A}$. In some embodiments, the target sequence is $p19^{ARF}$. In some embodiments, the target sequence comprises a mutation causing monogenic diabetes and examples of target genes are herein described.

In one aspect, the present invention provides a method for selective genomic editing in β-cells, comprising administering the composition of the present invention to a subject in need thereof, simultaneously or sequentially with (i) a fusion protein of a catalytically active CRISPR effector protein and at least one destabilization domain, or a polynucleotide encoding the fusion protein and (ii) a guide RNA hybridizable to a target sequence in the genome of the subject or a polynucleotide encoding the guide RNA, wherein binding of $Zn^{2+}$ to the chelating ligand in the β-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the catalytically active CRISPR effector protein to form a CRISPR complex with the guide RNA and the target sequence for genome editing in the β-cells. Fusion proteins comprising a catalytically active CRISPR effector protein and at least one destabilization domain are described in PCT/US2015/067177 filed Dec. 21, 2015 and U.S. 62/356,028 filed Jun. 29, 2016, each of which is incorporated by reference in its entirety. In some embodiments, the target sequence is a gene involved in β-cell proliferation. In some embodiments, the target sequence is $p16^{INK4A}$. In some embodiments, the target sequence is $p19^{ARF}$. In some embodiments, the target sequence comprises a mutation causing monogenic diabetes and examples of target genes are herein described.

In another aspect, the present invention provides a method for selective transcriptional activation or repression in β-cells, comprising administering the composition of the present invention to a subject in need thereof, simultaneously or sequentially with (i) a fusion protein of a catalytically inactive CRISPR effector protein, at least one destabilization domain, and at least one transcriptional activation domain or transcriptional repression domain, or a polynucleotide encoding the fusion protein, and (ii) a guide RNA hybridizable to a target sequence in genome of the subject or a polynucleotide encoding the guide RNA, wherein binding of $Zn^{2+}$ to the chelating ligand in the β-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the catalytically inactive CRISPR effector protein to form a CRISPR complex with the guide RNA and the target sequence for transcriptional activation or repression in the β-cells. Fusion proteins comprising a catalytically inactive CRISPR effector protein, at least one destabilization domain, and at least one transcriptional activation domain or transcriptional repression domain are described in PCT/US2015/067177 filed Dec. 21, 2015 and U.S. 62/356,028 filed Jun. 29, 2016, each of which is incorporated by reference in its entirety. In some embodiments, the target sequence is a gene involved in β-cell proliferation. In some embodiments, the target sequence is $p16^{INK4A}$. In some embodiments, the target sequence is $p19^{ARF}$. In some embodiments, the method comprises transcriptional repression of $p16^{INK4A}$ in β-cells. In some embodiments, the method comprises transcriptional repression of $p19^{ARF}$ in β-cells. In some embodiments, the method comprises transcriptional activation of EZH2 in β-cells. In some embodiments, the method comprises transcriptional activation of Cyclin Ds in β-cells. In some embodiments, the method comprises transcriptional activation of CDK4/CDK6 in β-cells. In some embodiments, the method comprises transcriptional activation of E2Fs in β-cells.

In yet another aspect, the present invention provides a method for selective transcriptional activation or repression in β-cells, comprising administering the composition of the present invention to a subject in need thereof, simultaneously or sequentially with (i) a catalytically inactive CRISPR effector protein or a polynucleotide encoding the CRISPR effector protein, (ii) a fusion protein of at least one destabilization domain, at least one aptamer ligand, and at least one transcriptional activation domain or transcriptional repression domain, and (iii) a guide RNA hybridizable to a target sequence in genome of the subject or a polynucleotide encoding the guide RNA, wherein the guide RNA comprises an aptamer sequence capable of binding to the transcriptional activation domain or transcriptional repression domain, wherein binding of $Zn^{2+}$ to the chelating ligand in the β-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the fusion protein to bind to the aptamer sequence of guide RNA for transcriptional activation or repression in the β-cells. Fusion proteins comprising at least one destabilization domain, at least one aptamer ligand, and at least one transcriptional activation domain or transcriptional repression domain are described in PCT/US2015/067177 filed Dec. 21, 2015 and U.S. 62/356,028 filed Jun. 29, 2016, each of which is herein incorporated by reference in its entirety. In some embodiments, the target sequence is a gene involved in β-cell proliferation. In some embodiments, the target sequence is $p16^{INK4A}$. In some embodiments, the target sequence is $p19^{ARF}$. In some embodiments, the method comprises transcriptional repression of $p16^{INK4A}$ in β-cells. In some embodiments, the method comprises transcriptional repression of $p19^{ARF}$ in β-cells. In some embodiments, the method comprises transcriptional activation of EZH2 in β-cells. In some embodiments, the method comprises transcriptional activation of Cyclin Ds in β-cells. In some embodiments, the method comprises transcriptional activation of CDK4/CDK6 in β-cells. In some embodiments, the method comprises transcriptional activation of E2Fs in β-cells.

In some embodiments, a multiplexing or multiplexed approach may be used. In some embodiments, one or more guide RNAs may be used. In some embodiments, two to more guide RNAs may be used, directed to either two to more distinct genes or to (or around) the same gene, including between exons or to flank exons (i.e. within intronic sequences) or to flank the entire coding sequence. In some embodiments, multiple, including paired, guides are envisaged. In some embodiments, multiple, including paired, guides are envisaged.

In one aspect, there is provided the present composition for use in any of the methods described herein, optionally in the treatment of diabetes.

In one aspect, there is provided use of the present composition for the manufacture of a medicament for use in any of the method described herein, optionally in the treatment of diabetes.

In some embodiments, the prodrug described herein is administered simultaneously or sequentially with a composition comprising a CRISPR effector protein or polynucleotides encoding it, optionally a Cas9 or a Cpf1 effector protein. In some embodiments, the CRISPR effector protein may be a split CRISPR effector protein, in particular a split Cas9 or a split Cpf1. A split CRISPR effector protein is, in some embodiments, is or is provided as an inducible system, optionally a non-naturally occurring or engineered system, for providing a CRISPR effector protein, the effector CRISPR protein being capable, in the presence of an inducer energy source, of forming a CRISPR complex with a target sequence and polynucleotides engineered to complex with the CRISPR protein and the target sequence, the inducible system comprising: (i) a first fusion protein, or polynucleotides encoding it; and (ii) a second fusion protein, or polynucleotides encoding it; wherein: the first fusion protein comprises a first portion of the CRISPR protein, a first half of an inducible dimer and one or more Nuclear Localization Sequences (NLS); and the second fusion protein comprises a second portion of the CRISPR protein, a second half of the inducible dimer and one or more Nuclear Export Sequences (NES); wherein contact with the inducer energy source brings the first and second portions of the inducible dimer together, so as to bring the first and second portions of the CRISPR protein together, such that the CRISPR protein is thereby capable of forming the CRISPR complex.

Accordingly, in some embodiments, the composition simultaneously or sequentially administered with the prodrug may comprise a first fusion protein, or polynucleotides encoding it, wherein the first fusion protein comprises a first portion of the CRISPR protein, a first half of an inducible dimer and one or more Nuclear Localization Sequences (NLS); and wherein contact with an inducer energy source brings the first half of the inducible dimer together with a second half of the inducible dimer, the second half of the inducible dimer is comprised within a second fusion protein which further comprises a second portion of the CRISPR protein and one or more Nuclear Export Sequences (NES), so as to bring the first and second portions of the CRISPR effector protein together, such that the CRISPR protein is thereby capable of forming, in the presence of the inducer energy source, a CRISPR complex with a target sequence and polynucleotides engineered to complex with the CRISPR effector protein and a target sequence.

In some embodiments, the composition simultaneously or sequentially administered with the prodrug may comprise a first fusion protein, or polynucleotides encoding it, wherein the first fusion protein comprises a first portion of the CRISPR protein, a first half of an inducible dimer and one or more Nuclear Export Sequences (NES) and wherein contact with an inducer energy source brings the first half of the inducible dimer together with a second half of the inducible dimer, the second half of the inducible dimer is comprised within a second fusion protein which further comprises a second portion of the CRISPR protein and one or more Nuclear Localization Sequences (NLS), so as to bring the first and second portions of the CRISPR effector protein together, such that the CRISPR protein is thereby capable of forming, in the presence of the inducer energy source, a CRISPR complex with a target sequence and polynucleotides engineered to complex with the CRISPR effector protein and a target sequence.

In some embodiments, the inducer energy source is delivered as the cargo compound of the prodrug. In some embodiments, the inducer energy source is Rapamycin (FKBP dimerizes with FRB in the presence of Rapamycin). In some embodiments, the inducer energy source is FK506 (FKBP dimerizes with CalcineurinA in the presence of FK506). In some embodiments, the inducer energy source is FKCsA (FKBP dimerizes with CyP-Fas in the presence of FKCsA). In some embodiments, the inducer energy source is Coumermycin (GyrB dimerizes with GryB in the presence of Coumermycin). In some embodiments, the inducer energy source is Gibberellin (GAI dimerizes with GID1 in the presence of Gibberellin). In some embodiments, the inducer energy source is HaXS (Snap-tag dimerizes with HaloTag in the presence of HaXS). In some embodiments, the inducer energy source is FK1012 (FKBP homo-dimerizes in the presence of FK1012).

Thus, in one aspect, there is provided an inducible system comprising the first fusion protein, or polynucleotides encoding it, as discussed here. In some embodiments, the system further comprises the second fusion protein, or polynucleotides encoding it, as discussed here. In some embodiments, the system may also comprise the inducer energy source deliverable as the cargo compound of the prodrug described herein, or this may be provided in a kit of parts whereby the kit comprises the inducible system and the inducer energy source. Thus, in one aspect, said kit is provided.

In some embodiments, the first fusion protein, or polynucleotides encoding it, may further comprise one or more Destabilization Domains (DDs). In some embodiments, the second fusion protein, or polynucleotides encoding it, may further comprise a Destabilization Domain (DD). In some embodiments, the first fusion protein, or polynucleotides encoding it, and the second fusion protein, or polynucleotides encoding it, may each further comprise a Destabilization Domain (DD). Exemplary DDs are described herein. This allows an additional degree of control to be applied, for example to an, or the, inducible system.

Accordingly, in some embodiments, the composition simultaneously or sequentially administered with the prodrug may comprise a first fusion protein, or polynucleotides encoding it, wherein the first fusion protein comprises a first portion of the CRISPR protein, a first half of an inducible dimer and one or more Nuclear Localization Sequences (NLS); and wherein contact with an inducer energy source brings the first half of the inducible dimer together with a second half of the inducible dimer, the second half of the inducible dimer is comprised within a second fusion protein which further comprises a second portion of the CRISPR protein and one or more Nuclear Export Sequences (NES), so as to bring the first and second portions of the CRISPR effector protein together, such that the CRISPR protein is thereby capable of forming, in the presence of the inducer energy source, a CRISPR complex with a target sequence and polynucleotides engineered to complex with the CRISPR effector protein and a target sequence, wherein the first fusion protein, or polynucleotides encoding it, and/or the second fusion protein, or polynucleotides encoding it, further comprise one or more Destabilization Domains (DDs).

In some embodiments, the composition simultaneously or sequentially administered with the prodrug may comprise a first fusion protein, or polynucleotides encoding it, wherein the first fusion protein comprises a first portion of the CRISPR protein, a first half of an inducible dimer and one or more Nuclear Export Sequences (NES) and wherein contact with an inducer energy source brings the first half of the inducible dimer together with a second half of the inducible dimer, the second half of the inducible dimer is comprised within a second fusion protein which further comprises a second portion of the CRISPR protein and one or more Nuclear Localization Sequences (NLS), so as to bring the first and second portions of the CRISPR effector protein together, such that the CRISPR protein is thereby capable of forming, in the presence of the inducer energy source, a CRISPR complex with a target sequence and polynucleotides engineered to complex with the CRISPR effector protein and a target sequence, wherein the first fusion protein, or polynucleotides encoding it, and/or the second fusion protein, or polynucleotides encoding it, further comprise one or more Destabilization Domains (DDs).

In some embodiments, the inducer energy source is delivered as the cargo compound of the prodrug. In some embodiments, the inducer energy source is Rapamycin (FKBP dimerizes with FRB in the presence of Rapamycin). In some embodiments, the inducer energy source is FK506 (FKBP dimerizes with CalcineurinA in the presence of FK506). In some embodiments, the inducer energy source is FKCsA (FKBP dimerizes with CyP-Fas in the presence of FKCsA). In some embodiments, the inducer energy source is Coumermycin (GyrB dimerizes with GryB in the presence of Coumermycin). In some embodiments, the inducer energy source is Gibberellin (GAI dimerizes with GID1 in the presence of Gibberellin). In some embodiments, the inducer energy source is HaXS (Snap-tag dimerizes with HaloTag in the presence of HaXS). In some embodiments, the inducer energy source is FK1012 (FKBP homo-dimerizes in the presence of FK1012).

Thus, in one aspect, there is provided an inducible system comprising the first fusion protein, or polynucleotides encoding it, as discussed here. In some embodiments, the system further comprises the second fusion protein, or polynucleotides encoding it, as discussed here. In some embodiments, the system may also comprise the inducer energy source and/or a stabilizing ligand, each deliverable as the cargo compound of the prodrug described herein, as discussed herein, or one or both of these may be provided in a kit of parts whereby the kit comprises the inducible system, the inducer energy source and/or the stabilizing ligand. Thus, in one aspect, said kit is provided.

The present invention leverages on several strengths of small molecules prodrugs. Small molecules are fast-acting, allow efficient dosage and temporal control, are reversible, and can be easily delivered to cells and tissues through passive diffusion. The ease of delivery is particularly important as most biologics fail to enter the core of islets. Finally, small molecules can be synthesized cheaply and can be homogenous, which reduces batch-to-batch variability.

The present invention provides methods and compositions for β-cell selective genomic editing, for example by coupling targeted delivery of a small molecule stabilizer or inducer with systematic or local delivery of a CRISPR-Cas effector protein. Targeted delivery of the small molecule stabilizer or inducer to β-cells can lead to β-cell selective activation of the CRISPR effector protein (e.g., Cas9 or Cpf1).

The loss of β-cell mass and/or function is a key pathogenic event in diabetes, and editing of specific genes in β-cells can resolve the loss of 3-cell mass and/or function. Choudhary et al., *Nature Review Drug Discovery* (2014) 13:278-289. In some embodiments, as a results of the targeted delivery of a small molecule stabilizer or inducer for a CRISPR-Cas effector protein, such CRISPR-mediated genomic editing is 3-cell specific, and it does not increase cellular proliferation in a nonselective way. Some embodiments provide methods and compositions specifically for β-cell selective genome editing, such as CRISPR-mediated targeted correction of a mutation causing monogenic diabetes (e.g., CRISPR-mediated targeted knockout of p16$^{INK4A}$ and/or p19$^{ARF}$. Beyond genome editing, CRISPR has been repurposed for epigenome editing, genome imaging, and for transcriptional activation or repression of genes. Wang, et. al., *Annual Review of Biochemistry* (2016) 85:227-264. The compositions of the present invention can be repurposed to effect β-cell specific epigenome editing and transcriptional regulation.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2. illustrates zinc ion catalyzed hydrolysis unmasked fluorescence in β-cells.

FIG. 3D is a confocal image of a single positive 3-cell.

FIG. 5 shows schematic of Zinc-based prodrug type systems (ZnPDs).

FIG. 8 shows the effect of different adenosine kinase inhibitors on EdU incorporation.

FIG. 9 shows the effect of harmine, a natural product and known DYRK1A inhibitor in human islet cells. FIG. 9A shows that harmine promotes β-cell proliferation in a dose-dependent manner. FIG. 9B shows that knocking down DYRK1A in human islet using shRNA also promotes 3-cell proliferation.

FIG. 10 shows an experiment for detecting serpinB1, a protease inhibitor that targets elastases. FIG. 10A shows experimental workflow for analysis of proteins from liver, liver explant conditioned media (LECM), hepatocyte-conditioned media (HCM), and plasma. FIG. 10B. shows the identification of serpinB1 by LC-MS/MS proteomics. Protein abundances were quantified based on spectral counts, and top differentially expressed proteins were plotted as log 2 ratio of LIRKO vs control (n=4 independent studies). Red bars correspond to serpinB1. FIG. 10C. shows relative liver serpinb1a mRNA by quantitative RT-PCR (normalized to TBP). Mean±SEM. *p<0.05, (n=6). FIG. 10D. shows quantification of serpinB1 protein (in E) in 12 wk-old male control and LIRKO mice. FIG. 10E. shows western blot of serpinB1 in liver. Normalized to acti; mean±SEM. *p<0.05, (n=4-5).

FIG. 11 shows serpinB1 promotes 3-cell proliferation. FIG. 11A shows fluorescent image of mouse islets treated with ovalbumin (negative control) or SerpinB1 and co-immunostained for Ki67, insulin and DAPI. FIG. 11B shows a dose-dependent effect of serpinB1 on the quantity of Ki67+ insulin+ cells (in A). Mean±SEM. **p<0.01, (n=6-12). FIG. 11C shows that inactive N-tagged serpin B1 construct from GeneCopoeia (1 g/ml) has no impact on the quantification of Ki67+ insulin+ cells in mouse islets treated ovalbumin, whereas insect cell derived untagged SerpinB1 promotes Ki67+ insulin+ cells. Mean±SEM, *p<0.05, (n=3). FIG. 11D shows that rSerpinB1 induces a dose-dependent increase in 3-cell proliferation from human islets. Mean±SEM. *p<0.05, **p<0.01, (n=7).

FIG. 12 shows synthesis of ZnPDs bearing 5-IT and sivelestat.

FIG. 15 shows a zinc-based prodrug system for selective genome editing.

FIG. 17 shows zinc-based prodrug system for TMP.

FIG. 31 shows $Zn^{2+}$-mediated release of harmine from prodrugs ML-172 and IL-173.

Figure 1:
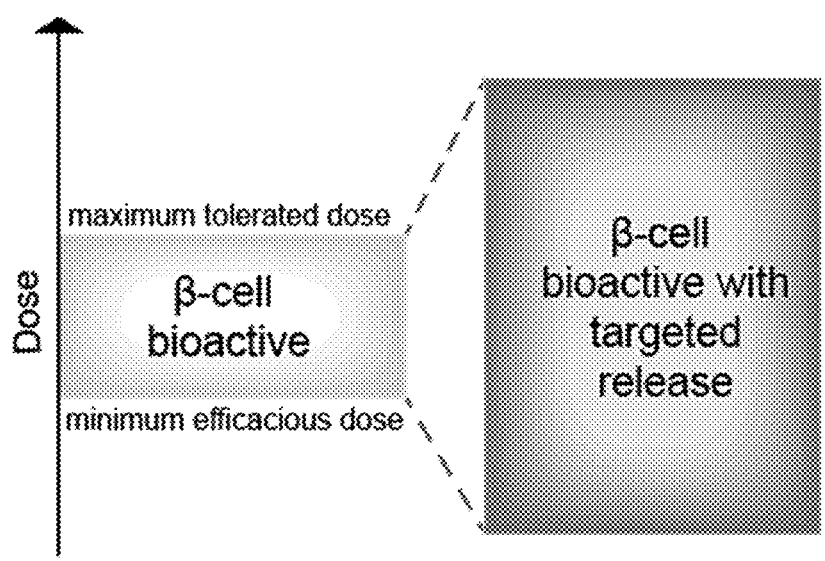
FIG. 1 shows the advantage of targeted release of small molecules to β-cells. Small molecules administered systemically have an intrinsic balance between efficacy and toxicity (e.g., by having effects on other cell types). Targeted release of a 3-cell bioactive will increase the therapeutic window by lowering the minimum efficacious dose and increasing the maximum tolerated dose of the therapeutic agent.

The figures herein are for illustrative purposes only and are not necessarily drawn to scale.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group can be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group.

The term "amine" (or "amino") as used herein refers to —NR'R" groups, wherein R' and R" are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH2, methylamino, dimethylamino, ethylamino, diethylamino, propylamino, isopropylamino, phenylamino, or benzylamino.

The term "ester" as used herein refers to —COOR'" and —C(O)O-G groups. R'" is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group CH3C(O)—.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well-known constant is described in many references, for instance, March, *Advanced Organic Chemistry* 251-59, McGraw Hill Book Company, New York, (1977). The Hammett constant values are generally negative for electron donating groups ($\sigma(P)=-0.66$ for $NH_2$) and positive for electron withdrawing groups ($\sigma(P)=0.78$ for a nitro group), $\sigma((P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like. By the terms "amino acid residue" and "peptide residue" is meant an amino acid or peptide molecule without the OH of its carboxyl group. In general the abbreviations used herein for designating the amino acids and the protective groups are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the $CH(NH_2)COOH$ portion, as defined by Kopple, *Peptides and Amino Acids* 2, 33 (W. A. Benjamin Inc., New York and Amsterdam, 1966); examples of such side chains of the common amino acids are —$CH_2CH_2SCH_3$ (the side chain of methionine), —$CH_2CH(CH_3)_2$ (the side chain of leucine) or —H (the side chain of glycine).

Specific examples of electron withdrawing group include, but are not limited to, $NR3+$, $SR2+$, $NH3+$, —$NO2$, —$SO2R$, —CN —$SO2Ar$, —COOH, —F, —Cl, —Br, —I, —Oar, —COOR, —OR, —COR, —SH, —SR, —OH, —CCR, —Ar and —C=$CR2$, wherein each R, individually, is a hydrogen, an alkyl or an aryl. Specific examples of electron donating group include, but are not limited to, —NH2, —OH, —CH3, —SH, —NHCO2, —OCOH, —OCH3, —N(CH3)2, and C1-C5 saturated alkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH–CH=$CH_2$, C=$CH_2$, or C=$CHCH_3$.

As used herein, "aryl" or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

Heteroalkyl group include straight and branched chain alkyl groups as defined above and further include 1, 2, 3, 4, 5, or 6 heteroatoms independently selected from oxygen, sulfur, and nitrogen. Thus, heteroalkyl groups include 1 to 12 carbon atoms, 1 to 10 carbons or, in some embodiments, from 1 to 8, or 1, 2, 3, 4, 5, or 6 carbon atoms, or any range therein (e.g., 1-4). Examples of heteroalkyl groups include, but are not limited to, —$(CH_2CH_2O)_{1-5}CH_3$, —$(CH_2)_{1-6}O(CH_2)_{1-6}$ $CH_3$, —$(CH_2)_{1-6}NR_a(CH_2)_{1-6}$ $CH_3$, —$(CH_2)_{1-6}S(CH_2)_{1-6}$ $CH_3$, —$(CH_2)_{1-6}O(CH_2)_{1-6}O(CH_2)_{1-6}$ $CH_3$, —$(CH_2)_{1-6}$ $NR_a(CH_2)_{1-6}$ $NR_a(CH_2)_{1-6}CH_3$, —$(CH_2)_{1-6}O(CH_2)_{1-6}O(CH_2)_{1-6}O(CH_2)_{1-6}CH_3$, —$(CH_2)_{1-6}NR_a(CH_2)_{1-6}NR_a(CH_2)_{1-6}NR_a(CH_2)_{1-6}CH_3$, with the total number of carbon atoms in the heteroalkyl group being 1 to 12 and Ra is a hydrogen or a substituted or unsubstituted alkyl, alkenyl, aryl or aralkyl group. Other examples of heteroalkyl groups include, but are not limited to, groups having different heteroatoms in a single group. Such examples of heteroalkyl groups include, but are not limited to, —$(CH_2)_{1-6}S(CH_2)_{1-6}O(CH_2)_{1-6}$, —$(CH_2)_{1-6}$ $NR_a(CH_2)_{1-6})$ $O(CH_2)_{1-6}$, —$(CH_2)_{1-6}O(CH_2)_{1-6}$ $NR_a(CH_2)_{1-6}S(CH_2)_{1-6}$, —$(CH_2)_{1-6}NR_a(CH_2)_{1-6}O(CH_2)_{1-6}S(CH_2)_{1-6}$, with the total number of carbon atoms in the heteroalkyl group being 1 to 12. In some embodiments, heteroalkyl groups include, but are not limited to, polyoxyethylene groups, such as —$(OCH_2CH_2—)_{1-5}CH_3$, for example, —$O(CH_2)_2$ $O(CH_2)_2OCH_3$, —$O(CH_2)_2O(CH_2)_2O(CH_2)_2OCH_3$, —$O(CH_2)_2O(CH_2)_2O(CH_2)_2O(CH_2)_2OCH_3$.

Aralkyl groups are substituted aryl groups in which an alkyl group as defined above has a hydrogen or carbon bond of the alkyl group replaced with a bond to an aryl group as defined above. In some embodiments, aralkyl groups contain 7 to 14 carbon atoms, 7 to 10 carbon atoms, e.g., 7, 8, 9, or 10 carbon atoms or any range therein (e.g., 7-8). Aralkyl groups may be substituted or unsubstituted. Substituted aralkyl groups may be substituted at the alkyl, the aryl or both the alkyl and aryl portions of the group. Representative substituted and unsubstituted alkaryl groups include but are not limited to alkylphenyl such as methylphenyl, (chloromethyl)phenyl, chloro(chloromethyl)phenyl, or fused alkaryl groups such as 5-ethylnaphthalenyl.

Heterocyclyl groups are non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass partially unsaturated and saturated ring systems, such as, for example, imidazolinyl and imidazolidinyl groups. The phrase also includes bridged polycyclic ring systems containing a heteroatom such as, but not limited to, quinuclidyl. The phrase also includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, pyrrolinyl, piperidyl, piperazinyl, morpholinyl, thiomorpholinyl, tetrahydropyranyl, and tetrahydrothiopyranyl groups. Representative substituted heterocyclyl groups may be mono-substituted or substituted more than once, such as, but not limited to, morpholinyl groups, which are 2-, 3-, 4-, 5-, or 6-substituted, or disubstituted with various substituents such as those listed above. The heteroatom(s) may also be in oxidized form, if chemically possible.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, imidazolyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds and also includes heteroaryl groups that have other groups bonded to one of the ring members, such as alkyl groups, referred to as "substituted heteroaryl groups." Representative substituted heteroaryl groups may be substituted one or more times with various substituents such as those listed above. The heteroatom(s) may also be in oxidized form, if chemically possible.

The term "halogen" or "halo" as used herein refers to bromine, chlorine, fluorine, or iodine. In some embodiments, the halogen is fluorine. In other embodiments, the halogen is chlorine or bromine. The term "halide" as used herein refers to the anion of a halogen, such as bromide, chloride, fluoride, and iodide. In some embodiments, the halide is chloride or iodide.

The terms "alkoxy" refers to a substituted or unsubstituted alkyl group bonded to an oxygen atom. Examples include but are not limited to methoxy and ethoxy. Representative substituted alkoxy groups may be substituted one or more times with substituents such as those listed above, such as methoxymethyl and fluoromethoxy.

The term "prodrug" refers to a compound which provides an active compound following administration to the individual in which it is used, by a chemical and/or biological process in vivo (e.g., by hydrolysis and/or an enzymatic conversion). The prodrug itself may be active, or it may be relatively inactive, then transformed into (e.g., either spontaneous or enzymatic) within the subject to release, or to convert (e.g., enzymatically, mechanically, electromagnetically, etc.) a more active compound. Prodrugs can be used to overcome issues associated with stability, toxicity, lack of specificity, or limited bioavailability and often offer advantages related to solubility, tissue compatibility, and/or delayed release (See e.g., Bundgard, Design of Prodrugs, pp. 7-9, 21-24, Elsevier, Amsterdam (1985); and Silverman, The Organic Chemistry of Drug Design and Drag Action, pp. 352-401, Academic Press, San Diego, CA (1992) both incorporated by reference for their teachings regarding the same). The present invention embraces prodrugs that comprise a chelating ligand and a cargo. Upon binding of $Zn^{2+}$ to the chelating ligand, $Zn^{2+}$ catalyzes cleavage of an ester, amide, or thioester group between the chelating ligand and the cargo, thereby releasing the cargo.

The term "ligand" refers to a species that interacts in some fashion with another species. In one example, a ligand may be a Lewis base that is capable of forming a coordinate bond with a Lewis acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. A Lewis base, when coordinated to a metal ion, is often referred to as a ligand. Further description of ligands relevant to the present invention is presented below. The terms "Lewis acid" and "Lewis acidic" are art-recognized and refer to chemical moieties which can accept a pair of electrons from a Lewis base as defined above.

The term "chelating ligand" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent form coordinate bonds with a single metal ion; however, in certain examples, a chelating agent may form coordinate bonds with more than one metal ion, with a variety of binding modes being possible.

The term "steric hindrance," refers to a steric effect occurs in the molecule arising from the crowding of substituent groups on the molecule. The steric hindrance may affect the reactivity of the molecule. The functional groups that introduce steric hindrance include, but are not limited to branched C4-C18 alkyl, C3-C8 cycloalkyl, and C6-C10 aryl, any of which may be substituted or unsubstituted, but for the most part will be unsubstituted. In some embodiments, specific examples of steric hindrance groups include: isobutyl, tert-butyl, n-pentyl, iso-pentyl, cyclopentyl, cyclohexyl, phenyl, norbornyl, cyclooctyl, (2,4,4'-trimethyl)pentyl, etc. steric hindrance groups may also include heterobicycles.

A "patient," "subject" or "host" to be treated by the subject method may mean either a human or non-human animal.

The term "treating" is an art-recognized term which includes curing as well as ameliorating at least one symptom of any condition or disease. Diagnostic applications are also examples of "treating".

The phrase "pharmaceutically acceptable" is art-recognized. In certain embodiments, the term includes compositions, ligands and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.*, 66:1-19 (1977).

The phrase "therapeutically effective amount" is an art-recognized term. In certain embodiments, the term refers to an amount of the therapeutic agent that produces some desired effect at a reasonable benefit/risk ratio applicable to any medical treatment. In certain embodiments, the term refers to that amount necessary or sufficient for diagnostic use of the subject compositions. One of ordinary skill in the art may empirically determine the effective amount of a particular compound without necessitating undue experimentation.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The phrases "parenteral administration" and "administered parenterally" are art-recognized terms, and include modes of administration other than enteral and topical administration, such as injections, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term dissociation constant "Kd" is a measure of how tightly the ligand and metal ion, e.g. $Zn^{2+}$ bind to one another. Lower values of Kd indicate a higher affinity, while higher values of Kd indicate weaker affinity.

The term "associated with" is used here in respect of how one molecule 'associates' with respect to another, for example between an adaptor protein and a functional domain, or between the CRISPR enzyme and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the CRISPR enzyme or adaptor protein is associated with a functional domain by binding thereto. In other embodiments, the CRISPR enzyme or adaptor protein is associated with a functional domain because the two are fused together, optionally via an intermediate linker.

Attachment of a domain or fusion protein can be via a linker, e.g., a flexible glycine-serine (GlyGlyGlySer) or (GGGS)3 or a rigid alpha-helical linker such as (Ala(GluAlaAlaAlaLys)Ala). Linkers such as (GGGGS)3 are preferably used herein to separate protein or peptide domains. (GGGGS)3 is preferable because it is a relatively long linker (15 amino acids). The glycine residues are the most flexible and the serine residues enhance the chance that the linker is on the outside of the protein. (GGGGS)6, (GGGGS)9 or (GGGGS)12 may preferably be used as alternatives. Other preferred alternatives are (GGGGS)1, (GGGGS)2, (GGGGS)4, (GGGGS)5, (GGGGS)7, (GGGGS)8, (GGGGS)10, or (GGGGS)11. Alternative linkers are available, e.g. the NLS of nucleoplasmin can be used as a linker.

The term "diabetes" or "diabetes mellitus" encompasses several different hyperglycemic states. These states include Type 1 (insulin-dependent diabetes mellitus or IDDM) and Type 2 (non-insulin-dependent diabetes mellitus or NIDDM) diabetes. The hyperglycemia present in individuals with Type I diabetes is associated with deficient, reduced, or nonexistent levels of insulin which are insufficient to maintain blood glucose levels within the physiological range. Treatment of Type 1 diabetes involves administration of replacement doses of insulin, generally by the parenteral route. The hyperglycemia present in individuals with Type II diabetes is initially associated with normal or elevated levels of insulin; however, these individuals are unable to maintain metabolic homeostasis due to a state of insulin resistance in peripheral-tissues and liver and, as the disease advances, due to a progressive deterioration of the pancreatic β-cells which are responsible for the secretion of insulin. Thus, initial therapy of Type 2 diabetes may be based on diet and lifestyle changes augmented by therapy with oral hypoglycemic agents such as sulfonylureas. Insulin therapy is often required, however, especially in the latter stages of the disease, in attempting to produce some control of hyperglycemia and minimize complications of the disease. Thus, many Type 2 diabetics ultimately require insulin in order to survive. Both type-1 and type-2 diabetes are contemplated by the present invention.

β-cells (β-cells or beta cells, used interchangeably) are a type of cells found in the pancreatic islet of the pancreas. They function as a sole source for providing insulin in response to the blood glucose level. After a meal, 1-cells are stimulated not only to secrete insulin but also to replenish the intracellular insulin stores by upregulation of proinsulin biosynthesis. As much as 20-50% of the total protein synthesized in a β-cell is proinsulin under stimulation conditions. Every six insulin molecules need two zinc ions to form a hexameric complex that is crystallized in the insulin secretory granules. As a result, β-cells have one of the highest zinc concentrations among mammalian cells, which can reach ~30 mM (~100 μM "free or loosely bound"). By contrast, most cells' $Zn^{2+}$ concentration is ~400 pM, while plasma $[Zn^{2+}]$ is ~1 nM. Thus, β-cells have over a million-fold higher $Zn^{2+}$ concentration than other cell types and plasma.

Zinc Prodrug for Tar Get Delivery to β-Cells and Other Cells

In one aspect, the present invention provides a composition comprising a prodrug comprising a chelating ligand having a selective affinity for at least one metal cation linked to a cargo compound via an ester, amide, or thioester group, wherein binding of the metal cation to the chelating ligand catalyzes cleavage of the ester, amide, or thioester group and release of the cargo compound. In some embodiments, the prodrug is represented by $(Car-H)_m$—S-$(L)_n$ (I-A), wherein L comprises a chelating ligand having a selective affinity for $Zn^{2+}$; S is a scaffold that comprises an optionally substitute aromatic or heteroaromatic ring or fused rings; H is a heteroatom selected from O, N, and S, which may be part of the aforementioned aromatic or heteroaromatic ring or fused rings; Car comprises (i) a cargo compound and optionally (ii) a self-immolative linker interconnecting the cargo group and H, wherein (i) or (ii) comprising an acyl group covalently bound to H to form an ester, amide, or thioester group; and each of m and n is at least one (e.g., 1, 2, 3, 4), wherein binding of $Zn^{2+}$ to the chelating ligand catalyzes cleavage of the ester, amide, or thioester group and release of the cargo compound.

In some embodiments, the prodrug is represented by Formula I-B: Car-$H_2$-SIM-$H_1$—S-L (I-B), wherein L comprises a chelating ligand having a selective affinity for $Zn^{2+}$; S is a scaffold that comprises a first optionally substituted aromatic or heteroaromatic ring or fused rings; Car is a cargo group that may comprises a second optionally substituted aromatic or heteroaromatic ring or fused rings; $H_1$ and $H_2$ are each a heteroatom independently, e.g. selected from O, N, and S, wherein $H_1$ may be part of the first aromatic or heteroaromatic ring or fused rings, and $H_2$ may be part of the second aromatic or heteroaromatic ring or fused rings; wherein SIM is a self-immolative linker comprising a first acyl group covalently bound to $H_1$ to form an ester, amide, or thioester group and a second acyl group covalently bound to $H_2$ to form an ester, amide, or thioester group. In some embodiments, $H_1$ and $H_2$ are each independently selected from O and N.

In some embodiments, the self-immolative linker can be linked to the chelating ligand via an ester, amide, or thioester group (which encompasses a carbamate, urea, carbonate, carbonothioate, or carbamothioate group linking the self-immolative linker and the chelating ligand), and the self-immolative linker can also be linked to the cargo group via an ester, amide, or thioester group (which encompasses a carbamate, urea, carbonate, carbonothioate, or carbamothioate group linking the self-immolative linker and the cargo group). In some embodiments wherein the prodrug does not comprise a self-immolative linker, the cargo group can be linked to the chelating ligand via an ester, amide, or thioester group (which encompasses a carbamate, urea, carbonate, carbonothioate, or carbamothioate group linking the cargo group and the chelating ligand). In some embodiments, the self-immolative linker comprises at least one optionally substituted aromatic or heteroaromatic ring or fused rings for improving stability. Self-immolative linkers are described in DeWit et al., J. Am. Chem. Soc. 131:18327-18334 (2009); Blencowe et al., Polym. Chem. 2:773-790 (2011); Wei Sheng, Self-Immolative Chemistry: Structural Features and Applications in Designing Smart Materials (Mich. St. Univ. 1/15/2014, available at www2.chemistry.msu.edu/courses/cem958/FS13_SS14/ Wei_Sheng.pdf), each of which is incorporated by reference in its entirety.

In some embodiments, the immolative linker is represented by Formula II-A:

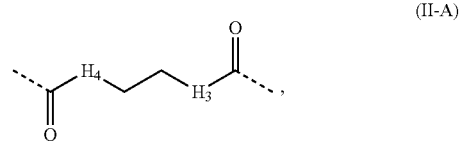

(II-A)

wherein $H_3$ and $H_4$ are each a heteroatom independently, e.g. selected from O, N, and S. In some embodiments, $H_3$ and $H_4$ are each independently selected from O and N. In some embodiments, $H_3$ and $H_4$ are each N, and $H_1$ and $H_2$ are each O.

In some embodiments, the immolative linker is represented by Formula II-B:

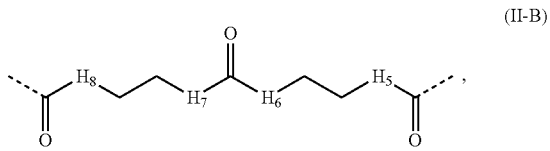

(II-B)

wherein $H_5$, $H_6$, $H_7$, and $H_8$ are each a heteroatom independently, e.g. selected from O, N, and S. In some embodiments, $H_5$, $H_6$, $H_7$, and $H_8$ are each independently selected from O and N. In some embodiments, $H_5$ and $H_6$ are each N, and $H_7$ and $H_8$ are each O or S. In some embodiments, $H_5$ and $H_6$ are each O or S, and $H_7$ and $H_8$ are each N.

In some embodiments, the immolative linker is represented by Formula II-C:

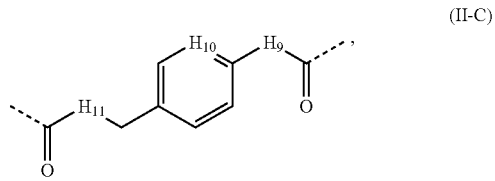

(II-C)

wherein $H_9$ and $H_{11}$ are each a heteroatom independently, e.g. selected from O, N, and S, and $H_{10}$ is C or N. In some embodiments, $H_9$ and $H_{11}$ are each independently selected from O and N. In some embodiments, $H_{11}$ is O. In some embodiments, $H_9$ and $H_{11}$ are each O, and $H_{10}$ is C.

In some embodiments, the immolative linker is represented by Formula II-D:

(II-D)

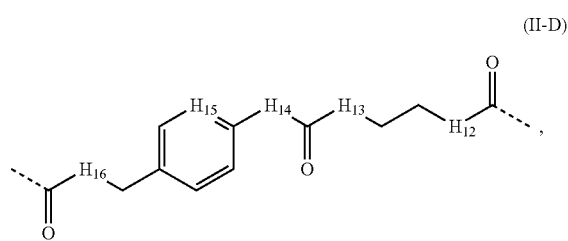

wherein $H_{12}$, $H_{13}$, $H_{14}$, and $H_{16}$ are each a heteroatom independently, e.g. selected from O, N, and S, and $H_{15}$ is C or N. In some embodiments, $H_{12}$, $H_{13}$, $H_{14}$, and $H_{16}$ are independently selected from O and N. In some embodiments, $H_{16}$ is O. In some embodiments, $H_{12}$ and $H_{13}$ are each N, $H_{14}$ and $H_{16}$ are each O, and $H_{15}$ is C.

In some embodiments, the immolative linker is represented by Formula II-E:

(II-E)

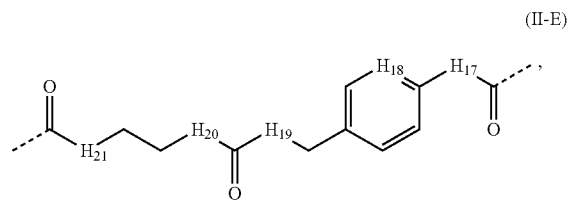

wherein $H_{17}$, $H_{19}$, $H_{20}$, and $H_{21}$ are each a heteroatom independently, e.g. selected from O, N, and S, and His is C or N. In some embodiments, $H_{17}$, $H_{19}$, $H_{20}$, and $H_{21}$ are each independently selected from O and N. In some embodiments, $H_{19}$ is O. In some embodiments, $H_{17}$ and $H_{19}$ are each O, $H_{20}$ and $H_{21}$ are each N, and His is C.

In some embodiments, S in Formula (I-A) comprises an optionally substituted phenyl ring, and H is O. In some embodiments, the prodrug is represented by Formula (III-A):

(III-A)

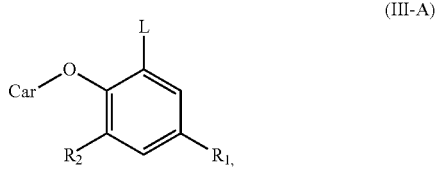

wherein Car and L have the same definitions as those of Formula (I-A); $R_1$ is H or comprises an electron withdrawing group or an electron donating group; and $R_2$ is H or comprises a chemical group conferring steric hindrance and/or reduction of electronic conjugation of the acyl group to the aromatic ring.

In some embodiments, the prodrug is represented by (III-A)

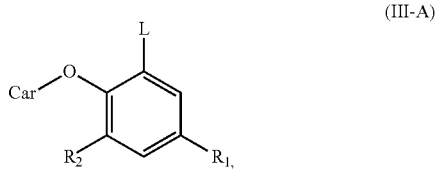

wherein Car and L have the same definitions as those of Formula (I-A); R1 is H or comprises an electron withdrawing group or an electron donating group; and R2 is H or comprises a chemical group conferring steric hindrance and/or reduction of electronic conjugation of the acyl group to the aromatic ring.

In some embodiments, the prodrug is represented by

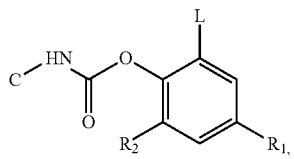

wherein R1 is H or comprises an electron withdrawing group or an electron donating group; and R2 is H or comprises a chemical group conferring steric hindrance and/or reduction of electronic conjugation of the acyl group to the aromatic ring.

In some embodiments, the prodrug is represented by Formula (III-B):

(III-B)

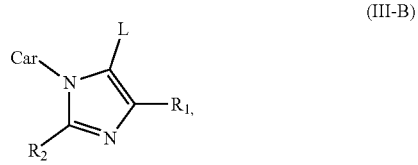

wherein Car and L have the same definitions as those of Formula (I-A); $R_1$ is H or comprises an electron withdrawing group or an electron donating group; and $R_2$ is H or comprises a chemical group conferring steric hindrance and/or reduction of electronic conjugation of the acyl group to the aromatic ring.

In some embodiments, the prodrug is represented by Formula (III-C):

(III-C)

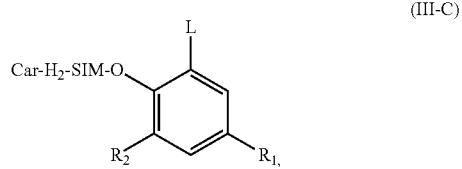

wherein Car, L, SIM, and $H_2$ have the same definitions as those in Formula (I-B); $R_1$ is H or comprises an electron withdrawing group or an electron donating group; and $R_2$ is H or comprises a chemical group conferring steric hindrance and/or reduction of electronic conjugation of the acyl group to the aromatic ring. In some embodiments, SIM is selected from Formulae II-A to II-E.

In some embodiments, the prodrug is represented by Formula (III-D):

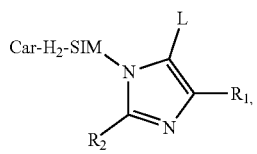

(III-D)

wherein Car, L, SIM, and H$_2$ have the same definitions as those in Formula (I-B); R$_1$ is H or comprises an electron withdrawing group or an electron donating group; and R$_2$ is H or comprises a chemical group conferring steric hindrance and/or reduction of electronic conjugation of the acyl group to the aromatic ring. In some embodiments, SIM is selected from Formulae II-A to II-E.

In some embodiments, the chelating ligand has a selective affinity for $Zn^{2+}$ over $Fe^{2+}$, $Cu^{2+}$, $Mn^{2+}$, $Co^{2+}$, and $Ni^{2+}$.

In some embodiments, the chelating ligand has a dissociation constant Kd for $Zn^{2+}$ of less than about 1 mM, less than about 100 µM, less than about 10 µM, less than about 1 µM, less than about 100 nM, less than about 10 nM, less about 1 nM, less than about 100 pM, less than about 10 pM, less than about 1 pM, less than about 0.1 pM. In some embodiments, the chelating ligand has a dissociation constant Kd for $Zn^{2+}$ of about 0.1 nM to about 1 mM, about 1 nM to about 100 µM, about 10 nM to about 10 µM, about 100 nM to about 1 µM, about 1 µM to about 10 µM. In some embodiments, the chelating ligand has a Kd for $Zn^{2+}$ of about 0.6 µM, about 0.7 nM, about 0.7 µM, about 1.5 µM, about 33 µM, or about 0.7 mM.

In some embodiments, the chelating ligand comprises numerous chemical moieties having a variety of structural, chemical and other characteristics capable of forming coordination bonds with zinc. The types of functional groups capable of forming coordinate complexes with zinc are generally known to those of skill in the art. For example, such moieties will generally include functional groups capable of interaction with metal center, i.e. zinc, for example, heteroatoms such as nitrogen, oxygen, sulfur, and phosphorus. In some embodiments, the chelating agent comprises amines (primary, secondary, and tertiary) and aromatic amines, amino groups, amido groups, nitro groups, nitroso groups, amino alcohols, nitrites, imino groups, isonitriles, cyanates, isocyanates, phosphates, phosphonates, phosphites, phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

In some embodiments, the chelating ligand comprises amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolamine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolamine, N-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines including di- and trialkylphosphines, such as tributylphosphine, triethylphosphine, triphenylphosphine, diphenylphosphine and the like; and monohydroxylic and polyhydroxylic alcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like; and heterocyclic compounds, including pyridine and the like.

In some embodiments, the chelating ligand comprises arsine, stilbenes, thioethers, selenoethers, telluroethers, thioketones, imines, phosphinimine, pyridines, pyrazoles, imidazoles, furans, oxazoles, oxazolines, thiophenes, thiazoles, isoxazoles, isothiazoles, amides, alkoxy, aryloxy, selenol, tellurol, siloxy, pyrazolylborates, carboxylate, acyl, amidates, triflates thiocarboxylate and the like.

In some embodiments, the chelating ligand is a bidentate ligand, comprises diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations thereof. In some embodiments, the chelating ligand is a tridentate ligand, comprises 2,5 diimino pyridyl ligands, tripyridyl moieties, tri-imidazolyl moieties, tris pyrazolyl moieties, and combinations thereof.

In some embodiments, the chelating ligand is sterically capable of forming four or more coordinate bonds to zinc. In some embodiments, the chelating ligand is capable of coordinating to zinc through at least one nitrogen atom.

In some embodiments, the chelating ligand comprises at least two secondary or ternary amines. In other embodiments, the chelating ligand comprises three secondary or tertiary amines. In some embodiments, the chelating ligand comprises a tertiary alkyl amine covalently bound to at least one pyridine ring.

In some embodiments, the chelating ligand is selected from the group consisting of:

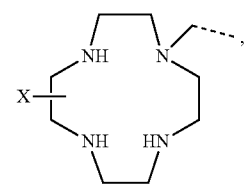

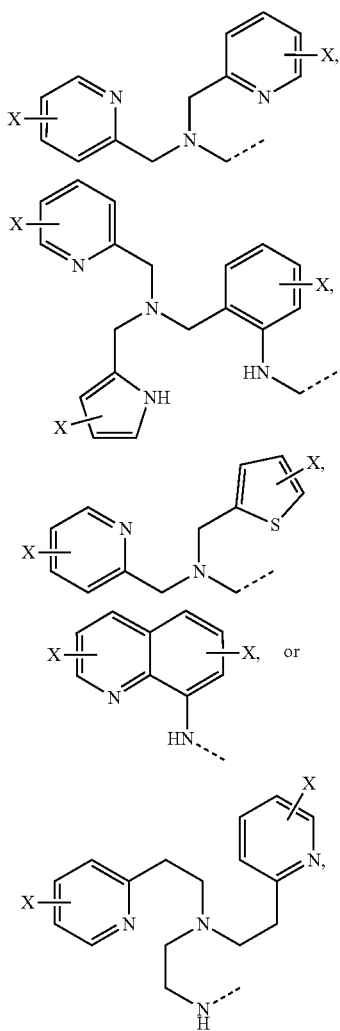

wherein X is independently H, NO$_2$, halogen, alkyl, alkoxy, haloalkyl, or aryl, provided that X does not interfere with coordination between nitrogen and zinc.

In some embodiments, the chelating ligand is selected from the group consisting of:

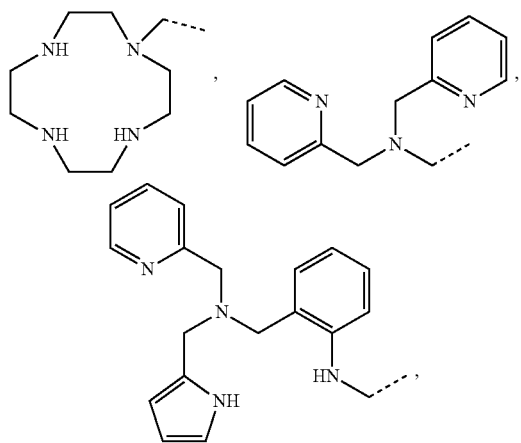

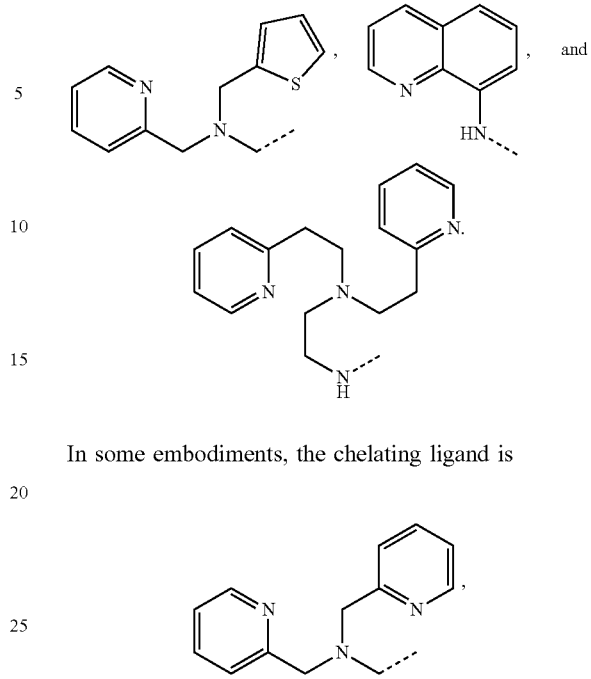

In some embodiments, the chelating ligand is

In some embodiments, the chelating ligand is designed to achieve a specific binding affinity for zinc. The method for designing chelating ligand to have different affinities are generally known those of ordinary skill in the art. See Que et al., *Chemical Reviews* (2008) 108(5):1517-1549.

In some embodiments, the cargo compound is a therapeutic or diagnostic agent that is physiologically inactive when covalently bound to the aromatic ring or aromatic fused rings. The covalent bond can be cleaved to release the therapeutic or diagnostic agent which can exhibit its known pharmacological or diagnostic effect, i.e. become active at the target delivery site. The releasing or activation of the therapeutic or diagnostic agent is achieved by a reaction mechanism that exists at the target delivery site. In some embodiments, the activation of the therapeutic or diagnostic agent is catalyzed by zinc. In some embodiments, the activation of the therapeutic or diagnostic agent is catalyzed by zinc, the covalent bond is an ester, amide, or thioester group, and the target delivery site is β-cell. β-cells can have much higher amounts of Zn$^{2+}$ in insulin vesicles, which can reach almost 30 mM (or about 100 μM free or loosely bound). By contrast, most cells' Zn$^{2+}$ concentration is about 400 pM, while plasma Zn$^{2+}$ is about 1 nM. Thus, β-cells can have over a million-fold higher Zn$^{2+}$ concentration than other cell types and plasma. Accordingly, in some embodiments, the inactive therapeutic or diagnostic agent that is covalently bound to the aromatic ring or aromatic fused rings, becomes activated upon zinc-catalyzed release at β-cell.

In some embodiments, selective release at the β-cell is achieved by controlling the cleavage of the covalent bond catalyzed by Zn$^{2+}$, i.e. the cargo release process. In some embodiments, the cargo release process is tailored by tuning the affinity of zinc chelating ligand. A high-affinity Zn$^{2+}$ chelating ligand facilitates cargo release, but may induce a premature release of the cargo at sites with low Zn$^{2+}$ concentration. High affinity ligands can also deplete Zn$^{2+}$ and may be toxic. On the other hand, a low-affinity Zn$^{2+}$ chelating ligand reduces efficiency of cargo release. Thus, in some embodiments, the prodrug comprises a chelating ligand that confers effective or optimum β-cell selectively which substantially avoiding toxicity.

In some embodiments, the cargo release process can be tailored by controlling the stability of the covalent bond being cleaved. In some embodiments, the prodrug is represented by

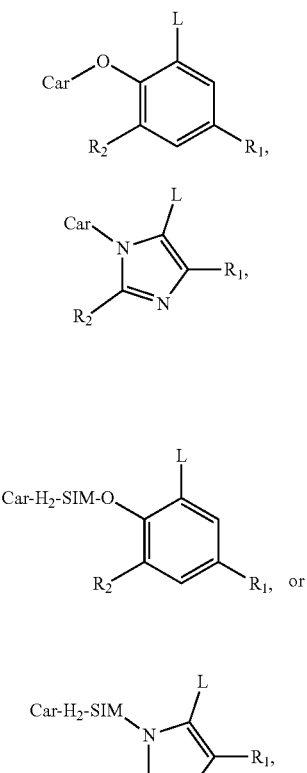

and the stability of the ester or amide group can be controlled by varying the R1 and R2 groups. In some embodiments, R1 is H. In other embodiments, R1 is an electron-withdrawing group that decreases the hydrolytic stability of the ester or amide group between the cargo (Car) and the aromatic ring. Non-limiting examples of electron-withdrawing group include NR3+, SR2+, NH3+, —NO2, —SO2R, —CN —SO2Ar, —COOH, —F, —Cl, —Br, —I, —Oar, —COOR, —OR, —COR, —SH, —SR, —OH, —CCR, —Ar and —C═CR2, wherein each R, individually, is a hydrogen, an alkyl or an aryl. In some embodiments, R1 is —CN or —NO2. In other embodiments, R1 is —Cl.

In some embodiments, R1 is an electron-donating group that increases the hydrolytic stability of the ester, amide, or thioester group between the cargo (Car) and the aromatic ring. Non-limiting examples of the electron-donating group include —NH2, —OH, —CH3, —SH, —NHCO2, —OCOH, —OCH3, —N(CH3)2, and C1-C5 saturated alkyl group.

In some embodiments, R2 is H or a halogen. In other embodiments, R2 is a chemical group conferring steric hindrance. In some embodiments, the steric hindrance group prevents the electronic conjugation of the acyl group to the aromatic ring and hinders water from approaching the reaction site. Non-limiting examples of the group conferring steric hindrance includes branched C4-C18 alkyl, C3-C8 cycloalkyl, and C6-C10 aryl, any of which may be substituted or unsubstituted, but for the most part will be unsubstituted. In some embodiments, specific examples of steric hindrance groups include iso-butyl, tert-butyl, n-pentyl, iso-pentyl, cyclopentyl, cyclohexyl, phenyl, norbornyl, cyclooctyl, (2,4,4'-trimethyl)pentyl, and heterobicycles.

In some embodiments, the composition further comprises a pharmaceutically acceptable carrier.

In some embodiments, the prodrug is an imaging agent comprising a masked fluorophore which can be unmasked by the cleavage of the ester, amide, or thioester group to emit a fluorescent signal. In some embodiments, the prodrug is represented by Formula (IV-A):

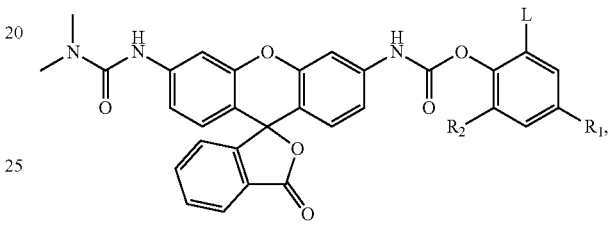

wherein R1 is H or comprises an electron withdrawing group or an electron donating group; and R2 is H or comprises a chemical group conferring steric hindrance and/or reduction of electronic conjugation of the acyl group to the aromatic ring.

In some embodiments, the prodrug is represented by Formula (IV-B):

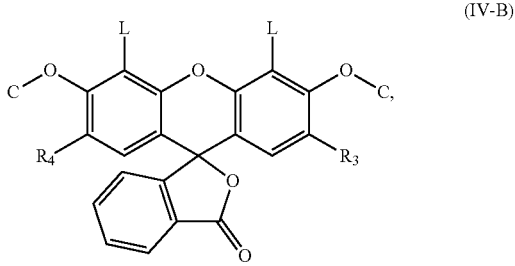

wherein each of R3 and R4 is H or comprises an electron withdrawing group, an electron donating group, or a chemical group conferring steric hindrance and/or reduction of electronic conjugation of the acyl group to the aromatic ring, and wherein C is an acyl group. In some embodiments, the prodrug is selected from:

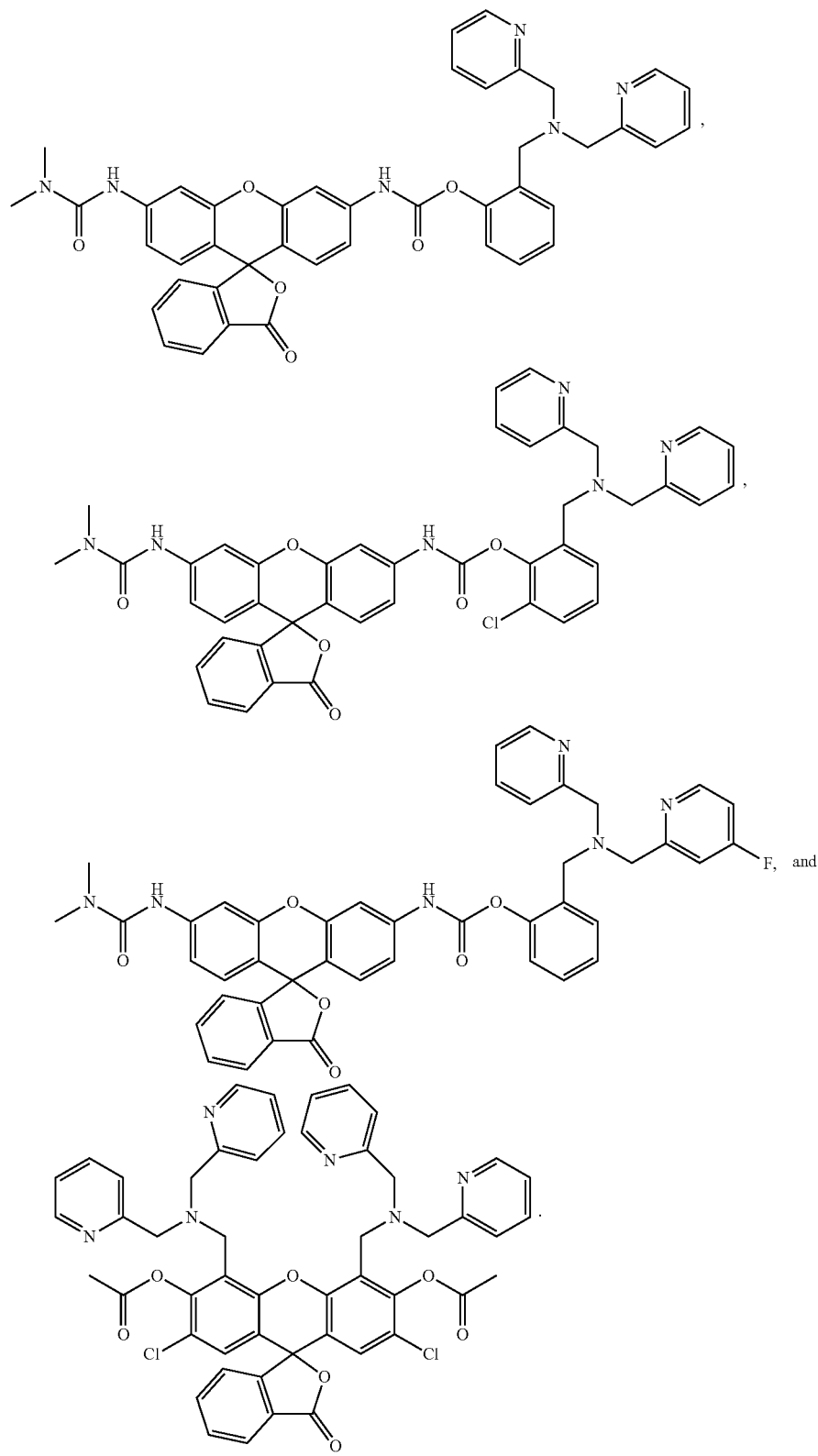

In some embodiments, as the steric crowding near the $Zn^{2+}$ binding site may affect the release of the cargo, the prodrug may additionally comprise an immolative linker. Immolative linkers that undergo cascades are preferred and these may include quinone methide, intramolecular cyclization, or hemiacetal degradation.

In some embodiments, the cargo compound is a therapeutic agent for treating diabetes. In some embodiments, the therapeutic agent promotes β-cell proliferation. In other embodiments, the therapeutic agent increases insulin secretion. In some embodiments, the therapeutic agent provides protection from β-cell death. In other embodiments, the therapeutic agent is an inhibitor of cytokine-induced β-cell apoptosis. In some embodiments, the therapeutic agent prevents glucolipotoxicity-induced β-cell apoptosis.

In some embodiments, the therapeutic agent is a CMGC kinase inhibitor. In some embodiments, the CMGC kinase is selected from the group consisting of DYRK1A, DYRK1B, DYRK2, CLK1, CLK2, and CLK4. In some embodiments, the therapeutic agent is a DYRK1A inhibitor. In some embodiments, the therapeutic agent is 5-IT or harmine.

In some embodiments, the therapeutic agent is an elastase inhibitor. Human neutrophil elastase (hNE), a member of the chymotrypsin superfamily of serine proteases is a 33-KDa enzyme stored in the azurophilic granules of the neutrophils. In neutrophils the concentration of NE exceeded 5 mM and its total cellular amount has been estimated to be up to 3 pg. Upon activation, NE is rapidly released from the granules into the extracellular space with some portion remaining bound to neutrophil plasma membrane (See Kawabat et al. 2002, *Eur. J. Phannacol.* 451, 1-10). The main intracellular physiological function of NE is degradation of foreign organic molecules phagocytosed by neutrophils, whereas the main target for extracellular elastase is elastin (Janoff and Scherer, 1968, *J. Exp. Med.* 128, 1137-1155). In some embodiments, the elastase inhibitor is serpinB1.

In some embodiments, the therapeutic agent is selected from the group consisting of: insulin analogues, pramlintide, metformin, sulphonylureas, meglitinides, thiazolidinediones (TZDs), glucagon-like peptide 1 (GLP1) analogues, dipeptidyl peptidase 4 (DPP4) inhibitors, alpha-glucosidase inhibitors, sodium-dependent glucose cotransporter 2(SGLT2) inhibitors, bromocriptine, diarylamide WS6, adenosine kinase inhibitor 5-iodotubercidin (5-IT), adenosine receptor agonist 5'-N-ethylcarboxamidoadenosine (NECA), sulphonylureas, TAK-875, gliptins, TUG891, AMG-151, MBX-2982, vorinostat, IL-1 receptor agonist anakinra, and HDAC inhibitors. In some embodiments, the therapeutic agent is selected from the group consisting of: DYRK1A inhibitors, elastase inhibitors, BRD0476, BRD3308, harmine, leucettine, 5-IT, sivelestat, and GNF4877.

In some embodiments, the cargo compound is a diagnostic agent for diabetes. In some embodiments, the diagnostic agent binds to a protein of the β-cells, and the expression of the protein can be used to diagnose diabetes, for example by its correlation to insulin secretion. In some embodiments, the diagnostic agent binds to a pancreatic zinc transporter, for example, ZnT8. In some embodiments, the diagnostic agent comprises a detectably labeled moiety that can be used to detect the expression level of the ZnT8 protein. In some embodiments, the detectably labeled moiety is a fluorophore. Upon binding of the prodrug to β-cell, the diagnostic agent is released by zinc catalyzed ester, amide, or thioester group cleavage, and binds to ZnT8. Thus, the expression level of ZnT8 can be detected via the detection of the fluorophore, and which is known to correlate with insulin secretion and thus can be used to diagnose diabetes. See Huang et al., *J. Bio. Chem.* (2017) 292(10): 4034-4043.

In some embodiments, the cargo compound is an imaging agent, which can be used to detect and/or monitor β-cells. In some embodiments, the cargo compound comprises a fluorescent molecule. Upon binding of the prodrug to β-cell, the imaging agent is released by zinc catalyzed ester, amide, or thioester group cleavage, and allows imaging of the β-cell.

In some embodiments, the imaging agent binds to a biomarker for islet beta cell, for example, GLP-1. In some embodiments, the imaging agent comprises a detectably labeled moiety that can be used to detect the expression level of the GLP-1 protein. In some embodiments, the detectably labeled moiety is a fluorophore. In some embodiments, upon binding of the prodrug to 3-cell, the imaging agent is released by zinc catalyzed ester, amide, or thioester group cleavage, and binds to GLP-1. Thus, the expression level of GLP-1 can be detected via the detection of the fluorophore. See Li et al., *Bioconjugate Chem.* (2015) 26: 1443-1450.

In one aspect, the present invention provides a method for selective delivery of a cargo compound to β-cells in vivo, comprising administering a composition of the present invention to a subject in need thereof, wherein binding of $Zn^{2+}$ to the chelating ligand of the prodrug in the 3-cells catalyzes cleavage of the ester, amide, or thioester group, thereby releasing the cargo compound in the β-cells.

In another aspect, the present invention provides a method for treating diabetes, comprising administering a composition of the present invention to a subject in need thereof, wherein binding of $Zn^{2+}$ to the chelating ligand of the prodrug in the 3-cells catalyzes cleavage of the ester, amide, or thioester group, thereby releasing the therapeutic agent in the β-cells.

In another aspect, the present invention provides a method for promoting 3-cell proliferation and/or regeneration, comprising administering a compositions of the present invention to a subject in need thereof, wherein binding of $Zn^{2+}$ to the chelating ligand in the β-cells catalyzes cleavage of the ester, amide, or thioester group, thereby releasing the therapeutic agent in the β-cells.

In yet another aspect, the present invention provides a method for imaging β-cells in vivo, comprising administering the composition of the present invention a subject thereof, wherein binding of $Zn^{2+}$ to the chelating ligand of the prodrug in the β-cells catalyzes cleavage of the ester, amide, or thioester group, thereby allowing the cargo compound or the optionally substitute aromatic ring or aromatic fused rings to emit a fluorescent signal in the β-cells, and detecting the fluorescent signal emitted from the cargo compound or the optionally substitute aromatic ring or aromatic fused rings.

In yet another aspect, the present invention provides a method for imaging β-cells in vitro, comprising contacting a composition of the present invention with a cell culture comprising β-cells, wherein binding of $Zn^{2+}$ to the chelating ligand of the prodrug in the β-cells catalyzes cleavage of the ester, amide, or thioester group, thereby allowing the cargo compound or the optionally substitute aromatic ring or aromatic fused rings to emit a fluorescent signal in the β-cells, and detecting the fluorescent signal emitted from the cargo compound or the optionally substitute aromatic ring or aromatic fused rings.

In yet another aspect, the present invention provides a method for detecting $Zn^{2+}$ contamination or concentration, comprising contacting a composition of the present invention with a sample, wherein binding of $Zn^{2+}$ to the chelating ligand catalyzes cleavage of the ester, amide, or thioester group between the chelating ligand and the cargo compound, thereby allowing the cargo compound or the optionally substitute aromatic or heteroaromatic ring or fused rings to emit a fluorescent signal; detecting an intensity of the fluorescent signal emitted; and determining the presence or a concentration of $Zn^{2+}$ in the sample based on the detected intensity of the fluorescent signal.

In yet another aspect, the present invention provides compositions and method for treating breast cancer. In breast cancer patients, previous studies showed a 72% increase in tissue zinc concentration in comparison with normal tissues (Chakravarty et al., Neoplasma. 1986, 33:85-90; Mulay et al., *J. Natl. Cancer Inst.* 1971, 47:1-13). In some embodiments, the zinc prodrug of the present invention specifically delivers a cargo compound to cancer cells, such as breast cancer cells. In some embodiments, the cargo compound is a therapeutic, diagnostic, or imaging agent for treating or diagnosing breast cancer.

In yet another aspect, the present invention provides compositions and method for delivering a cargo compound to prostate cells. Previous studies showed a nearly 10-fold greater zinc concentration in prostate tissue than in any other soft tissue (Zaichick et al., *Int. Urol. Nephrol.* 1997, 29:565-574; Franklin et al., *Mol. Cancer.* 2005, 4:32). In some embodiments, the cargo compound is a therapeutic, diagnostic, or imaging agent for treating or diagnosing a prostate disease or condition.

In yet another aspect, the present invention provides compositions and method for delivering a cargo compound to the brain or to neuronal tissues. $Zn^{2+}$ is present at significant levels in neuronal tissues, and is the second most abundant transition metal present in the brain (Huang, *Proc. Natl. Acad. Sci.* 1997, 94:13386-13387). $Zn^{2+}$ has been shown to have multiple routes of neuronal entry, including via voltage-gated $Ca^{2+}$ channels, via transporter-mediated exchange with intracellular $Na^+$, via NMDA receptor-gated channels, and via $Ca^{2+}$-permeable channels gated by certain subtypes of AMPA or kainite receptors (Sensi et al., *J. Neurosci.* 1997, 17:9554-9564). In some embodiments, the cargo compound is a therapeutic, diagnostic, or imaging agent for treating or diagnosing a brain or neurological disease or condition.

In yet another aspect, the present invention provides a method of inducing or enhancing human beta cell proliferation, the method comprising exposing human beta cells to a calcineurin activator and/or NFAT activator. In some embodiments, the calcineurin activator and/or NFAT activators are CMGC family kinase inhibitors. In some embodiments, the CMGC inhibitor is selected from the group consisting of DYRK1A inhibitors, DYRK1B inhibitors, DYRK2 inhibitors, CLK2 inhibitors, CLK3 inhibitors, and CLK4 inhibitors. In some embodiments, the method comprising administering the composition of the present invention.

In yet another aspect, the present invention provides a method of reducing hyperglycemia, the method comprising administering to a human subject in need thereof a kinase inhibitor, wherein the kinase inhibitor inhibits kinase activity in one or more CMGC family kinases.

Genome Editing and Transcriptional Modulation in β-Cells and Other Cells

In another aspect, the present invention provides compositions and methods for selective activation of a CRISPR effector protein in β-cells. In another aspect, the present invention provides compositions and methods for genome editing in β-cells. In yet another aspect, the present invention provides compositions and methods for selective transcriptional activation or repression in β-cells. In some embodiments the target gene in β-cells is a gene involved in β-cells proliferation. In some embodiments, the target gene is p16$^{INK4A}$, which has been reported to be involved in the senescence-mediated β-cell death. Krishnamurthy, et al., Nature (2006) 443:453-457; Helman et al., *Diabetes Obes. Metab.* (2016) 18 Suppl 1:58-62. In some embodiments, the target gene is p19$^{ARF}$. In some embodiments, the target gene comprises a mutation causing monogenic diabetes and examples of target genes are herein described.

In another aspect, the present invention provides compositions and methods for selective activation of a CRISPR effector protein in breast cancer cells. In another aspect, the present invention provides compositions and methods for genome editing in cancer cells, such as breast cancer cells. In yet another aspect, the present invention provides compositions and methods for selective transcriptional activation or repression in cancer cells such as breast cancer cells.

In another aspect, the present invention provides compositions and methods for selective activation of a CRISPR effector protein in prostate cells. In another aspect, the present invention provides compositions and methods for genome editing in prostate cells. In yet another aspect, the present invention provides compositions and methods for selective transcriptional activation or repression in prostate cells.

In some embodiments, the present invention provides a prodrug comprising a cargo compound which is a stabilizing ligand for a polypeptide comprising a destabilization domain (DD), wherein binding of the stabilizing ligand to the destabilization domain prevents proteasomal degradation of the polypeptide.

In some embodiments, the cargo compound is a stabilizing ligand for a destabilized dihydrofolate reductase (DHFR) or a destabilized estrogen receptor ligand binding domain (ERLBD). In some embodiments, the cargo compound is trimethoprim (TMP), 4-hydroxytamoxifen (4HT or 4OHT), or CMP8.

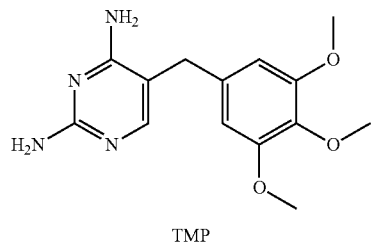

TMP

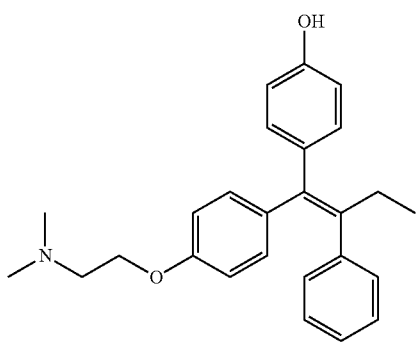

4OHT

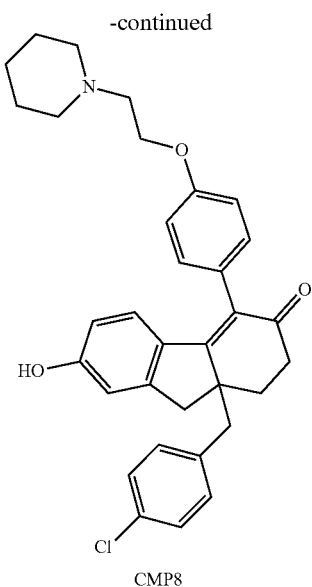

CMP8

In some embodiments, when DD is DHFR, a corresponding stabilizing ligand for this DD is, in some embodiments, TMP. As such, in some embodiments, one of the at least one DDs is DHFR and a stabilizing ligand therefor is TMP.

In some embodiments, when DD is ER50, a corresponding stabilizing ligand for this DD is, in some embodiments, 4HT. As such, in some embodiments, one of the at least one DDs is ER50 and a stabilizing ligand therefor is 4HT. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT.

In some embodiments, the destabilization domain is fused to a CRISPR effector protein, wherein binding of the stabilizing ligand to the destabilization domain increases activity of the CRISPR effector protein by at least one fold, at least 2 folds, at least 5 folds, at least 10 folds, at least 20 folds, at least 50 folds, or at least 100 folds.

In some embodiments, the CRISPR effector protein is Cas9, Cpf1, C2c1, C2c2, or Cas13b. In some embodiments, the CRISPR effector protein is a DNA-targeting CRISPR effector protein. In some embodiments, the CRISPR effector protein is a Type-II CRISPR effector protein such as Cas9. In some embodiments, the CRISPR effector protein is a Type-V CRISPR effector protein such as Cpf1 or C2c1. In some embodiments, the CRISPR effector protein is a RNA-targeting CRISPR effector protein. In some embodiments, the CRISPR effector protein is a Type-VI CRISPR effector protein such as C2c2 or Cas13b.

In some embodiments, the CRISPR effector protein forms a complex with a gRNA and upon binding of the said complex to the locus of interest the effector protein induces a modification of the sequences associated with or at the target locus of interest. In some embodiments, the locus of interest is the p16$^{INK4A}$ genomic locus. In some embodiments, the locus of interest is the p19$^{ARF}$ genomic locus.

In some embodiments, the destabilization domain is fused to (i) an aptamer ligand and (ii) a transcriptional activation domain or a transcriptional repression domain, wherein binding of the stabilizing ligand to the destabilization domain increases activity of the aptamer ligand by at least one fold, at least 2 folds, at least 5 folds, at least 10 folds, at least 20 folds, at least 50 folds, or at least 100 folds.

In some embodiments, the aptamer ligand is selected from MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, or PRR1. In some embodiments, the transcriptional activation domain or the transcriptional repression domain is selected from VP64, P65, MyoD1, HSF1, RTA, SET7/9, KRAB, NuE, NcoR, SID, or SID4X.

In one aspect, the present invention provides a method for selective activation of a CRISPR effector protein in β-cells, comprising administering the composition of the present invention to a subject in need thereof, simultaneously or sequentially with a fusion protein of a CRISPR effector protein and at least one destabilization domain, or a polynucleotide encoding the fusion protein, wherein binding of $Zn^{2+}$ to the chelating ligand in the 3-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the CRISPR effector protein to function in the β-cells. In some embodiments, the CRISPR effector protein forms a complex with a gRNA and upon binding of the said complex to the locus of interest the effector protein induces a modification of the sequences associated with or at the target locus of interest. In some embodiments, the locus of interest is the p16$^{INK4A}$ genomic locus. In some embodiments, the locus of interest is the p19$^{ARF}$ genomic locus.

In one aspect, the present invention provides a method for selective genomic editing in β-cells, comprising administering the composition of the present invention to a subject in need thereof, simultaneously or sequentially with (i) a fusion protein of a catalytically active CRISPR effector protein and at least one destabilization domain, or a polynucleotide encoding the fusion protein and (ii) a guide RNA hybridizable to a target sequence in genome of the subject or a polynucleotide encoding the guide RNA, wherein binding of $Zn^{2+}$ to the chelating ligand in the 3-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the catalytically active CRISPR effector protein to bind the guide RNA and the target sequence for genome editing in the β-cells. In some embodiments, the target sequence is a gene involved in β-cell proliferation. In some embodiments, the target sequence is p16$^{INK4A}$. In some embodiments, the target sequence is p19$^{ARF}$.

In another aspect, the present invention provides a method for selective transcriptional activation or repression in β-cells, comprising administering the composition of the present invention to a subject in need thereof, simultaneously or sequentially with (i) a fusion protein of a catalytically inactive CRISPR effector protein, at least one destabilization domain, and at least one transcriptional activation domain or transcriptional repression domain, or a polynucleotide encoding the fusion protein, and (ii) a guide RNA hybridizable to a target sequence in genome of the subject or a polynucleotide encoding the guide RNA, wherein binding of $Zn^{2+}$ to the chelating ligand in the β-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the catalytically inactive CRISPR effector protein to bind the guide RNA and the target sequence for transcriptional activation or repression in the β-cells. In some embodiments, the target sequence is a gene involved in β-cell proliferation. In some embodiments, the target sequence is $p16^{INK4A}$. In some embodiments, the target sequence is $p19^{ARF}$. In some embodiments, the method comprises transcriptional repression of $p16^{INK4A}$ in β-cells. In some embodiments, the method comprises transcriptional repression of $p19^{ARF}$ in β-cells. In some embodiments, the method comprises transcriptional activation of EZH2 in β-cells. In some embodiments, the method comprises transcriptional activation of Cyclin Ds in β-cells. In some embodiments, the method comprises transcriptional activation of CDK4/CDK6 in β-cells. In some embodiments, the method comprises transcriptional activation of E2Fs in β-cells.

In yet another aspect, the present invention provides a method for selective transcriptional activation or repression in β-cells, comprising administering the composition of the present invention to a subject in need thereof, simultaneously or sequentially with (i) a catalytically inactive CRISPR effector protein or a polynucleotide encoding the CRISPR effector protein, (ii) a fusion protein of at least one destabilization domain, at least one aptamer ligand, and at least one transcriptional activation domain or transcriptional repression domain, and (iii) a guide RNA hybridizable to a target sequence in genome of the subject or a polynucleotide encoding the guide RNA, wherein the guide RNA comprises an aptamer sequence capable of binding to the transcriptional activation domain or transcriptional repression domain, wherein binding of $Zn^{2+}$ to the chelating ligand in the β-cells catalyzes cleavage of the ester, amide, or thioester group, thereby releasing of the stabilizing ligand in the β-cells, and wherein binding of the stabilizing ligand to the destabilization domain prevents the fusion protein from proteasomal degradation and allows the fusion protein to bind to the aptamer sequence of guide RNA for transcriptional activation or repression in the β-cells. In some embodiments, the target sequence is a gene involved in β-cell proliferation. In some embodiments, the target sequence is $p16^{INK4A}$. In some embodiments, the target sequence is $p19^{ARF}$. In some embodiments, the method comprises transcriptional repression of $p16^{INK4A}$ in β-cells. In some embodiments, the method comprises transcriptional repression of $p19^{ARF}$ in β-cells. In some embodiments, the method comprises transcriptional activation of EZH2 in β-cells. In some embodiments, the method comprises transcriptional activation of Cyclin Ds in β-cells. In some embodiments, the method comprises transcriptional activation of CDK4/CDK6 in β-cells. In some embodiments, the method comprises transcriptional activation of E2Fs in β-cells.

Construction of Destabilized Domain—CRISPR Enzyme Fusion Protein

The prodrug composition described herein can be used to deliver a molecular stabilizer or inducer into beta cells to activate a destabilized or split CRISPR effector protein present in the beta cells. In one aspect, the invention provides a non-naturally occurring or engineered CRISPR enzyme associated with at least one destabilization domain (DD); and, for shorthand purposes, such a non-naturally occurring or engineered CRISPR enzyme associated with at least one destabilization domain (DD) is herein termed a "DD-CRISPR enzyme". In one aspect, the invention provides an engineered, non-naturally occurring DD-CRISPR-Cas system comprising a DD-CRISPR enzyme, wherein the CRISPR enzyme is a Cas protein (herein termed a "DD-Cas protein"), which is a type II DD-CRISPR Cas9 protein associated with at least one destabilization domain (herein termed a "DD-Cas9 protein" (or simply "DD-Cas9") and guide RNA that targets a nucleic acid molecule such as a DNA molecule, whereby the guide RNA targets the nucleic acid molecule, e.g., DNA molecule. The nucleic acid molecule, e.g., DNA molecule can encode a gene product. In some embodiments the DD-Cas protein may cleave the DNA molecule encoding the gene product. In some embodiments expression of the gene product is altered. The Cas protein and the guide RNA do not naturally occur together. The invention comprehends the guide RNA comprising a guide sequence fused to a tracr sequence. The invention further comprehends coding for the Cas protein being codon optimized for expression in a eukaryotic cell. In a preferred embodiment the eukaryotic cell is a mammalian cell and in a more preferred embodiment the mammalian cell is a human cell. Expression of the gene product may be decreased. The CRISPR effector protein may form part of a CRISPR-Cas system, which further comprises a guide RNA (sgRNA) comprising a guide sequence capable of hybridizing to a target sequence in a genomic locus of interest in a cell. In some embodiments, the functional CRISPR-Cas system binds to the target sequence. In some embodiments, the functional CRISPR-Cas system may edit the target sequence, e.g., the target sequence may comprise a genomic locus, and in some embodiments there may be an alteration of gene expression. In some embodiments, the functional CRISPR-Cas system may comprise further functional domains. In some embodiments, the invention provides a method for altering or modifying expression of a gene product. The method may comprise introducing into a cell containing a target nucleic acid, e.g., DNA molecule, or containing and expressing a target nucleic acid, e.g., DNA molecule; for instance, the target nucleic acid may encode a gene product or provide for expression of a gene product (e.g., a regulatory sequence). In some embodiments, the CRISPR effector protein is a Cas9, for instance SaCas9, SpCas9, StCas9, CjCas9 and so forth—any ortholog is envisaged. In some embodiments, the CRISPR effector protein is a Cpf1, for instance AsCpf1, LbCpf1, FnCpf1 and so forth—any ortholog is envisaged.

In some embodiments, The DD-CRISPR enzyme is a DD-Cas9. In some embodiments, the DD-CRISPR enzyme is an Sp DD-Cas9. In some embodiments, the CRISPR enzyme is an Sa DD-Cas9. In some embodiments, the CRISPR enzyme is an Cj, St or Fn DD-Cas9, although other orthologs are envisaged. Sp and Sa DD-Cas9s are particularly preferred, in some embodiments. In some embodiments, the DD-CRISPR enzyme cleave both strands of DNA to produce a double strand break (DSB). In some embodiments, the DD-CRISPR enzyme is a nickase. In some embodiments, the DD-CRISPR enzyme is a dual nickase. In some embodiments, the DD-CRISPR enzyme is a deadCas9, e.g., a Cas9 having substantially no nuclease activity, e.g., no more than 5% nuclease activity as compared with a wild-type Cas9 or Cas9 not having had mutations to it.

In some general embodiments, the DD-CRISPR enzyme is associated with one or more functional domains. In some more specific embodiments, the DD-CRISPR enzyme is a deadCas9 and/or is associated with one or more functional domains.

In some embodiments, the DD-CRISPR enzyme comprises a Rec2 or HD2 truncation. In some embodiments, the CRISPR enzyme is associated with the DD by way of a fusion protein. In some embodiments, the CRISPR enzyme is fused to the DD. In other words, the DD may be associated with the CRISPR enzyme by fusion with said CRISPR enzyme. In some embodiments, the enzyme may be considered to be a modified CRISPR enzyme, wherein the CRISPR enzyme is fused to at least one destabilization domain (DD). In some embodiments, the DD may be associated to the CRISPR enzyme via a connector protein, for example using a system such as a marker system such as the streptavidin-biotin system. As such, provided is a fusion of a CRISPR enzyme with a connector protein specific for a high affinity ligand for that connector, whereas the DD is bound to said high affinity ligand. For example, streptavidin may be the connector fused to the CRISPR enzyme, while biotin may be bound to the DD. Upon co-localization, the streptavidin will bind to the biotin, thus connecting the CRISPR enzyme to the DD. For simplicity, a fusion of the CRISPR enzyme and the DD is preferred in some embodiments. In some embodiments, the fusion may be to the N-terminal end of the CRISPR enzyme. In some embodiments, at least one DD is fused to the N-terminus of the CRISPR enzyme. In some embodiments, the fusion may be to the C-terminal end of the CRISPR enzyme. In some embodiments, at least one DD is fused to the C-terminus of the CRISPR enzyme. In some embodiments, one DD may be fused to the N-terminal end of the CRISPR enzyme with another DD fused to the C-terminal of the CRISPR enzyme. In some embodiments, the CRISPR enzyme is associated with at least two DDs and wherein a first DD is fused to the N-terminus of the CRISPR enzyme and a second DD is fused to the C-terminus of the CRISPR enzyme, the first and second DDs being the same or different. In some embodiments, the fusion may be to the N-terminal end of the DD. In some embodiments, the fusion may be to the C-terminal end of the DD. In some embodiments, the fusion may between the C-terminal end of the CRISPR enzyme and the N-terminal end of the DD. In some embodiments, the fusion may between the C-terminal end of the DD and N-terminal end of the CRISPR enzyme. Less background was observed with a DD comprising at least one N-terminal fusion than a DD comprising at least one C terminal fusion. Combining N- and C-terminal fusions had the least background but lowest overall activity. Advantageously a DD is provided through at least one N-terminal fusion or at least one N terminal fusion plus at least one C-terminal fusion. And of course, a DD can be provided by at least one C-terminal fusion.

In some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR. A corresponding stabilizing ligand for this DD is, in some embodiments, TMP. As such, in some embodiments, one of the at least one DDs is DHFR and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT.

In some embodiments, one or two DDs may be fused to the N-terminal end of the CRISPR enzyme with one or two DDs fused to the C-terminal of the CRISPR enzyme. In some embodiments, the at least two DDs are associated with the CRISPR enzyme and the DDs are the same DD, i.e. the DDs are homologous. Thus, both (or two or more) of the DDs could be ER50 DDs. This is preferred in some embodiments. Alternatively, both (or two or more) of the DDs could be DHFR DDs. This is also preferred in some embodiments. In some embodiments, the at least two DDs are associated with the CRISPR enzyme and the DDs are different DDs, i.e. the DDs are heterologous. Thus, one of the DDS could be ER50 while one or more of the or any other DDs could be DHFR. Having two or more DDs which are heterologous may be advantageous as it would provide a greater level of degradation control. A tandem fusion of more than one DD at the N or C-term may enhance degradation; and such a tandem fusion can be, for example ER50-ER50-Cas9 or DHFR-DHFR-Cas9 It is envisaged that high levels of degradation would occur in the absence of either stabilizing ligand, intermediate levels of degradation would occur in the absence of one stabilizing ligand and the presence of the other (or another) stabilizing ligand, while low levels of degradation would occur in the presence of both (or two of more) of the stabilizing ligands. Control may also be imparted by having an N-terminal ER50 DD and a C-terminal DHFR DD.

In some embodiments, the fusion of the CRISPR enzyme with the DD comprises a linker between the DD and the CRISPR enzyme. In some embodiments, the linker is a GlySer linker. In some embodiments, the DD-CRISPR enzyme further comprises at least one Nuclear Export Signal (NES). In some embodiments, the DD-CRISPR enzyme comprises two or more NESs. In some embodiments, the DD-CRISPR enzyme comprises at least one Nuclear Localization Signal (NLS). This may be in addition to an NES. In some embodiments, the CRISPR enzyme comprises or consists essentially of or consists of a localization (nuclear import or export) signal as, or as part of, the linker between the CRISPR enzyme and the DD. HA or Flag tags are also within the ambit of the invention as linkers. Applicants use NLS and/or NES as linker and use Glycine Serine linkers as short as GS up to (GGGGS)3.

In an aspect, the present invention provides a polynucleotide encoding the CRISPR enzyme and associated DD. In some embodiments, the encoded CRISPR enzyme and associated DD are operably linked to a first regulatory element. In some embodiments, a DD is also encoded and is operably linked to a second regulatory element. Advantageously, the DD here is to "mop up" the stabilizing ligand and so it is advantageously the same DD (i.e. the same type of Domain) as that associated with the enzyme, e.g., as herein discussed (with it understood that the term "mop up" is meant in the sense of performing so as to contribute or conclude activity. In some embodiments, the first regulatory element is a promoter and may optionally include an enhancer. In some embodiments, the second regulatory element is a promoter and may optionally include an enhancer. In some embodiments, the first regulatory element is an early promoter. In some embodiments, the second regulatory element is a late promoter. In some embodiments, the second regulatory element is or comprises or consists essentially of an inducible control element, optionally the tet system, or a repressible control element, optionally the tetr system. An inducible promoter may be favorable e.g. rTTA to induce tet in the presence of doxycycline.

In an aspect, the present invention provides a means for delivering the DD-CRISPR-Cas complex of the invention or polynucleotides discussed herein, e.g., particle(s) delivering component(s) of the complex, vector(s) comprising the polynucleotide(s) discussed herein (e.g., encoding the CRISPR enzyme, the DD; providing RNA of the CRISPR-Cas complex). In some embodiments, the vector may be a plasmid or a viral vector such as AAV, or lentivirus. Transient transfection with plasmids, e.g., into HEK cells may be advantageous, especially given the size limitations of AAV and that while SpCas9 fits into AAV, one may reach an upper limit with additional coding as to the association with the DD(s).

Also provided is a model that constitutively expresses the CRISPR enzyme and associated DD. The organism may be a transgenic and may have been transfected the present vectors or may be the offspring of an organism so transfected. In a further aspect, the present invention provides compositions comprising the CRISPR enzyme and associated DD or the polynucleotides or vectors described herein. Also provides are CRISPR-Cas systems comprising guide RNAs.

Also provided is a method of treating a subject, e.g., a subject in need thereof, comprising inducing gene editing by transforming the subject with the polynucleotide encoding the system or any of the present vectors and administering stabilizing ligand to the subject. A suitable repair template may also be provided, for example delivered by a vector comprising said repair template. Also provided is a method of treating a subject, e.g., a subject in need thereof, comprising inducing transcriptional activation or repression by transforming the subject with the polynucleotide encoding the present system or any of the present vectors, wherein said polynucleotide or vector encodes or comprises the catalytically inactive CRISPR enzyme and one or more associated functional domains; the method further comprising administering a stabilizing ligand to the subject. These methods may also include delivering and/or expressing excess DD to the subject. Where any treatment is occurring ex vivo, for example in a cell culture, then it will be appreciated that the term 'subject' may be replaced by the phrase "cell or cell culture."

Compositions comprising the present system for use in said method of treatment are also provided. A separate composition ay comprise the stabilizing ligand. A kit of parts may be provided including such compositions. Use of the present system in the manufacture of a medicament for such methods of treatment are also provided. Use of the present system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again. Using an inducible Cas9 activator allows one to induce transcription right before the screen and therefore minimizes the chance of false negative hits. Accordingly, by use of the instant invention in screening, e.g., gain of function screens, the chance of false negative results may be minimized.

In one aspect, the invention provides an engineered, non-naturally occurring CRISPR-Cas system comprising a DD-Cas9 protein and a guide RNA that targets a DNA molecule encoding a gene product in a cell, whereby the guide RNA targets the DNA molecule encoding the gene product and the Cas9 protein cleaves the DNA molecule encoding the gene product, whereby expression of the gene product is altered; and, wherein the Cas9 protein and the guide RNA do not naturally occur together. The invention comprehends the guide RNA comprising a guide sequence fused to a tracr sequence. The Cas protein is a type II CRISPR-Cas protein and is a Cas9 protein. The invention further comprehends coding for the Cas9 protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

Where functional domains and the like are "associated" with one or other part of the enzyme, these are typically fusions. The term "associated with" is used here in respect of how one molecule 'associates' with respect to another, for example between parts of the CRISPR enzyme and a functional domain. The two may be considered to be tethered to each other. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (e.g. between the enzyme and the functional domain or between the adaptor protein and the functional domain). Thus, in some embodiments, the part of the CRISPR enzyme is associated with a functional domain by binding thereto. In other embodiments, the CRISPR enzyme is associated with a functional domain because the two are fused together, optionally via an intermediate linker. Examples of linkers include the GlySer linkers discussed herein. While a non covalent bound DD may be able to initiate degradation of the associated Cas9, proteasome degradation involves unwinding of the protein chain; and, a fusion is preferred as it can provide that the DD stays connected to Cas9 upon degradation. However the CRISPR enzyme and DD are brought together, in the presence of a stabilizing ligand specific for the DD, a stabilization complex is formed. This complex comprises the stabilizing ligand bound to the DD. The complex also comprises the DD associated with the CRISPR enzyme. In the absence of said stabilizing ligand, degradation of the DD and its associated CRISPR enzyme is promoted.

Destabilizing domains have general utility to confer instability to a wide range of proteins; see, e.g., Miyazaki, *J Am Chem Soc.* Mar. 7, 2012; 134(9): 3942-3945, and Chung H *Nature Chemical Biology* Vol. 11 Sep. 2015 pgs 713-720, incorporated herein by reference. CMP8 or 4-hydroxytamoxifen can be destabilizing domains. More generally, a temperature-sensitive mutant of mammalian DHFR (DHFRts), a destabilizing residue by the N-end rule, was found to be stable at a permissive temperature but unstable at 37° C. The64dditionn of methotrexate, a high-affinity ligand for mammalian DHFR, to cells expressing DHFRts inhibited degradation of the protein partially. This was an important demonstration that a small molecule ligand can stabilize a protein otherwise targeted for degradation in cells. A rapamycin derivative was used to stabilize an unstable mutant of the FRB domain of mTOR (FRB*) and restore the function of the fused kinase, GSK-3β. 6,7. This system demonstrated that ligand-dependent stability represented an attractive strategy to regulate the function of a specific protein in a complex biological environment. A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with a CRISPR enzyme confers to the CRISPR protein degradation of the entire fusion protein by the proteasome. Shield-1 and TMP bind to and stabilize the DD in a dose-dependent manner. The estrogen receptor ligand binding domain (ERLBD, residues 305-549 of ERS1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known. There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to a CRISPR enzyme and its stability can be regulated or perturbed using a ligand, whereby the CRISPR enzyme has a DD. Another DD can be a 12-kDa (107-amino-acid) tag based on a mutated FKBP protein, stabilized by Shield1 ligand; see, e.g., Nature Methods 5, (2008). For instance a DD can be a modified FK506 binding protein 12 (FKBP12) that binds to and is reversibly stabilized by a synthetic, biologically inert small molecule, Shield-1; see, e.g., Banaszynski L A, Chen L C, Maynard-Smith L A, Ooi A G, Wandless T J. A rapid, reversible, and tunable method to regulate protein function in living cells using synthetic small molecules. Cell. 2006; 126:995-1004; Banaszynski L A, Sellmyer M A, Contag C H, Wandless T J, Thorne S H. Chemical control of protein stability and function in living mice. Nat Med. 2008; 14:1123-1127; Maynard-Smith L A, Chen L C, Banaszynski L A, Ooi A G, Wandless T J. A directed approach for engineering conditional protein stability using biologically silent small molecules. The Journal of biological chemistry. 2007; 282:24866-24872; and Rodriguez, Chem Biol. Mar. 23, 2012; 19(3): 391-398—all of which are incorporated herein by reference and may be employed in the practice of the invention in selected a DD to associate with a CRISPR enzyme in the practice of this invention. As can be seen, the knowledge in the art includes a number of DDs, and the DD can be associated with, e.g., fused to, advantageously with a linker, to a CRISPR enzyme, whereby the DD can be stabilized in the presence of a ligand and when there is the absence thereof the DD can become destabilized, whereby the CRISPR enzyme is entirely destabilized, or the DD can be stabilized in the absence of a ligand and when the ligand is present the DD can become destabilized; the DD allows the CRISPR enzyme and hence the CRISPR-Cas complex or system to be regulated or controlled-turned on or off so to speak, to thereby provide means for regulation or control of the system, e.g., in an in vivo or in vitro environment. For instance, when a protein of interest is expressed as a fusion with the DD tag, it is destabilized and rapidly degraded in the cell, e.g., by proteasomes. Thus, absence of stabilizing ligand leads to a D associated Cas9 being degraded. When a new DD is fused to a protein of interest, its instability is conferred to the protein of interest, resulting in the rapid degradation of the entire fusion protein. Peak activity for Cas9 is sometimes beneficial to reduce off-target effects. Thus, short bursts of high activity are preferred. The present invention is able to provide such peaks. In some senses the system is inducible. In some other senses, the system repressed in the absence of stabilizing ligand and de-repressed in the presence of stabilizing ligand. Without wishing to be bound by any theory and without making any promises, other benefits of the invention may include that it is:

Dosable (in contrast to a system that turns on or off, e.g., can allow for variable CRISPR-Cas system or complex activity).

Orthogonal, e.g., a ligand only affects its cognate DD so two or more systems can operate independently, and/or the CRISPR enzymes can be from one or more orthologs.

Transportable, e.g., may work in different cell types or cell lines.

Rapid.

Temporal Control.

Able to reduce background or off target Cas9 or Cas9 toxicity or excess build up of Cas9 by allowing the Cas9 to be degraded.

Cheap—the stabilizing ligands are widely available and typically not expensive.

While the DD can be at N and/or C terminal(s) of the Cas9 or CRISPR enzyme, including a DD at one or more sides of a split e.g. Cas9(N)-linker-DD-linker-Cas9(C) is also a way to introduce a DD. In some embodiments, if using only one terminal association of DD to the CRISPR enzyme is to be used, then it is preferred to use ER50 as the DD. In some embodiments, if using both N- and C-terminals, then use of either ER50 and/or DHFR is preferred. Particularly good results were seen with the N-terminal fusion, which is surprising. Having both N and C terminal fusion may be synergistic. The size of Destabilization Domain varies but is typically approx.-approx. 100-300 amino acids in size. The DD is preferably an engineered destabilizing protein domain. DDs and methods for making DDs, e.g., from a high affinity ligand and its ligand binding domain. The invention may be considered to be "orthogonal" as only the specific ligand will stabilize its respective (cognate) DD, it will have no effect on the stability of non-cognate DDs. A commercially available DD system is the CloneTech, ProteoTuner™ system; the stabilizing ligand is Shield1, which is also preferred for use in the present invention. Suitable split sites with respect to SpCas9 are discussed below.

In some embodiments, the stabilizing ligand is a 'small molecule'. In some embodiments, the stabilizing ligand is cell-permeable. It has a high affinity for its corresponding DD. Suitable DD—stabilizing ligand pairs are known in the art. In general, the stabilizing ligand may be removed by:

Natural processing (e.g., proteasome degradation), e.g., in vivo;

Mopping up, e.g. ex vivo/cell culture, by:

Provision of a preferred binding partner; or

Provision of XS substrate (DD without Cas9).

Advantageously, the DD may "mop up" the stabilizing ligand and so it is the same DD (i.e. the same type of DD) as that associated with the enzyme. By mopping up the stabilizing ligand with excess DD that is not associated with the CRISPR enzyme, greater degradation of the CRISPR enzyme will be seen. It is envisaged, without being bound by theory, that as additional or excess un-associated DD is added that the equilibrium will shift away from the stabilizing ligand complexing or binding to the DD associated with the CRISPR enzyme and instead move towards more of the stabilizing ligand complexing or binding to the free DD (i.e. that not associated with the CRISPR enzyme). Thus, provision of excess or additional unassociated (or free) DD is preferred when it is desired to reduce CRISPR enzyme activity through increased degradation of the CRISPR enzyme. An excess of free DD will bind residual ligand and also takes away bound ligand from DD-Cas9 fusion. Therefore it accelerates DD-Cas9 degradation and enhances temporal control of Cas9 activity.

Attachment or association can be via a linker, e.g., a flexible glycine-serine (GlyGlyGlySer) or (GGGS)$_3$ or a rigid alpha-helical linker such as (Ala(GluAlaAlaAlaLys)Ala). Linkers such as (GGGGS)$_3$ are preferably used herein to separate protein or peptide domains. (GGGGS)$_3$ is preferable because it is a relatively long linker (15 amino acids). The glycine residues are the most flexible and the serine residues enhance the chance that the linker is on the outside of the protein. (GGGGS)$_6$, (GGGGS)$_9$, or (GGGGS)$_{12}$ may preferably be used as alternatives. Other preferred alternatives are (GGGGS)$_1$, (GGGGS)$_2$, (GGGGS)$_4$, (GGGGS)$_5$, (GGGGS)$_7$, (GGGGS)$_8$, (GGGGS)$_{10}$, or (GGGGS)$_{11}$. Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a (GGGGS)$_3$ linker may be used here (or the 6, 9, or 12 repeat versions therefore) or the NLS of nucleoplasmin can be used as a linker between Cas9 and the functional domain.

In some embodiments, the CRISPR enzyme comprises a Rec2 or HD2 truncation. The Rec2 or HD2 domains are known in Sp Cas9 from the crystal structure provided by Nishimasu et al. and the herein cited materials; corresponding domains are envisaged in orthologs. Such mutants may be advantageous where there is a desire to reduce the package size as this can assist with delivery, especially with the larger Cas9s such as Sp Cas9.

It will be appreciated that truncation may include removal of the domain, in some embodiments. In some embodiments, the truncation includes replacement with a different amino acid sequence, for example a linker. In some embodiments, the linker is branched or otherwise allows for tethering of the DD and/or a functional domain to the CRISPR enzyme. Functional domains are discussed further herein. HD2, the Helical Domain 2, is dispensable (meaning that at least 10% functional CRISPR enzyme activity is retained, preferably at least 30% and most preferably at least 50% functional CRISPR enzyme activity is retained in the truncated CRISPR enzyme). An exemplary DNA sequence encoding it in Sp Cas9 is provided below and suitable equivalents will be readily apparent in orthologs of Sp via sequence comparison, using programs such as BLAST. HD2 domain in Sp Cas9:

```
CTGAACCCCGACAACAGCGACGTGGACAAGCTGTTCATCCAGCTGGTGCA

GACCTACAACCAGCTGTTCGAGGAAAACCCCATCAACGCCAGCGGCGTGG

ACGCCAAGGCCATCCTGTCTGCCAGACTGAGCAAGAGCAGACGGCTGGAA

AATCTGATCGCCCAGCTGCCCGGCGAGAAGAAGAATGGCCTGTTCGGAAA

CCTGATTGCCCTGAGCCTGGGCCTGACCCCCAACTTCAAGAGCAACTTCG

ACCTGGCCGAGGATGCCAAACTGCAGCTGAGCAAGGACACCTACGACGAC
```

-continued
```
GACCTGGACAACCTGCTGGCCCAGATCGGCGACCAGTACGCCGACCTGTT

TCTGGCCGCCAAGAACCTGTCCGACGCCATCCTGCTGAGCGACATCCTGA

GAGTGAACACCGAG
```

In an aspect the invention involves a split CRISPR-Cas effector (e.g., split Cas9) system, providing an additional level of control on top of the DD-Cas9 of the present invention, as in Zetsche et al (Zetsche et al., "A split-Cas9 architecture for inducible genome editing and transcription modulation," Nature Biotechnology 33:139-142, DOI: 10.1038/nbt.3149 (Published online 2 Feb. 2015)). For example, the invention can provide a non-naturally occurring or engineered inducible CRISPR-Cas system, comprising: a first CRISPR enzyme fusion construct attached to a first half of an inducible dimer and a second CRISPR enzyme fusion construct attached to a second half of the inducible dimer,
  wherein the first CRISPR enzyme fusion construct comprises a first part of a CRISPR enzyme of the present invention and is operably linked to one or more nuclear localization signals,
  wherein the second CRISPR enzyme fusion construct comprises a second part of a CRISPR enzyme of the present invention is operably linked to one or more nuclear export signals,
  wherein contact with an inducer energy source brings the first and second halves of the inducible dimer together,
  wherein bringing the first and second halves of the inducible dimer together brings the first and second parts of the CRISPR enzyme together and thereby allows the first and second CRISPR enzyme fusion constructs to constitute a functional CRISPR-Cas system,
  wherein the CRISPR-Cas system comprises a guide RNA (sgRNA) comprising a guide sequence capable of hybridizing to a target sequence in a genomic locus of interest in a cell, and
  wherein the functional CRISPR-Cas system binds to the target sequence and, optionally, edits the genomic locus to alter gene expression.

In an aspect of the invention in the inducible CRISPR-Cas system, the CRISPR enzyme comprises two parts of a split CRISPR enzyme. With regard to the inducible system, the terms CRISPR enzyme and split CRISPR enzyme may be used interchangeably. In an aspect of the invention in the inducible CRISPR-Cas system, the inducible dimer is or comprises or consists essentially of or consists of an inducible heterodimer. In an aspect, in inducible CRISPR-Cas system, the first half or a first portion or a first fragment of the inducible heterodimer is or comprises or consists of or consists essentially of an FKBP, optionally FKBP12. In an aspect of the invention, in the inducible CRISPR-Cas system, the second half or a second portion or a second fragment of the inducible heterodimer is or comprises or consists of or consists essentially of FRB. In an aspect of the invention, in the inducible CRISPR-Cas system, the arrangement of the first CRISPR enzyme fusion construct is or comprises or consists of or consists essentially of N-terminal Cas9 part-FRB-NES. In an aspect of the invention, in the inducible CRISPR-Cas system, the arrangement of the first CRISPR enzyme fusion construct is or comprises or consists of or consists essentially of NES-N-terminal Cas9 part-FRB-NES. In an aspect of the invention, in the inducible CRISPR-Cas system, the arrangement of the second CRISPR enzyme fusion construct is or comprises or consists essentially of or consists of C-terminal Cas9 part-FKBP-NLS. In an aspect the invention provides in the inducible CRISPR-Cas system, the arrangement of the second CRISPR enzyme fusion construct is or comprises or consists of or consists essentially of NLS-C-terminal Cas9 part-FKBP-NLS. In an aspect, in inducible CRISPR-Cas system there can be a linker that separates the Cas9 part from the half or portion or fragment of the inducible dimer. In an aspect, in the inducible CRISPR-Cas system, the inducer energy source is or comprises or consists essentially of or consists of rapamycin. In an aspect, in inducible CRISPR-Cas system, the inducible dimer is an inducible homodimer. In an aspect, in inducible CRISPR-Cas system, the CRISPR enzyme is Cas9, e.g., SpCas9 or SaCas9.

Inducer for split CRISPR-Cas effector (e.g., Split Cas9): An inducer energy source may be considered to be an inducer or a dimerizing agent, which can be delivered using the prodrug composition described herein. The term 'inducer energy source' is used herein throughout for consistency. The inducer energy source (or inducer) acts to reconstitute the Cas9. In some embodiments, the inducer energy source brings the two parts of the Cas9 together through the action of the two halves of the inducible dimer. The two halves of the inducible dimer therefore are brought tougher in the presence of the inducer energy source. The two halves of the dimer will not form into the dimer (dimerize) without the inducer energy source. Thus, the two halves of the inducible dimer cooperate with the inducer energy source to dimerize the dimer. This in turn reconstitutes the Cas9 by bringing the first and second parts of the Cas9 together. Suitable examples include rapamycin.

Split Position: In an aspect in inducible CRISPR-Cas system, the Cas9 is split into two parts at any one of the following split points, according or with reference to SpCas9: a split position between 202A/203S; a split position between 255F/256D; a split position between 310E/311I; a split position between 534R/535K; a split position between 572E/573C; a split position between 713S/714G; a split position between 1003L/104E; a split position between 1054G/1055E; a split position between 1114N/1115S; a split position between 1152K/1153S; a split position between 1245K/1246G; or a split between 1098 and 1099. Cas9 can be split into two distinct fragments, which reconstitute a functional full-length Cas9 nuclease when brought back together using chemical induction. The split Cas9 architecture will be useful for a variety of applications. For example, split Cas9 may enable genetic strategies for restricting Cas9 activity to intersectional cell populations by putting each fragment under a different tissue specific promoter. Additionally, different chemically inducible dimerization domains such as APA and gibberellin may also be employed. The split position or location is the point at which the first part of the Cas9 enzyme is separated from the second part. In some embodiments, the first will comprise or encode amino acids 1 to X, whilst the second part will comprise or encode amino acids X+1 to the end. In this example, the numbering is contiguous, but this may not always be necessary as amino acids (or the nucleotides encoding them) could be trimmed from the end of either of the split ends, provided that sufficient DNA binding activity and, if required, DNA nickase or cleavage activity is retained, for example at least 40%, 50%, 60%, 70%, 80%, 90% or 95% activity compared to wildtype Cas9.

The exemplary numbering provided herein may be in reference to the wildtype protein, preferably the wildtype SpCas9 protein. However, it is envisaged that mutants of the wildtype SpCas9 protein can be used. For example, in the crystal data paper itself, a deadCas9 was used and these are preferred in some embodiments, see the discussion elsewhere herein. The numbering may also not follow exactly the Sp Cas9 numbering as, for instance, some N- or C-terminal truncations or deletions may be used, but this can be addressed suing standard sequence alignment tools. Orthologs are also preferred as a sequence alignment tool. Thus, the split position may be selected using ordinary skill in the art, for instance based on the crystal data provided in the herein cited materials. A number of split positions in SpCas9, which reconstitute Cas9 with inducible dimerization domains, include as tabulated below (showing Amino Acid position of split in Sp Cas9 (1368 a.a. in total)):

| Fusion Side | Structure | Domain |
| --- | --- | --- |
| 202A/203S | Outside loop | Rec 2 |
| 255F/256D | Outside loop | Rec 2 |
| 310E/311I | Outside loop | Rec 1 |
| 534R/535K | Outside loop | Rec 1 |
| 572E/573C | Unstructured | Rec 1 |
| 713S/714G | Unstructured | Rec 1 |
| 1003L/104E | Unstructured | RuvC3 |
| 1054G/1055E | Unstructured | RuvC3 |
| 1114N/1115S | Unstructured | PI |
| 1152K/1153S | Outside loop | PI |
| 1245K/1246G | Unstructured | PI |

The following split positions may also be advantageously employed (Amino Acid position of split in Sp Cas9 (1368 a.a. in total)):

| Split number | Amino Acid position of Sp Cas9 (1368 a.a. in total) | Domain | Split in Loop (L) or Unstructured Region (UR)? |
| --- | --- | --- | --- |
| 1 | 203 | Rec 2 | L |
| 2 | 256 | Rec 2 | L |
| 3 | 311 | Rec 1 | L |
| 4 | 535 | Rec 1 | L |
| 5 | 573 | Rec 1 | UR |
| 6 | 714 | Rec 1 | UR |
| 7 | 1004 | RuvC3 | UR |
| 8 | 1055 | RuvC3 | UR |
| 9 | 1115 | PI | UR |
| 10 | 1153 | PI | L |
| 11 | 1246 | PI | UR |

Identifying potential split sides is most simply done with the help of a crystal structure. For Sp mutants, it should be readily apparent what the corresponding position for, for example, a sequence alignment. For non-Sp enzymes one can use the crystal structure of an ortholog if a relatively high degree of homology exists between the ortholog and the intended Cas9.

The split position may be located within a region or loop. Preferably, the split position occurs where an interruption of the amino acid sequence does not result in the partial or full destruction of a structural feature (e.g. alpha-helixes or β-sheets). Unstructured regions (regions that did not show up in the crystal structure because these regions are not structured enough to be "frozen" in a crystal) are often preferred options. Splits in all unstructured regions that are exposed on the surface of SpCas9 are envisioned in the practice of the invention. The positions within the unstructured regions or outside loops may not need to be exactly the numbers provided above, but may vary by, for example 1, 2, 3, 4, 5, 6, 7, 8, 9, or even 10 amino acids either side of the position given above, depending on the size of the loop, so long as the split position still falls within an unstructured region of outside loop.

A split in an outside loop of the Rec 2 domain is preferred in some embodiments. In other embodiments, a split in an outside loop of Rec 1 is preferred. In other embodiments, a split in an outside loop of PI is preferred. In other embodiments, a split in an unstructured region of Rec 1 is preferred. In other embodiments, a split in an unstructured region of RuvC3 is preferred. In other embodiments, a split in an unstructured region of PI is preferred.

Splits 4, 5 and 6 in Table 2 above are beneficial in one aspect, in that there is some advantage to keeping the two parts (either side of the split) roughly the same length for packing purposes. For example, it is thought to be easier to maintain stoichiometry between both pieces when the transcripts are about the same size.

The N- and C-term pieces of human codon-optimized S. pyogenes Cas9 may be fused to FRB and FKBP dimerization domains, respectively. This arrangement is preferred. They may be switched over (i.e. N-term to FKBP and C-term to FRB), this arrangement worked as well but there is a suggestion that this switched arrangement brings the two parts of the Cas9 further apart.

Linkers such as (GGGGS)3 are preferably used herein to separate the Cas9 fragment from the dimerization domain. (GGGGS)3 is preferable because it is a relatively long linker (15 amino acids). The glycine residues are the most flexible and the serine residues enhance the chance that the linker is on the outside of the protein. (GGGGS)6, (GGGGS)9, or (GGGGS)12 may preferably be used as alternatives. Other preferred alternatives are (GGGGS)1, (GGGGS)2, (GGGGS)4, (GGGGS)5, (GGGGS)7, (GGGGS)8, (GGGGS)10, or (GGGGS) 11. For example, (GGGGS)3 may be used between the N-term Cas9 fragment and FRB. Such a linker may also be used between FKB and the C-term Cas9 fragment. Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. A linker, such as any of the linkers discussed herein, can also be used between the Cas9 and any functional domain. Again, a (GGGGS)3 linker may be used here (or the 6, 9, or 12 repeat versions therefore) or the NLS of nucleoplasmin can be used as a linker between Cas9 and the functional domain.

In some embodiments, the FRB/FKBP system is preferred. However, alternatives to the FRB/FKBP system are envisaged. For example the ABA and gibberellin system. Accordingly, preferred examples of the FKBP family are any one of the following inducible systems. FKBP which dimerizes with CalcineurinA (CNA), in the presence of FK506; FKBP which dimerizes with CyP-Fas, in the presence of FKCsA; FKBP which dimerizes with FRB, in the presence of Rapamycin; GyrB which dimerizes with GryB, in the presence of Coumermycin; GAI which dimerizes with GID1, in the presence of Gibberellin; or Snap-tag which dimerizes with HaloTag, in the presence of HaXS. Alternatives within the FKBP family itself are also preferred. For example, FKBP, which homo-dimerizes (i.e. one FKBP dimerizes with another FKBP) in the presence of FK1012. Thus, also provided is a non-naturally occurring or engineered inducible CRISPR-Cas system, comprising: a first CRISPR enzyme fusion construct attached to a first half of an inducible homodimer and a second CRISPR enzyme fusion construct attached to a second half of the inducible homodimer, wherein the first CRISPR enzyme fusion construct is operably linked to one or more nuclear localization signals, wherein the second CRISPR enzyme fusion construct is operably linked to a (optionally one or more) nuclear export signal(s), wherein contact with an inducer energy source brings the first and second halves of the inducible homodimer together, wherein bringing the first and second halves of the inducible homodimer together allows the first and second CRISPR enzyme fusion constructs to constitute a functional CRISPR-Cas system, wherein the CRISPR-Cas system comprises a guide RNA (sgRNA) comprising a guide sequence capable of hybridizing to a target sequence in a genomic locus of interest in a cell, and wherein the functional CRISPR-Cas system binds to the target sequence and, optionally, edits the genomic locus to alter gene expression.

In one embodiment, the homodimer is preferably FKBP and the inducer energy source is preferably FK1012. In another embodiment, the homodimer is preferably GryB and the inducer energy source is preferably Coumermycin. In another embodiment, the homodimer is preferably ABA and the inducer energy source is preferably Gibberellin. In other embodiments, the dimer is a heterodimer. Preferred examples of heterodimers are any one of the following inducible systems: FKBP which dimerizes with CalcineurinA (CNA), in the presence of FK506; FKBP which dimerizes with CyP-Fas, in the presence of FKCsA; FKBP which dimerizes with FRB, in the presence of Rapamycin, in the presence of Coumermycin; GAI which dimerizes with GID1, in the presence of Gibberellin; or Snap-tag which dimerizes with HaloTag, in the presence of HaXS. FKBP/FRB is advantageous as it is well characterized and both domains are sufficiently small (<100 amino acids) to assist with packaging. Furthermore, rapamycin has been used for a long time and side effects are well understood. Large dimerization domains (>300 aa) should work too but may require longer linkers to make enable Cas9 reconstitution.

Teachings in Paulmurugan and Gambhir (Cancer Res, Aug. 15, 2005 65; 7413) may be used in combination with herein teachings to exemplify the FRB/FKBP/Rapamycin system in the practice of the invention; see also Crabtree et al. (Chemistry & Biology 13, 99-107, January 2006).

A single vector can be used. An expression cassette (plasmid) was constructed as follows. The split Cas9 construct was based on a first CRISPR enzyme fusion construct, flanked by NLSs, with FKBP fused to C terminal part of the split Cas9 via a GlySer linker; and a second CRISPR enzyme fusion construct, flanked by NESs, with FRB fused with the N terminal part of the split Cas9 via a GlySer linker. To separate the first and second CRISPR enzyme fusion constructs, P2A was used splitting on transcription. The Split Cas9 showed indel formation similar to wildtype in the presence of rapamycin, but markedly lower indel formation than the wildtype in the absence of rapamycin. Accordingly, a single vector is provided. The vector comprises: a first CRISPR enzyme fusion construct attached to a first half of an inducible dimer and a second CRISPR enzyme fusion construct attached to a second half of the inducible dimer, wherein the first CRISPR enzyme fusion construct is operably linked to one or more nuclear localization signals, wherein the second CRISPR enzyme fusion construct is operably linked to one or more nuclear export signals, wherein contact with an inducer energy source brings the first and second halves of the inducible heterodimer together, wherein bringing the first and second halves of the inducible heterodimer together allows the first and second CRISPR enzyme fusion constructs to constitute a functional CRISPR-Cas system, wherein the CRISPR-Cas system comprises a guide RNA (sgRNA) comprising a guide sequence capable of hybridizing to a target sequence in a genomic locus of interest in a cell, and wherein the functional CRISPR-Cas system binds to the target sequence and, optionally, edits the genomic locus to alter gene expression. These elements are preferably provided on a single construct, for example an expression cassette.

The first CRISPR enzyme fusion construct is preferably flanked by at least one nuclear localization signal at each end. The second CRISPR enzyme fusion construct is preferably flanked by at least one nuclear export signal at each end.

Applicants have determined split sites for SaCas9.

| Fusion Side | Structure | Domain |
| --- | --- | --- |
| 430/431 | Unstructured loop | Between REC and NUC lobes (between 3'/C' terminal end of Rec Domain and 5'/N' terminal end of RuvCII domain). |
| 739/740 | Unstructured region | RuvCIII domain |

Table showing Amino Acid position of split in a Cas9 (1053 a.a. in total)

In some embodiments, with any Cas9, the split is preferably positioned in an unstructured loop or an unstructured region.

In some embodiments, with split SaCas9, the split is preferably positioned at or around amino acid position 430 or 431, in particular between 430 and 431.

In some embodiments, with split SaCas9, the split is preferably positioned at or around amino acid position 739 or 740, in particular between 739 and 740.

With split SaCas9, a certain amount of variation should be tolerated on each side of each split. For example, for split point 1: −4 to +2 amino acid positions is ideal. In some embodiments, the split is positioned at (ideally C' terminal to) amino acid positions 426, 427, 428, 429 or 430. In some embodiments, the split is positioned at (ideally C' terminal to) amino acid positions 431, 432 or even 433. In some embodiments, the split is positioned at (ideally C' terminal to) amino acid positions 426-433.

Without being bound by theory, it is understood that any further towards the N' terminal than −4 and the split position gets too close to the sgRNA. Further towards the C' terminal than +2 and the split position gets too close to an alpha-helix.

For split point 2: the split point at 739-740 may be moved within −7 to +4 amino acid positions. In some embodiments, the split is positioned at (ideally C' terminal to) amino acid positions 732, 733, 734, 735, 736, 737, 738, or 739. In some embodiments, the split is positioned at (ideally C' terminal to) amino acid positions 740, 471, 742, 743, 744 or even 745. In some embodiments, the split is positioned at (ideally C' terminal to) amino acid positions 732-745.

Without being bound by theory, it is understood that split 2 is located in the middle of an unstructured region flanked by alpha-helixes.

Corresponding positions in other orthologues are also envisaged

The promoter used for SaCas9 splits is CBh and bGHpA is the polyA signal in all constructs cloned so far and we planning to clone. However, we know that CMV, EF1alpha and EFS (minimal EF1α promoter) work well for SpCas9 and will also work for SaCas9. In an aspect, the promoter used for SaCas9 splits is CBh. In other aspects, CMV, EF1alpha and EFS (minimal EF1α promoter) may be used as promoters. In an aspect, a polyA tail such as bGHpA may be used.

Also provided is a split SaCas9 with specific split points. In an aspect the invention provides a non-naturally occurring or engineered inducible CRISPR-Cas system, comprising:
a first CRISPR enzyme fusion construct attached to a first half of an inducible dimer and
a second CRISPR enzyme fusion construct attached to a second half of the inducible dimer,
wherein the first CRISPR enzyme fusion construct comprises a first part of a CRISPR enzyme,
wherein the second CRISPR enzyme fusion construct comprises a second part of a CRISPR enzyme,
wherein contact with an inducer energy source brings the first and second halves of the inducible dimer together,
wherein bringing the first and second halves of the inducible dimer together brings the first and second parts of the CRISPR enzyme together and thereby allows the first and second CRISPR enzyme fusion constructs to constitute a functional CRISPR-Cas system,
wherein the CRISPR-Cas system comprises a guide RNA (sgRNA) comprising a guide sequence capable of hybridizing to a target sequence in a genomic locus of interest in a cell, and
wherein the functional CRISPR-Cas system binds to the target sequence and, optionally, edits the genomic locus to alter gene expression, and
wherein the two parts of the Cas9 are split between amino acid positions amino acid positions 426-433 or amino acid positions 732-745, or positions corresponding thereto.

In an aspect, the Cas9 is SaCas9. In an aspect, the Cas9 is an ortholog of SaCas9. In an aspect, the first CRISPR enzyme fusion construct comprises a first part of a CRISPR enzyme and is operably linked to one or more, preferably two or more nuclear localization signals (NLS). In an aspect, the first CRISPR enzyme fusion construct comprises a first part of a CRISPR enzyme and is operably linked to one or more, preferably two or more nuclear export signals (NES). In an aspect, the second CRISPR enzyme fusion construct comprises a second part of a CRISPR enzyme and is operably linked to one or more, preferably two or more nuclear localization signals. In an aspect, the second CRISPR enzyme fusion construct comprises a second part of a CRISPR enzyme and is operably linked to one or more, preferably two or more nuclear export signals. In an aspect, the first CRISPR enzyme fusion construct comprises a first part of a CRISPR enzyme and is operably linked to one or more, preferably two or more nuclear localization signals and the second CRISPR enzyme fusion construct comprises a second part of a CRISPR enzyme and is operably linked to one or more, preferably two or more nuclear export signals. In an aspect, the first CRISPR enzyme fusion construct comprises a first part of a CRISPR enzyme and is operably linked to one or more, preferably two or more nuclear export signals and the second CRISPR enzyme fusion construct comprises a second part of a CRISPR enzyme and is operably linked to one or more, preferably two or more nuclear localization signals.

In an aspect, two NLS are operably linked to one part, and one NES operably is operably linked to the other part. In a further aspect, one or two NLS are operably linked to one part, and one or two NES operably are also operably linked to the other part.

In addition as to Split Cas9, in an aspect, in the inducible CRISPR-Cas system, one or more functional domains, as discussed herein are associated, with one or both parts of the Cas9 enzyme. For example, the functional domains may optionally include a transcriptional activator, a transcriptional or a nuclease such as a Fok1 nuclease. Further examples are provided herein. In an aspect, in the inducible CRISPR-Cas system, the functional CRISPR-Cas system binds to the target sequence and the enzyme is a deadCas9, optionally having a diminished nuclease activity of at least 97%, or 100% (or no more than 3% and advantageously 0% nuclease activity) as compared with the CRISPR enzyme not having the at least one mutation. In an aspect, in the inducible CRISPR-Cas system, the deadCas9 (CRISPR enzyme) comprises two or more mutations wherein two or more of D10, E762, H840, N854, N863, or D986 according to SpCas9 protein or any corresponding ortholog or N580 according to SaCas9 protein are mutated, or the CRISPR enzyme comprises at least one mutation, e.g., wherein at least H840 is mutated.

In some embodiments, the one or more DDs may be used. Each DD may be associated with one of the two parts of the split CRISPR enzyme.

Where one DD is used, it is preferred in some embodiments, that the NES is associated with the same part of the split CRISPR enzyme as the DD. This may help to ensure cytoplasmic location of the DD.

Where more than one DD is used, it is preferred in some embodiments, that the NES is associated with the same part of the split CRISPR enzyme as at least one of the DDs. Again, this may help to ensure cytoplasmic location of the DD.

In some embodiments, where one part of the split CRISPR enzyme comprises two or more DDs, there may be one DD associated with the N-terminal of the split CRISPR enzyme and one DD associated with the C-terminal of the CRISPR enzyme.

In some embodiments, two DDs may be used. Both may be associated with the same part of the split CRISPR enzyme, or one DD may be associated with one part of the split CRISPR enzyme (N- or C-terminal) and the other DD may be associated with the other part of the split CRISPR enzyme (N- or C-terminal).

In some embodiments, three DDs may be used. All three may be associated with the same part of the split CRISPR enzyme (N- or C-terminal or a mixture), or one DD may be associated with one part of the split CRISPR enzyme (N- or C-terminal) and the other two DDs may be associated with the other part of the split CRISPR enzyme (N- or C-terminal or a mixture).

In some embodiments, four DDs may be used. All four may be associated with the same part of the split CRISPR enzyme (N- or C-terminal or a mixture), or one DD may be associated with one part of the split CRISPR enzyme (N- or C-terminal) and the other three DDs may be associated with the other part of the split CRISPR enzyme (N- or C-terminal or a mixture).

In some embodiments, four DDs may be used and two DDs may be associated with one part of the split CRISPR enzyme (N- or C-terminal or a mixture) and the other two DDs may be associated with the other part of the split CRISPR enzyme (N- or C-terminal or a mixture). In some embodiments using four DDs, one DD may be associated with each end of the two split CRISPR enzyme parts. This paired approach is preferred as it allows one DD at each end of both parts of the split CRISPR enzyme.

As such, in some embodiments, one DD is associated with the N-terminal of the first part of the split CRISPR enzyme and one DD is associated with the C-terminal of the first part of the CRISPR enzyme; and one DD is associated with the N-terminal of the second part of the split CRISPR enzyme and one DD is associated with the C-terminal of the second part of the CRISPR enzyme. The invention further comprehends and an aspect of the invention provides, a polynucleotide encoding the inducible CRISPR-Cas system as herein discussed.

The invention comprehends a DD-CRISPR Cas complex comprising a DD-CRISPR enzyme and a guide RNA (sgRNA), wherein the DD-CRISPR enzyme comprises at least one mutation, such that the DD-CRISPR enzyme has no more than 5% of the nuclease activity of the CRISPR enzyme not having the at least one mutation and, optional, at least one or more nuclear localization sequences; the guide RNA (sgRNA) comprises a guide sequence capable of hybridizing to a target sequence in a genomic locus of interest in a cell; and wherein: the DD-CRISPR enzyme is associated with two or more functional domains; or at least one loop of the sgRNA is modified by the insertion of distinct RNA sequence(s) that bind to one or more adaptor proteins, and wherein the adaptor protein is associated with two or more functional domains; or the DD-CRISPR enzyme is associated with one or more functional domains and at least one loop of the sgRNA is modified by the insertion of distinct RNA sequence(s) that bind to one or more adaptor proteins, and wherein the adaptor protein is associated with one or more functional domains. The invention comprehends the use of modified guides such as in Konermann et al., "Genome-scale transcription activation by an engineered CRISPR-Cas9 complex," doi:10.1038/nature14136, incorporated herein by reference, or PCT/US14/70175, filed Dec. 12, 2014.

Construction of Destabilization Domain —Transcriptional/Translational Activation/Repression Domain Fusion Protein The prodrug composition described herein can be used to deliver a molecular stabilizer into beta cells to activate a destabilized fusion protein of an aptamer ligand and a transcriptional or translational activation or repression domain present in the beta cells. In one aspect, the invention provides a fusion protein comprising one or more destabilization domains (DD), one or more adaptor proteins capable of binding to a DNA- or RNA guided (endo)nuclease system guide RNA or guide DNA, such as in certain embodiments a CRISPR/Cas system guide RNA (gRNA) or guide DNA (gDNA), and optionally one or more functional domains. In certain embodiments, the RNA-guided or DNA-guided (endo)nuclease (also called "effector protein") may itself also be associated with a destabilizing domain. Such non-naturally occurring or engineered effector protein associated with at least one destabilization domain (DD); and, for shorthand purposes, such a non-naturally occurring or engineered CRISPR enzyme associated with at least one destabilization domain (DD) is herein termed a "DD-effector".

In one aspect, the invention provides an engineered, non-naturally occurring DD-CRISPR-Cas system comprising a fusion protein according to the invention as defined herein associated with at least one destabilization domain, a CRISPR enzyme, wherein the CRISPR enzyme is a Cas protein, which is a type II DD-CRISPR Cas protein and guide RNA that targets a nucleic acid molecule such as a DNA or RNA molecule, whereby the guide RNA targets the nucleic acid molecule, e.g., DNA or RNA molecule. The nucleic acid molecule, e.g., DNA or RNA molecule can encode a gene product. In some embodiments the Cas protein may cleave the DNA molecule encoding the gene product. In some embodiments expression of the gene product is altered. The Cas protein and the guide RNA do not naturally occur together. The invention comprehends the guide RNA comprising a guide sequence fused to a tracr sequence in case the particular Cas protein requires the presence of a tracr. The invention further comprehends coding for the Cas protein being codon optimized for expression in a eukaryotic cell.

In a preferred embodiment the eukaryotic cell is a mammalian cell and in a more preferred embodiment the mammalian cell is a human cell. Expression of the gene product may be decreased. The CRISPR enzyme may form part of a CRISPR-Cas system, which further comprises a guide RNA (gRNA) comprising a guide sequence capable of hybridizing to a target sequence in a genomic locus of interest in a cell. The gRNA may be functionalized such as being capable of binding to the fusion protein according to the invention, in particular binding to the adaptor protein of the fusion protein. In some embodiments, the functional CRISPR-Cas system binds to the target sequence. In some embodiments, the functional CRISPR-Cas system may edit the target sequence, e.g., the target sequence may comprise a genomic locus, and in some embodiments there may be an alteration of gene expression. In some embodiments, the functional CRISPR-Cas system may comprise further functional domains. In some embodiments, the invention provides a method for altering or modifying expression of a gene product. The method may comprise introducing into a cell containing a target nucleic acid, e.g., DNA or RNA molecule, or containing and expressing a target nucleic acid, e.g., DNA or RNA molecule; for instance, the target nucleic acid may encode a gene product or provide for expression of a gene product (e.g., a regulatory sequence).

The CRISPR enzyme may be a Cas9, Cpf1, C2c1, C2c2, C2c3, or Cas13b. In some embodiments, the CRISPR enzyme is an Sp DD-Cas9. In some embodiments, the CRISPR enzyme is an Sa DD-Cas9. In some embodiments, the CRISPR enzyme is a Cj, St or Fn DD-Cas9, although other orthologs are envisaged. Sp and Sa DD-Cas9s are particularly preferred, in some embodiments. In some embodiments, the CRISPR enzyme cleave both strands of DNA to produce a double strand break (DSB). In some embodiments, the CRISPR enzyme is a nickase. In some embodiments, the CRISPR enzyme is a dual nickase. In some embodiments, the CRISPR enzyme is a deadCas, e.g., a Cas having substantially no nuclease activity, e.g., no more than 5% nuclease activity as compared with a wild-type Cas or Cas not having had mutations to it.

In some general embodiments, the CRISPR enzyme is associated with one or more functional domains. In some more specific embodiments, the CRISPR enzyme is a deadCas and/or is associated with one or more functional domains.

In some embodiments, the CRISPR enzyme comprises a Rec2 or HD2 truncation. In some embodiments, the CRISPR enzyme is associated with the DD by way of a fusion protein. In some embodiments, the CRISPR enzyme is fused to the DD. In other words, the DD may be associated with the CRISPR enzyme by fusion with said CRISPR enzyme. In some embodiments, the enzyme may be considered to be a modified CRISPR enzyme, wherein the CRISPR enzyme is optionally fused to at least one destabilization domain (DD).

In some embodiments, the DD of the fusion protein according to the invention, or of the CRISPR enzyme may be associated therewith via a connector protein, for example using a system such as a marker system such as the streptavidin-biotin system. As such, provided is a fusion of a fusion protein according to the invention, or CRISPR enzyme with a connector protein specific for a high affinity ligand for that connector, whereas the DD is bound to said high affinity ligand. For example, streptavidin may be the connector fused to the fusion protein or CRISPR enzyme, while biotin may be bound to the DD. Upon co-localization, the streptavidin will bind to the biotin, thus connecting the fusion protein or CRISPR enzyme to the DD. For simplicity, a fusion of the fusion protein and/or CRISPR enzyme with the DD is preferred in some embodiments. In some embodiments, the fusion may be to the N-terminal end of the fusion protein or CRISPR enzyme.

In some embodiments, at least one DD is fused to the N-terminus of the fusion protein or CRISPR enzyme. In some embodiments, the fusion may be to the C-terminal end of the fusion protein or CRISPR enzyme. In some embodiments, at least one DD is fused to the C-terminus of the fusion protein or CRISPR enzyme. In some embodiments, one DD may be fused to the N-terminal end of the fusion protein or CRISPR enzyme with another DD fused to the C-terminal of the fusion protein or CRISPR enzyme. In some embodiments, the fusion protein or CRISPR enzyme is associated with at least two DDs and wherein a first DD is fused to the N-terminus of the fusion protein or CRISPR enzyme and a second DD is fused to the C-terminus of the fusion protein or CRISPR enzyme, the first and second DDs being the same or different. In some embodiments, the fusion may be to the N-terminal end of the DD. In some embodiments, the fusion may be to the C-terminal end of the DD. In some embodiments, the fusion may between the C-terminal end of the fusion protein or CRISPR enzyme and the N-terminal end of the DD. In some embodiments, the fusion may between the C-terminal end of the DD and N-terminal end of the fusion protein or CRISPR enzyme. Less background was observed with a DD fused to the CRISPR protein comprising at least one N-terminal fusion than a DD comprising at least one C terminal fusion. Combining N- and C-terminal CRISPR protein fusions had the least background but lowest overall activity. Advantageously a DD is provided through at least one N-terminal fusion or at least one N terminal fusion plus at least one C-terminal fusion. And of course, a DD can be provided by at least one C-terminal fusion.

In some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR. A corresponding stabilizing ligand for this DD is, in some embodiments, TMP. As such, in some embodiments, one of the at least one DDs is DHFR and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT.

In some embodiments, one or two DDs may be fused to the N-terminal end of the fusion protein or CRISPR enzyme with one or two DDs fused to the C-terminal of the fusion protein or CRISPR enzyme. In some embodiments, the at least two DDs are associated with the fusion protein or CRISPR enzyme and the DDs are the same DD, i.e. the DDs are homologous. Thus, both (or two or more) of the DDs could be ER50 DDs. This is preferred in some embodiments. Alternatively, both (or two or more) of the DDs could be DHFR DDs. This is also preferred in some embodiments. In some embodiments, the at least two DDs are associated with the fusion protein or CRISPR enzyme and the DDs are different DDs, i.e. the DDs are heterologous. Thus, one of the DDS could be ER50 while one or more of the or any other DDs could be DHFR. Having two or more DDs which are heterologous may be advantageous as it would provide a greater level of degradation control. A tandem fusion of more than one DD at the N or C-term may enhance degradation; and such a tandem fusion can be, for example ER50-ER50-adaptor (or CRISPR) protein or DHFR-DHFR-adaptor (or CRISPR). High levels of degradation occur in the absence of either stabilizing ligand, intermediate levels of degradation occur in the absence of one stabilizing ligand and the presence of the other (or another) stabilizing ligand, while low levels of degradation occur in the presence of both (or two of more) of the stabilizing ligands. Control may also be imparted by having an N-terminal ER50 DD and a C-terminal DHFR DD, or vice versa.

In some embodiments, the fusion of the fusion protein or CRISPR enzyme with the DD comprises a linker between the DD and the fusion protein or CRISPR enzyme. In some embodiments, the linker is a GlySer linker. In some embodiments, the fusion protein and/or CRISPR enzyme further comprises at least one Nuclear Export Signal (NES). In some embodiments, the fusion protein and/or CRISPR enzyme comprises two or more NESs. In some embodiments, the fusion protein and/or CRISPR enzyme comprises at least one Nuclear Localization Signal (NLS). This may be in addition to an NES. In some embodiments, the fusion protein and/or CRISPR enzyme comprises or consists essentially of or consists of a localization (nuclear import or export) signal as, or as part of, the linker between the fusion protein or CRISPR enzyme and the DD. HA or Flag tags are also within the ambit of the invention as linkers. Applicants use NLS and/or NES as linker and use Glycine Serine linkers as short as GS up to (GGGGS)3.

In an aspect, the present invention provides a polynucleotide encoding the fusion protein according to the invention as described herein, minimally containing the DD and the adaptor protein, optionally a functional domain. In some embodiments, the encoded adaptor protein and associated DD are operably linked to a first regulatory element. In some embodiments, a DD is also encoded and is operably linked to a second regulatory element. [0301] Advantageously, the DD here is to "mop up" the stabilizing ligand and so it is advantageously the same DD (i.e. the same type of Domain) as that associated with the enzyme, e.g., as herein discussed (with it understood that the term "mop up" is meant in the sense of performing so as to contribute or conclude activity. In some embodiments, the first regulatory element is a promoter and may optionally include an enhancer. In some embodiments, the second regulatory element is a promoter and may optionally include an enhancer. In some embodiments, the first regulatory element is an early promoter. In some embodiments, the second regulatory element is a late promoter. In some embodiments, the second regulatory element is or comprises or consists essentially of an inducible control element, optionally the tet system, or a repressible control element, optionally the tetr system. An inducible promoter may be favorable e.g. rTTA to induce tet in the presence of doxycycline.

In an aspect, the present invention provides a means for delivering the DD-CRISPR-Cas complex of the invention or polynucleotides discussed herein, e.g., particle(s) delivering component(s) of the complex, vector(s) comprising the polynucleotide(s) discussed herein (e.g., encoding the CRISPR enzyme, the DD; providing RNA of the CRISPR-Cas complex). In some embodiments, the vector may be a plasmid or a viral vector such as AAV, or lentivirus. Transient transfection with plasmids, e.g., into HEK cells may be advantageous, especially given the size limitations of AAV and that while SpCas9 fits into AAV, one may reach an upper limit with additional coding as to the association with the DD(s).

Also provided is a model that constitutively expresses the fusion protein and/or CRISPR enzyme and associated DD. The organism may be a transgenic and may have been transfected the present vectors or may be the offspring of an organism so transfected. In a further aspect, the present invention provides compositions comprising the fusion protein and/or CRISPR enzyme and associated DD or the polynucleotides or vectors described herein. Also provides are CRISPR-Cas systems comprising guide RNAs.

Where functional domains and the like are "associated" with one or other part of the enzyme, these are typically fusions. The term "associated with" is used here in respect of how one molecule 'associates' with respect to another, for example between parts of the fusion protein or CRISPR enzyme and a functional domain. The two may be considered to be tethered to each other. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit.

Alternatively, this may essentially be viewed as binding between two molecules or direct linkage, such as a fusion protein. In any event, the fusion protein may include a linker between the two subunits of interest (e.g. between the enzyme and the functional domain or between the adaptor protein and the functional domain). Thus, in some embodiments, the part of the fusion protein or CRISPR enzyme is associated with a functional domain by binding thereto. In other embodiments, the fusion protein and/or CRISPR enzyme is associated with a functional domain because the two are fused together, optionally via an intermediate linker. Examples of linkers include the GlySer linkers discussed herein. While a non covalent bound DD may be able to initiate degradation of the associated fusion protein or effector protein, proteasome degradation involves unwinding of the protein chain; and, a fusion is preferred as it can provide that the DD stays connected to fusion protein or effector protein upon degradation. However the fusion protein or CRISPR enzyme and DD are brought together, in the presence of a stabilizing ligand specific for the DD, a stabilization complex is formed. This complex comprises the stabilizing ligand bound to the DD. The complex also comprises the DD associated with the fusion protein and/or CRISPR enzyme. In the absence of said stabilizing ligand, degradation of the DD and its associated fusion protein or CRISPR enzyme is promoted.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Reference is also made to Magalhaes ("A general RNA motif for cellular transfection."), the contents of which are hereby incorporated by reference. This paper described the use of aptamers such as Otter and C1, as well as their minimal versions: OtterMin and C1Min. In some embodiments, one or more, preferably two, of Otter and/or C1 are used in the present invention as the escort RNA aptamer sequence. In some embodiments, OtterMin may replace Otter. In some embodiments, C1Min may replace C1. In some embodiments, 2× Otter, 2×C1, 2×C1Min, or 2× Otter-Min may be used. Combinations of two of any of the four are also preferred in some embodiments. In some embodiments, it is preferred to have one of Otter or OtterMin, and one of C1 or C1Min. Where a certain aptamer is used as an escort RNA aptamer sequence, then it will be appreciated that the corresponding RNA (escort RNA aptamer sequence) will be required.

In some embodiments, the present invention relates to an escort RNA aptamer sequence. For example, the escort RNA aptamer may be part of the guide RNA of a CRISPR-Cas system. For example, the activity and destination of the CRISPR-Cas system or complex or guide may be controlled by an escort RNA aptamer sequence that has binding affinity for an aptamer ligand, such as a cell surface protein or other localized cellular component. Alternatively, the escort aptamer (escort RNA aptamer sequence) may for example be responsive to, i.e. activated or inactivated by, an aptamer effector on or in the cell.

It will be appreciated that the terms "escort RNA aptamer sequence" and "escort aptamer" are used interchangeably herein. In some embodiments, the escort RNA aptamer sequence comprises an aptamer sequence and is fused to the guide at one or more of the tetraloop and/or stem loop 2. Preferably, the escort RNA aptamer sequence is completely RNA although it may comprise DNA or other nucleotides: preferably it is predominantly, i.e. at least 50%, RNA. Examples of aptamers comprised within the escort RNA aptamer sequence include Otter and C1, as well as their minimal versions: OtterMin and C1Min.

In some embodiments, the escort RNA aptamer sequence is responsive to a localized aptamer effector on or in the cell. In some embodiments, the aptamer effector is localized on the cell, for example so that it is at least partially available on the extra-cellular face or side of the cell membrane. The aptamer effector may therefore be one part of a fusion protein, one other part of the fusion protein having a membrane anchor or membrane-spanning domain. In some embodiments, the aptamer effector is in the cell. For example, the the aptamer effector may be internalised within a cell, i.e. within (beyond) the cell membrane, for example in the cytoplasm, within an organelle (including mitochondria), within an endosome, or in the nucleus (if the cell has one, i.e. it is a eukaryotic cell).

In some embodiments, the (escort) RNA aptamer sequence is 'responsive to' the aptamer effector such that the escort RNA aptamer sequence is activated. Optionally, this results in greater nicking or cleavage in the case of nickases and nucleases. In other embodiments, the escort RNA aptamer sequence is 'responsive to' the aptamer effector such that the escort RNA aptamer sequence is de-activated and, optionally, the guide itself is de-activated so that target recognition and hybridization and optionally, recruitment of the CRISPR protein is decreased. Optionally, this results in reduced nicking or cleavage in the case of nickases and nucleases.

In some embodiments, the (escort) aptamer (escort RNA aptamer sequence) may for example change conformation in response to an interaction with the aptamer ligand or effector in the cell. In some embodiments, it may have specific binding affinity for the aptamer ligand.

In one aspect, the present invention relates to aptamers that specifically bind to an activator or repressor. For example, in some embodiments, one guide with a first aptamer/RNA-binding protein pair can be linked or fused to an activator, while a second guide with a second aptamer/RNA-binding protein pair can be linked or fused to a repressor. The guides are for different targets (loci), so this allows one gene to be activated and one repressed. For example, the following schematic shows such an approach:

Guide 1—MS2 aptamer-------MS2 RNA-binding protein fused to DD-------VP64 activator; and Guide 2—PP7 aptamer-------PP7 RNA-binding protein fused to DD-------SID4x repressor.

The present invention also relates to orthogonal PP7/MS2 gene targeting. In this example, gRNA targeting different loci are modified with distinct RNA loops in order to recruit MS2-VP64 or PP7-SID4X, which activate and repress their target loci, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, a gRNA targeting locus A can be modified with MS2 loops, recruiting MS2-VP64 activators, while another gRNA targeting locus B can be modified with PP7 loops, recruiting PP7-SID4X repressor domains. In the same cell, dead effector proteins can thus mediate orthogonal, locus-specific modifications. This principle can be extended to incorporate other orthogonal RNA-binding proteins such as Q-β.

A PP7 variant may be used in some embodiments. For example, Applicants found that the PP7 *Pseudomonas* bacteriophage coat protein (with amino acids 68-69 mutated to SG and amino acids 70-75 deleted from the wild type protein as described in Wu, Bin, Jeffrey A. Chao, and Robert H.

Singer. "Fluorescence fluctuation spectroscopy enables quantitative imaging of single mRNAs in living cells. "Biophysical journal 102.12 (2012): 2936-2944. and Chao, Jeffrey A., et al. "Structural basis for the coevolution of a viral RNA-protein complex." Nature structural & molecular biology 15.1 (2007): 103-105.), worked well. As such, in some embodiments, where the adaptor protein is an RNA-binding protein and that RNA-binding protein is PP7, the PP7 may be the variant described above, i.e. with amino acids 68-69 mutated to SG and/or amino acids 70-75 deleted from the wild type protein.

Similarly, an MS2 variant may also be used, such as the N55 mutant, especially the N55K mutant. This is the N55K mutant of the MS2 bacteriophage coat protein (shown to have higher binding affinity than wild type MS2 in Lim, F., M. Spingola, and D. S. Peabody. "Altering the RNA binding specificity of a translational repressor." Journal of Biological Chemistry 269.12 (1994): 9006-9010.)

An alternative option for orthogonal repression includes incorporating non-coding RNA loops with transactive repressive function into the guide (either at similar positions to the MS2/PP7 loops integrated into the guide or at the 3' terminus of the guide). For instance, guides were designed with non-coding (but known to be repressive) RNA loops (e.g., using the Alu repressor (in RNA) that interferes with RNA polymerase II in mammalian cells). The Alu RNA sequence was located: in place of the MS2 RNA sequences as used herein (e.g., at tetraloop and/or stem loop 2); and/or at 3' terminus of the guide. This gives possible combinations of MS2, PP7 or Alu at the tetraloop and/or stemloop 2 positions, as well as, optionally, addition of Alu at the 3' end of the guide (with or without a linker).

The use of two different aptamers (each associated with a distinct RNA) allows an activator-adaptor protein fusion and a repressor-adaptor protein fusion to be used, with different guides, to activate expression of one gene, while repressing another. They, along with their different guides can be administered together, or substantially together, in a multiplexed approach. A large number of such modified guides can be used all at the same time, for example 10 or 20 or 30 and so forth, while only one (or at least a minimal number) of CRISPR effectors to be delivered, as a comparatively small number of effectors can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, while the other might be p65, although these are just examples and other transcriptional activators are envisaged. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the Gly-Ser linker.

It is also envisaged that the enzyme-guide complex as a whole may be associated with two or more functional domains. For example, there may be two or more functional domains associated with the fusion protein or enzyme, or preferably there may be two or more functional domains associated with the guide (via one or more adaptor proteins), or there may be one or more functional domains associated with the enzyme and one or more functional domains associated with the guide (via one or more adaptor proteins).

The fusion between the adaptor protein and the activator or repressor may include a linker. For example, GlySer linkers GGGS can be used. They can be used in repeats of 3 ((GGGGS)$_3$) or 6, 9 or even 12 or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

The invention comprehends a DD-CRISPR Cas complex comprising a DD-fusion protein (optionally comprising one or more further functional domains), a CRISPR enzyme (optionally also comprising a DD and/or functional domain) and a guide RNA (gRNA) or guide DNA (gDNA), wherein the CRISPR enzyme comprises at least one mutation, such that the CRISPR enzyme has no more than 5% of the nuclease activity of the CRISPR enzyme not having the at least one mutation and, optional, at least one or more nuclear localization sequences; the guide RNA/DNA comprises a guide sequence capable of hybridizing to a target sequence in a genomic locus of interest in a cell; and wherein: the CRISPR enzyme is optionally associated with one or more functional domains; and at least one loop of the gRNA/gDNA is modified by the insertion of distinct RNA/DNA sequence(s) that bind to one or more adaptor proteins, and wherein the adaptor protein is associated with at least one DD, and optionally with one or more additional functional domain; or the CRISPR enzyme is associated with one or more functional domains and at least one loop of the gRNA is modified by the insertion of distinct RNA sequence(s) that bind to one or more adaptor proteins, and wherein the adaptor protein is associated with one or more DD and optionally one or more functional domains. The invention comprehends the use of modified guides such as in Konermann et al., "Genome-scale transcription activation by an engineered CRISPR-Cas9 complex," doi:10.1038/nature14136, incorporated herein by reference, or PCT/US14/70175, filed Dec. 12, 2014.

In some embodiments, one or more functional domains are associated with an adaptor protein, for example as used with the modified guides of Konermann et al. (Nature 517, 583-588, 29 Jan. 2015).

For the purposes of the following discussion, reference to a functional domain could be a functional domain associated with the CRISPR enzyme or a functional domain associated with the adaptor protein.

In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. Other references herein to activation (or activator) domains in respect of those associated with the CRISPR enzyme include any known transcriptional activation domain and specifically VP64, p65, MyoD1, HSF1, RTA, SET7/9 or a histone acetyltransferase.

In some embodiments, the one or more functional domains is a transcriptional repressor domain. In some embodiments, the transcriptional repressor domain is a KRAB domain. In some embodiments, the transcriptional repressor domain is a NuE domain, NcoR domain, SID domain or a SID4X domain.

In some embodiments, the one or more functional domains have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

In some embodiments, the one or more functional domains are selected from transcription or translation activator, transcription or translation repressor, methyltransferase, methylase, demethylase, DNA hydroxylmethylase, histone acetylase, histone deacetylases, transcription or translation release factor domain, histone modification domain, nuclease, single-strand RNA cleavage domain, double-strand RNA cleavage domain, single-strand DNA cleavage domain, double-strand DNA cleavage domain, nucleic acid binding domain, a protein acetyltransferase, a protein deacetylase, a protein methyltransferase, a protein deaminase, a protein kinase, a protein phosphatase, transposase, integrase, recombinase, resolvase, invertase, protease, repressor, activator, nuclear-localization signal, nuclear export signal, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase, histone tail protease, HDACs, histone methyltransferases (HMTs), histone acetyltransferase (HAT) inhibitors, HDAC and HMT recruiting proteins, HDAC effector Domains, HDAC recruiter effector domains, histone methyltransferase (HMT) effector domains, histone methyltransferase (HMT) recruiter effector domains, histone acetyltransferase inhibitor effector domains, or domains having molecular switch activity or chemical inducibility or light inducibility.

Histone modifying domains are also preferred in some embodiments. Exemplary histone modifying domains are discussed below. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains. Histone acetyltransferases are preferred in some embodiments.

In some embodiments, the DNA cleavage activity is due to a nuclease. In some embodiments, the nuclease comprises a Fok1 nuclease.

In some embodiments, the one or more functional domains is attached to the CRISPR enzyme so that upon binding to the gRNA and target the functional domain is in a spatial orientation allowing for the functional domain to function in its attributed function.

In some embodiments, the one or more functional domains is attached to the adaptor protein so that upon binding of the CRISPR enzyme to the gRNA and target, the functional domain is in a spatial orientation allowing for the functional domain to function in its attributed function.

In an aspect the invention provides a composition as herein discussed wherein the one or more functional domains is attached to the CRISPR enzyme or adaptor protein via a linker, optionally a GlySer linker, as discussed herein.

Endogenous transcriptional repression is often mediated by chromatin modifying enzymes such as histone methyltransferases (HMTs) and deacetylases (HDACs). Repressive histone effector domains are known and an exemplary list is provided below. In the exemplary table, preference was given to proteins and functional truncations of small size to facilitate efficient viral packaging (for instance via AAV). In general, however, the domains may include HDACs, histone methyltransferases (HMTs), and histone acetyltransferase (HAT) inhibitors, as well as HDAC and HMT recruiting proteins. The functional domain may be or include, in some embodiments, HDAC Effector Domains, HDAC Recruiter Effector Domains, Histone Methyltransferase (HMT) Effector Domains, Histone Methyltransferase (TIN/T) Recruiter Effector Domains, or Histone Acetyltransferase Inhibitor Effector Domains.

| HDAC Effector Domains | | | | | | | |
|---|---|---|---|---|---|---|---|
| Subtype/ Complex | Name | Substrate (if known) | Modification (if known) | Organism | Full size (aa) | Selected truncation (aa) | Final size (aa) | Catalytic domain |
| HDAC I | HDAC8 | — | — | X. laevis | 325 | 1-325 | 325 | 1-272: HDAC |
| HDAC I | RPD3 | — | — | S. cerevisiae | 433 | 19-340 (Vannier) | 322 | 19-331: HDAC |
| HDAC IV | MesoLo4 | — | — | M. loti | 300 | 1-300 (Gregoretti) | 300 | — |
| HDAC IV | HDAC11 | — | — | H. sapiens | 347 | 1-347 (Gao) | 347 | 14-326: HDAC |
| HD2 | HDT1 | — | — | A. thaliana | 245 | 1-211 (Wu) | 211 | — |
| SIRT I | SIRT3 | H3K9Ac H4K16Ac H3K56Ac | — | H. sapiens | 399 | 143-399 (Scher) | 257 | 126-382: SIRT |
| SIRT I | HST2 | — | — | C. albicans | 331 | 1-331 (Hnisz) | 331 | — |
| SIRT I | CobB | — | — | E. coli (K12) | 242 | 1-242 (Landry) | 242 | — |
| SIRT I | HST2 | — | — | S. cerevisiae | 357 | 8-298 (Wilson) | 291 | — |

HDAC Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| SIRT III | SIRT5 | H4K8Ac H4K16Ac | — | H. sapiens | 310 | 37-310 (Gertz) | 274 | 41-309: SIRT |
| SIRT III | Sir2A | — | — | P. falciparum | 273 | 1-273 (Zhu) | 273 | 19-273: SIRT |
| SIRT IV | SIRT6 | H3K9Ac H3K56Ac | — | H. sapiens | 355 | 1-289 (Tennen) | 289 | 35-274: SIRT |

Accordingly, the repressor domains of the present invention may be selected from histone methyltransferases (HMTs), histone deacetylases (HDACs), histone acetyltransferase (HAT) inhibitors, as well as HDAC and HMT recruiting proteins.

The HDAC domain may be any of those in the table above, namely: HDAC8, RPD3, MesoLo4, HDAC11, HDT1, SIRT3, HST2, CobB, HST2, SIRT5, Sir2A, or SIRT6.

In some embodiments, the functional domain may be a HDAC Recruiter Effector Domain. Preferred examples include those in the Table below, namely MeCP2, MBD2b, Sin3a, NcoR, SALL1, RCOR1. NcoR is exemplified in the present Examples and, although preferred, it is envisaged that others in the class will also be useful.

Table of HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | MeCP2 | — | — | R. norvegicus | 492 | 207-492 (Nan) | 286 | — |
| Sin3a | MBD2b | — | — | H. sapiens | 262 | 45-262 (Boeke) | 218 | — |
| Sin3a | Sin3a | — | — | H. sapiens | 1273 | 524-851 (Laherty) | 328 | 627-829: HDAC1 interaction |
| NcoR | NcoR | — | — | H. sapiens | 2440 | 420-488 (Zhang) | 69 | — |
| NuRD | SALL1 | — | — | M. musculus | 1322 | 1-93 (Lauberth) | 93 | — |
| CoREST | RCOR1 | — | — | H. sapiens | 482 | 81-300 (Gu, Ouyang) | 220 | — |

In some embodiments, the functional domain may be a Methyltransferase (TNT) Effector Domain. Preferred examples include those in the Table below, namely NUE, vSET, EHMT2/G9A, SUV39H1, dim-5, KYP, SUVR4, SET4, SET1, SETD8, and TgSET8. NUE is exemplified in the present Examples and, although preferred, it is envisaged that others in the class will also be useful.

Table of Histone Methyltransferase (HMT) Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| SET | NUE | H2B, H3, H4 | — | C. trachomatis | 219 | 1-219 (Pennini) | 219 | |
| SET | vSET | — | H3K27me3 | P. bursaria chlorella virus | 119 | 1-119 (Mujtaba) | 119 | 4-112: SET2 |
| SUV39 family | EHMT2/G9A | H1.4K2, H3K9, H3K27 | H3K9me1/2, HlK25me1 | M. musculus | 1263 | 969-1263 (Tachibana) | 295 | 1025-1233: preSET, SET, postSET |
| SUV39 | SUV39H1 | — | H3K9me2/3 | H. sapiens | 412 | 79-412 (Snowden) | 334 | 172-412: preSET, SET, postSET |

Table of Histone Methyltransferase (HMT) Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Suvar3-9 | dim-5 | — | H3K9me3 | N. crassa | 331 | 1-331 (Rathert) | 331 | 77-331: preSET, SET, postSET |
| Suvar3-9 (SUVH subfamily) | KYP | — | H3K9me1/2 | A. thaliana | 624 | 335-601 | 267 (Jackson) | — |
| Suvar3-9 (SUVR subfamily) | SUVR4 | H3K9me1 | H3K9me2/3 | A. thaliana | 492 | 180-492 | 313 (Thorstensen) | 192-462: preSET, SET, postSET |
| Suvar4-20 | SET4 | — | H4K20me3 | C. elegans | 288 | 1-288 (Vielle) | 288 | — |
| SET8 | SET1 | — | H4K20me1 | C. elegans | 242 | 1-242 (Vielle) | 242 | — |
| SET8 | SETD8 | — | H4K20me1 | H. sapiens | 393 | 185-393 | 209 (Couture) | 256-382: SET |
| SET8 | TgSET8 | — | H4K20me1/2/3 | T. gondii | 1893 | 1590-1893 (Sautel) | 304 | 1749-1884: SET |

In some embodiments, the functional domain may be a Histone Methyltransferase (HMT) Recruiter Effector Domain. Preferred examples include those in the Table below, namely Hp1a, PHF19, and NIPP1.

Table of Histone Methyltransferase (HMT) Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| — | Hp1a | — | H3K9me3 | M. musculus | 191 | 73-191 | 119 (Hathaway) | 121-179: chromoshadow |
| — | PHF19 | — | H3K27me3 | H. sapiens | 580 | (1-250) + GGSG linker + (500-580) | 335 (Ballaré) | 163-250: PHD2 |
| — | NIPP1 | — | H3K27me3 | H. sapiens | 351 | 1-329 (Jin) | 329 | 310-329: EED |

In some embodiments, the functional domain may be Histone Acetyltransferase Inhibitor Effector Domain. Preferred examples include SET/TAF-1β listed in the Table below.

Table of Histone Acetyltransferase Inhibitor Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| — | SET/TAF-1β | — | — | M. musculus | 289 | 1-289 (Cervoni) | 289 | — |

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100 kb away. Targeting of known control elements can be used to activate or repress the gene of interest. In some cases, a single control element can influence the transcription of multiple target genes. Targeting of a single control element could therefore be used to control the transcription of multiple genes simultaneously.

Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100 kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome readout by e.g. RNAseq or microarray. This would allow for the identification of likely candidate genes involved in the disease phenotype. Such candidate genes could be useful as novel drug targets.

Histone acetyltransferase (HAT) inhibitors are mentioned herein. However, an alternative in some embodiments is for the one or more functional domains to comprise an acetyltransferase, preferably a histone acetyltransferase. These are useful in the field of epigenomics, for example in methods of interrogating the epigenome. Methods of interrogating the epigenome may include, for example, targeting epigenomic sequences. Targeting epigenomic sequences may include the guide being directed to an epigenomic target sequence. Epigenomic target sequence may include, in some embodiments, include a promoter, silencer or an enhancer sequence.

Use of a functional domain linked to a fusion protein according to the invention as described herein, and/or a CRISPR-Cas enzyme as described herein, preferably a dead-Cas, to target epigenomic sequences can be used to activate or repress promoters, silencer or enhancers.

Examples of acetyltransferases are known but may include, in some embodiments, histone acetyltransferases. In some embodiments, the histone acetyltransferase may comprise the catalytic core of the human acetyltransferase p300 (Gerbasch & Reddy, Nature Biotech 6 Apr. 2015).

In some preferred embodiments, the functional domain is linked to a fusion protein according to the invention and/or dead-Cas9 enzyme to target and activate epigenomic sequences such as promoters or enhancers. One or more guides directed to such promoters or enhancers may also be provided to direct the binding of the CRISPR enzyme to such promoters or enhancers.

Method of Treatment

The present invention, provides compositions and methods for the treatment of diabetes (e.g., type 1 diabetes, type 2 diabetes, gestational diabetes, obese diabetes) and for the prophylaxis or treatment of impaired glucose tolerance (IGT); an agent for preventing progression from impaired glucose tolerance to diabetes and the like. The present invention can also be used for prophylaxis or treatment of diabetic complications, such as neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hyperacusis, cerebrovascular disorder, peripheral blood circulation disorder, diabetic cachexia, insulin resistance syndrome and the like.

In some embodiments, the present invention can be formulated into a biological preparation, a liposome preparation, an emulsion or a microemulsion preparation. Examples of the dosage forms of the present invention for oral administration include oral preparations such as tablet (including sugar-coated tablet, film-coated tablet, sublingual tablet, buccal tablet, mouth cavity quick-integrating tablet), pill, granule, powder, capsule (including soft capsule, microcapsule), syrup, emulsion, suspension and films (e.g., mouth cavity mucous membrane adhesion film), powder, microgranule, nanogranule, gel capsule, spray and the like. The compositions of the present invention may comprise additionally additives such as excipient, binder, disintegrant, lubricant, sweetening agent, surfactant, suspending agent, emulsifier, dispersing agent, thickener, diluent, penetration enhancer, which are generally used in the technical field of preparations, can be appropriately added in suitable amounts, where necessary.

In some embodiments, the composition of the present invention may be administered to a subject in need thereof, via modes of administration such as enteral and topical administration, as well as injections, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

In some embodiments, a pharmaceutically effective amount of the composition of the present invention is administered. For administration, effective amounts and therapeutically effective amounts (also referred to herein as doses) can be initially estimated based on results from in vitro assays and/or animal model studies. For example, a dose can be formulated in animal models to achieve a circulating concentration range that includes the IC50 as determined in cell culture. Such information can be used to more accurately determine useful doses in subjects of interest.

The actual dose amount administered to a particular subject can be determined by a physician, veterinarian or researcher taking into account parameters such as physical and physiological factors including body weight, severity of condition, type of disease, previous or concurrent therapeutic interventions, idiopathy of the subject and route of administration.

Useful doses often range from 0.1 to 5 mg/kg/day or from 0.5 to 1 mg/kg/day or from 0.1 to 5 pg/kg/day or from 0.5 to 1 pg/kg/day. In other non-limiting examples, a dose can comprise 1 g/kg/day, 5 g/kg/day, 10 g/kg/day, 50 g/kg/day, 100 g/kg/day, 200 g/kg/day, 350 g/kg/day, 500 g/kg/day, 1 mg/kg/day, 5 mg/kg/day, 10 mg/kg/day, 50 mg/kg/day, 100 mg/kg/day, 200 mg/kg/day, 350 mg/kg/day, 500 mg/kg/day or 1000 mg/kg/day.

Therapeutically effective amounts can be achieved by administering single or multiple doses during the course of a treatment regimen (days, weeks, months, etc.). [0358] Some embodiments comprise inducing or enhancing human β-cell proliferation. Some embodiments comprise treating diabetes or a symptom thereof in a human subject by inducing or enhancing β-cell proliferation.

In some embodiments, β-cell proliferation is induced or enhanced by inhibiting proteins and/or nucleic acids associated with decreased and/or suppressed β-cell proliferation. For instance, some embodiments comprise administering an inhibitor of one or more CMGC family kinases (e.g., DYRK1A, DYRK1B, DYRK2, CLK1, CLK2, and/or CLK4). Some embodiments comprise administering an activator of one or more proteins and/or nucleic acids associated with 3-cell proliferation (e.g., NFAT and/or calcineurin).

In some embodiments, expression of proteins and/or nucleic acids associated with decreased and/or suppressed β-cell proliferation is decreased. For instance, expression can be decreased with inhibitory nucleic acids, which can include small interfering RNAs (e.g., shRNA), antisense oligonucleutides (e.g. antisense RNAs), and/or CRISPR-Cas.

Inhibitory Nucleic Acids

Some embodiments comprise decreasing protein expression (e.g., inhibition of a CMGC family kinase expression, such as DYRK1A, DYRK1B, DYRK2, CLK1, CLK2, and/or CLK4 expression) with inhibitory nucleic acids. Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), ribozymes, and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro interfering RNA (miRNA); a small temporal RNA (stRNA); or a short, hairpin RNA (shRNA); small RNA-induced gene activation (RNAa); small activating RNAs (saRNAs), or combinations thereof. See, e.g., WO 2010040112; Burnett and Rossi (2012) Chem Biol. 19 (1):60-71; and WO2015130968, which is incorporated herein by reference in its entirety.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range there within.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 8,604,192; 8,697,663; 8,703,728; 8,796,437; 8,865,677; and 8,883,752 each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2'-O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 (known as a methylene(methylimino) or MMI backbone], CH2-O—N (CH3)-CH2, CH2-N(CH3)-N(CH3)-CH2 and O—N(CH3)-CH2-CH2 backbones, wherein the native phosphodiester backbone is represented as O—P—O—CH); amide backbones (De Mesmaeker (1995) Ace. Chem. Res. 28:366-374); morpholino backbone structures (Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, Nielsen (1991) Science 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'-alkylene phosphonates and chiral phosphonates, phosphinates, phosphoramidates comprising 3'-amino phosphoramidate and aminoalkylphosphoramidates, phosphonoacetate phosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey (2002) Biochemistry 41(14), 4503-4510); Genesis, volume 30, issue 3, 2001; Heasman, (2002) Dev. Biol. 243, 209-214; Nasevicius (2000) Nat. Genet. 26, 216-220; Lacerra (2000) Proc. Natl. Acad. Sci. 97, 9591-9596; and U.S. Pat. No. 5,034,506, issued Jul. 23, 1991. Cyclohexenyl nucleic acid oligonucleotide mimetics are described in Wang (2000) Am. Chem. Soc. 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564;

5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,677,439; and 8,927,513 each of which is herein incorporated by reference.

One or more substituted sugar moieties can also be included, e.g., one of the following at the 2' position: OH, SH, SCH$_3$, F, OCN, OCH$_3$, OCH$_3$ O(CH$_2$)n CH$_3$, O(CH$_2$)n NH$_2$ or O(CH$_2$)n CH$_3$ where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin (1995) Helv. Chim. Acta 78, 486). Other preferred modifications include 2'-methoxy (2'-O—CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentiobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, 2,6-diaminopurine; 5-ribosyluracil (Carlile (2014) Nature 515 (7525): 143-6). Kornberg, A., DNA Replication, W. H. Freeman & Co., San Francisco, 1980, pp 75-77; Gebeyehu (1987) Nucl. Acids Res. 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide. In some embodiments, both the nucleobase and backbone may be modified to enhance stability and activity (El-Sagheer (2014) Chem Sci 5:253-259).

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen (1991) Science 254, 1497-1500; and Shi (2015).

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandte Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger (1989) Proc. Natl. Acad. Sci. USA 86, 6553-6556), cholic acid (Manoharan (1994) Bioorg. Med. Chem. Let. 4, 1053-1060), a thioether, e.g., hexyl-S-tritylthiol (Manoharan (1992) Ann. N. Y. Acad. Sci. 660, 306-309; Manoharan (1993) Bioorg. Med. Chem. Let. 3, 2765-2770), a thiocholesterol (Oberhauser (1992) Nucl. Acids Res. 20, 533-538), an aliphatic chain, e.g., dodecanediol or undecyl residues (Kabanov (1990) FEBS Lett. 259, 327-330; Svinarchuk (1993) Biochimie 75, 49-54), a phospholipid, e.g., di-hexadecyl-rac-glycerol or triethylammonium 1, 2-di-O-hexadecyl-rac-glycero-3-H-phosphonate (Manoharan (1995) Tetrahedron Lett. 36, 3651-3654; Shea (1990) Nucl. Acids Res. 18, 3777-3783), a polyamine or a polyethylene glycol chain (Mancharan (1995) Nucleosides & Nucleotides 14, 969-973), or adamantane acetic acid (Manoharan (1995) Tetrahedron Lett. 36, 3651-3654), a palmityl moiety (Mishra (1995) Biochim. Biophys. Acta 1264, 229-237), or an octadecylamine or hexylamino-carbonyl-t oxycholesterol moiety (Crooke (1996) J. Pharmacol. Exp. Ther. 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928; 5,688,941, 8,865,677; 8,877,917 each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecanediol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to the target lncRNA, i.e., hybridize sufficiently well and with sufficient specificity, to give the desired effect. "Complementary" in this context refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a lncRNA, then the bases are considered to be complementary to each other at that position. 100% complementarity is not required.

In some embodiments, the location on a target lncRNA to which an inhibitory nucleic acids hybridizes is defined as a target region to which a protein binding partner binds. These regions are likely to include the protein binding sequences. Routine methods can be used to design an inhibitory nucleic acid that binds to this sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments 5-500 nucleotides in length comprising a stretch of at least five (5) consecutive nucleotides within the protein binding region, or immediately adjacent thereto, are considered to be suitable for targeting as well. Target segments can include sequences that comprise at least the 5 consecutive nucleotides from the 5'-terminus of one of the protein binding regions (the remaining nucleotides being a consecutive stretch of the same RNA beginning immediately upstream of the 5'-terminus of the binding segment and continuing until the inhibitory nucleic acid contains about 5 to about 100 nucleotides). Similarly preferred target segments are represented by RNA sequences that comprise at least the 5 consecutive nucleotides from the 3'-terminus of one of the illustrative preferred target segments (the remaining nucleotides being a consecutive stretch of the same lncRNA beginning immediately downstream of the 3'-terminus of the target segment and continuing until the inhibitory nucleic acid contains about 5 to about 100 nucleotides). One having skill in the art armed with the sequences provided herein will be able, without undue experimentation, to identify further preferred protein binding regions to target.

Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target RNAs), to give the desired effect.

Making and Using Inhibitory Nucleic Acids

The inhibitory nucleic acids used to practice the methods described herein, whether RNA, cDNA, genomic DNA, vectors, viruses or hybrids thereof, can be isolated from a variety of sources, genetically engineered, amplified, and/or expressed, generated recombinantly or synthetically by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; Maier (2000) Org Lett 2(13):1819-1822; Egeland (2005) Nucleic Acids Res 33(14):e125; Krotz (2005) Pharm Dev Technol 10(2):283-90 U.S. Pat. No. 4,458,066. Recombinant nucleic acid sequences can be individually isolated or cloned and tested for a desired activity. Any recombinant expression system can be used, including e.g. in vitro bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion or "seamless cloning", ligation, transformation, plasmid purification, and DNA sequencing, for example as described in Sambrook et al. "Molecular Cloning: A Laboratory Manual." (1989)), Coffin et al. (Retroviruses. (1997)) and "RNA Viruses: A Practical Approach" (Alan J. Cann, Ed., Oxford University Press, (2000)). "Seamless cloning" allows joining of multiple fragments of nucleic acids in a single, isothermal reaction (Gibson (2009) Nat Methods 6:343-345; Werner (2012) Bioeng Bugs 3:38-43; Sanjana (2012) Nat Protoc 7:171-192). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus (Warnock (2011) Methods in Molecular Biology 737:1-25). The recombinant vectors capable of expressing the nucleic acids of the invention can be delivered as described herein, and persist in target cells (e.g., stable transformants).

This can be achieved, for example, by administering an inhibitory nucleic acid, e.g., antisense oligonucleotides complementary to a CMGC family kinase (e.g., DYRK1A, DYRK1B, DYRK2, CLK1, CLK2, and/or CLK4). Other inhibitory nucleic acids for use in practicing the methods described herein and that are complementary to a CMGC family kinase (e.g., DYRK1A, DYRK1B, DYRK2, CLK1, CLK2, and/or CLK4) can be those which inhibit post-transcriptional processing of a CMGC family kinase (e.g., DYRK1A, DYRK1B, DYRK2, CLK1, CLK2, and/or CLK4), such as inhibitors of mRNA translation (antisense), agents of RNA interference (RNAi), catalytically active RNA molecules (ribozymes), and RNAs that bind proteins and other molecular ligands (aptamers). Additional methods exist to inhibit endogenous microRNA (miRNA) activity through the use of antisense-miRNA oligonucleotides (antagomirs) and RNA competitive inhibitors or decoys (miRNA sponges).

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions a CMGC family kinase (e.g., DYRK1A, DYRK1B, DYRK2, CLK1, CLK2, and/or CLK4). Thus, oligonucleotides are chosen that are sufficiently complementary to the target, i.e., that hybridize sufficiently well and with sufficient specificity, to give the desired effect, while striving to avoid significant off-target effects i.e. must not directly bind to, or directly significantly affect expression levels of, transcripts other than the intended target. The optimal length of the antisense oligonucleotide may very but it should be as short as possible while ensuring that its target sequence is unique in the transcriptome i.e. antisense oligonucleotides may be as short as 12-mers (Seth (2009) J Med Chem 52:10-13) to 18-22 nucleotides in length.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

It is understood in the art that a complementary nucleic acid sequence need not be 100% complementary to that of its target nucleic acid to be specifically hybridisable. A complementary nucleic acid sequence of the invention is specifically hybridisable when binding of the sequence to the target DNA or RNA molecule interferes with the normal function of the target DNA or RNA to cause a loss of activity, and there is a sufficient degree of complementarity to avoid non-specific binding of the sequence to non-target sequences under conditions in which specific binding is desired, i.e., under physiological conditions in the case of in vivo assays or therapeutic treatment, and in the case of in vitro assays, under conditions in which the assays are performed under suitable conditions of stringency. The antisense oligonucleotides useful in the methods described herein have at least 80% sequence complementarity to a target region within the target nucleic acid, e.g., 90%, 95%, or 100% sequence complementarity to the target region within a CMGC family kinase (e.g., DYRK1A, DYRK1B, DYRK2, CLK1, CLK2, and/or CLK4) (e.g., a target region comprising the seed sequence). Percent complementarity of an antisense compound with a region of a target nucleic acid can be determined routinely using basic local alignment search tools (BLAST programs) (Altschul (1990) J. Mol. Biol. 215, 403-410; Zhang and Madden (1997) Genome Res. 7, 649-656). The specificity of an antisense oligonucleotide can also be determined routinely using BLAST program against the entire genome of a given species.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art. For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York, Hilario (2007) Methods Mol Biol 353:27-38.

Inhibitory nucleic acids for use in the methods described herein can include one or more modifications, e.g., be stabilized against nucleolytic degradation such as by the incorporation of a modification, e.g., a nucleotide modification. For example, inhibitory nucleic acids can include a phosphorothioate at least the first, second, or third internucleotide linkage at the 5' or 3' end of the nucleotide sequence. As another example, inhibitory nucleic acids can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the inhibitory nucleic acids can include at least one 2'-O-methyl-modified nucleotide, and in some embodiments, all of the nucleotides include a 2'-O-methyl modification.

Modifications

Chemical modifications, particularly the use of locked nucleic acids (LNAs) (Okiba (1997) Tetrahedron Lett 39:5401-5404; Singh (1998) Chem Commun 4:455-456), 2'-O-methoxyethyl (2'-O-MOE) (Martin (1995) Helv Chim Acta 78:486-504; You (2006) Nucleic Acids Res 34(8):e60; Owczarzy (2011) Biochem 50(43):9352-9367), constrained ethyl BNA (cET) (Murray (2012) Nucleic Acids Res 40:6135-6143), and gapmer oligonucleotides, which contain 2-5 chemically modified nucleotides (LNA, 2'-O-MOE RNA or cET) at each terminus flanking a central 5-10 base "gap" of DNA (Monia (1993) J Biol Chem 268:14514-14522; Wahlestedt (2000) PNAS 97:5633-5638), improve antisense oligonucleotide binding affinity for the target RNA, which increases the steric block efficiency. Antisense oligos that hybridize to a CMGC family kinase (e.g., DYRK1A, DYRK1B, DYRK2, CLK1, CLK2, and/or CLK4), can be identified through experimentation.

Techniques for the manipulation of inhibitory nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual $3^{rd}$ ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Modified Bases Locked Nucleic Acids (LNAs)

In some embodiments, the inhibitory nucleic acids are "locked," i.e., comprise nucleic acid analogues in which the ribose ring is "locked" by a methylene bridge connecting the 2'-0 atom and the 4'-C atom (see, e.g., Kaupinnen (2005) Drug Disc. Today 2(3):287-290; Koshkin (1998) J. Am. Chem. Soc. 120(50):13252-13253). For additional modifications see US 20100004320, US 20090298916, and US 20090143326.

siRNA/shRNA

In some embodiments, the nucleic acid sequence that is complementary to a CMGC family kinase (e.g., DYRK1A, DYRK1B, DYRK2, CLK1, CLK2, and/or CLK4) can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference. RNA interference may cause translational repression and degradation of target mRNAs with imperfect complementarity or sequence-specific cleavage of perfectly complementary mRNAs.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. After the siRNA has cleaved its target, it is released from that RNA to search for another target and can repeatedly bind and cleave new targets (Brummelkamp (2002) Science 296:550-553; Lee (2002) Nature Biotechnol., 20, 500-505; Miyagishi and Taira (2002) Nature Biotechnol 20:497-500; Paddison (2002) Genes & Dev. 16:948-958; Paul (2002) Nature Biotechnol 20, 505-508; Sui (2002) Proc. Natl. Acad. Sd. USA 99(6), 5515-5520; Yu (2002) Proc Natl Acad Sci USA 99:6047-6052; Peer and Lieberman (2011) Gen Ther 18, 1127-1133).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target. shRNAs that are constitutively expressed form promoters can ensure long-term gene silencing. Most methods commonly used for delivery of siRNAs rely on commonly used techniques for introducing an exogenous nucleic acid into a cell including calcium phosphate or calcium chloride precipitation, microinjection, DEAE-dextrin-mediated transfection, lipofection, commercially available cationic polymers and lipids and cell-penetrating peptides, electroporation or stable nucleic acid-lipid particles (SNALPs), all of which are routine in the art. siRNAs can also be conjugated to small molecules to direct binding to cell-surface receptors, such as cholesterol (Wolfrum (2007) Nat Biotechnol 25:1149-1157), alpha-tocopherol (Nishina (2008) Mol Ther 16:734-40), lithocholic acid or lauric acid (Lorenz (2004) Bioorg Med Chem Lett 14:4975-4977), polyconjugates (Rozema (2007) PNAS 104:12982-12987). A variation of conjugated siRNAs are aptamer-siRNA chimeras (McNamara (2006) Nat Biotechnol 24:1005-1015; Dassie (2009) Nat Biotechnol 27:839-849) and siRNA-fusion protein complexes, which is composed of a targeting peptide, such as an antibody fragment that recognizes a cell-surface receptor or ligand, linked to an RNA-binding peptide that can be complexed to siRNAs for targeted systemic siRNA delivery (Yao (2011) Sci Transl Med 4(130):130ra48.

Ribozymes

Trans-cleaving enzymatic nucleic acid molecules can also be used; they have shown promise as therapeutic agents for human disease (Usman & McSwiggen, (1995) Ann. Rep. Med. Chem. 30, 285-294; Christoffersen and Marr (1995) J. Med. Chem. 38, 2023-2037; Weng (2005) Mol Cancer Ther 4, 948-955; Armado (2004) Hum Gene Ther 15, 251-262; Macpherson (2005) J Gene Med 7, 552-564; Muhlbacher (2010) Curr Opin Pharmacol 10(5):551-6). Enzymatic nucleic acid molecules can be designed to cleave specific CMGC family kinase (e.g., DYRK1A, DYRK1B, DYRK2, CLK1, CLK2, and/or CLK4) targets within the background of cellular RNA. Such a cleavage event renders the CMGC family kinase (e.g., DYRK1A, DYRK1B, DYRK2, CLK1, CLK2, and/or CLK4) non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel (1979) Proc. R. Soc. London B 205, 435) have been used to evolve new nucleic acid catalysts with improved properties, new functions and capable of catalyzing a variety of reactions, such as cleavage and ligation of phosphodiester linkages and amide linkages, (Joyce (1989) Gene 82, 83-87; Beaudry (1992) Science 257, 635-641; Joyce (1992) Scientific American 267, 90-97; Breaker (1994) TIBTECH 12, 268; Bartel (1993) Science 261:1411-1418; Szostak (1993) TIBS 17, 89-93; Kumar (1995) FASEB J. 9, 1183; Breaker (1996) Curr. Op. Biotech. 1, 442; Scherer (2003) Nat Biotechnol 21, 1457-1465; Berens (2015) Curr. Op. Biotech. 31, 10-15). Ribozymes can also be engineered to be allosterically activated by effector molecules (riboswitches, Liang (2011) Mol Cell 43, 915-926; Wieland (2010) Chem Biol 17, 236-242; U.S. Pat. No. 8,440,810). The development of ribozymes that are optimal for catalytic activity would contribute significantly to any strategy that employs RNA-cleaving ribozymes for the purpose of regulating gene expression. The most common ribozyme therapeutics are derived from either hammerhead or hairpin/paperclip motifs. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Ribozymes can be delivered to target cells in RNA form or can be transcribed from vectors. Due to poor stability of fully-RNA ribozymes, ribozymes often require chemical modification, such as, 5'-PS backbone linkage, 2'-O-Me, 2'-deoxy-2'-C-allyl uridine, and terminal inverted 3'-3' deoxyabasic nucleotides (Kobayashi (2005) Cancer Chemother Pharmacol 56, 329-336).

CRISPR Cas, TALENs, and Zinc Finger Nucleases (ZFNs)

As mentioned above, some embodiments comprise methods gene targeting and/or genome editing. Such methods are useful, e.g., in the context of decreasing protein expression in vivo and/or modifying cells in vitro (e.g., in the context of adoptive cell therapies). In some embodiments, genes are targeting and/or edited using DNA binding proteins.

In some embodiments, the methods described herein include the use of transcription activator-like effector nucleases (TALENs), Clustered Regularly Interspaced Short Palindromic Repeats (CRISPR) Cas RNA-guided nucleases (RGNs), or zinc finger nucleases (ZFNs) to inhibit expression of a CMGC family kinase (e.g., DYRK1A, DYRK1B, DYRK2, CLK1, CLK2, and/or CLK4). In these methods, engineered nucleases are used to specifically target and disrupt expression of a CMGC family kinase (e.g., DYRK1A, DYRK1B, DYRK2, CLK1, CLK2, and/or CLK4). Methods for using CRISPR, TALENs, and ZFNs are well known in the art.

Gene Targeting and Genome Editing

As mentioned above, some embodiments comprise methods gene targeting and/or genome editing. Such methods are useful, e.g., in the context of decreasing protein expression in vivo and/or modifying cells in vitro (e.g., in the context of adoptive cell therapies). In some embodiments, genes are targeting and/or edited using DNA binding proteins.

In certain embodiments, the DNA binding protein is a (endo)nuclease or a variant thereof having altered or modified activity (i.e. a modified nuclease, as described herein elsewhere). In certain embodiments, said nuclease is a targeted or site-specific or homing nuclease or a variant thereof having altered or modified activity. In certain embodiments, said nuclease or targeted/site-specific/homing nuclease is, comprises, consists essentially of, or consists of a (modified) CRISPR/Cas system or complex, a (modified) Cas protein, a (modified) zinc finger, a (modified) zinc finger nuclease (ZFN), a (modified) transcription factor-like effector (TALE), a (modified) transcription factor-like effector nuclease (TALEN), or a (modified) meganuclease. In certain embodiments, said (modified) nuclease or targeted/site-specific/homing nuclease is, comprises, consists essentially of, or consists of a (modified) RNA-guided nuclease. As used herein, the term "Cas" generally refers to a (modified) effector protein of the CRISPR/Cas system or complex, and can be without limitation a (modified) Cas9, or other enzymes such as Cpf1, The term "Cas" may be used herein interchangeably with the terms "CRISPR" protein, "CRISPR/Cas protein", "CRISPR effector", "CRISPR/Cas effector", "CRISPR enzyme", "CRISPR/Cas enzyme" and the like, unless otherwise apparent, such as by specific and exclusive reference to Cas9. It is to be understood that the term "CRISPR protein" may be used interchangeably with "CRISPR enzyme", irrespective of whether the CRISPR protein has altered, such as increased or decreased (or no) enzymatic activity, compared to the wild type CRISPR protein. Likewise, as used herein, in certain embodiments, where appropriate and which will be apparent to the skilled person, the term "nuclease" may refer to a modified nuclease wherein catalytic activity has been altered, such as having increased or decreased nuclease activity, or no nuclease activity at all, as well as nickase activity, as well as otherwise modified nuclease as defined herein elsewhere, unless otherwise apparent, such as by specific and exclusive reference to unmodified nuclease.

As used herein, the term "targeting" of a selected nucleic acid sequence means that a nuclease or nuclease complex is acting in a nucleotide sequence specific manner. For instance, in the context of the CRISPR/Cas system, the guide RNA is capable of hybridizing with a selected nucleic acid sequence. As uses herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

In certain embodiments, the DNA binding protein is a (modified) transcription activator-like effector nuclease (TALEN) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y.

Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference. By means of further guidance, and without limitation, naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26. The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

In certain embodiments, the nucleic acid modification is effected by a (modified) zinc-finger nuclease (ZFN) system. The ZFN system uses artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference. By means of further guidance, and without limitation, artificial zinc-finger (ZF) technology involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In certain embodiments, the nucleic acid modification is effected by a (modified) meganuclease, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

In certain embodiments, the nucleic acid modification is effected by a (modified) CRISPR/Cas complex or system. With respect to general information on CRISPR/Cas Systems, components thereof, and delivery of such components, including methods, materials, delivery vehicles, vectors, particles, and making and using thereof, including as to amounts and formulations, as well as Cas9 CRISPR/Cas-expressing eukaryotic cells, Cas-9 CRISPR/Cas expressing eukaryotes, such as a mouse, reference is made to: U.S. Pat. Nos. 8,999,641, 8,993,233, 8,697,359, 8,771,945, 8,795, 965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183, 512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), WO2015/058052 (PCT/US2014/061077), WO2015070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO/2016/04925 (PCT/US2015/051830), WO/2016/094867 (PCT/US2015/065385), WO/2016/094872 (PCT/US2015/065393), WO/2016/094874 (PCT/US2015/065396), WO/2016/106244 (PCT/US2015/067177).

Reference is further made to Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L.A., & Zhang, F. Science February 15; 339(6121):819-23 (2013); RNA-guided editing of bacterial genomes using CRISPR-Cas systems. Jiang W., Bikard D., Cox D., Zhang F, Marraffini L A. Nat Biotechnol March; 31(3):233-9 (2013); One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013); Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23; Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell August 28. pii: S0092-8674(13)01015-5. (2013); DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, T J., Marraffini, LA., Bao, G., & Zhang, F. Nat Biotechnol doi: 10.1038/nbt.2647 (2013); Genome engineering using the CRISPR-Cas9 system. Ran, FA., Hsu, PD., Wright, J., Agarwala, V., Scott, DA., Zhang, F. Nature Protocols November; 8(11):2281-308. (2013); Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science December 12. (2013). [Epub ahead of print]; Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell Feb. 27. (2014). 156(5):935-49; Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) Apr. 20. doi: 10.1038/nbt.2889; CRISPR-Cas9 Knockin Mice for Genome Editing and Cancer Modeling, Platt et al., Cell 159(2): 440-455 (2014) DOI: 10.1016/j.cell.2014.09.014; Development and Applications of CRISPR-Cas9 for Genome Engineering, Hsu et al, Cell 157, 1262-1278 (Jun. 5, 2014) (Hsu 2014); Genetic screens in human cells using the CRISPR/Cas9 system, Wang et al., Science. 2014 Jan. 3; 343(6166): 80-84. doi:10.1126/science.1246981; Rational design of highly active sgRNAs for CRISPR-Cas9-mediated gene inactivation, Doench et al., Nature Biotechnology 32(12):1262-7 (2014) published online 3 Sep. 2014; doi:10.1038/nbt.3026, and In vivo interrogation of gene function in the mammalian brain using CRISPR-Cas9, Swiech et al, Nature Biotechnology 33, 102-106 (2015) published online 19 Oct. 2014; doi:10.1038/nbt.3055, Cpf1 Is a Single RNA-Guided Endonuclease of a Class 2 CRISPR-Cas System, Zetsche et al., Cell 163, 1-13 (2015); Discovery and Functional Characterization of Diverse Class 2 CRISPR-Cas Systems, Shmakov et al., Mol Cell 60(3): 385-397 (2015); Each of these publications, patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Preferred DNA binding proteins are CRISPR/Cas enzymes or variants thereof. In certain embodiments, the CRISPR/Cas protein is a class 2 CRISPR/Cas protein. In certain embodiments, said CRISPR/Cas protein is a type II, type V, or type VI CRISPR/Cas protein. The CRISPR/Cas system does not require the generation of customized proteins to target specific sequences but rather a single Cas protein can be programmed by an RNA guide (gRNA) to recognize a specific nucleic acid target, in other words the Cas enzyme protein can be recruited to a specific nucleic acid target locus (which may comprise or consist of RNA and/or DNA) of interest using said short RNA guide.

In general, the CRISPR/Cas or CRISPR system is as used herein foregoing documents refers collectively to elements involved in the expression of or directing the activity of CRISPR-associated ("Cas") proteins or genes, including sequences encoding a Cas protein and a guide RNA. In this context of the guide RNA this may include one or more of, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), In general, a CRISPR system is characterized by elements that promote the formation of a CRISPR complex at the site of a target sequence. In the context of formation of a CRISPR complex, "target sequence" refers to a sequence to which a guide sequence is designed to have complementarity, where hybridization between a target DNA sequence and a guide sequence promotes the formation of a CRISPR complex.

In certain embodiments, the gRNA comprises a guide sequence fused to a tracr mate sequence (or direct repeat), and a tracr sequence In particular embodiments, the guide sequence fused to the tracr mate and the tracr sequence are provided or expressed as discrete RNA sequences. In preferred embodiments, the gRNA is a chimeric guide RNA or single guide RNA (sgRNA), comprising a guide sequence fused to the tracr mate which is itself linked to the tracr sequence. In particular embodiments, the CRISPR/Cas system or complex as described herein does not comprise and/or does not rely on the presence of a tracr sequence (e.g. if the Cas protein is Cpf1).

As used herein, the term "guide sequence" in the context of a CRISPR/Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay.

A guide sequence, and hence a nucleic acid-targeting guide RNA may be selected to target any target nucleic acid sequence. The target sequence may be DNA. The target sequence may be genomic DNA. The target sequence may be mitochondrial DNA.

In certain embodiments, the gRNA comprises a stem loop, preferably a single stem loop. In certain embodiments, the direct repeat sequence forms a stem loop, preferably a single stem loop. In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In particular embodiments, the CRISPR/Cas system requires a tracrRNA. The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and gRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop may correspond to the tracr mate sequence, and the portion of the sequence 3' of the loop then corresponds to the tracr sequence. In a hairpin structure the portion of the sequence 5' of the final "N" and upstream of the loop may alternatively correspond to the tracr sequence, and the portion of the sequence 3' of the loop corresponds to the tracr mate sequence. In alternative embodiments, the CRISPR/Cas system does not require a tracrRNA, as is known by the skilled person.

In certain embodiments, the guide RNA (capable of guiding Cas to a target locus) may comprise (1) a guide sequence capable of hybridizing to a target locus and (2) a tracr mate or direct repeat sequence (in 5' to 3' orientation, or alternatively in 3' to 5' orientation, depending on the type of Cas protein, as is known by the skilled person). In particular embodiments, the CRISPR/Cas protein is characterized in that it makes use of a guide RNA comprising a guide sequence capable of hybridizing to a target locus and a direct repeat sequence, and does not require a tracrRNA. In particular embodiments, where the CRISPR/Cas protein is characterized in that it makes use of a tracrRNA, the guide sequence, tracr mate, and tracr sequence may reside in a single RNA, i.e. an sgRNA (arranged in a 5' to 3' orientation or alternatively arranged in a 3' to 5' orientation), or the tracr RNA may be a different RNA than the RNA containing the guide and tracr mate sequence. In these embodiments, the tracr hybridizes to the tracr mate sequence and directs the CRISPR/Cas complex to the target sequence.

In particular embodiments, the DNA binding protein is a catalytically active protein. In these embodiments, the formation of a nucleic acid-targeting complex (comprising a guide RNA hybridized to a target sequence results in modification (such as cleavage) of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest). The skilled person will be aware of specific cut sites for selected CRISPR/Cas systems, relative to the target sequence, which as is known in the art may be within the target sequence or alternatively 3' or 5' of the target sequence.

Accordingly, in particular embodiments, the DNA binding protein has nucleic acid cleavage activity. In some embodiments, the nuclease as described herein may direct cleavage of one or both nucleic acid (DNA, RNA, or hybrids, which may be single or double stranded) strands at the location of or near a target sequence, such as within the target sequence and/or within the complement of the target sequence or at sequences associated with the target sequence. In some embodiments, the nucleic acid-targeting effector protein may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be blunt (e.g. for Cas9, such as SaCas9 or SpCas9). In some embodiments, the cleavage may be staggered (e.g. for Cpf1), i.e. generating sticky ends. In some embodiments, the cleavage is a staggered cut with a 5' overhang. In some embodiments, the cleavage is a staggered cut with a 5' overhang of 1 to 5 nucleotides, preferably of 4 or 5 nucleotides. In some embodiments, the cleavage site is upstream of the PAM. In some embodiments, the cleavage site is downstream of the PAM.

In certain embodiments, the target sequence should be associated with a PAM (protospacer adjacent motif) or PFS (protospacer flanking sequence or site); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. Further, engineering of the PAM Interacting (PI) domain may allow programing of PAM specificity, improve target site recognition fidelity, and increase the versatility of the Cas, e.g. Cas9, genome engineering platform. Cas proteins, such as Cas9 proteins may be engineered to alter their PAM specificity, for example as described in Kleinstiver B P et al. Engineered CRISPR-Cas9 nucleases with altered PAM specificities. Nature. 2015 Jul. 23; 523(7561):481-5. doi: 10.1038/nature14592. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. The skilled person will understand that other Cas proteins may be modified analogously.

In some embodiments, the nucleic acid-targeting effector protein may be mutated with respect to a corresponding wild-type enzyme such that the mutated nucleic acid-targeting effector protein lacks the ability to cleave one or both DNA strands of a target polynucleotide containing a target sequence. As a further example, two or more catalytic domains of a Cas protein (e.g. RuvC I, RuvC II, and RuvC III or the HNH domain of a Cas9 protein) may be mutated to produce a mutated Cas protein which cleaves only one DNA strand of a target sequence.

In particular embodiments, the nucleic acid-targeting effector protein may be mutated with respect to a corresponding wild-type enzyme such that the mutated nucleic acid-targeting effector protein lacks substantially all DNA cleavage activity. In some embodiments, a nucleic acid-targeting effector protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form.

As used herein, the term "modified" Cas generally refers to a Cas protein having one or more modifications or mutations (including point mutations, truncations, insertions, deletions, chimeras, fusion proteins, etc.) compared to the wild type Cas protein from which it is derived. By derived is meant that the derived enzyme is largely based, in the sense of having a high degree of sequence homology with, a wildtype enzyme, but that it has been mutated (modified) in some way as known in the art or as described herein.

As detailed above, in certain embodiments, the nuclease as referred to herein is modified. As used herein, the term "modified" refers to which may or may not have an altered functionality. By means of example, and in particular with reference to Cas proteins, modifications which do not result in an altered functionality include for instance codon optimization for expression into a particular host, or providing the nuclease with a particular marker (e.g. for visualization). Modifications with may result in altered functionality may also include mutations, including point mutations, insertions, deletions, truncations (including split nucleases), etc., as well as chimeric nucleases (e.g. comprising domains from different orthologues or homologues) or fusion proteins. Fusion proteins may without limitation include for instance fusions with heterologous domains or functional domains (e.g. localization signals, catalytic domains, etc.). Accordingly, in certain embodiments, the modified nuclease may be used as a generic nucleic acid binding protein with fusion to or being operably linked to a functional domain. In certain embodiments, various different modifications may be combined (e.g. a mutated nuclease which is catalytically inactive and which further is fused to a functional domain, such as for instance to induce DNA methylation or another nucleic acid modification, such as including without limitation a break (e.g. by a different nuclease (domain)), a mutation, a deletion, an insertion, a replacement, a ligation, a digestion, a break or a recombination). As used herein, "altered functionality" includes without limitation an altered specificity (e.g. altered target recognition, increased (e.g. "enhanced" Cas proteins) or decreased specificity, or altered PAM recognition), altered activity (e.g. increased or decreased catalytic activity, including catalytically inactive nucleases or nickases), and/or altered stability (e.g. fusions with destablilization domains). Suitable heterologous domains include without limitation a nuclease, a ligase, a repair protein, a methyltransferase, (viral) integrase, a recombinase, a transposase, an argonaute, a cytidine deaminase, a retron, a group II intron, a phosphatase, a phosphorylase, a sulfurylase, a kinase, a polymerase, an exonuclease, etc. Examples of all these modifications are known in the art. It will be understood that a "modified" nuclease as referred to herein, and in particular a "modified" Cas or "modified" CRISPR/Cas system or complex preferably still has the capacity to interact with or bind to the polynucleic acid (e.g. in complex with the gRNA).

By means of further guidance and without limitation, in certain embodiments, the nuclease may be modified as detailed below. As already indicated, more than one of the indicated modifications may be combined. For instance, codon optimization may be combined with NLS or NES fusions, catalytically inactive nuclease modifications or nickase mutants may be combined with fusions to functional (heterologous) domains, etc.

In certain embodiments, the nuclease, and in particular the Cas proteins of prokaryotic origin, may be codon optimized for expression into a particular host (cell). An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/

093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid. Codon optimization may be for expression into any desired host (cell), including mammalian, plant, algae, or yeast.

In certain embodiments, the nuclease, in particular the Cas protein, may comprise one or more modifications resulting in enhanced activity and/or specificity, such as including mutating residues that stabilize the targeted or non-targeted strand (e.g. eCas9; "Rationally engineered Cas9 nucleases with improved specificity", Slaymaker et al. (2016), Science, 351(6268):84-88, incorporated herewith in its entirety by reference). In certain embodiments, the altered or modified activity of the engineered CRISPR protein comprises increased targeting efficiency or decreased off-target binding. In certain embodiments, the altered activity of the engineered CRISPR protein comprises modified cleavage activity. In certain embodiments, the altered activity comprises increased cleavage activity as to the target polynucleotide loci. In certain embodiments, the altered activity comprises decreased cleavage activity as to the target polynucleotide loci. In certain embodiments, the altered activity comprises decreased cleavage activity as to off-target polynucleotide loci. In certain embodiments, the altered or modified activity of the modified nuclease comprises altered helicase kinetics. In certain embodiments, the modified nuclease comprises a modification that alters association of the protein with the nucleic acid molecule comprising RNA (in the case of a Cas protein), or a strand of the target polynucleotide loci, or a strand of off-target polynucleotide loci. In an aspect of the invention, the engineered CRISPR protein comprises a modification that alters formation of the CRISPR complex. In certain embodiments, the altered activity comprises increased cleavage activity as to off-target polynucleotide loci. Accordingly, in certain embodiments, there is increased specificity for target polynucleotide loci as compared to off-target polynucleotide loci. In other embodiments, there is reduced specificity for target polynucleotide loci as compared to off-target polynucleotide loci. In certain embodiments, the mutations result in decreased off-target effects (e.g. cleavage or binding properties, activity, or kinetics), such as in case for Cas proteins for instance resulting in a lower tolerance for mismatches between target and gRNA. Other mutations may lead to increased off-target effects (e.g. cleavage or binding properties, activity, or kinetics). Other mutations may lead to increased or decreased on-target effects (e.g. cleavage or binding properties, activity, or kinetics). In certain embodiments, the mutations result in altered (e.g. increased or decreased) helicase activity, association or formation of the functional nuclease complex (e.g. CRISPR/Cas complex). In certain embodiments, the mutations result in an altered PAM recognition, i.e. a different PAM may be (in addition or in the alternative) be recognized, compared to the unmodified Cas protein (see e.g. "Engineered CRISPR-Cas9 nucleases with altered PAM specificities", Kleinstiver et al. (2015), Nature, 523(7561):481-485, incorporated herein by reference in its entirety). Particularly preferred mutations include positively charged residues and/or (evolutionary) conserved residues, such as conserved positively charged residues, in order to enhance specificity. In certain embodiments, such residues may be mutated to uncharged residues, such as alanine.

In certain embodiments, the nuclease, in particular the Cas protein, may comprise one or more modifications resulting in a nuclease that has reduced or no catalytic activity, or alternatively (in case of nucleases that target double stranded nucleic acids) resulting in a nuclease that only cleaves one strand, i.e. a nickase. By means of further guidance, and without limitation, for example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As further guidance, where the enzyme is not SpCas9, mutations may be made at any or all residues corresponding to positions 10,762,840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a Cas is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Thus, the Cas may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the Cas or has a mutation as otherwise as discussed herein.

In certain embodiments, the nuclease is a split nuclease (see e.g. "A split-Cas9 architecture for inducible genome editing and transcription modulation", Zetsche et al. (2015), Nat Biotechnol. 33(2):139-42, incorporated herein by reference in its entirety). In a split nuclease, the activity (which may be a modified activity, as described herein elsewhere), relies on the two halves of the split nuclease to be joined, i.e. each half of the split nuclease does not possess the required activity, until joined. As further guidance, and without limitation, with specific reference to Cas9, a split Cas9 may result from splitting the Cas9 at any one of the following split points, according or with reference to SpCas9: a split position between 202A/203 S; a split position between 255F/256D; a split position between 310E/311I; a split position between 534R/535K; a split position between 572E/573C; a split position between 713S/714G; a split position between 1003L/104E; a split position between 1054G/1055E; a split position between 1114N/1115S; a split position between 1152K/1153S; a split position between 1245K/1246G; or a split between 1098 and 1099. Identifying potential split sides is most simply done with the help of a crystal structure. For Sp mutants, it should be readily apparent what the corresponding position for, for example, a sequence alignment. For non-Sp enzymes one can use the crystal structure of an ortholog if a relatively high degree of homology exists between the ortholog and the intended Cas9. Ideally, the split position should be located within a region or loop. Preferably, the split position occurs where an interruption of the amino acid sequence does not result in the partial or full destruction of a structural feature (e.g. alpha-helixes or β-sheets). Unstructured regions (regions that did not show up in the crystal structure because these regions are not structured enough to be "frozen" in a crystal) are often preferred options. In certain embodiments, a functional domain may be provided on each of the split halves, thereby allowing the formation of homodimers or heterodimers. The functional domains may be (inducible) interact, thereby joining the split halves, and reconstituting (modified) nuclease activity. By means of example, an inducer energy source may inducibly allow dimerization of the split halves, through appropriate fusion partners. An inducer energy source may be considered to be simply an inducer or a dimerizing agent. The term 'inducer energy source' is used herein throughout for consistency. The inducer energy source (or inducer) acts to reconstitute the Cas9. In some embodiments, the inducer energy source brings the two parts of the Cas9 together through the action of the two halves of the inducible dimer. The two halves of the inducible dimer therefore are brought tougher in the presence of the inducer energy source. The two halves of the dimer will not form into the dimer (dimerize) without the inducer energy source. Thus, the two halves of the inducible dimer cooperate with the inducer energy source to dimerize the dimer. This in turn reconstitutes the Cas9 by bringing the first and second parts of the Cas9 together. The CRISPR enzyme fusion constructs each comprise one part of the split Cas9. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer. The Cas9 is split in the sense that the two parts of the Cas9 enzyme substantially comprise a functioning Cas9. That Cas9 may function as a genome editing enzyme (when forming a complex with the target DNA and the guide), such as a nickase or a nuclease (cleaving both strands of the DNA), or it may be a deadCas9 which is essentially a DNA-binding protein with very little or no catalytic activity, due to typically two or more mutations in its catalytic domains as described herein further.

In certain embodiments, the nuclease may comprise one or more additional (heterologous) functional domains, i.e. the modified nuclease is a fusion protein comprising the nuclease itself and one or more additional domains, which may be fused C-terminally or N-terminally to the nuclease, or alternatively inserted at suitable and appropriate sited internally within the nuclease (preferably without perturbing its function, which may be an otherwise modified function, such as including reduced or absent catalytic activity, nickase activity, etc.). any type of functional domain may suitably be used, such as without limitation including functional domains having one or more of the following activities: (DNA or RNA) methyltransferase activity, methylase activity, demethylase activity, DNA hydroxylmethylase domain, histone acetylase domain, histone deacetylases domain, transcription or translation activation activity, transcription or translation repression activity, transcription or translation release factor activity, histone modification activity, nuclease activity, single-strand RNA cleavage activity, double-strand RNA cleavage activity, single-strand DNA cleavage activity, double-strand DNA cleavage activity, nucleic acid binding activity, a protein acetyltransferase, a protein deacetylase, a protein methyltransferase, a protein deaminase, a protein kinase, a protein phosphatase, transposase domain, integrase domain, recombinase domain, resolvase domain, invertase domain, protease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase, histone tail protease, HDACs, histone methyltransferases (HMTs), and histone acetyltransferase (HAT) inhibitors, as well as HDAC and HMT recruiting proteins, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains. In some embodiments, the functional domain is an epigenetic regulator; see, e.g., Zhang et al., U.S. Pat. No. 8,507,272 (incorporated herein by reference in its entirety). In some embodiments, the functional domain is a transcriptional activation domain, such as VP64, p65, MyoD1, HSF1, RTA, SET7/9 or a histone acetyltransferase. In some embodiments, the functional domain is a transcription repression domain, such as KRAB. In some embodiments, the transcription repression domain is SID, or concatemers of SID (eg SID4X), NuE, or NcoR. In some embodiments, the functional domain is an epigenetic modifying domain, such that an epigenetic modifying enzyme is provided. In some embodiments, the functional domain is an activation domain, which may be the P65 activation domain. In some embodiments, the functional domain comprises nuclease activity. In one such embodiment, the functional domain may comprise Fok1. Mention is made of U.S. Pat. Pub. 2014/0356959, U.S. Pat. Pub. 2014/0342456, U.S. Pat. Pub. 2015/0031132, and Mali, P. et al., 2013, Science 339(6121):823-6, doi: 10.1126/science.1232033, published online 3 Jan. 2013 and through the teachings herein the invention comprehends methods and materials of these documents applied in conjunction with the teachings herein. It is to be understood that also destabilization domains or localization domains as described herein elsewhere are encompassed by the generic term "functional domain". In certain embodiments, one or more functional domains are associated with the nuclease itself. In some embodiments, one or more functional domains are associated with an adaptor protein, for example as used with the modified guides of Konnerman et al. (Nature 517(7536): 583-588, 2015; incorporated herein by reference in its entirety), and form part of a Synergistic activator mediator (SAM) complex. The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. These adaptor proteins or orthogonal RNA binding proteins can further recruit effector proteins or fusions which comprise one or more functional domains.

In certain embodiments, the nuclease, in particular the Cas protein, may comprise one or more modifications resulting in a destabilized nuclease when expressed in a host (cell). Such may be achieved by fusion of the nuclease with a destabilization domain (DD). Destabilizing domains have general utility to confer instability to a wide range of proteins; see, e.g., Miyazaki, J Am Chem Soc. Mar. 7, 2012; 134(9): 3942-3945, incorporated herein by reference. CMP8 or 4-hydroxytamoxifen can be destabilizing domains. More generally, A temperature-sensitive mutant of mammalian DHFR (DHFRts), a destabilizing residue by the N-end rule, was found to be stable at a permissive temperature but unstable at 37° C. The addition of methotrexate, a high-affinity ligand for mammalian DHFR, to cells expressing DHFRts inhibited degradation of the protein partially. This was an important demonstration that a small molecule ligand can stabilize a protein otherwise targeted for degradation in cells. A rapamycin derivative was used to stabilize an unstable mutant of the FRB domain of mTOR (FRB*) and restore the function of the fused kinase, GSK-3β.6,7. This system demonstrated that ligand-dependent stability represented an attractive strategy to regulate the function of a specific protein in a complex biological environment. A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with a CRISPR enzyme confers to the CRISPR protein degradation of the entire fusion protein by the proteasome. Shield-1 and TMP bind to and stabilize the DD in a dose-dependent manner. The estrogen receptor ligand binding domain (ERLBD, residues 305-549 of ERS1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known. There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to a CRISPR enzyme and its stability can be regulated or perturbed using a ligand, whereby the CRISPR enzyme has a DD. Another DD can be a 12-kDa (107-amino-acid) tag based on a mutated FKBP protein, stabilized by Shield1 ligand; see, e.g., Nature Methods 5, (2008). For instance a DD can be a modified FK506 binding protein 12 (FKBP12) that binds to and is reversibly stabilized by a synthetic, biologically inert small molecule, Shield-1; see, e.g., Banaszynski L A, Chen L C, Maynard-Smith L A, Ooi A G, Wandless T J. A rapid, reversible, and tunable method to regulate protein function in living cells using synthetic small molecules. Cell. 2006; 126:995-1004; Banaszynski L A, Sellmyer M A, Contag C H, Wandless T J, Thorne S H. Chemical control of protein stability and function in living mice. Nat Med. 2008; 14:1123-1127; Maynard-Smith L A, Chen L C, Banaszynski L A, Ooi A G, Wandless T J. A directed approach for engineering conditional protein stability using biologically silent small molecules. The Journal of biological chemistry. 2007; 282:24866-24872; and Rodriguez, Chem Biol. Mar. 23, 2012; 19(3): 391-398-all of which are incorporated herein by reference and may be employed in the practice of the invention in selected a DD to associate with a CRISPR enzyme in the practice of this invention. As can be seen, the knowledge in the art includes a number of DDs, and the DD can be associated with, e.g., fused to, advantageously with a linker, to a CRISPR enzyme, whereby the DD can be stabilized in the presence of a ligand and when there is the absence thereof the DD can become destabilized, whereby the CRISPR enzyme is entirely destabilized, or the DD can be stabilized in the absence of a ligand and when the ligand is present the DD can become destabilized; the DD allows the CRISPR enzyme and hence the CRISPR-Cas complex or system to be regulated or controlled-turned on or off so to speak, to thereby provide means for regulation or control of the system, e.g., in an in vivo or in vitro environment. For instance, when a protein of interest is expressed as a fusion with the DD tag, it is destabilized and rapidly degraded in the cell, e.g., by proteasomes. Thus, absence of stabilizing ligand leads to a D associated Cas being degraded. When a new DD is fused to a protein of interest, its instability is conferred to the protein of interest, resulting in the rapid degradation of the entire fusion protein. Peak activity for Cas is sometimes beneficial to reduce off-target effects. Thus, short bursts of high activity are preferred. The present invention is able to provide such peaks. In some senses the system is inducible. In some other senses, the system repressed in the absence of stabilizing ligand and de-repressed in the presence of stabilizing ligand. By means of example, and without limitation, in some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR. A corresponding stabilizing ligand for this DD is, in some embodiments, TMP. As such, in some embodiments, one of the at least one DDs is DHFR and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT. More than one (the same or different) DD may be present, and may be fused for instance C-terminally, or N-terminally, or even internally at suitable locations. Having two or more DDs which are heterologous may be advantageous as it would provide a greater level of degradation control.

In some embodiments, the fusion protein as described herein may comprise a linker between the nuclease and the fusion partner (e.g. functional domain). In some embodiments, the linker is a GlySer linker. Attachment of a functional domain or fusion protein can be via a linker, e.g., a flexible glycine-serine (GlyGlyGlySer) or (GGGS)3 or a rigid alpha-helical linker such as (Ala(GluAlaAlaAlaLys) Ala). Linkers such as (GGGGS)3 are preferably used herein to separate protein or peptide domains. (GGGGS)3 is preferable because it is a relatively long linker (15 amino acids). The glycine residues are the most flexible and the serine residues enhance the chance that the linker is on the outside of the protein. (GGGGS)6, (GGGGS)9, or (GGGGS)12 may preferably be used as alternatives. Other preferred alternatives are (GGGGS)1, (GGGGS)2, (GGGGS)4, (GGGGS)5, (GGGGS)7, (GGGGS)8, (GGGGS)10, or (GGGGS)11. Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a (GGGGS)3 linker may be used here (or the 6, 9, or 12 repeat versions therefore) or the NLS of nucleoplasmin can be used as a linker between Cas9 and the functional domain.

In some embodiments, the nuclease is fused to one or more localization signals, such as nuclear localization sequences (NLSs), such as about or more than about 1, 2, 3, 4, 5, 6, 7, 8, 9, 10, or more NLSs. In some embodiments, the nuclease comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the nuclease comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV; the NLS from nucleoplasmin (e.g. the nucleoplasmin bipartite NLS with the sequence KRPAATKKAGQAKKKK); the c-myc NLS having the amino acid sequence PAAKRVKLD or RQRRNELKRSP; the hRNPA1 M9 NLS having the sequence NQSSNFGPMKGGNFGGRSSGPYGGGGQYFAK-PRNQGGY; the sequence RMRIZFKNKGKDTAEL-RRRRVEVSVELRKAKKDEQILKRRNV of the IBB domain from importin-alpha; the sequences VSRKRPRP and PPKKARED of the myoma T protein; the sequence POPKKKPL of human p53; the sequence SALIKKKKK-MAP of mouse c-abl IV; the sequences DRLRR and PKQKKRK of the influenza virus NS1; the sequence RKLKKKIKKL of the Hepatitis virus delta antigen; the sequence REKKKFLKRR of the mouse Mxl protein; the sequence KRKGDEVDGVDEVAKKKSKK of the human poly(ADP-ribose) polymerase; and the sequence RKCLQAGMNLEARKTKK of the steroid hormone receptors (human) glucocorticoid.

With particular reference to the CRISPR/Cas system as described herein, besides the Cas protein, in addition or in the alternative, the gRNA and/or tracr (where applicable) and/or tracr mate (or direct repeat) may be modified. Suitable modifications include, without limitation dead guides, escorted guides, protected guides, or guides provided with aptamers, suitable for ligating to, binding or recruiting functional domains (see e.g. also elsewhere herein the reference to synergistic activator mediators (SAM)). Mention is also made of WO/2016/049258 (FUNCTIONAL SCREENING WITH OPTIMIZED FUNCTIONAL CRISPR-CAS SYSTEMS (SAM)), WO/2016/094867 (PROTECTED GUIDE RNAS (PGRNAS); WO/2016/094872 (DEAD GUIDES FOR CRISPR TRANSCRIPTION FACTORS); WO/2016/094874 (ESCORTED AND FUNCTIONALIZED GUIDES FOR CRISPR-CAS SYSTEMS); all incorporated herein by reference. In certain embodiments, the tracr sequence (where appropriate) and/or tracr mate sequence (direct repeat), may comprise one or more protein-interacting RNA aptamers. The one or more aptamers may be located in the tetraloop and/or stemloop 2 of the tracr sequence. The one or more aptamers may be capable of binding MS2 bacteriophage coat protein. In certain embodiments, the gRNA (or trace or tracr mate) is modified by truncations, and/or incorporation of one or more mismatches vis-à-vis the intended target sequence or sequence to hybridize with.

By means of further guidance, and without limitation, in certain embodiments, the gRNA is a dead gRNA (dgRNA), which are guide sequences which are modified in a manner which allows for formation of the CRISPR complex and successful binding to the target, while at the same time, not allowing for successful nuclease activity (i.e. without nuclease activity/without indel activity). These dead guides or dead guide sequences can be thought of as catalytically inactive or conformationally inactive with regard to nuclease activity. Several structural parameters allow for a proper framework to arrive at such dead guides. Dead guide sequences are shorter than respective guide sequences which result in active Cas-specific indel formation. Dead guides are 5%, 10%, 20%, 30%, 40%, 50%, shorter than respective guides directed to the same Cas protein leading to active Cas-specific indel formation. Guide RNA comprising a dead guide may be modified to further include elements in a manner which allow for activation or repression of gene activity, in particular protein adaptors (e.g. aptamers) as described herein elsewhere allowing for functional placement of gene effectors (e.g. activators or repressors of gene activity). One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g. an activator or repressor; dimerized MS2 bacteriophage coat proteins as fusion proteins with an activator or repressor), or a protein which itself binds an effector (e.g. activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional up-regulation, for example for Neurog2. Other transcriptional activators are, for example, VP64. P65, HSF1, and MyoD1. By mere example of this concept, replacement of the MS2 stem-loops with PP7-interacting stem-loops may be used to recruit repressive elements.

By means of further guidance, and without limitation, in certain embodiments, the gRNA is an escorted gRNA (egRNA). By "escorted" is meant that the CRISPR-Cas system or complex or guide is delivered to a selected time or place within a cell, so that activity of the CRISPR-Cas system or complex or guide is spatially or temporally controlled. For example, the activity and destination of the CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, or an external energy source that is applied to the cell at a particular time. The escorted Cpf1 CRISPR-Cas systems or complexes have a gRNA with a functional structure designed to improve gRNA structure, architecture, stability, genetic expression, or any combination thereof. Such a structure can include an aptamer. Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

By means of further guidance, and without limitation, in certain embodiments, the gRNA is a protected guide. Protected guides are designed to enhance the specificity of a Cas protein given individual guide RNAs through thermodynamic tuning of the binding specificity of the guide RNA to target nucleic acid. This is a general approach of introducing mismatches, elongation or truncation of the guide sequence to increase/decrease the number of complimentary bases vs. mismatched bases shared between a target and its potential off-target loci, in order to give thermodynamic advantage to targeted genomic loci over genomic off-targets. In certain embodiments, the guide sequence is modified by secondary structure to increase the specificity of the CRISPR-Cas system and whereby the secondary structure can protect against exonuclease activity and allow for 3' additions to the guide sequence. In certain embodiments, a "protector RNA" is hybridized to a guide sequence, wherein the "protector RNA" is an RNA strand complementary to the 5' end of the guide RNA (gRNA), to thereby generate a partially double-stranded gRNA. In an embodiment of the invention, protecting the mismatched bases with a perfectly complementary protector sequence decreases the likelihood of target binding to the mismatched basepairs at the 3' end. In certain embodiments, additional sequences comprising an extended length may also be present.

Guide RNA (gRNA) extensions matching the genomic target provide gRNA protection and enhance specificity. Extension of the gRNA with matching sequence distal to the end of the spacer seed for individual genomic targets is envisaged to provide enhanced specificity. Matching gRNA extensions that enhance specificity have been observed in cells without truncation. Prediction of gRNA structure accompanying these stable length extensions has shown that stable forms arise from protective states, where the extension forms a closed loop with the gRNA seed due to complimentary sequences in the spacer extension and the spacer seed. These results demonstrate that the protected guide concept also includes sequences matching the genomic target sequence distal of the 20mer spacer-binding region. Thermodynamic prediction can be used to predict completely matching or partially matching guide extensions that result in protected gRNA states. This extends the concept of protected gRNAs to interaction between X and Z, where X will generally be of length 17-20 nt and Z is of length 1-30 nt. Thermodynamic prediction can be used to determine the optimal extension state for Z, potentially introducing small numbers of mismatches in Z to promote the formation of protected conformations between X and Z. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E'" and EL are used interchangeably to correspond to the term extended length (ExL) which represents the number of nucleotides by which the target sequence is extended. An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nucleotides in length. In a more preferred embodiment the ExL is 4 nucleotides in length. The extension sequence may or may not be complementary to the target sequence. An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence. Addition of gRNA mismatches to the distal end of the gRNA can demonstrate enhanced specificity. The introduction of unprotected distal mismatches in Y or extension of the gRNA with distal mismatches (Z) can demonstrate enhanced specificity. This concept as mentioned is tied to X, Y, and Z components used in protected gRNAs. The unprotected mismatch concept may be further generalized to the concepts of X, Y, and Z described for protected guide RNAs.

In certain embodiments, any of the nucleases, including the modified nucleases as described herein, may be used in the methods, compositions, and kits according to the invention. In particular embodiments, nuclease activity of an unmodified nuclease may be compared with nuclease activity of any of the modified nucleases as described herein, e.g. to compare for instance off-target or on-target effects. Alternatively, nuclease activity (or a modified activity as described herein) of different modified nucleases may be compared, e.g. to compare for instance off-target or on-target effects.

Also provided herein are compositions for use in carrying out the methods of the invention. More particularly, non-naturally occurring or engineered compositions are provided which comprise one or more of the elements required to ensure genomic perturbation. In particular embodiments, the compositions comprise one or more of the (modified) DNA binding protein, and/or a guide RNA. In particular embodiments, the composition comprises a vector. In further particular embodiments, the vector comprises a polynucleotide encoding a gRNA. In particular embodiments, the vector comprises two or more guide RNAs. Said two or more guide RNAs may target a different target (so as to ensure multiplex targeting) or the same target, in which case the different guide RNAs will target different sequences within the same target sequence. Where provided in a vector the different guide RNAs may be under common control of the same promotor, or may be each be under control of the same or different promoters.

Further Embodiments

Embodiment 1. A composition comprising a prodrug, the prodrug comprising a cargo group, a chelating ligand, and optionally a self-immolative linker interconnecting the cargo group and the chelating ligand; wherein binding of $Zn^{2+}$ to the chelating ligand catalyzes cleavage of at least one ester, amide, or thioester, amide, or thioester group between the chelating ligand and the cargo group, thereby releasing the cargo compound.

Embodiment 2. The composition of Embodiment 1, wherein the prodrug is represented by Formula I-A:

$$(Car-H)_m—S-(L)_n \qquad (I-A), wherein:$$

L comprises a chelating ligand having a selective affinity for $Zn^{2+}$;
S comprises an optionally substituted aromatic or heteroaromatic ring or fused rings;
H is a heteroatom selected from O, N, and S;
Car comprises (i) a cargo group and optionally (ii) a self-immolative linker interconnecting the cargo group and H, wherein the optional self-immolative linker comprises an acyl group covalently bound to H to form an ester, amide, or thioester group; and
each of m and n is at least one;

or wherein the prodrug is represented by Formula I-B:

$$Car-H_2-SIM-H_1—S-L \qquad (I-B), wherein:$$

L comprises a chelating ligand having a selective affinity for $Zn^{2+}$;
S comprises a first optionally substituted aromatic or heteroaromatic ring or fused rings;
Car is a cargo group, optionally comprising a second optionally substituted aromatic or heteroaromatic ring or fused rings; and
$H_1$ and $H_2$ are each a heteroatom independently, e.g. selected from O, N, and S, wherein $H_1$ is optionally part of the first aromatic or heteroaromatic ring or fused rings, and $H_2$ is optionally part of the second aromatic or heteroaromatic ring or fused rings; and
wherein SIM is a self-immolative linker comprising a first acyl group covalently bound to $H_1$ to form an ester, amide, or thioester group and a second acyl group covalently bound to $H_2$ to form an ester, amide, or thioester group.

Embodiment 3. The composition of Embodiment 2, wherein the self-immolative linker is represented by any of Formulae II-A to II-E:

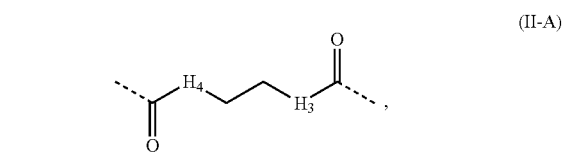
(II-A)

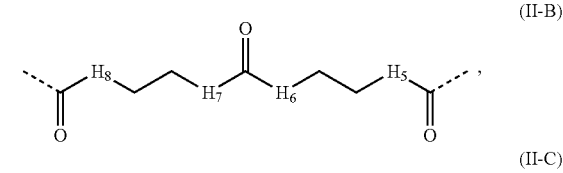
(II-B)

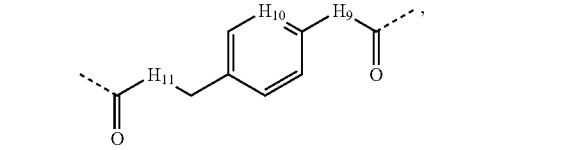
(II-C)

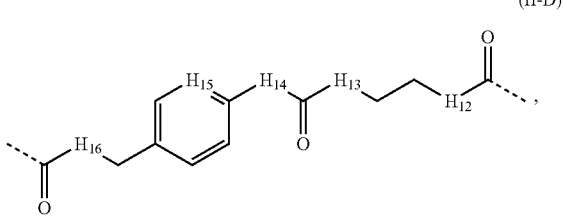
(II-D)

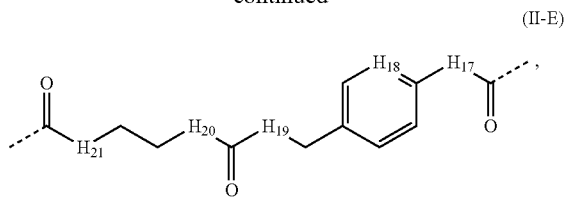

(II-E)

wherein $H_3$, $H_4$, $H_5$, $H_6$, $H_7$, $H_8$, $H_9$, $H_{11}$, $H_{12}$, $H_{13}$, $H_{14}$, $H_{16}$, $H_{17}$, $H_{19}$, $H_{20}$, and $H_{21}$ are independently, e.g. selected from O, N, and S; and wherein $H_{10}$, $H_{15}$, and $H_{18}$ are each independently selected from C and N.

Embodiment 4. The composition of Embodiment 2, wherein the prodrug is represented by any of Formulae III-A to III-D:

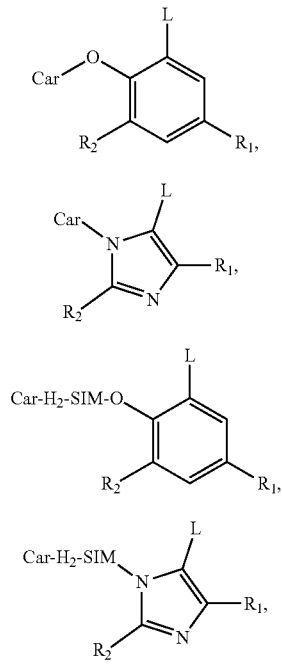

wherein:
R1 is H or comprises an electron withdrawing group or an electron donating group; and
R2 is H or comprises a chemical group conferring steric hindrance and/or reduction of electronic conjugation of the acyl group to the aromatic ring.

Embodiment 5. The composition of any of Embodiments 1-4, wherein the chelating ligand has a selective affinity for $Zn^{2+}$ over $Fe^{2+}$, $Cu^{2+}$, $Mn^{2+}$, $Co^{2+}$, and $Ni^{2+}$.

Embodiment 6. The composition of any of Embodiments 1-5, wherein the chelating ligand has a $K_d$ for $Zn^{2+}$ of about 1 nM and about 100 μM.

Embodiment 7. The composition of any of Embodiments 1-6, wherein the chelating ligand comprises at least two secondary or tertiary amines or at least three secondary or tertiary amines.

Embodiment 8. The composition of any of Embodiments 1-7, wherein the chelating ligand comprises a tertiary alkyl amine covalently bound to at least one pyridine ring.

Embodiment 9. The composition of any of Embodiments 1-8, wherein the chelating ligand is

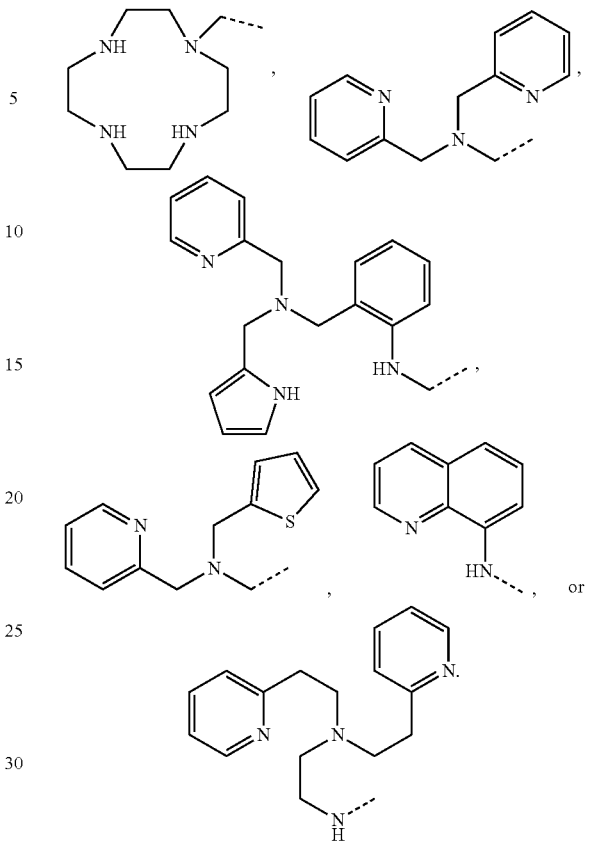

Embodiment 10. The composition of any of Embodiments 1-9, wherein the chelating ligand is Embodiment 11. The composition of any of Embodiments 1-10, wherein the cargo compound is a therapeutic or diagnostic agent that is physiologically inactive when covalently bound to the aromatic or heteroaromatic ring or fused rings.

Embodiment 12. The composition of Embodiment 11, wherein the cargo compound is a therapeutic agent for treating diabetes.

Embodiment 13. The composition of Embodiment 10, wherein the cargo compound promotes β-cell proliferation and/or regeneration.

Embodiment 14. The composition of Embodiment 12 or 13, wherein the cargo compound is a CMGC kinase inhibitor.

Embodiment 15. The composition of Embodiment 14, wherein the cargo compound is an inhibitor for a CMGC kinase selected from the group consisting of DYRK1A, DYRK1B, DYRK2, CLK1, CLK2, and CLK4.

Embodiment 16. The composition of Embodiment 15, wherein the cargo compound is a DYRK1A inhibitor.

Embodiment 17. The composition of Embodiment 12 or 13, wherein the cargo compound is an elastase inhibitor.

Embodiment 18. The composition of Embodiment 12 or 13, wherein the cargo compound is 5-iodotubercidin, sivelestat, GNF 4877, harmine, or leucettine.

Embodiment 19. The composition of any of Embodiments 1-9, wherein the cargo compound is a stabilizing ligand for a polypeptide comprising a destabilization domain, wherein binding of the stabilizing ligand to the destabilization domain prevents proteasomal degradation of the polypeptide.

Embodiment 20. The composition of Embodiment 19, wherein the cargo compound is a stabilizing ligand for a destabilized dihydrofolate reductase (DHFR) or a destabilized estrogen receptor ligand binding domain (ERLBD).

Embodiment 21. The composition of Embodiment 20, wherein the cargo compound is trimethoprim (TMP), 4-hydroxytamoxifen (4HT), or CMP8.

Embodiment 22. The composition of any of Embodiments 19-21, wherein the destabilization domain is fused to a CRISPR effector protein.

Embodiment 23. The composition of Embodiment 22, wherein binding of the stabilizing ligand to the destabilization domain increases activity of the CRISPR effector protein by at least one-fold.

Embodiment 24. The composition of Embodiment 22 or 23, wherein the CRISPR effector protein is Cas9, Cpf1, C2c1, C2c2, or Cas13b.

Embodiment 25. The composition of Embodiment 24, wherein the CRISPR effector protein is Cas9 or Cpf1.

Embodiment 26. The composition of any of Embodiments 19-21, wherein the destabilization domain is fused to (i) an aptamer ligand and/or (ii) a transcriptional activation domain or a transcriptional repression domain.

Embodiment 27. The composition of Embodiment 26, wherein binding of the stabilizing ligand to the destabilization domain increases activity of the aptamer ligand by at least one-fold.

Embodiment 28. The composition of Embodiment 26 or 27, wherein the aptamer ligand is selected from MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1.

Embodiment 29. The composition of any of Embodiments 26-28, wherein the transcriptional activation domain or the transcriptional repression domain is selected from VP64, P65, MyoD1, HSF1, RTA, SET7/9, KRAB, NuE, NcoR, SID, and SID4X.

Embodiment 30. The composition of any of Embodiments 1-9, wherein the cargo compound is capable of inducing dimerization of a first half of an inducible dimer and a second half of an inducible dimer.

Embodiment 31. The composition of Embodiment 30, wherein the first half of the inducible dimer is FK506 binding protein 12 (FKBP), and the second half of the inducible dimer is FKBP rapamycin binding domain (FRB).

Embodiment 32. The composition of Embodiment 31, wherein the cargo compound is Rapamycin.

Embodiment 33. The composition of any of Embodiments 30-32, wherein the first half of the inducible dimer is fused to a first portion of a CRISPR effector protein, and the second half of the inducible dimer is fused to a second portion of the CRISPR effector protein.

Embodiment 34. The composition of Embodiment 33, wherein the cargo compound induces dimerization of the first half of the inducible dimer and the second half of the inducible dimer to bring the first and second portions of the CRISPR effector protein together, allowing the CRISPR effector protein to function in β-cells.

Embodiment 35. The composition of Embodiment 33 or 34, wherein the CRISPR effector protein is Cas9, Cpf1, C2c1, C2c2, or Cas13b.

Embodiment 36. The composition of Embodiment 35, wherein the CRISPR effector protein is Cas9.

Embodiment 37. The composition of any of Embodiments 1-36, wherein the cargo compound or the optionally substitute aromatic or heteroaromatic ring or fused rings comprises a masked fluorophore that is unmasked upon cleavage of the ester, amide, or thioester group.

Embodiment 38. The composition of any of Embodiments 2-37, wherein R1 is H.

Embodiment 39. The composition of any of Embodiments 2-37, wherein R1 is an electron withdrawing group.

Embodiment 40. The composition of Embodiment 39, wherein R1 is —CN or —NO$_2$.

Embodiment 41. The composition of any of Embodiments 2-37, wherein R1 is an electron donating group.

Embodiment 42. The composition of Embodiment 41, wherein R1 is —OCH$_3$ or —N(CH$_3$)$_2$.

Embodiment 43. The composition of any of Embodiments 2-37, wherein at least one of R1 and R2 is a halogen.

Embodiment 44. The composition of Embodiment 43, wherein at least one of R1 and R2 is a Cl or F.

Embodiment 45. The composition of any of Embodiments 1-37, wherein the composition further comprises a pharmaceutically acceptable carrier.

Embodiment 46. A method for selective delivery of a cargo compound to β-cells in vivo, comprising administering the composition of any of Embodiments 1-45 to a subject in need thereof, wherein binding of $Zn^{2+}$ to the chelating ligand of the prodrug in the β-cells catalyzes cleavage of the ester, amide, or thioester group, thereby releasing the cargo compound in the β-cells.

Embodiment 47. A method for treating diabetes, comprising administering the composition of any of Embodiments 10-18 to a subject in need thereof, wherein binding of $Zn^{2+}$ to the chelating ligand of the prodrug in the β-cells catalyzes cleavage of the ester, amide, or thioester group, thereby releasing the therapeutic agent in the β-cells.

Embodiment 48. A method for promoting β-cell proliferation and/or regeneration, comprising administering the composition of any of Embodiments 10-18 to a subject in need thereof, wherein binding of $Zn^{2+}$ to the chelating ligand in the β-cells catalyzes cleavage of the ester, amide, or thioester group, thereby releasing the therapeutic agent in the β-cells.

Embodiment 49. A method for selective activation of a CRISPR effector protein in β-cells, comprising administering the composition of any of Embodiments 19-25 to a subject in need thereof, simultaneously or sequentially with a fusion protein of a CRISPR effector protein and at least one destabilization domain, or a polynucleotide encoding the fusion protein, wherein binding of $Zn^{2+}$ to the chelating ligand in the β-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the CRISPR effector protein to function in the β-cells.

Embodiment 50. A method for selective activation of a CRISPR effector protein in β-cells, comprising administering the composition of any of Embodiments 30-36 to a subject in need thereof, simultaneously or sequentially with (i) a first fusion protein comprising a first half of an inducible dimer and a first portion of a CRISPR effector protein, or a polynucleotide encoding the first fusion protein, and (ii) a second fusion protein comprising a second half of the inducible dimer and a second portion of the CRISPR effector protein, or a polynucleotide encoding the second fusion protein, wherein binding of $Zn^{2+}$ to the chelating ligand in the β-cells catalyzes cleavage of the ester, amide, or thioester group, thereby releasing the cargo compound in the β-cells, and wherein cargo compound induces dimerization of the first half of the inducible dimer and the second half of the inducible dimer to bring the first and second portions of the CRISPR effector protein together, allowing the CRISPR effector protein to function in β-cells.

Embodiment 51. A method for selective genomic editing in β-cells, comprising administering the composition of any of Embodiments 19-25 to a subject in need thereof, simultaneously or sequentially with (i) a fusion protein of a catalytically active CRISPR effector protein and at least one destabilization domain, or a polynucleotide encoding the fusion protein and (ii) a guide RNA hybridizable to a target sequence in genome of the subject or a polynucleotide encoding the guide RNA, wherein binding of $Zn^{2+}$ to the chelating ligand in the β-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the catalytically active CRISPR effector protein to bind the guide RNA and the target sequence for genome editing in the β-cells.

Embodiment 52. A method for selective genomic editing in β-cells, comprising administering the composition of any of Embodiments 30-36 to a subject in need thereof, simultaneously or sequentially with (i) a first fusion protein comprising a first half of an inducible dimer and a first portion of a catalytically active CRISPR effector protein, or a polynucleotide encoding the first fusion protein, (ii) a second fusion protein comprising a second half of the inducible dimer and a second portion of the CRISPR effector protein, or a polynucleotide encoding the second fusion protein, and (iii) a guide RNA hybridizable to a target sequence in genome of the subject or a polynucleotide encoding the guide RNA, wherein binding of $Zn^{2+}$ to the chelating ligand in the β-cells catalyzes cleavage of the ester, amide, or thioester group, thereby releasing the cargo compound in the β-cells, and wherein cargo compound induces dimerization of the first half of the inducible dimer and the second half of the inducible dimer to bring the first and second portions of the CRISPR effector protein together, allowing the catalytically active CRISPR effector protein to bind the guide RNA and the target sequence for genome editing in the β-cells.

Embodiment 53. A method for selective transcriptional activation or repression in β-cells, comprising administering the composition of any of Embodiments 19-25 to a subject in need thereof, simultaneously or sequentially with (i) a fusion protein of a catalytically inactive CRISPR effector protein, at least one destabilization domain, and at least one transcriptional activation domain or transcriptional repression domain, or a polynucleotide encoding the fusion protein, and (ii) a guide RNA hybridizable to a target sequence in genome of the subject or a polynucleotide encoding the guide RNA, wherein binding of $Zn^{2+}$ to the chelating ligand in the β-cells catalyzes cleavage of the ester, amide, or thioester group, thereby releasing the stabilizing ligand in the β-cells, and wherein binding of the stabilizing ligand to the destabilization domain prevents the fusion protein from proteasomal degradation and allows the catalytically inactive CRISPR effector protein to bind the guide RNA and the target sequence for transcriptional activation or repression in the β-cells.

Embodiment 54. A method for selective transcriptional activation or repression in β-cells, comprising administering the composition of any of Embodiments 30-36 to a subject in need thereof, simultaneously or sequentially with (i) a first fusion protein comprising a first half of an inducible dimer and a first portion of a catalytically inactive CRISPR effector protein, or a polynucleotide encoding the first fusion protein, (ii) a second fusion protein comprising a second half of the inducible dimer and a second portion of the CRISPR effector protein, or a polynucleotide encoding the second fusion protein, and (iii) a guide RNA hybridizable to a target sequence in genome of the subject or a polynucleotide encoding the guide RNA, wherein at least one of the first fusion protein and the second fusion protein further comprises at least one transcriptional activation domain or transcriptional repression domain, wherein binding of $Zn^{2+}$ to the chelating ligand in the β-cells catalyzes cleavage of the ester, amide, or thioester group, thereby releasing the cargo compound in the β-cells, and wherein cargo compound induces dimerization of the first half of the inducible dimer and the second half of the inducible dimer to bring the first and second portions of the CRISPR effector protein together, allowing the catalytically inactive CRISPR effector protein to bind the guide RNA and the target sequence for transcriptional activation or repression in the β-cells.

Embodiment 55. A method for selective transcriptional activation or repression in β-cells, comprising administering the composition of any of Embodiments 19-21 and 26-29 to a subject in need thereof, simultaneously or sequentially with (i) a catalytically inactive CRISPR effector protein or a polynucleotide encoding the CRISPR effector protein, (ii) a fusion protein of at least one destabilization domain, at least one aptamer ligand, and at least one transcriptional activation domain or transcriptional repression domain, and (iii) a guide RNA hybridizable to a target sequence in genome of the subject or a polynucleotide encoding the guide RNA, wherein the guide RNA comprises an aptamer sequence capable of binding to the transcriptional activation domain or transcriptional repression domain, wherein binding of $Zn^{2+}$ to the chelating ligand in the β-cells catalyzes cleavage of the ester, amide, or thioester group, thereby releasing of the stabilizing ligand in the β-cells, and wherein binding of the stabilizing ligand to the destabilization domain prevents the fusion protein from proteasomal degradation and allows the fusion protein to bind to the aptamer sequence of guide RNA for transcriptional activation or repression in the β-cells.

Embodiment 56. A method for imaging β-cells in vivo, comprising administering the composition of Embodiment 37 to a subject thereof, wherein binding of $Zn^{2+}$ to the chelating ligand of the prodrug in the β-cells catalyzes cleavage of the ester, amide, or thioester group, thereby allowing the cargo compound or the optionally substitute aromatic or heteroaromatic ring or fused rings to emit a fluorescent signal in the β-cells, and detecting the fluorescent signal emitted from the cargo compound or the optionally substitute aromatic or heteroaromatic ring or fused rings.

Embodiment 57. A method for imaging β-cells in vitro, comprising contacting the composition of Embodiment 37 with a cell culture comprising β-cells, wherein binding of $Zn^{2+}$ to the chelating ligand of the prodrug in the β-cells catalyzes cleavage of the ester, amide, or thioester group, thereby allowing the cargo compound or the optionally substitute aromatic or heteroaromatic ring or fused rings to emit a fluorescent signal in the β-cells, and detecting the fluorescent signal emitted from the cargo compound or the optionally substitute aromatic or heteroaromatic ring or fused rings.

Embodiment 58. A method for selective delivery of a cargo compound to breast cancer cells in vivo, comprising administering the composition of any of Embodiments 1-45 to a subject in need thereof, wherein binding of $Zn^{2+}$ to the chelating ligand of the prodrug in the breast cancer cells catalyzes cleavage of the ester, amide, or thioester group, thereby releasing the cargo compound in the breast cancer cells.

Embodiment 59. A method for selective delivery of a cargo compound to prostate cells in vivo, comprising administering the composition of any of Embodiments 1-45 to a subject in need thereof, wherein binding of $Zn^{2+}$ to the chelating ligand of the prodrug in the prostate cells catalyzes cleavage of the ester, amide, or thioester group, thereby releasing the cargo compound in the prostate cells.

Embodiment 60. The method of any of Embodiments 46-56 and 58-59, wherein the composition is administered parenterally.

Embodiment 61. The method of any of Embodiments 46-56 and 58-59, wherein the composition is administered intravenously.

Embodiment 62. The method of any of Embodiments 46-56 and 58-59, wherein the composition is administered intramuscularly.

Embodiment 63. A method of inducing or enhancing human beta cell proliferation, the method comprising exposing human beta cells to a kinase inhibitor, wherein the kinase inhibitor inhibits kinase activity of one or more CMGC family kinases.

Embodiment 64. A method of reducing hyperglycemia, the method comprising administering to a human subject in need thereof a kinase inhibitor, wherein the kinase inhibitor inhibits kinase activity of one or more CMGC family kinases.

Embodiment 65. A method of treating diabetes, the method comprising administering to a human subject in need thereof a kinase inhibitor, wherein the kinase inhibitor inhibits kinase activity of one or more CMGC family kinases.

Embodiment 66. A method of inducing or enhancing human beta cell proliferation, the method comprising exposing human beta cells to a calcineurin activator and/or NFAT activator, wherein optionally the calcineurin activator and/or NFAT activator are CMGC family kinase inhibitors.

Embodiment 67. The method of any of Embodiments 63-66, wherein the CMGC family kinase is selected from the group consisting of DYRK1A, DYRK1B, DYRK2, CLK2, CLK3, and CLK4.

Embodiment 68. The method of any of Embodiments 63-67, wherein the method comprises administering to a subject in need thereof a CMGC inhibitor.

Embodiment 69. The method of Embodiment 68, wherein the CMGC inhibitor is selected from the group consisting of DYRK1A inhibitors, DYRK1B inhibitors, DYRK2 inhibitors, CLK2 inhibitors, CLK3 inhibitors, and CLK4 inhibitors.

Embodiment 70. The method of any of Embodiments 63-69, wherein the method comprising administering the composition of any of Embodiments 1-45.

Embodiment 71. The composition of any one of Embodiments 1-45 for use in a method of any one of Embodiments 46-69, optionally in the treatment of diabetes.

Embodiment 72. Use of the composition of any one of Embodiments 1-45 for the manufacture of a medicament for use in a method of any one of Embodiments 46-69, optionally in the treatment of diabetes.

EXAMPLES

Example 1. Optimize the Scaffold and Ligand End of ZnPDs

Figure 2A:
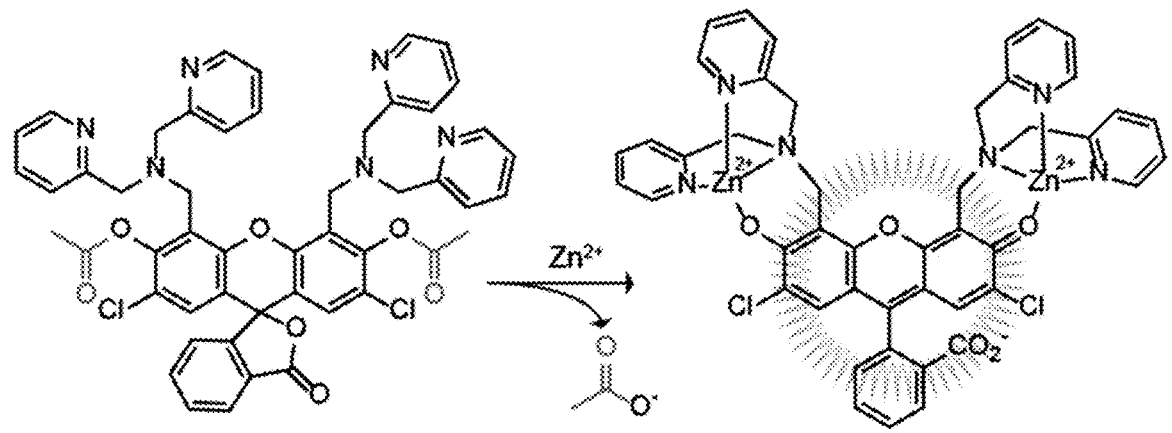
FIG. 2A. shows that fluorescence of DA-ZP1 reaction-based probe is unmasked by removal of acetyl groups (in red) by $Zn^{2+}$.

Zn2+ is redox inactive, but is a powerful Lewis acid. Reaction-based probes were developed to image Zn2+ in tissue. [28,29] In these reaction-based probes, Zn2+ activates the fluorescence of a caged probe by catalyzing the removal of the acetyl groups from the molecule (in red in FIG. 2A). Further, the Zn2+ specificity of this reaction over those of other metal ions, including Fe2+, Cu2+, Mn2+, Co2+, and Ni2+, is high.

Figure 2B:
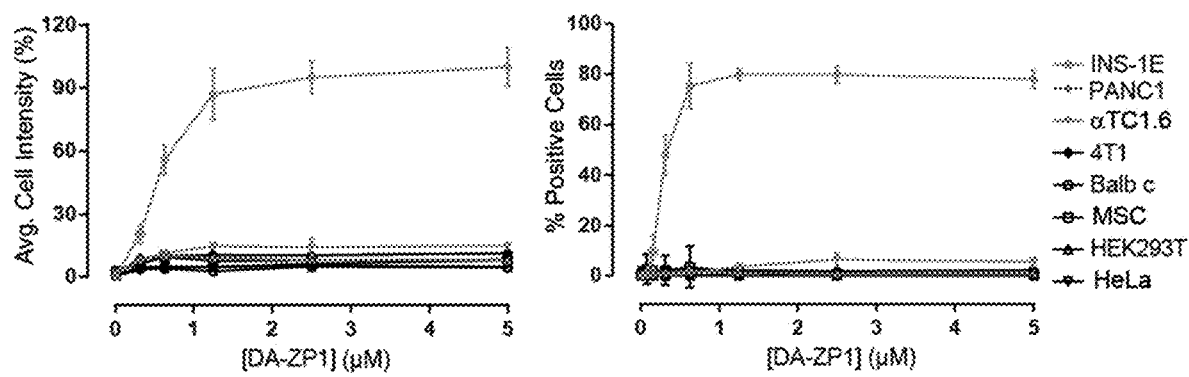
FIG. 2B. shows that $Zn^{2+}$ selectively unmasks DA-ZP1 fluorescence in INS-1E cells compared to other cells as confirmed by high average fluorescent cell intensity and high % fluorescence-positive cells.
Figure 2C:
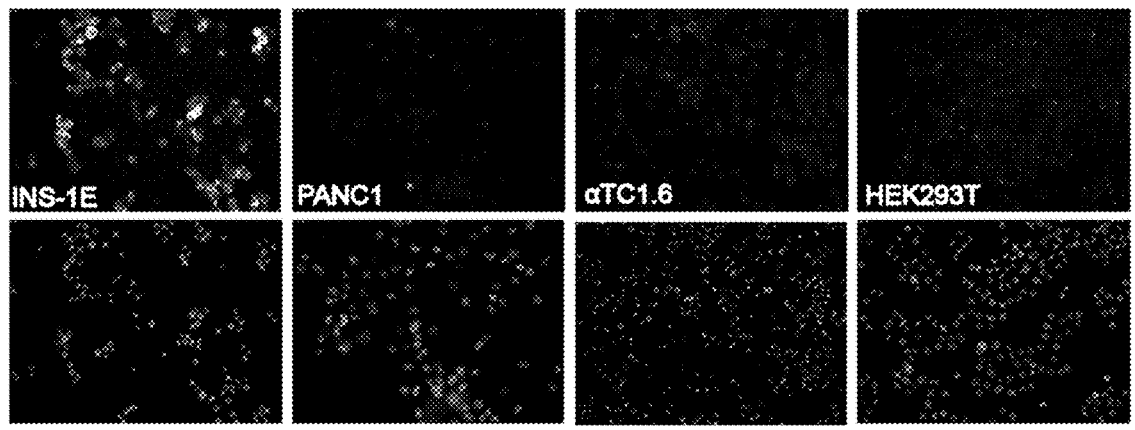
FIG. 2C. illustrates representative DA-ZP1 images (top panel) for INS-1E, PANC1, aTC1.6, and HEK293T cells and nuclear staining (DAPI) for the same cells (bottom panel).

To demonstrate that high intracellular Zn2+ concentration can indeed be used to selectively release cargo in β-cells, the reaction-based probe was incubated in a β-cell line (INS-1E), an alpha cell line (aTC1.6), an acinar cell line (PANC1), and cells of other lineages (FIG. 2B). It was found that β-cells were highly fluorescent compared to other cell types, which yielded minimal background fluorescence (FIG. 2C).

Figure 3:
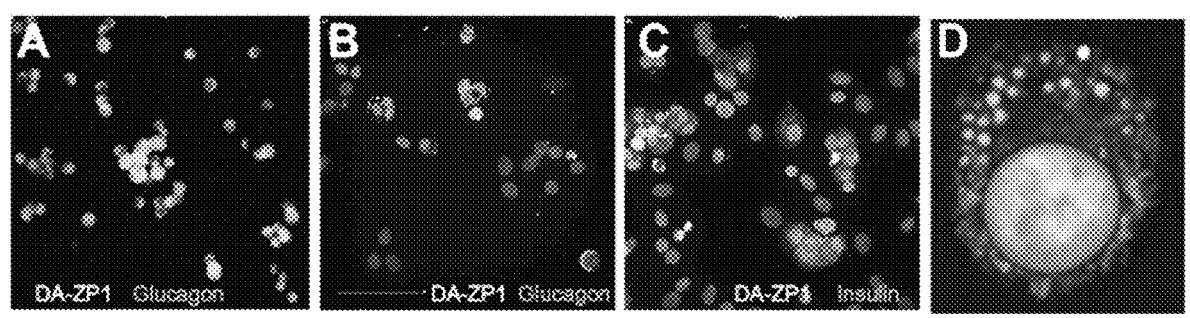
FIG. 3. shows $Zn^{2+}$ triggered selective fluorescence release in β-cells of human islets. Dissociated (A) rat or (B-D) human islets were incubated with DA-ZP1 followed by immunostaining reaction, for (A,B) glucagon and (C,D) insulin.
Figure 4:
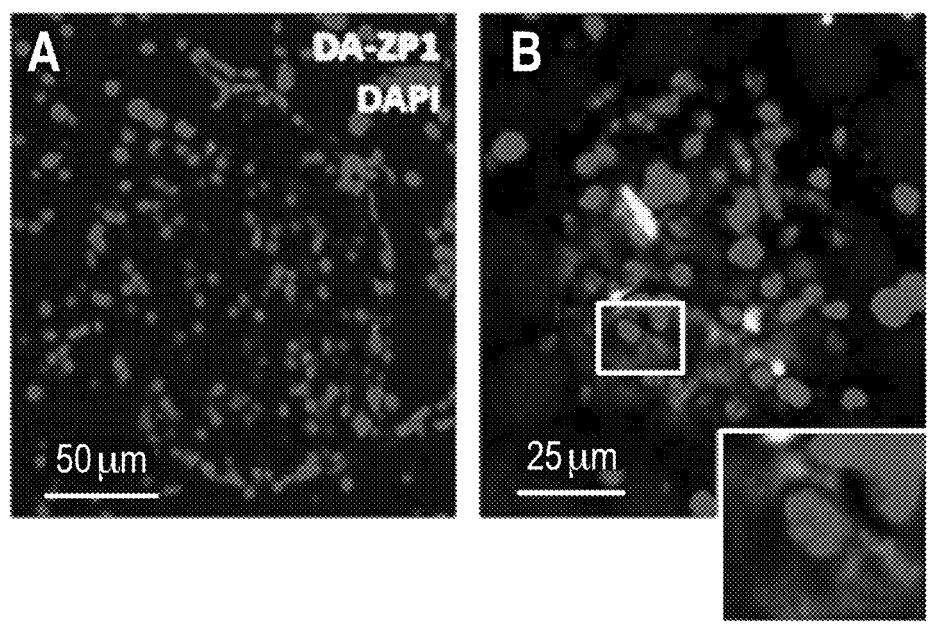
FIG. 4. shows fluorescence image of paraffin-embedded sections of islets from mice treated with (A) DMSO or (B) 50 mg/kg DA-ZP1. One hour after intraperitoneal injection, sections of islets were stained with an anti-fluorescein antibody and counter-stained with DAPI. Inset shows cell highlighted by the white square.

Next, this probe was incubated in dissociated rat or human islets, co-staining for insulin to identify β-cells and glucagon to identify alpha cells. Using different Zn2+ dyes, very little to no overlap was observed between glucagon-positive and zinc probe-positive cells, while there was a high degree of overlap between insulin-positive and zinc probe-positive cells (FIG. 3A-C). Using confocal microscopy, distinct green-fluorescent vesicles were observed within β-cells (FIG. 3D), showing the high degree of resolution for the localization of this probe. Finally, 10-12-week old C57BL/6 mice were injected intraperitoneally with a single dose of 50 mg/kg DA-ZP1 or DMSO. Fluorescence was detected in islet sections from DA-ZP1-treated mice, but not in DMSO-treated mice (FIG. 4).

All the imaging experiments were performed in 96 well plate. INS-1E, PANC1, αTC1.6, HEK293T and other cell types were plated in 96 well plate. 70 µL, 4×PFA was added in each well to fix the cells. After 15 minutes, all the wells were washed with PBS. After washing with PBS, 70 µL DAPI (1×) (nuclear stain) was added along with appropriate concentration of DAZP-1. The staining process was continued for 20 minute and 100 µL PBS as was added in each well.

These studies demonstrate that the high concentration of Zn2+ can be exploited for selective cargo release in β-cells in vitro.

Figure 5A:
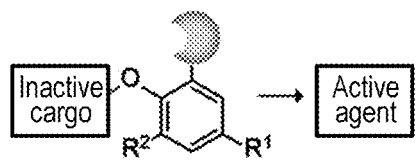
FIG. 5A shows that zinc catalyzes cleavage of the scissile bond (red) and releases active agent.
Figure 5B:
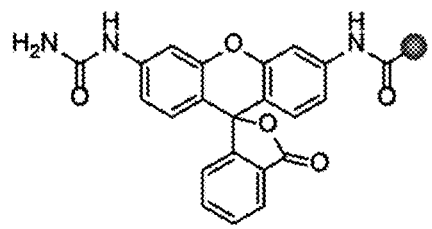
FIG. 5B shows Rhodamine-based pro-fluorophore with the point of attachment marked with purple circle.
Figure 5C:
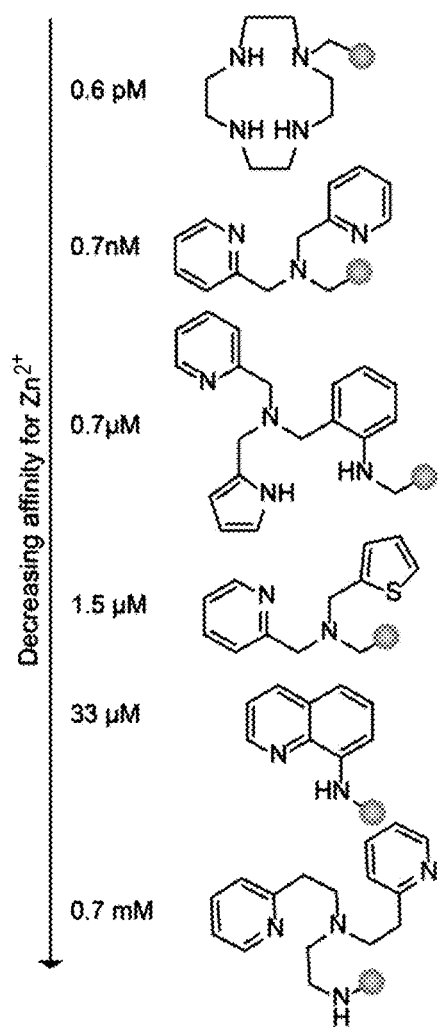
FIG. 5C. shows chelating ligands with different affinities for $Zn^{2+}$. The site of attachment to the scaffold is shown with blue sphere.

Example 2. Synthesis and Biochemical Studies on ZnPDs, Using a Fluorophore as Cargo and Ligands with Varying Zn2+ Affinity The reaction-based probe scaffold was designed as a cargo release scaffold (FIG. 5A) which uses, as cargo, a pro-fluorophore (FIG. 5B) that is activated upon zinc-catalyzed release from the scaffold to give a strongly fluorescent molecule. β-cell-selective release of the active agent is via β-cell-selective cleavage of the scissile bond (FIG. 5A, shown in red). Without being bound by theory, is it believed that such selectivity is obtained due to the ability to fine-tune the chemical stability of the scissile bond on the cargo release scaffold. The first control site is a Zn2+ chelating ligand (FIG. 5A, shown in blue). A high-affinity Zn2+ chelating ligand facilitates cargo release, but may induce a premature release of the cargo at sites with low Zn2+ concentration. High-affinity ligands can also deplete Zn2+ and may be toxic. On the other hand, a very low-affinity Zn2+ chelating scaffold will reduce the efficiency of scissile bond cleavage and will adversely affect the efficiency of cargo release. Therefore, the optimal affinity is investigated to avoid these consequences. To identify the chelating ligand that confers the most β-cell selectivity, a large corpus (>50) of reported Zn2+ ligands with affinities ranging from pM to mM (FIG. 5C) will be tested. [29] Zn2+ ligands with wide-ranging affinities were identified, which are compatible with the reaction-based probe system.

The second control of the stability of the scissile bond is through a classic Hammett-type chemistry and involves positioning appropriate groups at the R1 site (FIG. 5A). Installation of electron-withdrawing groups (—CN, —NO2) at this site decreases the hydrolytic stability of the bond, while installation of electron-donating groups (—OMe, —NMe2) increases stability. If these two sites fail to provide the desired selectivity, a third control site can be employed (labelled as R2, FIG. 5A) that will affect bond stability by steric hindrance—a large group will prevent the electronic conjugation of the acyl group to the aromatic ring and also hinder water's approach to the reaction site.

As a first step, the ligands on the cargo release scaffold are systematically varied (FIG. 5A) with the fluorophore (FIG. 5B) as the cargo. Next, using buffered solutions containing various concentrations of Zn2+, photophysical characterization of the ZnPDs is perform. Specifically, the concentration of Zn2+ that results in the release of half of the maximal fluorescence is determined. R1 is also systematically varied with the ultimate goal of generating a pool of ~15 fluorophore-release scaffolds with Zn2+ affinities ranging from ~100 μM down to ~1 nM, which is [Zn2+ ] in plasma. Finally, ZnPDs are confirmed to retain selectivity over Zn2+ compared to other divalent metal ions, including Fe2+, Cu2+, Mn2+, Co2+, and Ni2+. Buffered solutions containing these other metals exhibit no fluorescence.

Example 3. Identify Fluorophore-Bearing ZnPDs with Maximum Specificity for β-Cells and Test Fluorophore-Release ZnPDs on Human Islets Over 30 cell lines of various lineages (including those described in FIG. 2B) have been identified and are available through the Cell Line Factory at the Broad Institute. As was done for the reaction-based probe, DA-ZP1 (FIG. 2B, C), fluorescence of the probes synthesized according to the present invention will be quantified in these cells using high-throughput fluorescence assay which is currently run in a 96-well format, an automated high-content imaging microscope and an automated image analysis system.

The fluorophore-bearing ZnPDs according to the present invention is assessed in human islets using high-content imaging. After dissociation of the islet cells with Accutase, cells are seeded on 96-well plates coated with an extracellular matrix derived from the HTB9 bladder carcinoma cell line.[31,32] Cells are then treated for 30 minutes with various concentrations of each ZnPDs, and fixed for simultaneous immunofluorescence for insulin and glucagon. The calculation of percent positive β- or α-cells enables determination of the specificity and sensitivity of the various zinc affinities of each ligand. The β-cells in the culture system will be labeled with relevant high sensitivity and specificity, i.e. non-β-cells in the culture system will not be labeled. Detection of fluorescence in an electron microscopy (EM) will show the subcellular localization of the fluorophore-bearing ZnPDs in the insulin granules.

An optimal Zn2+ affinity ligand and scaffold will be identified for selective fluorescent labeling of β-cells, with no labeling of other non-β-cells in the culture system. These results will help define the optimal ligand and scaffold for conjugating small molecules that can promote β-cell proliferation in human islets. Since the fluorescent probes are fine-tuned to the Zn2+ concentration found in β-cells, the probes are superior to zinc dyes currently used for performing quality-control studies on islets used clinically or in research settings. As such, the present invention provides next-generation, highly specific probes for fluorescent labeling of live β-cells.

It is noted that $Zn^{2+}$, while mostly present at pM levels in tissues, is present at significant levels in mammary, prostate, and neuronal tissue, which may result in off-site delivery. However, the fluorescence signal from a breast cancer cell line (4T1) is very low compared to that of β-cells (FIG. 2B), which indicates that the ZnPDs of the present invention will work well. The addition of an additional layer of specificity to our zinc-based release system may ameliorate such non-selectivity, and can be accomplished by appending exendin-4 (Ex-4). Thus, the present invention also contemplate using an Ex-4 sequence and conjugation chemistry that was used for β-cell imaging in vivo by the Weisseleder and Kulkarni laboratories, which is incorporated herein by reference. [33]

The concentration of Zn2+ in the interstitial space during insulin secretion is considerably high (~10 μM), which may also trigger premature cargo release. To avoid such scenarios, experiments under low-glucose conditions will be performed. In one aspect, highly potent ligands that are able to strip protein-bound catalytic Zn2+ are not used. There is significant heterogeneity in the concentration of Zn2+ in β-cells in islets. For example, dysfunctional or dedifferentiated β-cells do not have very high Zn2+ and the delivery system may not work in these cells. Finally, co-staining for organelle markers and markers of insulin granules is performed if there is difficulty with assessing cellular localization using EM.

Example 4. Effects of Small Molecules on β-Cell Replication

A human islet cell-culture system and proliferation assay developed by Wagner et al. was used to not only of preserve β-cell function over 7-10 days in culture, but also identify conditions that increase β-cell division.[32] The thymidine analog 5-ethinyl-2'-deoxyuridine (EdU) was used, which, when reacted with an azide-conjugated fluorophore, enables rapid and high-quality imaging of cells that have ever gone through S phase.[34] The detection was paired with insulin immunofluorescence, followed by automated imaging and analysis to identify EdU+ins+ cells after compound treatment. Islet cells were incubated with EdU for 6 days, consistent with the low rate of human β-cell proliferation. Under these conditions, most islet donor samples possessed low but non-zero levels of β-cell proliferation in cell culture. The quality of the assay was verified by using as a positive control adenoviral overexpression of human CDK6 and cyclin D1.[35]

Figure 6:
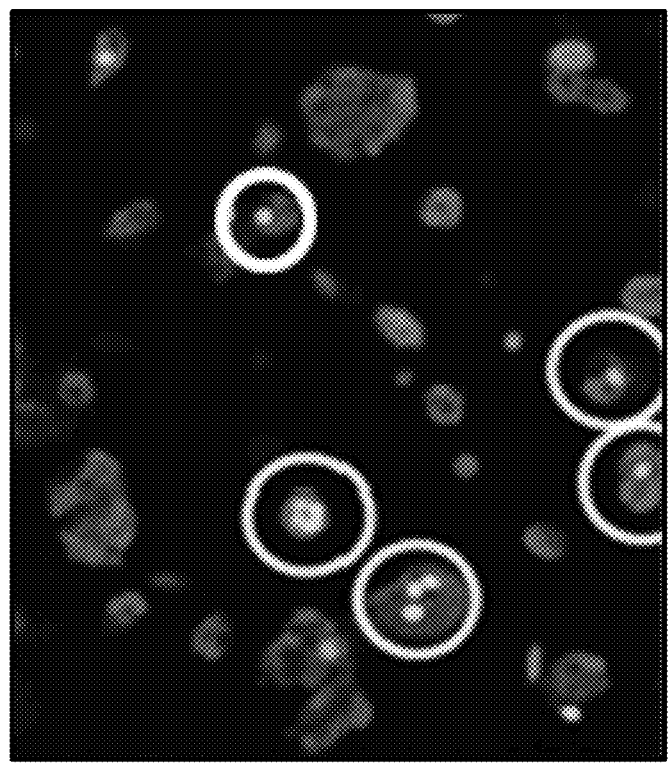
FIG. 6 shows that the effects of DYRK1A inhibitors promote 3-cell proliferation. Fluorescent image of human islet cells treated for 6 days with 1p M 5-iodotubercidin (5-IT) and stained for 5-ethinyl-2'-deoxyuridine (EdU) (green) and insulin (red). Replicating cells are circled.

This assay is useful for testing reagents (e.g., peptide factors or small molecules) described in the literature, some of which proved to be nonselective.[36,37] The effects of 5-iodotubercidin (5-IT), an adenosine kinase inhibitor that has been reported to increase proliferation of mouse, rat, and porcine β-cells was then tested on EdU incorporation in human islet cells. [38] After 6 days of treatment, a ~10-fold increase in proliferation was observed, with a maximal effect at 1 μM 5-IT (FIG. 6). This effect was consistent across >20 human islet donors, irrespective of age, gender, BMI, or cause of death. Concentrations of 5-IT greater than 1 μM appeared to be toxic to cells. This proliferation is characterized by many "doublets", consisting of two adjacent EdU+ins+ cells, suggesting recent cell division. Importantly, 5-IT did not induce proliferation of the other cell types in the heterogeneous culture system, suggesting a β-cell-selective effect.

Figure 7:
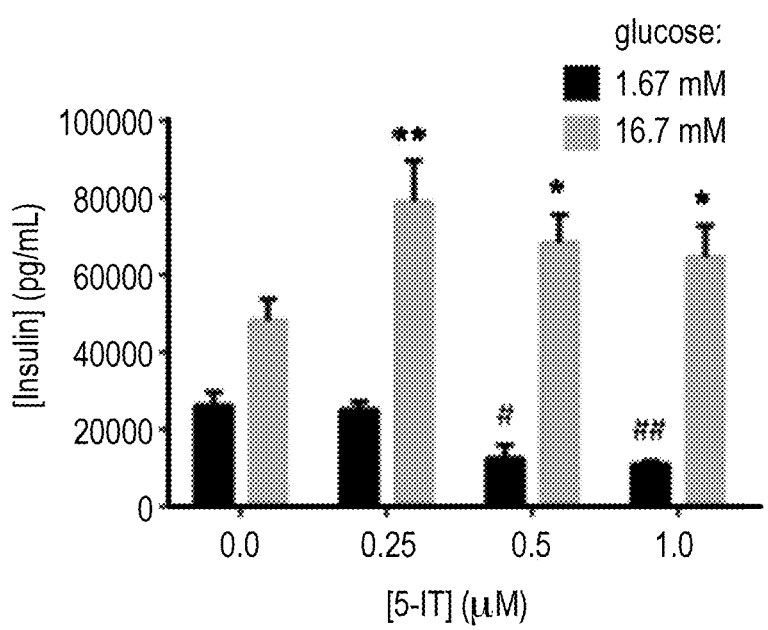
FIG. 7 shows the glucose responsiveness measured by glucose-stimulated insulin secretion (GSIS) of 3-cells treated with 5-IT for 12 days.

To evaluate whether the proliferation induced in human β-cells caused loss of function, glucose-stimulated insulin secretion (GSIS) on cells treated for 12 days with 5-IT was measured. In the DMSO-treated state, glucose stimulated ~2-fold increase in insulin secretion in dissociated islet cells. After treatment with 5-IT, an increase in GSIS was observed (FIG. 7). On the other hand, baseline secretion under low-glucose conditions decreased somewhat in a dose-dependent manner. Although incompletely understood, the loss of basal secretion may be due to cell-death effects on other cells in the culture system. These results indicate that the human β-cells are viable and functioning appropriately in terms of glucose responsiveness after 12 days.

Figure 8A:
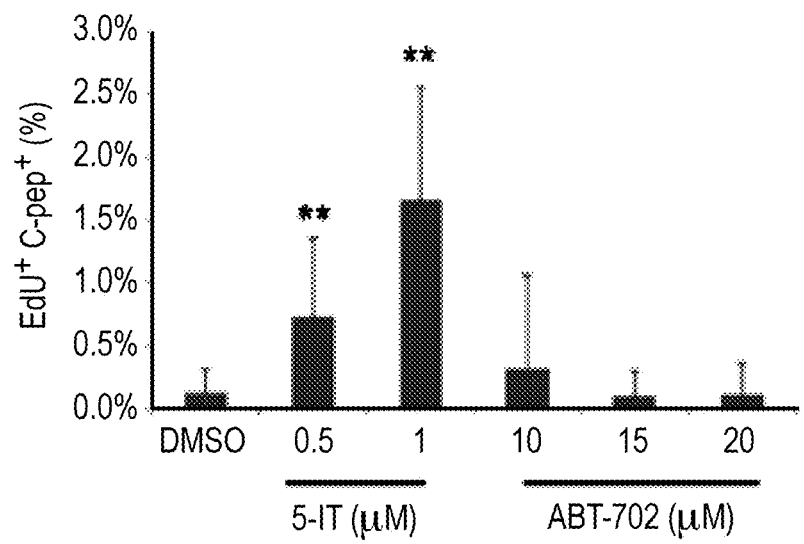
FIG. 8A shows that while 5-IT promotes 3-cell proliferation, another adenosine kinase inhibitor ABT-702 does not.
Figure 8B:
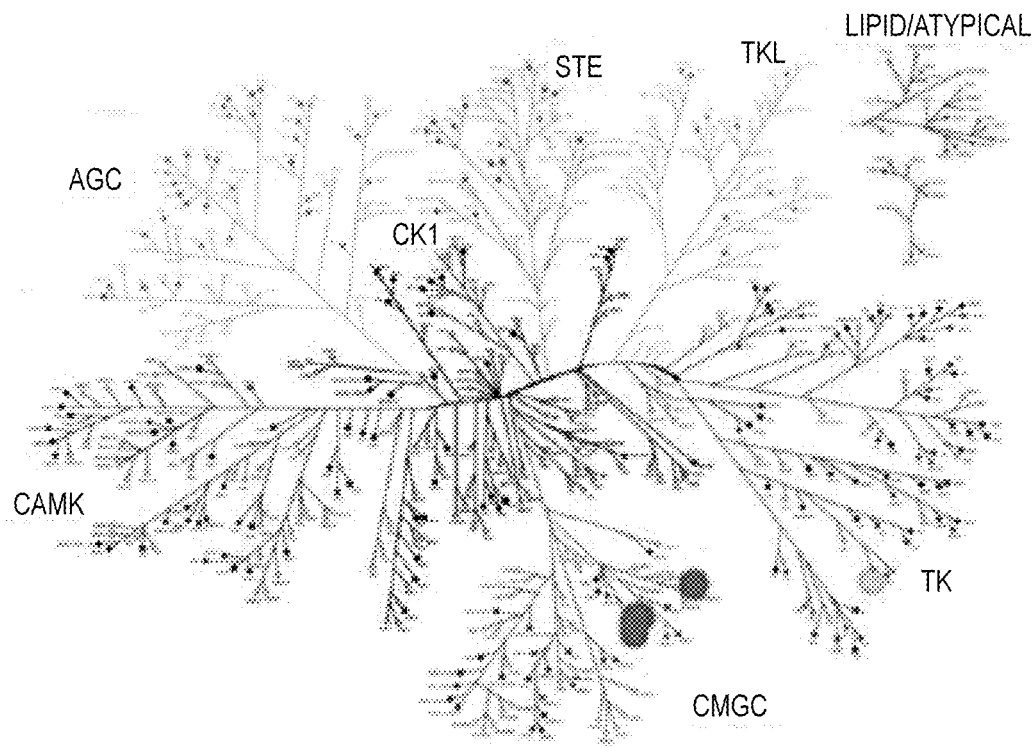
FIG. 8B shows the kinome profiling across 253 human kinases with 5-IT (red dots) and ABY-702 (green dot).

Since 5-IT is primarily annotated as an adenosine kinase inhibitor, the effects of the structurally unrelated adenosine kinase inhibitor ABT-702 was tested. [38, 39] ABT-702 had no effect on EdU incorporation (FIG. 8A), suggesting that the mechanism of 5-IT in human β-cells is different. Because 5-IT is a close analog of adenosine itself, its mechanism may involve kinase inhibition. Thus, the effects of 100 nM 5-IT with 500 nM ABT-702 on the activity of 253 human kinases were compared. 5-IT strongly inhibited a related set of CMGC family kinases: DYRK1A, DYRK1B, DYRK2, CLK1, CLK2, and CLK4 (FIG. 8B), with IC50 values of 13, 10, 6, 36, 10, and 14 nM, respectively. These results suggest that the stimulation of human β-cell proliferation by 5-IT is due to inhibition of this subset of the CMGC kinase family. To test this hypothesis, the effects of harmine, a natural product and known DYRK1A inhibitor, was measured in human islet cells. Harmine induced a dose-dependent increase in EdU+ins+ cells at 5 and 10 μM after 6-days treatment (FIG. 9A), suggesting that DYRK1A was the relevant target. Because DYRK1A targets NFAT, FK506, an inhibitor of calcineurin and NFAT activation was tested for its ability to suppress the stimulation of proliferation. One μM FK506 completely blocked the effects of 1 μM 5-IT or 10 μM harmine, resulting in the absence of EdU+ins+ β-cells in the treated cultures (data not shown). DYRK1A was then knocked down in human islets using shRNA, and an increase in β-cell proliferation was found (FIG. 9B). The data support the role for acute inhibition of human DYRK1A in adult β-cells as an effective strategy to induce β-cell proliferation and regeneration.

Example 5. Effects of Elastase Inhibitors on β-Cell Proliferation

The liver insulin receptor knockout (LIRKO) mouse is profoundly insulin resistant, but displays remarkable islet hyperplasia.[40] Liver was found as the source of a secreted factor in this model that can induce β-cell proliferation in mouse and human islets.[24] A proteomics effort using liver, liver explant-conditioned media, hepatocyte-conditioned media, and plasma led to the discovery that serpin B1, a protease inhibitor that targets elastases, is enriched in serum from LIRKO mice (FIG. 10).[1] To address whether serpinB1 promotes β-cell proliferation, mouse islets were cultured in the presence of recombinant human serpinB1 or ovalbumin (negative control) and measured proliferation using the marker Ki67. rSerpinB1-treated islets exhibited a dose-dependent effect, and a 2-fold increase in the percentage of Ki67+ins+ cells was observed at the dose of 1 μg/mL (FIG. 11 A, B). The activity of serpin B1 appeared dependent upon elastase activity, as an inactive N-tagged serpin B1 construct had no impact on the percentage of Ki67+ cells (FIG. 11C). Finally, rSerpinB1 induced a dose-dependent increase in β-cell proliferation from human islets (FIG. 11D). These results indicate that serpinB1 can be harnessed to enhance endogenous human β-cell proliferation.

Figures 12A, 12B, 12C, 12D:
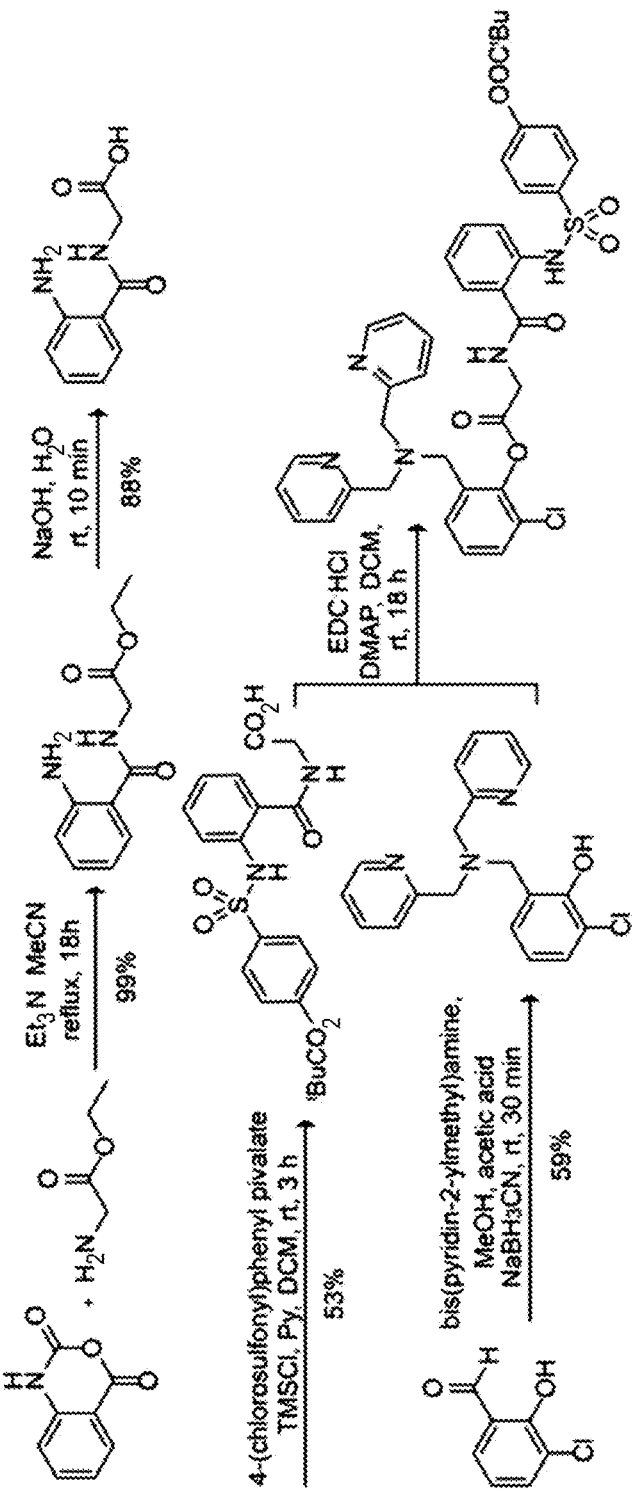
FIG. 12A shows proposed attachment point for 5-IT.
FIG. 12B shows proposed attachment point for Sivelestat.
FIG. 12C shows proposed attachment point for GNF 4877.
FIG. 12D shows optimized conditions for the synthesis of sivelestat-bearing ZnPDs.

Example 6. Synthesis and Biochemical Studies on ZnPDs Bearing 5-IT and Sivelestat To ensure that the cargo is inactive when conjugated to the scaffold, the large body of medicinal chemistry data available for these compounds were examined to identify conjugation sites where any perturbation disrupts biological activity (shown in purple, FIG. 12A-C). Furthermore, the cargoes and the zinc scaffold were conjugated (with appropriate protecting groups) to yield the final ZnPDs. The synthesis of sivelestat ZnPDs was successfully optimized (FIG. 12D). Specifically, ammonolysis of isatoic anhydride with glycine ethyl ester was followed by hydrolysis, and in situ TMS protection and sulfonylation to yield sivelestat with an overall yield of 46%. A final coupling step between sivelestat and the ligand-bearing scaffold afforded the ZnPD. After the synthesis of 5-IT- and sivelestat-bearing ZnPDs, cargo release in buffered solutions containing various concentrations of $Zn^{2+}$ was confirmed. The scaffold was found to retain selectivity over $Zn^{2+}$ compared to other divalent metal ions, including $Fe^{2+}$, $Cu^{2+}$, $Mn^{2+}$, $Co^{2+}$, and $Ni^{2+}$. Here, buffered solutions of metal ions were used and the cleavage reaction was followed using LC-MS.

Example 7. Test Effects of Zinc-Catalyzed Probes on Human Islets

To test effects of ZnPDs in human islets, cells are treated for six days in the absence or presence of various concentrations of each conjugated zinc ligand and EdU. As positive controls, the unconjugated small molecules are tested in parallel. Testing each compound at multiple concentrations allows determining if lower concentrations of ZnPDs are required for activity. Cells are fixed for simultaneous immunofluorescence for insulin and detection of EdU incorporation. ImageXpress Micro automated microscopy system as well as the Phenix system from PerkinElmer are used for high-throughput confocal microscopy. Automated image acquisition and analysis are used to test many different conditions in a rapid manner. The calculation of percent EdU-positive β-cells shows the specificity and sensitivity of the various zinc affinities of each ligand.

In order to confirm cell specificity of the ZnPD probes, intact human islets are treated with the compounds and sort p and alpha cells using flow cytometry. Gene-expression profiling by RNA-seq is performed to determine the level of cell-cycle regulation as a result of compound treatment. Studies of 5-IT showed that a set of genes enriched in regulation of the cell cycle, DNA synthesis, and cell division are upregulated in human islets after compound treatment. [2] This experiment confirms that the cargo is being delivered to β-cells selectively.

Example 8. Measure In Vitro and In Vivo Pharmacokinetics Properties of Zinc-Catalyzed Probes Key physicochemical (e.g., solubility, permeability) and pharmacokinetic (e.g., microsomal stability, plasma binding) properties of Zinc-catalyzed probes are tested for downstream development. Ideal characteristics include solubility>50 µM in PBS buffer; plasma stability, with >75% parent molecule remaining after 1-hour incubation with mouse or human plasma; membrane permeability, as measured by the Caco-2 permeability assay; and liver microsome stability, such that >50% parent molecule remains after 1-hour incubation with mouse or human liver microsomes. The in vivo pharmacokinetics of the ZnPDs will be assessed, by administering a single dose orally, intraperitoneally, or intravenously, followed by monitoring the plasma levels of compound by LC/MS over 24 hours. This experiment informs the optimal dose and route to be used in the following examples, and compares the exposure of ZnPDs with unconjugated compounds. To demonstrate selective delivery, the tissue distribution of β-cell mitogens (FIG. 3D-F) with and without ZnPDs are compared. These quantitative measurements inform medicinal chemistry efforts to optimize further the activity, selectivity, stability, and toxicity of the proliferation system.

The conjugated zinc-based probes of 5-IT and sivelestat will induce β-cell proliferation, but not proliferation of the other cell types (including alpha cells, other endocrine cells, fibroblasts, endothelial cells) in our islet cell-culture system. Moreover, gene-expression profiling will elucidate the level of cell-cycle regulation in β-cells after compound treatment, which will be absent in sorted alpha cells. Finally, pharmacokinetic studies will inform the optimal dose and route of administration.

As alternative to 5-IT or sivelestat, other inhibitors of DYRK1A and elastase with varying potency are used in synthesizing conjugated ZnPDS (e.g., GNF 4877 (FIG. 12C). Similarly, other elastase inhibitors with lower molecular weight are also used. Further, steric crowding near the Zn2+-binding site may affect the release of the compounds. Here, self-immolative linkers, which have less sterics are used. The possible immolation cascades include those of quinone methide, intramolecular cyclization, or hemiacetal degradation.[41]

Example 9. Effects of Small Molecules on Human β-Cell Proliferation In Vivo

1) Establishing a humanized mouse model: The humanized mouse model is established according to Kulkarni et al.[22,23] Briefly, the immunodeficient NOD.Cg-Prkdc$^{scid}$Il2rg$^{tm1Wjl}$SzJ mouse strain, commonly known as NOD-scid gamma (NSG), combines features of the NOD/ShiLtJ background and Prkcd mutation, known as the severe combined immune deficiency mutation (scid), which essentially eliminates adaptive immunity. [42,43] This strain has utility in studies of hematopoietic and cancer stem cells and of islet transplantation. [44-46]

2) Human islet transplantation and follow-up studies: For studies to test 5-IT, NSG mice were transplanted with healthy human islets (1000 islet equivalents, IEQ) obtained from the Integrated Islet Distribution Program (IIDP) into the subrenal capsular space.[23,47] 5-IT was injected at a dose of 0.625 mg/kg intraperitoneally (i.p.). A separate group of mice with human islet transplants were injected with DMSO as vehicle controls, and sham-operated animals were used as an additional control group. The injection was repeated twice a week for 3 weeks. In the final week, we injected BrdU (100 mg/kg) daily for 4 days, and six hours after the last BrdU injection the pancreas was harvested. β-cell replication was assessed using previously described protocols.[23] For sivelestat experiments, osmotic pumps loaded with compound (300 µg/kg/day) were implanted into mice, and were treated for 14 days. Mice were provided BrdU in drinking water and injected i.p. on days 8, 11, and 14. Islets were harvested five hours after the last BrdU injection.

Figure 13A:
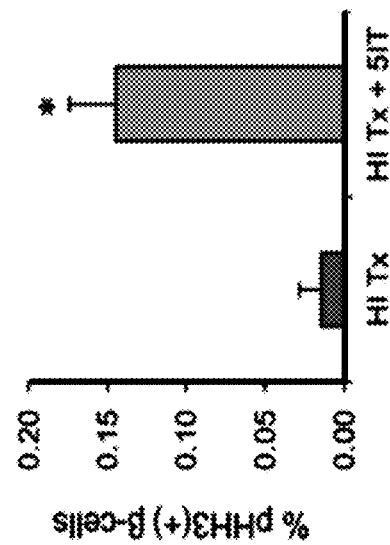
FIG. 13A BrdU/insulin, FIG. 13B Ki67/insulin and FIG. 13C pHH3/insulin double positive cells. Up to 2000 β-cells were counted. Mean±SEM, n=4. *p<0.05 and **p<0.01.
Figure 13B:
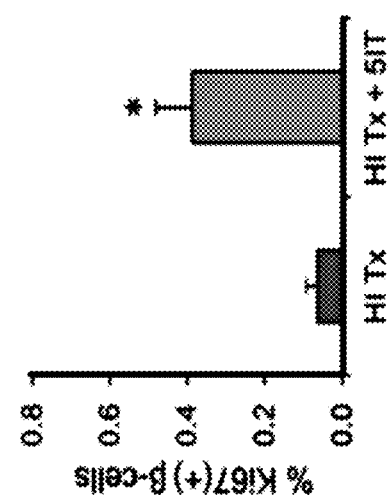
FIG. 13 shows quantification of proliferating β-cells from human islets treated with 5-IT.
Figure 13C:
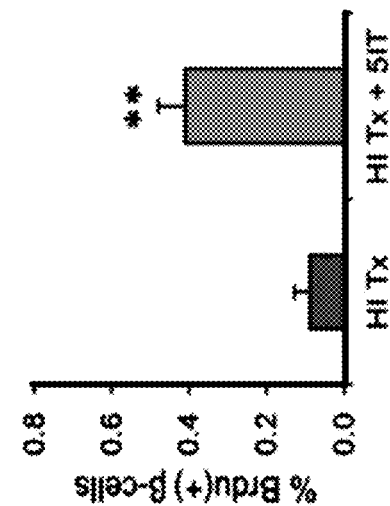

Immunohistochemical analysis of kidney sections bearing human islet grafts showed a ~5-fold increase in BrdU incorporation in the 5-IT treated group, indicating a transition from G1 to S-phase of the cell cycle (FIG. 13A). The enhanced mitosis was confirmed using Ki67 (FIG. 13B) and pHH3 immunostaining (FIG. 13C). No significant differences between control and 5-IT-treated mice in the proliferation of liver, adipose, muscle, and kidney tissue were observed.

Figure 14:
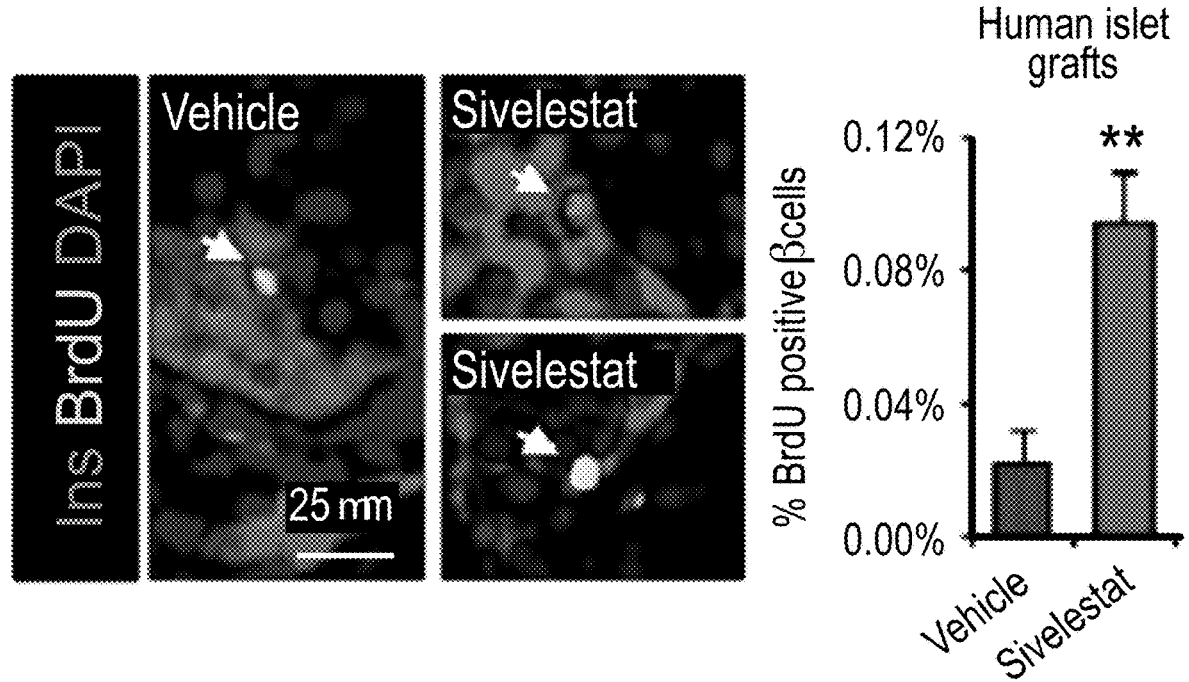
FIG. 14 shows representative fluorescent images and quantification of human islet grafts retrieved from mice treated with sivelestat or vehicle and co-immunostained for BrdU, insulin, and DAPI.
Figures 15A, 15B:
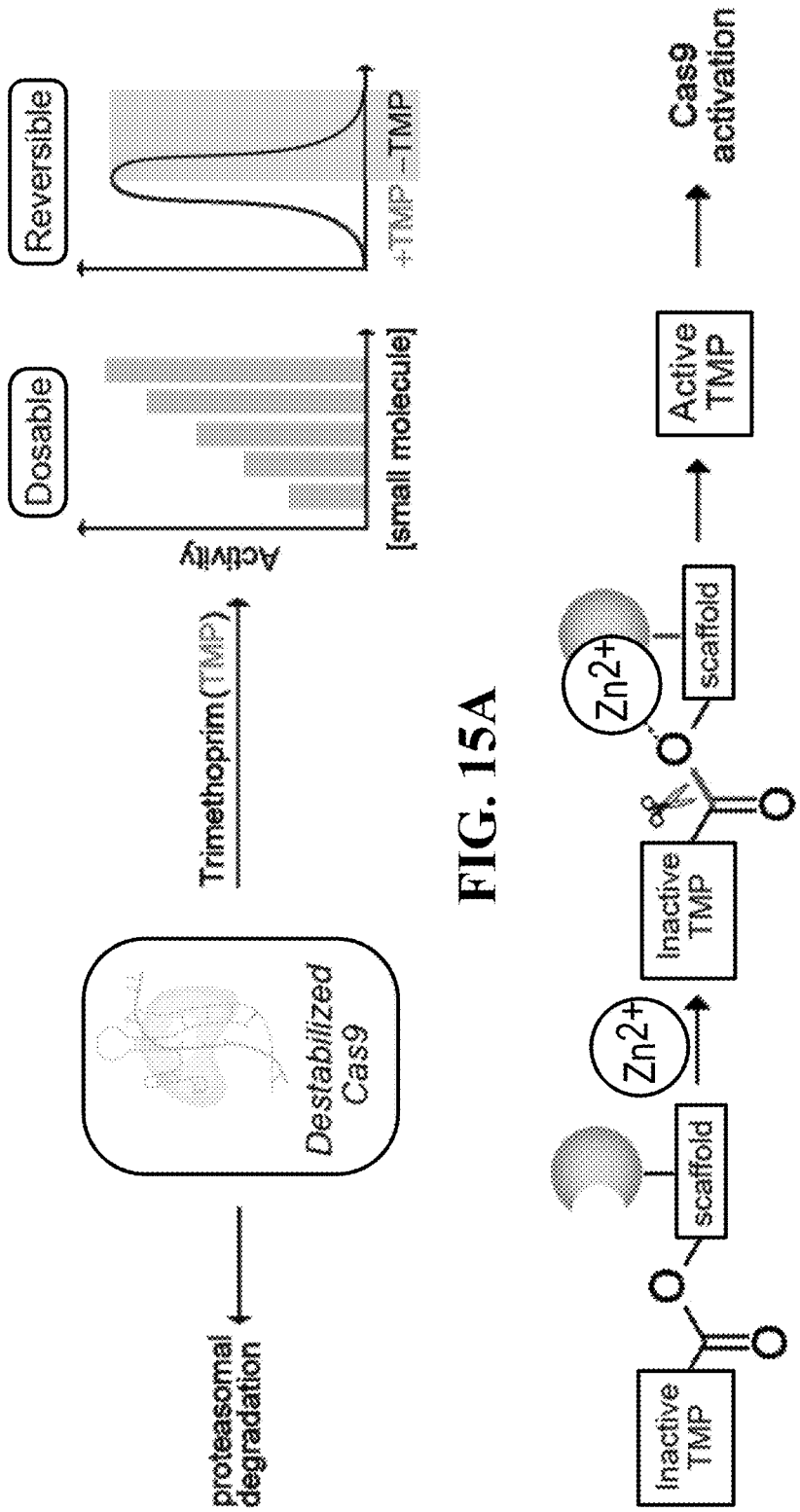
FIG. 15A shows small-molecule activated Cas9 variant, as an exemplary CRISPR effector protein, that affords dose- and temporal-control of Cas9 activity.
FIG. 15B shows a zinc-based prodrug (ZnPD) system that consists of three components: an inactive form of the trimethoprim to be delivered, a $Zn^{2+}$-binding ligand. (shown in blue), and a scaffold linking these two components. Upon zinc binding and ZnPD cleavage in the R-cell, the inactive trimethoprim now becomes the active agent, with activity only in cells with high $Zn^{2+}$ levels (i.e., β-cells).

Next, sivelestat, a small-molecule inhibitor of elastinolytic proteases and thus a partial mimic of serpinB1 activity, was tested for β-cell proliferation. Treatment of mouse islets with sivelestat increased β-cell proliferation, without a significant effect on the liver, skeletal muscle, visceral and subcutaneous adipose tissue, spleen, or kidney (data not shown), suggesting a β-cell-selective effect. Similar to its effect on mouse islets, sivelestat also increased proliferation of human β-cells (FIG. 14). Thus, small molecules promote β-cell proliferation in human islets transplanted in vivo by targeting two independent pathways.

Example 10. Treat Wild-Type Animals with Zinc-Catalyzed Probes

Human islets under the kidney capsule of 8-week-old NOD-SCIDIL-2rγnull (NSG) model male mice as described are transplanted.[2,23,48,49] Two weeks after transplantation, mice are tested for graft functionality by glucose tolerance tests (GTT) and glucose-stimulated insulin secretion (GSIS). Subsequently, the mice are separated into two groups and treated (n=8 per group) with an intra-peritoneal injection of the ZnPDs linked to 5-IT or sivelestat (starting with 0.625 mg/kg and 0.3 mg/kg, respectively, based on work with unconjugated compounds) dissolved in 50% DMSO twice a week for 12 weeks. Mice that are injected i.p. with DMSO only (vehicle control) and a separate sham-operated cohort serve as controls. Six weeks after the injection, a GTT is performed and the animals are bleed for measuring blood glucose, human insulin and human C-peptide. After 12 weeks, mice are injected daily with BrdU intra-peritoneally (100 mg/kg) for 3 days; 6 h after the final injection, the mice are sacrificed. Islet grafts and the endogenous mouse pancreas are rapidly dissected, fixed and sectioned. The sections from both the grafts and the pancreas are processed. The "n" numbers are determined for statistical significance.

Next, whether the expanded β-cell numbers following treatment with the zinc-catalyzed probes function to correct hyperglycemia is investigated. To this end, effects of injecting the zinc-catalyzed probes on β-cell replication in a diabetic "milieu" are examined by transplanting human islets in the NRG/Akita model that develops spontaneous hyperglycemia.[50] GTT and GSIS tests are performed every 4 weeks; it is also contemplated that the duration of the study is extended for longer than 12 weeks to allow an adequate increase in β-cell numbers to effectively correct the hyperglycemia.

Phenotype Animals and Islets after Treatment.

i. Physiological characterization: Body weights and blood glucose are measured weekly. Blood glucose is measured using a Glucometer Elite. Blood is collected in chilled heparinized tubes, centrifuged, and the supernatant stored at −8° C. for human insulin or C-peptide (Linco ELISA). A fraction of the blood sample in tubes containing aprotinin (10,000 IU/mL) is also collected for detection of glucagon by RIA (Linco). GTT and GSIS are performed using standard protocols.[23,40,51] All experiments are performed in accordance with and following approval by the Joslin IACUC.

ii. Measurement of β-cell mass: Pancreata is rapidly dissected, weighed, fixed in Z-fix and embedded in paraffin. Alterations in β-cell mass are determined using previously described methods. [23,52-56] Briefly, 5 µm sections are immunostained for non-β-cells using a cocktail of antibodies against non-β-cell hormones for 3 h at RT. At least 3 sections separated by 200 µm are obtained from the pancreas and depending on the amount of graft material, at least 2 sections are obtained. Sections are analyzed systematically using a grid covering at least 200 fields/mouse. Relative volumes are calculated for β-cells, non-β-cells and exocrine tissue. Contaminating tissue are recorded to correct for pancreatic weight. β-cell mass is given by the formula=relative β-cell volume X corrected pancreatic weight. [23,40,54,57-59]

iii. Evaluation of β-cell proliferation, neogenesis, and apoptosis: Pancreas and graft sections are fixed in Z-fix overnight, and paraffin-embedded sections are stained for BrdU using anti-BrdU antibody (Amersham). These sections are co-immunostained with antibodies to non-β-cells or β-cells40,58 to determine the proliferating cell type. At least 1000 nuclei are counted, and the positive cells are scored as % of the total number of β-cells counted. In parallel, Ki67 (Pharmingen) or phospho-histone H3 are immunostained for. To examine whether treatment with the small molecules alters neogenesis, sections with antibodies to insulin or glucagon are immunostained. Single and positive cells and a cluster of 8 cells or less are counted and taken as an indication of extra-endocrine neogenesis.[59] Every alternate field at 420 µm final magnification is scored (100 fields/mouse are counted). The presence of apoptosis is assessed using the nonradioactive terminal deoxynucleotidyl transferase-mediated deoxyuridine triphosphate nick end labeling (TUNEL) reagent (Roche). To examine the cell type in which apoptosis is occurring, pancreas sections are immunostained for non-β-cell hormones or for insulin. At least 1000 nuclei are counted, and β-cell apoptosis is expressed as % of counted cells. As an alternative we propidium iodide staining is used.[60] Since TUNEL only identifies cells actively undergoing apoptosis and due to rapid clearance of dead cells, pre-apoptotic cells are determined using anti-activated caspase 3 and 6 antibodies (Upstate).

iv. Evaluation of other tissues: To confirm specificity, in each of the in vivo studies, other metabolic tissues are collected including the liver, white and brown adipose, skeletal muscle, kidney, and brain for alterations in proliferation and apoptosis. A similar approach as in (iii) is adopted to examine % of cells exhibiting growth or cell death.

In studies using the NSG model, the zinc-catalyzed probes will enhance replication of β-cells and promote an increase in human insulin secretion compared to controls. Hyperglycemia will be gradually reversed in the NRG/Akita mice. Limited human islets which cannot be used for transplantations are used for in vitro stimulation studies. The availability of human islets from the IIDP from donors of different ages provides an opportunity to examine effects on proliferation at varied ages. Kulkarni et al. has access to the human EndoC-PH1 cell line,[61,22,40,54] In the event of no reversal of hyperglycemia, a higher dose of the probes, a longer follow-up period are used, or NSG males rendered diabetic by multiple doses of streptozotocin (STZ) are used. [25,62] Human islets from both genders are used to address gender-specific effects. Islets from different aged donors are used, since the ability of β-cells to proliferate is known to change in older humans. [63] For sivelestat which is conjugated to the scaffold via an ester bond, because plasma has significant esterase activity, which may non-specifically release sivelestat, a carbamate linkage is proposed for 5-IT if need. It is worthwhile to note that the ester bond in DA-ZP1 like environment is not easily accessible to esterase as we do not observe non-specific labeling in cells (FIG. 2).

Figure 16:
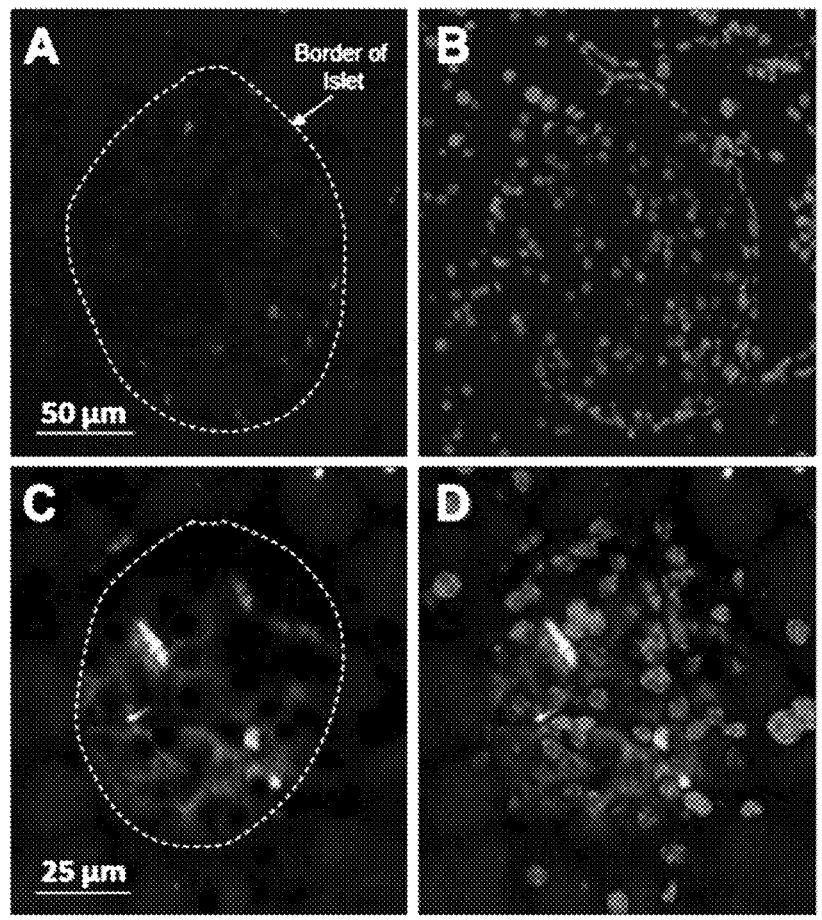
FIG. 16 shows paraffin-embedded sections of islets from mice treated with DMSO (A,B) or DA-ZP1 (C,D).
Figure 17A:
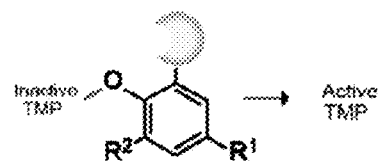
FIG. 17A shows zinc-based prodrug with TMP as cargo.
Figure 17B:
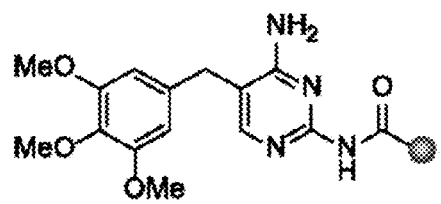
FIG. 17B shows TMP-based Cas9 activator with the point of attachment marked with purple circle.
Figure 17C:
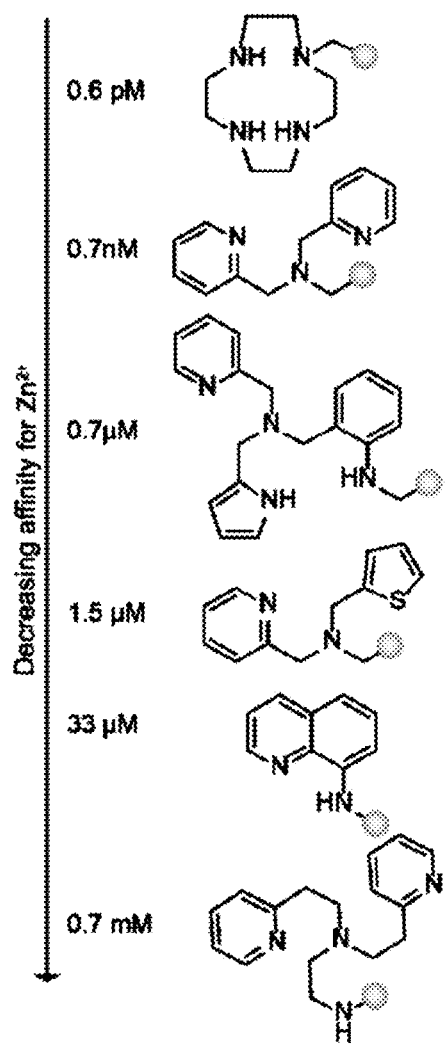
FIG. 17C shows chelating ligands with different affinities for Zn2+. The site of attachment to the scaffold is shown with blue sphere.
Figure 18:
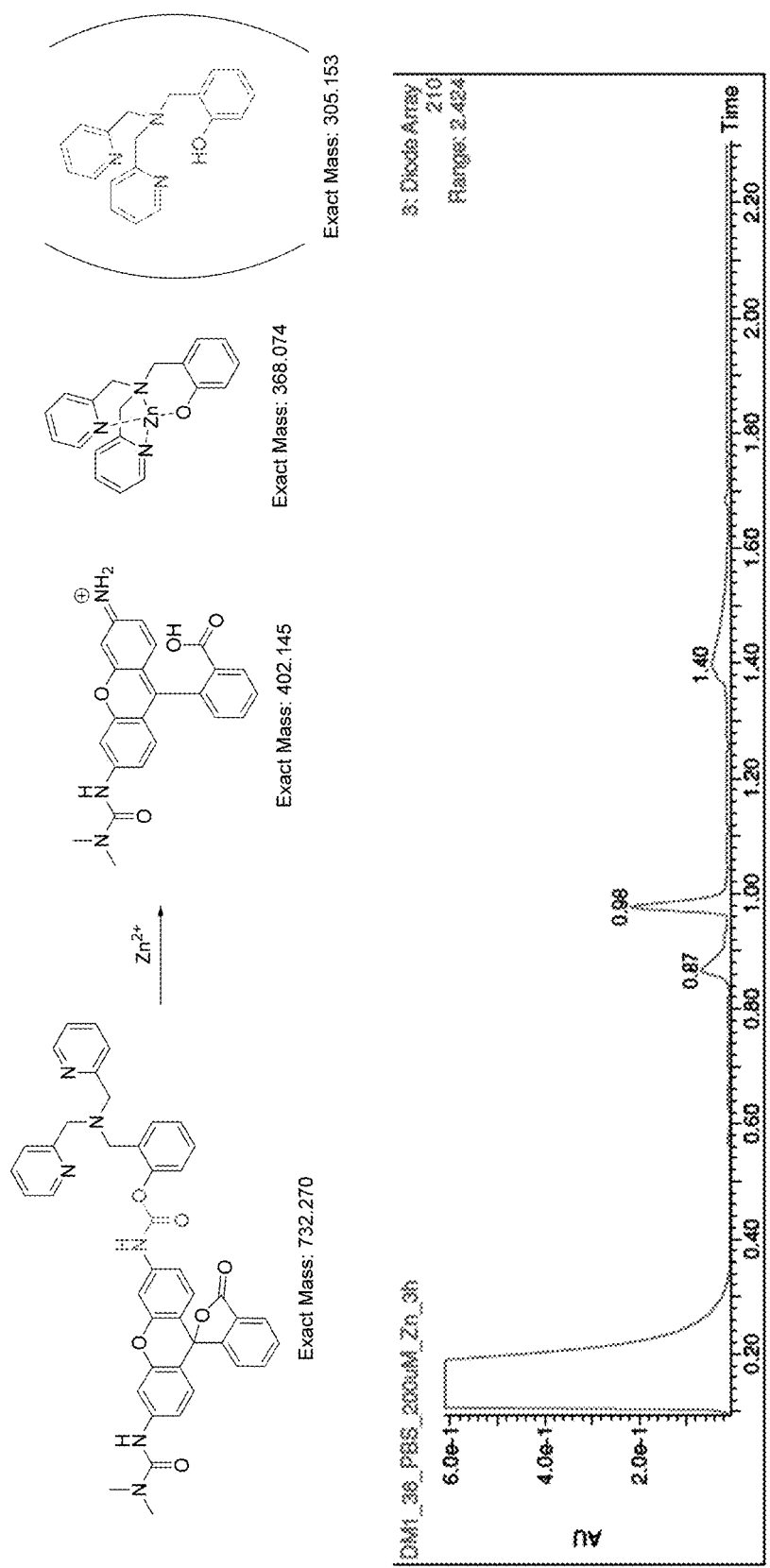
FIG. 18 shows IPLC Chromatogram of samples of Zn2+-catalyzed hydrolysis.
Figure 19:
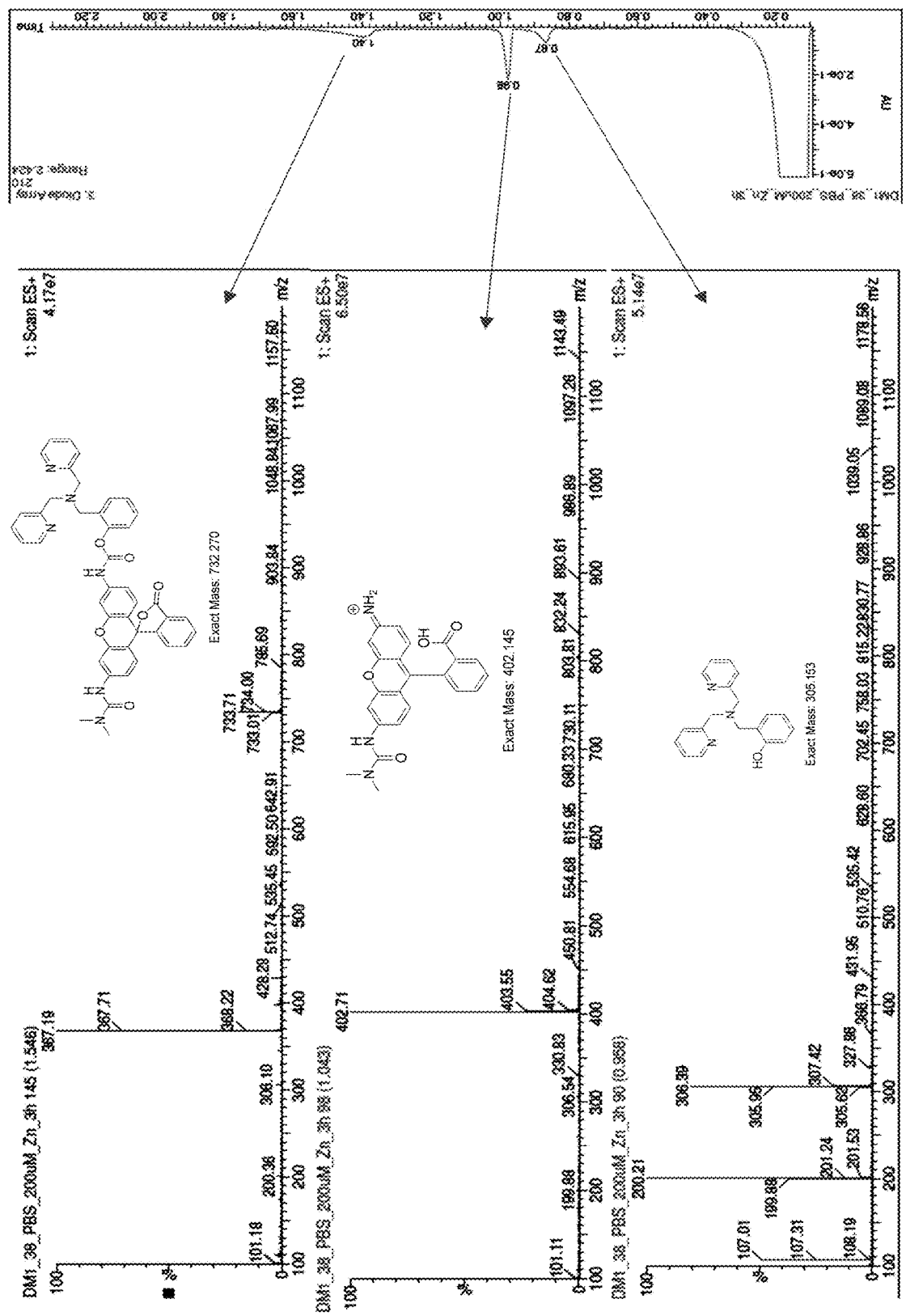
FIG. 19 shows mass spectrometry of the samples of Zn2+-catalyzed hydrolysis.
Figure 20:
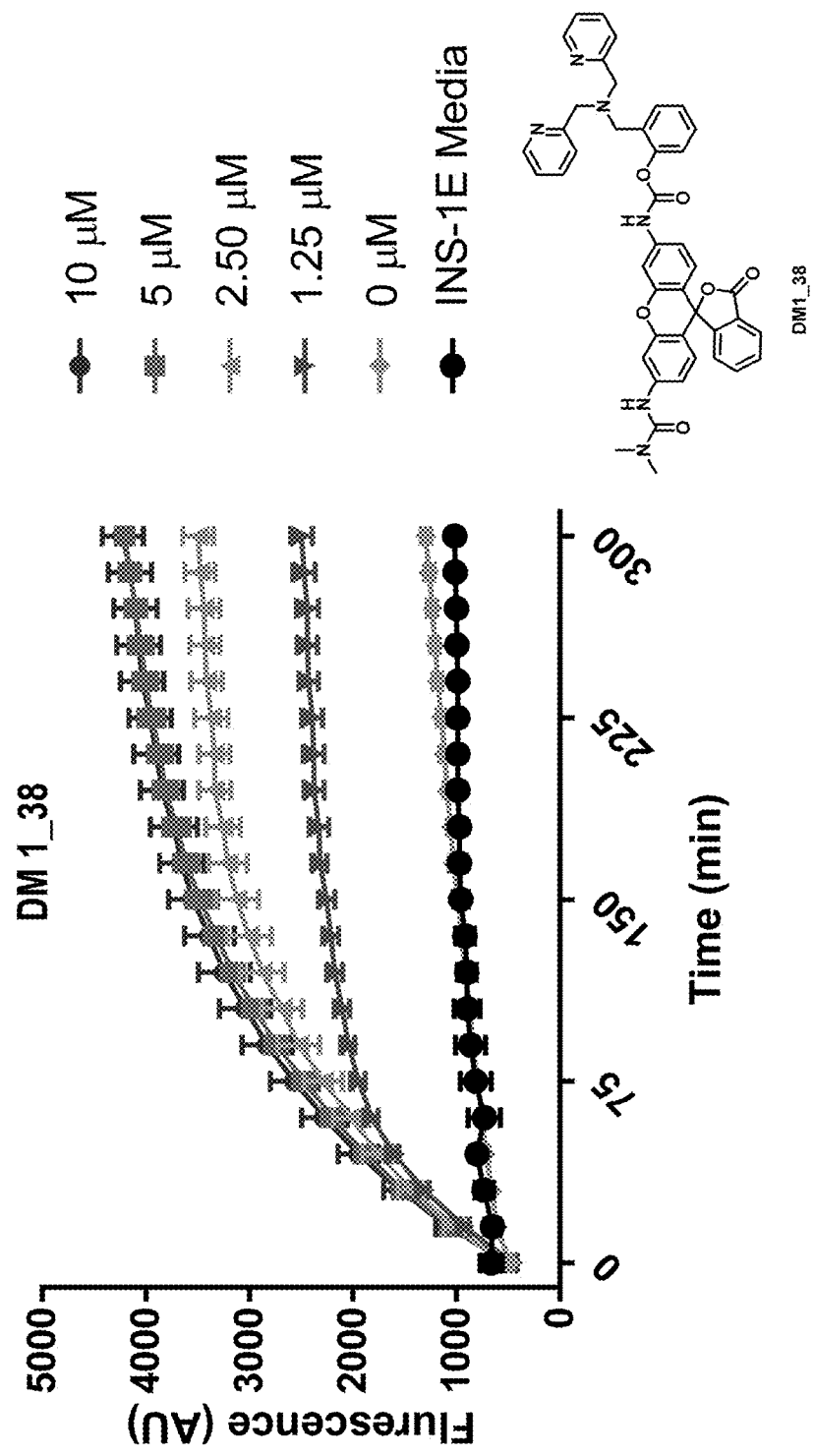
FIG. 20 shows fluorescence spectrum of $Zn^{2+}$-catalyzed hydrolysis of DM1_38 at different concentrations of $Zn^{2+}$ and INS-1E media.
Figure 21:
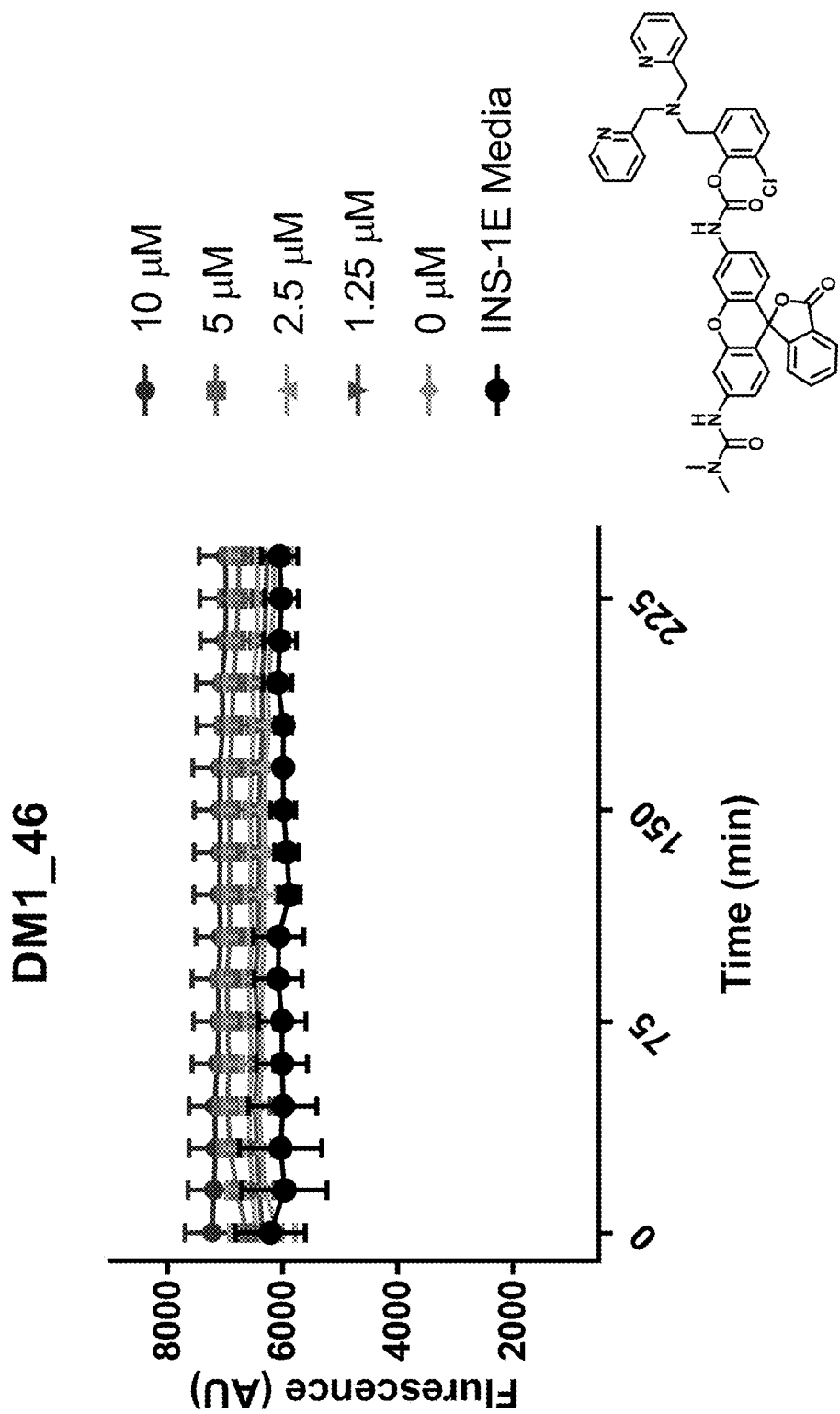
FIG. 21 shows fluorescence spectrum of $Zn^{2+}$-catalyzed hydrolysis of DM1_46 at different concentrations of $Zn^{2+}$ and INS-1E media.
Figure 22:
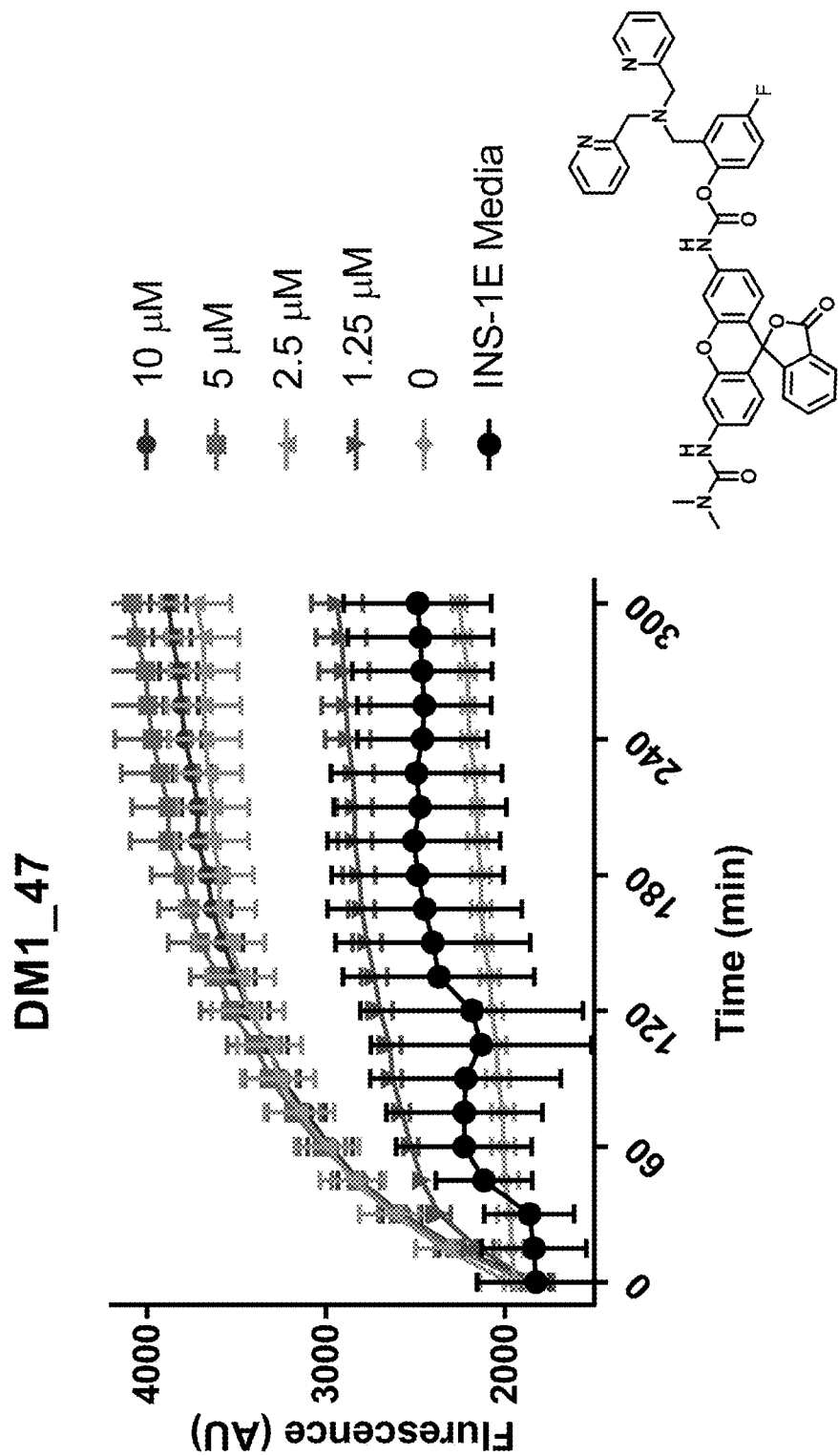
FIG. 22 shows fluorescence spectrum of $Zn^{2+}$-catalyzed hydrolysis of DM1_47 at different concentrations of $Zn^{2+}$ and INS-1E media.
Figure 23:
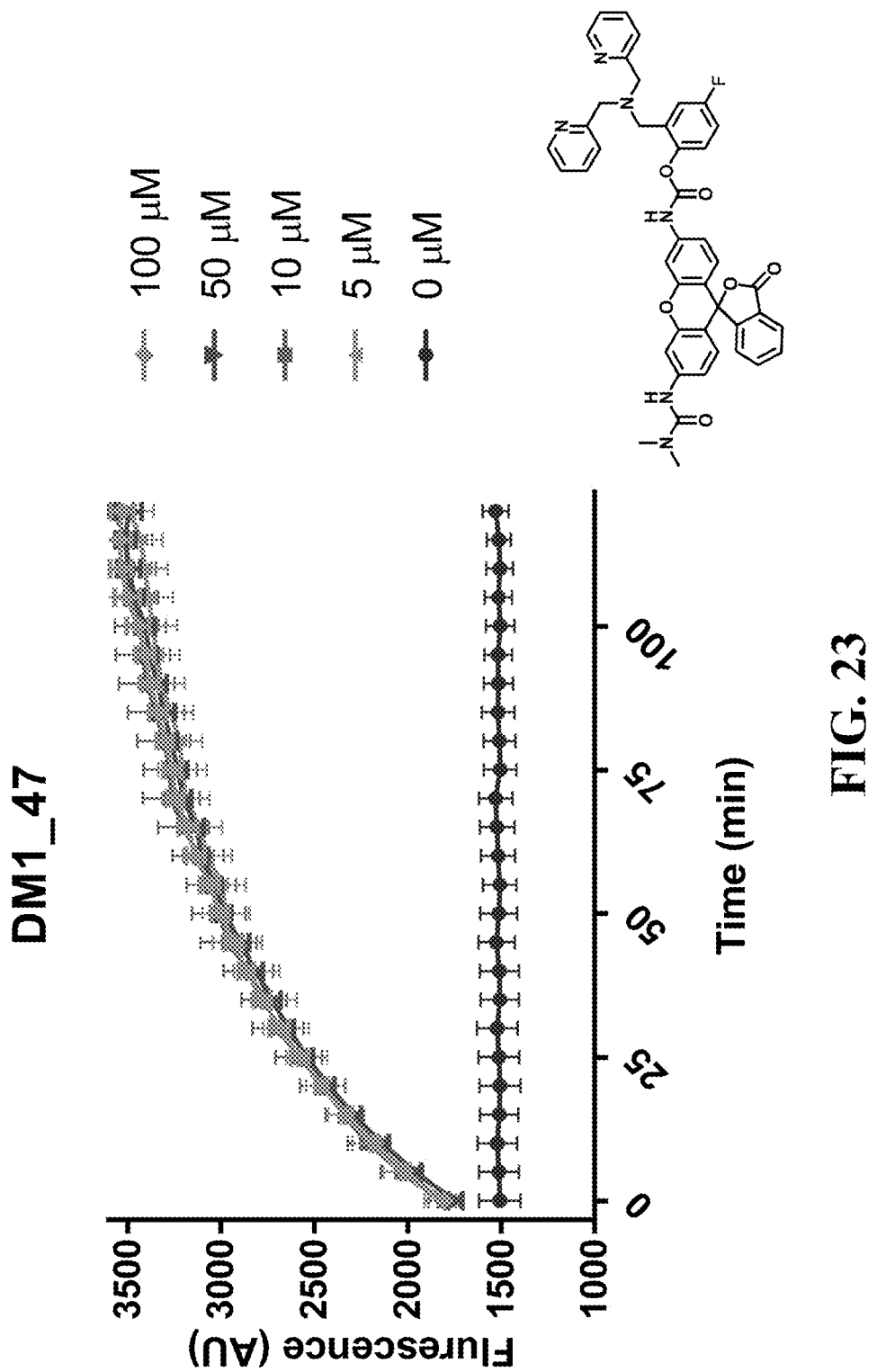
FIG. 23 shows fluorescence spectrum of $Zn^{2+}$-catalyzed hydrolysis of DM1_47 at different concentrations of $Zn^{2+}$.
Figure 24A:
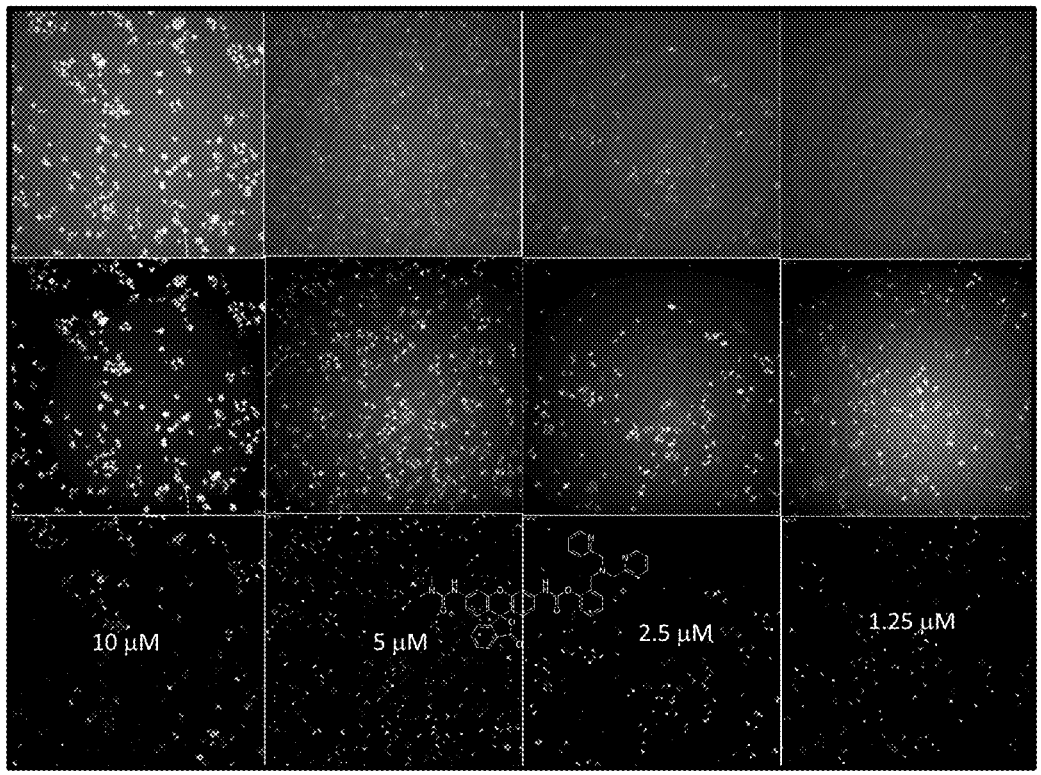
FIG. 24 shows dose-dependent fluorescent cargo release from DM1_38 in INS-1E cells.
Figure 24B:
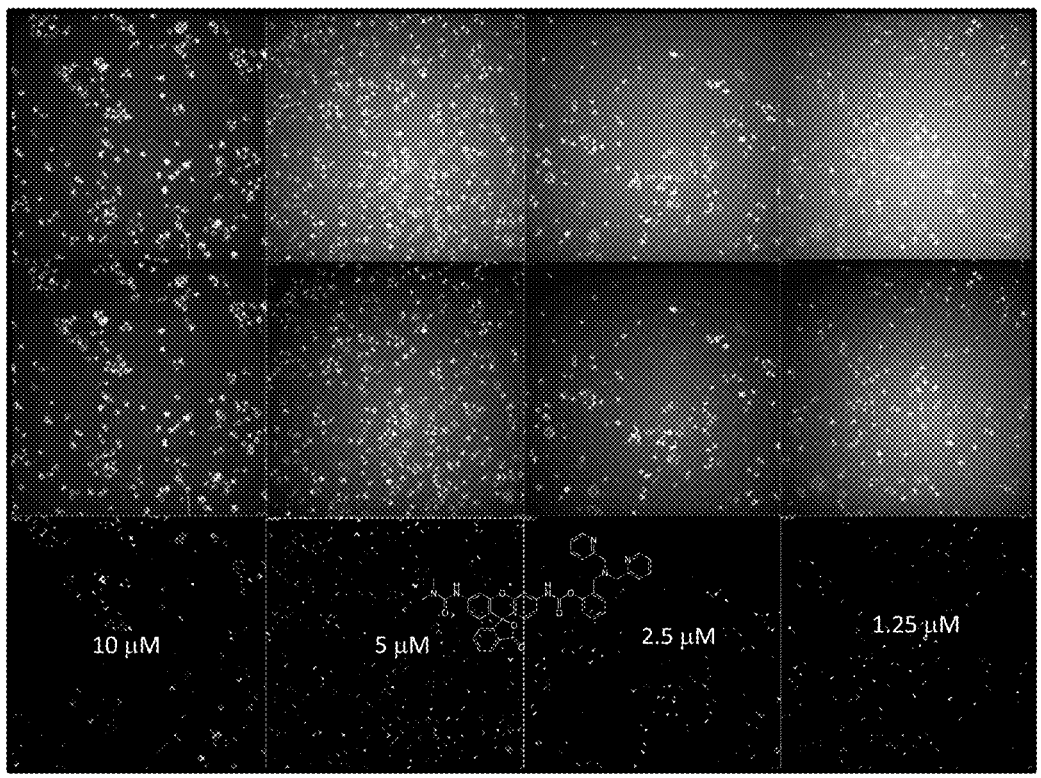
Figure 25:
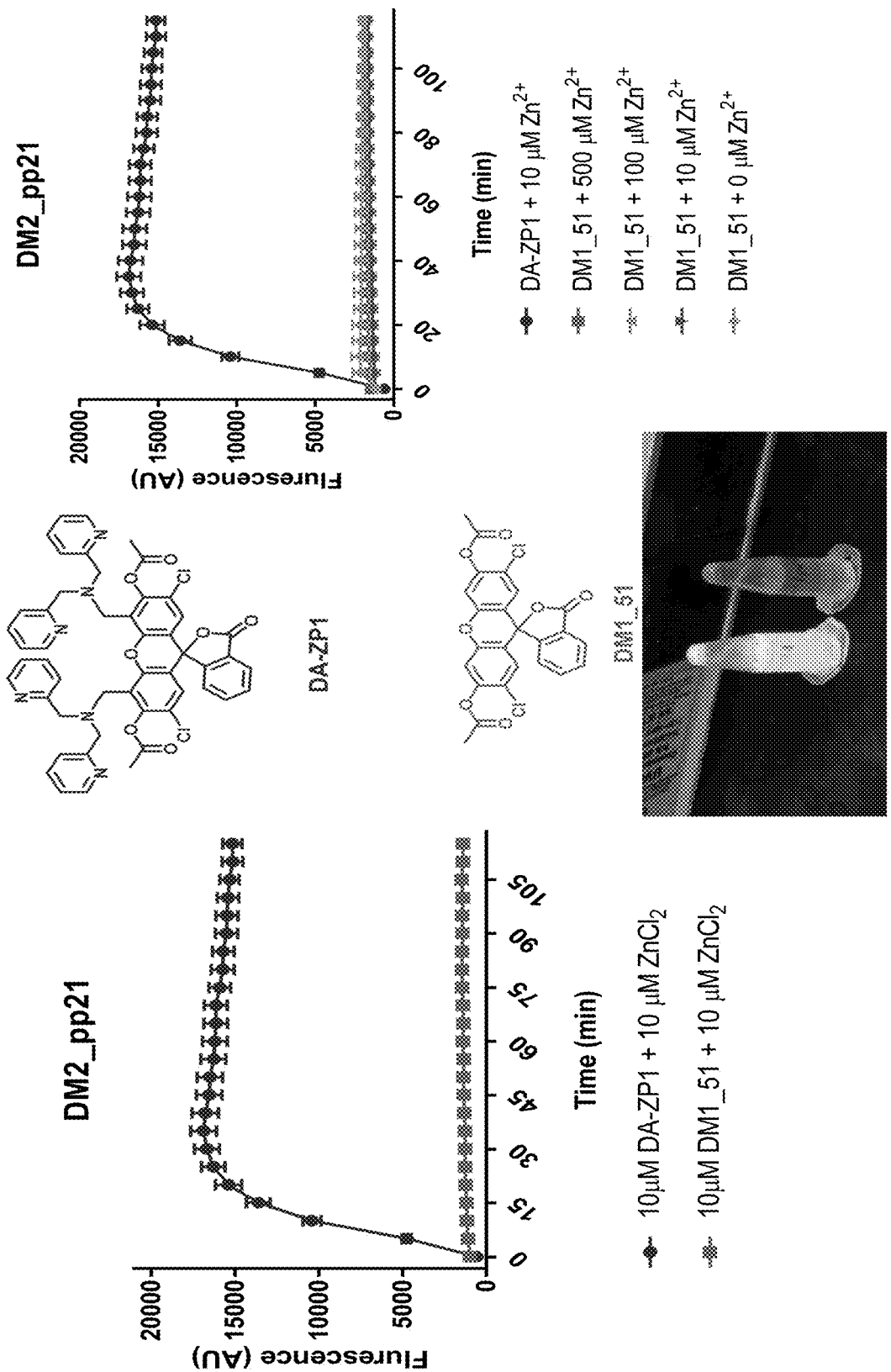
FIG. 25 shows effect of chelating group for $Zn^{2+}$-catalyzed hydrolysis.
Figure 26:
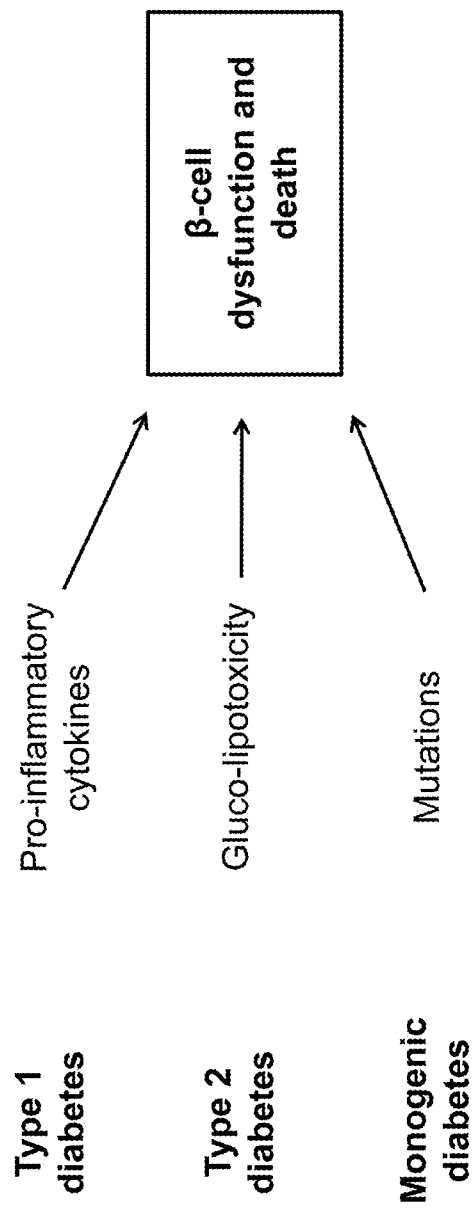
FIG. 26 shows β-cell dysfunction and death as a hallmark of different types of diabetes.
Figure 27:
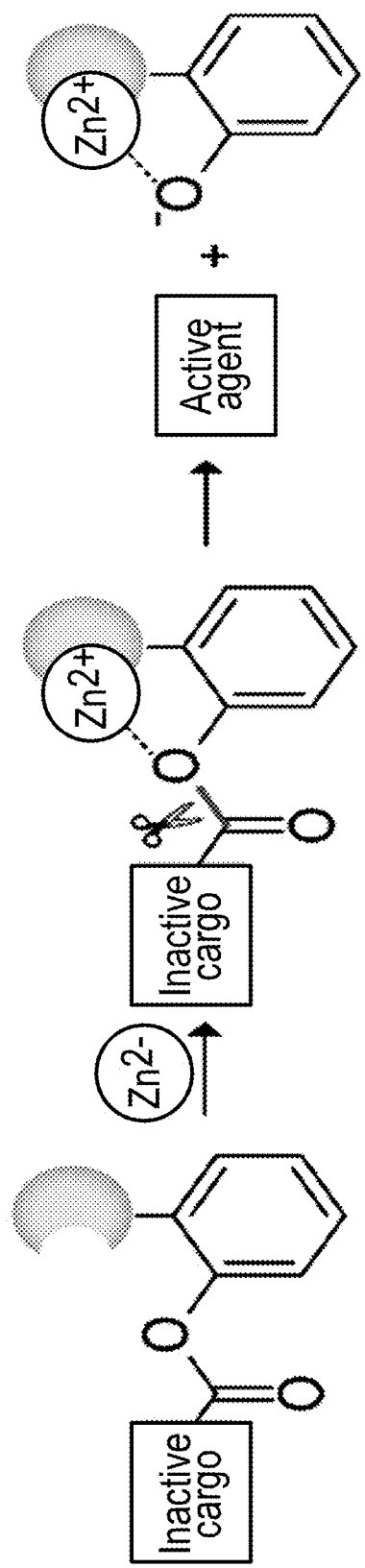
FIG. 27 shows schematic of $Zn^{2+}$-catalyzed cleavage of ester bonds of prodrugs and release of active agents.

Example 11. Synthesis and Biochemical Studies on ZnPDs, Using TMP as Cargo and Ligands with Varying Zn2+ Affinity The reaction-based probe scaffold paired with a cargo release scaffold (FIG. 16A) was synthesized, with cargo, a caged version of TMP (FIG. 16B), the small molecule activator of Cas9 activity that is uncaged upon zinc-catalyzed release from the scaffold. 3-cell-selective release of the active agent requires β-cell-selective cleavage of the scissile bond (FIG. 16A, shown in red). Without being bound by theory, it is believed that such selectivity is attained by fine-tuning the chemical stability of the scissile bond on the cargo release scaffold. The first control site is a Zn2+ chelating ligand (FIG. 16A, shown in blue). A high-affinity Zn2+ chelating ligand will facilitate cargo release but may induce a premature release of the cargo at sites with low Zn2+ concentration. High-affinity ligands can also deplete Zn2+ and may be toxic. On the other hand, a very low-affinity Zn2+ chelating scaffold will reduce the efficiency of scissile bond cleavage and will adversely affect the efficiency of cargo release. Therefore, the optimal affinity is determined to avoid these consequences. To identify the chelating ligand that confers the most β-cell selectivity, a large corpus (>50) of reported Zn2+ ligands with affinities ranging from pM to mM (FIG. 16C) are tested. Que et al., J. Chem. Rev. (2008) 108:1517-1549. Zn2+ ligands with wide-ranging affinities that are compatible with the reaction-based probe system were identified.

The second control of the stability of the scissile bond is through a classic Hammett-type chemistry and will involve positioning appropriate groups at the R1 site (FIG. 16A). Installation of electron-withdrawing groups (—CN, —NO2)

at this site decreases the hydrolytic stability of the bond, while installation of electron-donating groups (—OMe, —NMe2) increases stability. If these two sites fail to provide the desired selectivity, a third control site is employed (labelled as R2, FIG. 16A) that affects bond stability by steric hindrance—a large group prevents the electronic conjugation of the acyl group to the aromatic ring and also hinder water's approach to the reaction site. As a first step, the ligands on the cargo release scaffold (FIG. 16A) are systematically varied with the caged TMP (FIG. 16B) as the cargo. Attachment of TMP to the zinc scaffold through the site shown with purple circle renders TMP inactive. β-cell specificity is tested by quantitating Cas9 activity in over 10 cell lines of various lineages described in FIG. 2B using Next Generation sequencing (NGS) techniques. Maji et al., *Nat. Chem. Biol.* (2017) 13:9-11. Concomitantly with the studies in cell lines, the TMP-bearing ZnPD is tested in human islets. After dissociation of the islet cells with Accutase, cells are seeded on 96-well plates coated with an extracellular matrix derived from the HTB9 bladder carcinoma cell line. Walpita et al., *J. Biomol. Screen.* (2012) (4):509-518; Walpita et al., *Protoc. Chem. Biol.* (2014) 6:157-168. Islets are treated with various concentrations of each ZnPDs following transfection of Cas9 and guide RNA plasmids. Guide RNAs that have been employed various screening libraries are used. After ~72 hrs post-transfection, β- and/or α-cells are sorted before extracting their genomic DNA before performing NGS experiments. The calculation of percent cells with insertion/deletion (indel) in the β-cells compared to other cells shows the specificity and sensitivity of the various zinc affinities of each ligand. It is important to balance between high sensitivity, where indel is induce in every β-cell in the culture system, with high specificity, where inducing indels in non-β-cells is refrained from in the culture system. An acyl-imidazole-based zinc-scaffold is also contemplated where $Zn^{2+}$ catalyzes the hydrolysis of a carbamate bond. Miki et al., *Nat. Methods* (2016) 13(11): 931-937.

Example 12. β-Cell Selective Genome Editing In Vivo

CRISPR mediated gene knockout in several systems has been reported.[17,18] Specifically, CRISPR is delivered via adeno-associated virus (AAV) using Cas9 packaged in the AAV and programmed to target the p16ink4a genomic locus. After generating the plasmids targeting Ai9 and p16ink4a loci, AAVs encoding Cas9 and Ai9 gRNAS or p16ink4a gRNAS in a dual vector system using the Gene Transfer Vector Core (Schepens Eye Research Institute, Boston) is constructed. AAV9 is available from U Penn Vector Core. Dual AAV vectors (and vehicle) are injected intra-peritoneally in 10-week-old male C57Bl/6 mice. The animals are followed after 3-4 weeks and the pancreas harvested for immunohistochemistry.

Sections for markers of proliferation and cell death are examined using methods routinely available. El Ouaamari et al., *Cell Metabolism*, (2016) 19:194-205; Dirice et al., *Diabetes* (2016) 65(6):1660-1671. To confirm the specificity of Cas9 activation, other metabolic tissues are collected including the liver, white and brown adipose, skeletal muscle, kidney, and brain for alterations in proliferation and apoptosis. Further, genomic DNA is extracted and determined for indels in these tissues.

$Zn^{2+}$, while mostly present at pM levels in tissues, is present at significant levels in mammary, prostate, and neuronal tissue, which may result in off-site Cas9 activation. However, the fluorescence signal from a breast cancer cell line (4T1) is very low compared to that of β-cells (FIG. 2B). Thus, the ZnPDs of the present invention will work well. The concentration of $Zn^{2+}$ in the interstitial space during insulin secretion is considerably high (~10 μM), which may also trigger premature cargo release. To avoid such scenarios, in some embodiments, low-glucose conditions are used. In some embodiments, protein-bound catalytic $Zn^{2+}$ can be stripped by highly potent ligands, and which will not be used. There is significant heterogeneity in the concentration of $Zn^{2+}$ in β-cells in islets. For example, dysfunctional or dedifferentiated β-cells do not have very high $Zn^{2+}$ and the delivery system may not work in these cells. Thus, smaller Cas9 variants are also contemplated (e.g., SaCas9).

REFERENCES

1. El Ouaamari A, Dirice E, Gedeon N, Hu J, Zhou J Y, Shirakawa J, Hou L, Goodman J, Karampelias C, Qiang G, Boucher J, Martinez R, Gritsenko M A, De Jesus D F, Kahraman S, Bhatt S, Smith R D, Beer H D, Jungtrakoon P, Gong Y, Goldfine A B, Liew C W, Doria A, Andersson O, Qian W J, Remold-O'Donnell E, Kulkarni R N. SerpinB1 promotes pancreatic β-cell proliferation. (2016) Cell Metabolism 23: 194-205.
2. Dirice E, Walpita D, Vetere A, Meier B C, Kahraman S, Hu J, Dancik V, Burns S M, Gilbert T J, Olson D E, Clemons P A, Kulkarni R N, Wagner B K. Inhibition of DYRK1A stimulates human beta-cell proliferation. (2016) Diabetes 65:1660-1671.
3. Li Y V. Zinc and insulin in pancreatic beta-cells. (2014) Endocrine 45: 178-189.
4. Wang P, Alvarez-Perez J C, Felsenfeld D P, Liu H, Sivendran S, Bender A, Kumar A, Sanchez R, Scott D K, Garcia-Ocana A, Stewart A F. (2015) A high-throughput chemical screen reveals that harmine-mediated inhibition of DYRK1A increases human pancreatic beta cell replication. Nat Med 21: 383-388.
5. Shen W, Taylor B, Jin Q, Nguyen-Tran V, Meeusen S, Zhang Y Q, Kamireddy A, Swafford A, Powers A F, Walker J, Lamb J, Bursalaya B, DiDonato M, Harb G, Qiu M, Filippi C M, Deaton L, Turk C N, Suarez-Pinzon W L, Liu Y, Hao X, Mo T, Yan S, Li J, Herman A E, Hering B J, Wu T, Martin Seidel H, McNamara P, Glynne R, Laffitte B. (2015) Inhibition of DYRK1A and GSK3B induces human β-cell proliferation. Nat Comm 6: 8372.
6. Shapiro A M, Lakey J R, Ryan E A, Korbutt G S, Toth E, Warnock G L, Kneteman N M, Rajotte R V. (2000) Islet transplantation in seven patients with type 1 diabetes mellitus using a glucocorticoid-free immunosuppressive regimen. N Engl J Med 343: 230-238.
7. Shapiro A M, Ricordi C, Hering B J, Auchincloss H, Lindblad R, Robertson R P, Secchi A, Brendel M D, Berney T, Brennan D C, Cagliero E, Alejandro R, Ryan E A, DiMercurio B, Morel P, Polonsky K S, Reems J A, Bretzel R G, Bertuzzi F, Froud T, Kandaswamy R, Sutherland D E, Eisenbarth G, Segal M, Preiksaitis J, Korbutt G S, Barton F B, Viviano L, Seyfert-Margolis V, Bluestone J, Lakey J R. (2006) International trial of the Edmonton protocol for islet transplantation. N Engl J Med 355: 1318-1330.
8. Meier J J, Butler A E, Saisho Y, Monchamp T, Galasso R, Bhushan A, Rizza R A, Butler P C. (2008) β-cell replication is the primary mechanism subserving the postnatal expansion of β-cell mass in humans. Diabetes 57: 1584-1594.

9. Keenan H A, Sun J K, Levine J, Doria A, Aiello L P, Eisenbarth G, Bonner-Weir S, King G L. (2010) Residual insulin production and pancreatic ss-cell turnover after 50 years of diabetes: Joslin Medalist Study. Diabetes 59: 2846-2853.
10. Oram R A, Jones A G, Besser R E, Knight B A, Shields B M, Brown R J, Hattersley A T, McDonald T J. (2014) The majority of patients with long-duration type 1 diabetes are insulin microsecretors and have functioning beta cells. Diabetologia 57: 187-191.
11. Rautio J, Kumpulainen H, Heimbach T, Oliyai R, Oh D, Jarvinen T, Savolainen J. (2008) Prodrugs: design and clinical applications. Nat Rev Drug Discov 7: 255-270.
12. Meunier B, Robert A. (2010) Heme as trigger and target for trioxane-containing antimalarial drugs. Acc Chem Res 43: 1444-1451.
13. Li, Y. V., Zinc and insulin in pancreatic beta-cells. Endocrine, (2014). 45: 178-89.
14. Bozym, R. A., et al., Free zinc ions outside a narrow concentration range are toxic to a variety of cells in vitro. Exp Biol Med (Maywood), (2010). 235: 741-50.
15. Ichii H, Inverardi L, Pileggi A, Molano R D, Cabrera O, Caicedo A, Messinger S, Kuroda Y, Berggren P O, Ricordi C. (2005) A novel method for the assessment of cellular composition and beta-cell viability in human islet preparations. Am J Transplant 5: 1635-1645.
16. Lukowiak B, Vandewalle B, Riachy R, Kerr-Conte J, Gmyr V, Belaich S, Lefebvre J, Pattou F. (2001) Identification and purification of functional human beta-cells by a new specific zinc-fluorescent probe. J Histochem Cytochem 49: 519-528.
17. Laurent D, Vinet L, Lamprianou S, Daval M, Filhoulaud G, Ktorza A, Wang H, Sewing S, Juretschke H P, Glombik H, Meda P, Boisgard R, Nguyen D L, Stasiuk G J, Long N J, Montet X, Hecht P, Kramer W, Rutter G A, Hecksher-Sorensen J. (2016) Pancreatic (3-cell imaging in humans: fiction or option? Diab Obes Metab 18: 6-15.
18. Wadman M. (2010) 'Cure acceleration' funds woven into health reform legislation. Nat Med 16:135.
19. Chou D H-C, Vetere A, Choudhary A, Scully S S, Schenone M, Tang A, Gomez R, Burns S M, Lundh M, Vital T, Comer E, Faloon P W, Dancik V, Ciarlo C, Paulk J, Dai M, Reddy C, Sun H, Young M, Donato N, Jaffe, JD, Clemons P A, Palmer M A, Carr S A, Schreiber S L, Wagner B K. (2015) Kinase-independent small-molecule inhibition of JAK-STAT signaling. J Am Chem Soc 137: 7929-7934.
20. Fomina-Yadlin D, Kubicek S, Walpita D, Dancik V, Hecksher-Sorensen J, Bittker J A, Sharifnia T, Shamji A, Clemons P A, Wagner B K, and Schreiber S L. (2010) Small-molecule inducers of insulin expression in pancreatic alpha cells. Proc Natl Acad Sci USA 107: 15099-15104.
21. Yuan Y, Hartland K, Boskovic Z, Wang Y, Walpita D, Lysy P A, Zhong C, Young D W, Kim Y K, Tolliday N J, Sokal E M, Schreiber S L, Wagner B K. (2013) A small-molecule inducer of PDX1 expression identified by high-throughput screening. Chem Biol 20: 1513-1522.
22. Wagner F F, Lundh M, Kaya T, McCarren P, Zhang Y L, Chattopadhyay S, Gale J P, Galbo T, Fisher S L, Meier B C, Vetere A, Richardson S, Morgan N G, Christensen D P, Gilbert T J, Hooker J M, Leroy M, Walpita D, Mandrup-Poulsen T, Wagner B K, Holson E B. (2016) An isochemogenic set of inhibitors to define the therapeutic potential of histone deacetylases in β-cell protection. ACS Chem Biol 11: 363-374.
23. Assmann A, Hinault C, Kulkarni R N. (2009) Growth factor control of pancreatic islet regeneration and function. Pediatr Diabetes 10: 14-32.
24. Flier S N, Kulkarni R N, Kahn C R. (2001) Evidence for a circulating islet cell growth factor in insulin-resistant states. Proc Natl Acad Sci USA 98: 7475-7480.
25. El Ouaamari A, Kawamori D, Dirice E, Liew C W, Shadrach J L, Hu J, Katsuta H, Hollister-Lock J, Qian W J, Wagers A J, Kulkarni R N. (2013) Liver-derived systemic factors drive β-cell hyperplasia in insulin-resistant states. Cell Rep 3: 401-410.
26. Dirice E, Kahraman S, Jiang W, El O A, De Jesus D F, Teo A K, Hu J, Kawamori D, Gaglia J L, Mathis D, Kulkarni R N. (2014) Soluble factors secreted by T cells promote (3-cell proliferation. Diabetes 63: 188-202.
27. Dhawan S, Dirice E, Kulkarni R N, Bhushan A. (2016) Inhibition of TGF-β signaling promotes human pancreatic β-cell replication. Diabetes 65: 1208-18.
28. Bhatt S, Gupta M K, Khamaisi M, Martinez R, Gritsenko M A, Wagner B K, Guye P, Busskamp V, Shirakawa J, Wu G, Liew C W, Clauss T R, Valdez I, El Ouaamari A, Dirice E, Takatani T, Keenan H A, Smith R D, Church G, Weiss R, Wagers A J, Qian W J, King G L, Kulkarni R N. (2015) Preserved DNA damage checkpoint pathway protects against complications in long-standing type 1 diabetes. Cell Metab. 22: 239-52.
29. Zastrow M L, Radford R J, Chyan W, Anderson C T, Zhang D Y, Loas A, Tzounopoulos T, Lippard S J. (2016) Reaction-based probes for imaging mobile zinc in live cells and tissues. ACS Sensors 1: 32-39.
30. Que E L, Domaille D W, Chang C J. (2008) Metals in neurobiology: probing their chemistry and biology with molecular imaging. Chem Rev 108: 1517-1549.
31. Maolanon A R, Madsen A S, Olsen C A. (2016) Innovative strategies for selective inhibition of histone deacetylases. Cell Chem Biol 23: 759-68.
32. Lavis, L. D., T. Y. Chao, and R. T. Raines, Fluorogenic label for biomolecular imaging. ACS Chem Biol, 2006. 1: 252-60.
33. Walpita D, Hasaka T, Spoonamore J, Vetere A, Takane K K, Fomina-Yadlin D, Fiaschi-Taesch N, Shamji A, Clemons P A, Stewart A F, Schreiber S L, and Wagner B K. (2012) A human islet cell-culture system for high-throughput screening. J Biomol Screen 17: 509-518.
34. Walpita D, Wagner B K. (2014) Evaluation of compounds in primary human islet cell culture. Curr Prot Chem Biol 6: 157-168.
35. Wagner, F. F., et al., An Isochemogenic Set of Inhibitors To Define the Therapeutic Potential of Histone Deacetylases in 3-Cell Protection. ACS Chemical Biology, (2016) 11: 363-374.
36. Franklin, R. B., et al., Zinc and zinc transporters in normal prostate and the pathogenesis of prostate cancer. Front Biosci, (2005). 10: 2230-9.
37. Reiner T, Thurber G, Gaglia J, Vinegoni C, Liew C W, Upadhyay R, Kohler R H, Li L, Kulkarni R N, Benoist C, Mathis D, Weissleder R. (2011) Accurate measurement of pancreatic islet beta-cell mass using a second-generation fluorescent exendin-4 analog. Proc Natl Acad Sci USA 108: 12815-12820.
38. Annes J P, Ryu J H, Lam K, Carolan P J, Utz K, Hollister-Lock J, Arvanites A C, Rubin L L, Weir G, Melton D A. (2012) Adenosine kinase inhibition selectively promotes rodent and porcine islet β-cell replication. Proc Natl Acad Sci USA 109: 3915-3920.
39. Jarvis M F, Yu H, Kohlhaas K, Alexander K, Lee C H, Jiang M, Bhagwat S S, Williams M, Kowaluk E A. (2000)

ABT-702 (4-amino-5-(3-bromophenyl)-7-(6-morpholino-pyridin-3-yl)pyrido[2, 3-d]pyrimidine), a novel orally effective adenosine kinase inhibitor with analgesic and anti-inflammatory properties: I. In vitro characterization and acute antinociceptive effects in the mouse. J Pharmacol Exp Ther 295: 1156-1164.
40. Michael M D, Kulkarni R N, Postic C, Previs S F, Shulman G I, Magnuson M A, Kahn C R. (2000) Loss of insulin signaling in hepatocytes leads to severe insulin resistance and progressive hepatic dysfunction. Mol Cell 6: 87-97.
41. Tranoy-Opalinski I, Fernandes A, Thomas M, Gesson J P, Papot S. (2008) Design of self-self-immolative linkers for tumour-activated prodrug therapy. Anticancer Agents Med Chem 8: 618-37.
42. Shultz L D, Lyons B L, Burzenski L M, Gott B, Chen X, Chaleff S, Kotb M, Gillies S D, King M, Mangada J, Greiner D L, Handgretinger R. (2005) Human lymphoid and myeloid cell development in NOD/LtSz-scid IL2R gamma null mice engrafted with mobilized human hemopoietic stem cells. J Immunol 174: 6477-6489.
43. Greiner D L, Hesselton R A, Shultz L D. (1998) SCID mouse models of human stem cell engraftment. Stem Cells 16: 166-177.
44. King M, Pearson T, Shultz L D, Leif J, Bottino R, Trucco M, Atkinson M A, Wasserfall C, Herold K C, Woodland R T, Schmidt M R, Woda B A, Thompson M J, Rossini A A, Greiner D L. (2008) A new Hu-PBL model for the study of human islet alloreactivity based on NOD-scid mice bearing a targeted mutation in the IL-2 receptor gamma chain gene. Clin Immunol 126: 303-314.
45. Whitfield-Larry F, Young E F, Talmage G, Fudge E, Azam A, Patel S, Largay J, Byrd W, Buse J, Calikoglu A S, Shultz L D, Frelinger J A. (2011) HLA-A2-matched peripheral blood mononuclear cells from type 1 diabetic patients, but not nondiabetic donors, transfer insulitis to NOD-scid/gamma(null)/HLA-A2 transgenic mice concurrent with the expansion of islet-specific CD8+ T cells. Diabetes 60: 1726-1733.
46. Agliano A, Martin-Padura I, Mancuso P, Marighetti P, Rabascio C, Pruneri G, Shultz LD, Bertolini F. (2008) Human acute leukemia cells injected in NOD/LtSz-scid/IL-2Rgamma null mice generate a faster and more efficient disease compared to other NOD/scid-related strains. Int J Cancer 123: 2222-2227.
47. Levitt H E, Cyphert T J, Pascoe J L, Hollern D A, Abraham N, Lundell R J, Rosa T, Romano L C, Zou B, O'Donnell C P, Stewart A F, Garcia-Ocana A, Alonso L C. (2011) Glucose stimulates human β-cell replication in vivo in islets transplanted into NOD-severe combined immunodeficiency (SCID) mice. Diabetologia 54: 572-582.
48. Fiaschi-Taesch N M, Berman D M, Sicari B M, Takane K K, Garcia-Ocana A, Ricordi C, Kenyon N S, Stewart A F. (2008) Hepatocyte growth factor enhances engraftment and function of nonhuman primate islets. Diabetes 57: 2745-54.
49. Racki W J, Covassin L, Brehm M, Pino S, Ignotz R, Dunn R, Laning J, Graves S K, Rossini A A, Shultz L D, Greiner D L. (2010) NOD-scid IL2rgamma(null) mouse model of human skin transplantation and allograft rejection. Transplantation 89: 527-536.
50. Pearson T, Shultz L D, Lief J, Burzenski L, Gott B, Chase T, Foreman O, Rossini A A, Bottino R, Trucco M, Greiner D L. (2008) A new immunodeficient hyperglycaemic mouse model based on the Ins2Akita mutation for analyses of human islet and beta stem and progenitor cell function. Diabetologia. 51: 1449-56.
51. Ueki K, Okada T, Hu J, Liew C W, Assmann A, Dahlgren G M, Peters J L, Shackman J G, Zhang M, Artner I, Satin L S, Stein R, Holzenberger M, Kennedy R T, Kahn C R, Kulkarni R N. (2006) Total insulin and IGF-I resistance in pancreatic β-cells causes overt diabetes. Nat Genet 38: 583-588.
52. Davalli A M, Ogawa Y, Ricordi C, Scharp D W, Bonner-Weir S, Weir G C. (1995) A selective decrease in the β-cell mass of human islets transplanted into diabetic nude mice. Transplantation 59: 817-820.
53. Montana E, Bonner-Weir S, Weir G C. (1993) Beta-cell mass and growth after syngeneic islet cell transplantation in normal and streptozotocin diabetic C57BL/6 mice. J Clin Invest 91: 780-787.
54. Kulkarni R N, Almind K, Goren H J, Winnay I N, Ueki K, Okada T, Kahn C R. (2003) Impact of genetic background on development of hyperinsulinemia and diabetes in insulin receptor/insulin receptor substrate-1 double heterozygous mice. Diabetes 52: 1528-1534.
55. Weibel E R. (1969) Stereological principles for morphometry in electron microscopic cytology. Int Rev Cytol 26: 235-302.
56. Montana E, Bonner Weir S, Weir G C. (1994) Transplanted β-cell response to increased metabolic demand. Changes in β-cell replication and mass. J Clin Invest 93: 1577-1582.
57. Kulkarni R N, Holzenberger M, Shih D Q, Ozcan U, Stoffel M, Magnuson M A, Kahn C R. (2002) β-cell-specific deletion of the Igf1 receptor leads to hyperinsulinemia and glucose intolerance but does not alter β-cell mass. Nat Genet 31: 111-115.
58. Kulkarni R N, Winnay J N, Daniels M, Bruning J C, Flier S N, Hanahan D, Kahn C R. (1999) Altered function of insulin receptor substrate-1-deficient mouse islets and cultured β-cell lines. J Clin Invest 104: R69-R75.
59. Xu G, Stoffers D A, Habener J F, Bonner-Weir S. (1999) Exendin-4 stimulates both β-cell replication and neogenesis, resulting in increased β-cell mass and improved glucose tolerance in diabetic rats. Diabetes 48: 2270-2276.
60. Trivedi N, Hollister-Lock J, Lopez-Avalos M D, O'Neil J J, Keegan M, Bonner-Weir S, Weir G C. (2001) Increase in beta-cell mass in transplanted porcine neonatal pancreatic cell clusters is due to proliferation of beta-cells and differentiation of duct cells. Endocrinology 142: 2115-22.
61. Ravassard P, Hazhouz Y, Pechberty S, Bricout-Neveu E, Armanet M, Czernichow P, Scharfmann R. (2011) A genetically engineered human pancreatic β-cell line exhibiting glucose-inducible insulin secretion. J Clin Invest 121: 3589-3597.
62. Yin D, Tao J, Lee D D, Shen J, Hara M, Lopez J, Kuznetsov A, Philipson L H, Chong A S. (2006) Recovery of islet β-cell function in streptozotocin-induced diabetic mice: an indirect role for the spleen. Diabetes 55:3256-3263.
63. Gregg B E, Moore P C, Demozay D, Hall B A, Li M, Husain A, Wright A J, Atkinson M A, Rhodes C J. (2012) Formation of a human β-cell population within pancreatic islets is set early in life. J Clin Endocrinol Metab 97: 3197-3206.

Example 13. Synthesis of Additional Prodrugs

Figure 28:
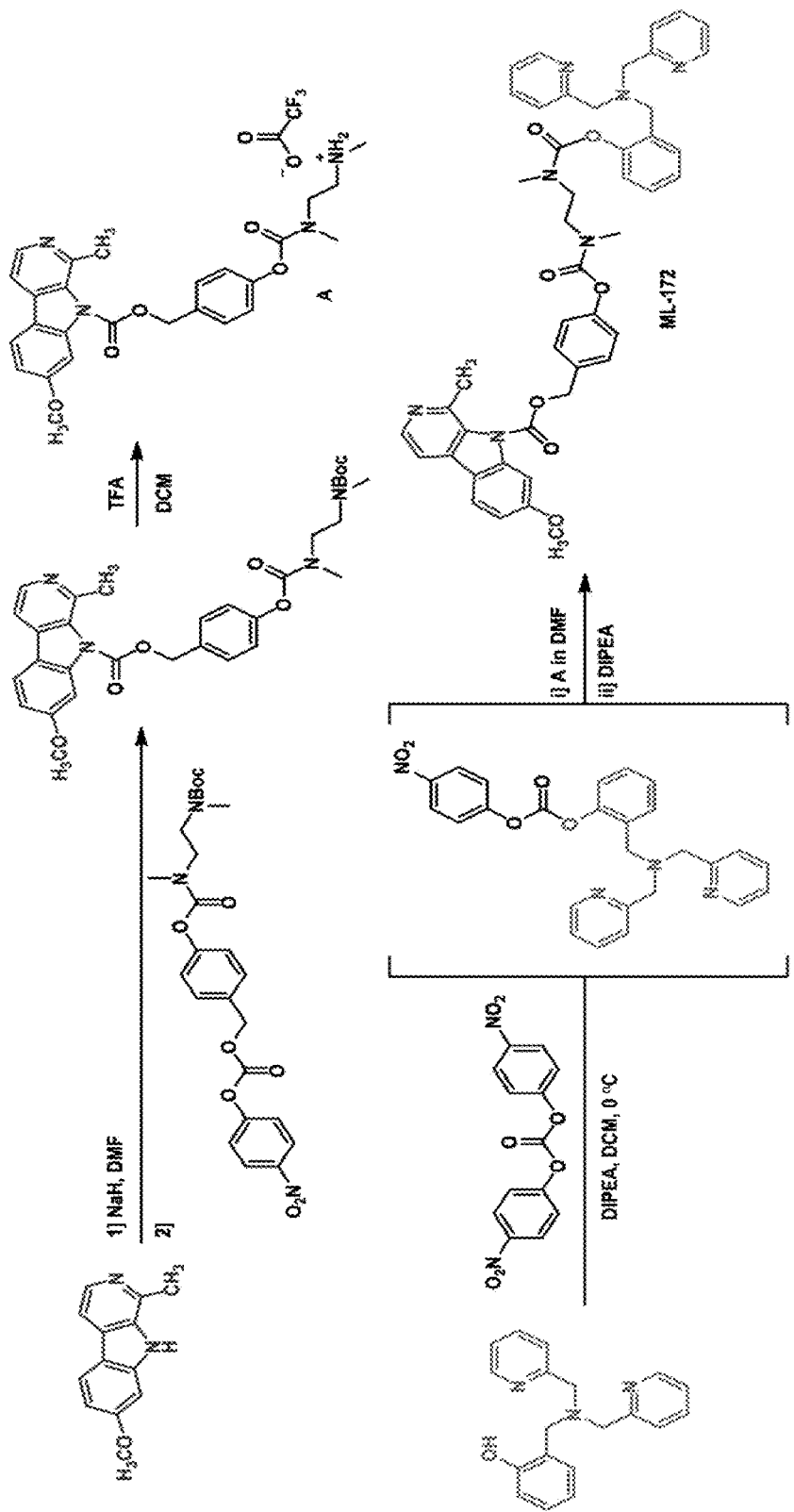
FIG. 28 shows a synthesis scheme for prodrug ML-172.

As shown in FIG. 28, prodrug ML-172 has been synthesized which comprises a cargo group (harmine), a chelating ligand, and a self-immolative linker. The self-immolative linker is covalently linked to the chelating ligand via a first carbamate group, is covalently linked to the cargo group via a second carbamate group, and further comprises (i) an aromatic ring between the first and second carbamate group which improves stability and (ii) a third carbamate group between the aromatic ring and the first carbamate group.

Figure 29:
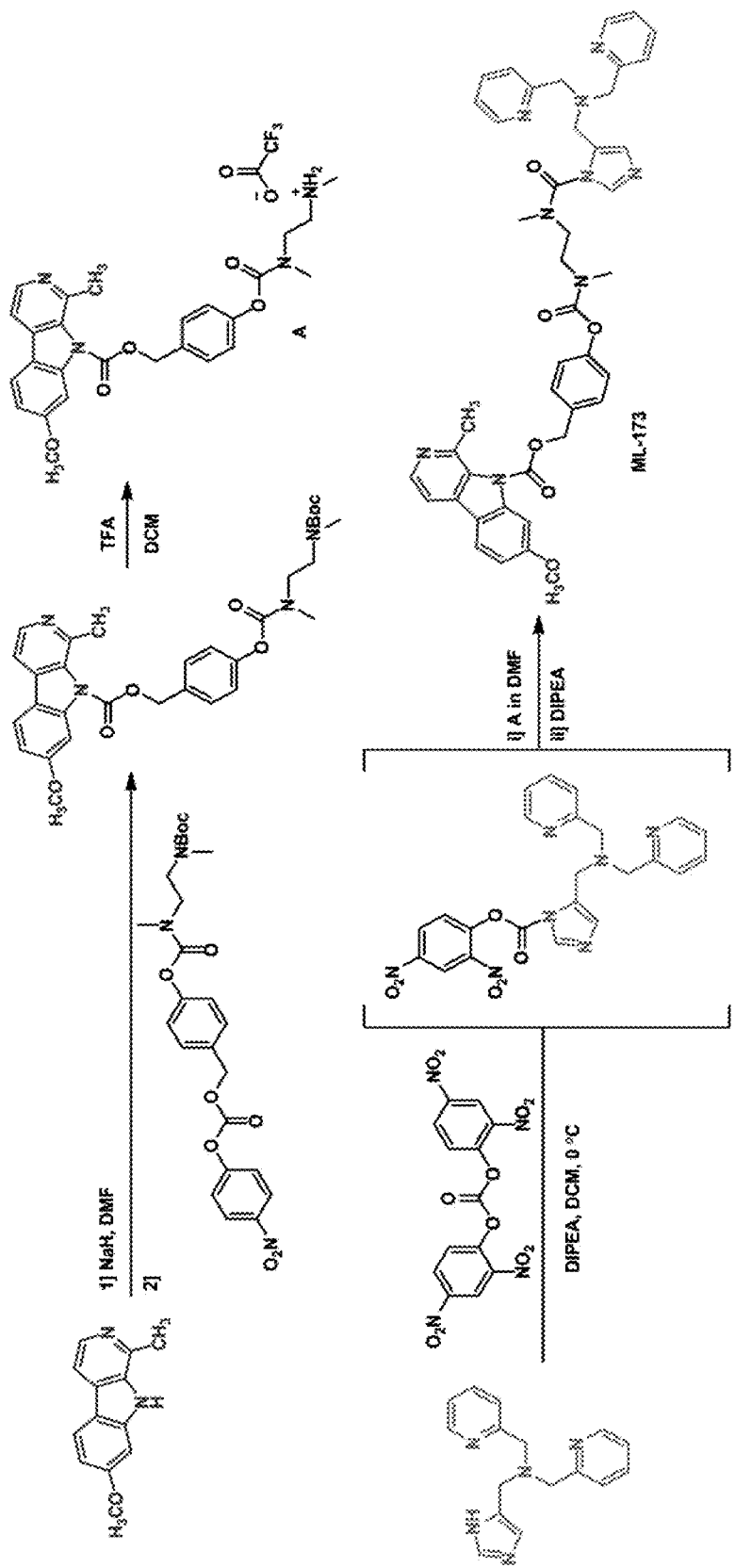
FIG. 29 shows a synthesis scheme for prodrug ML-173.

As shown in FIG. 29, prodrug ML-173 has been synthesized which comprises a cargo group (harmine), a chelating ligand, and a self-immolative linker. The self-immolative linker is covalently linked to the chelating ligand via a urea group, is covalently linked to the cargo group via a first carbamate group, and further comprises (i) an aromatic ring between the urea group and the first carbamate group which improves stability and (ii) a second carbamate group between the aromatic ring and the urea group.

Figure 30:
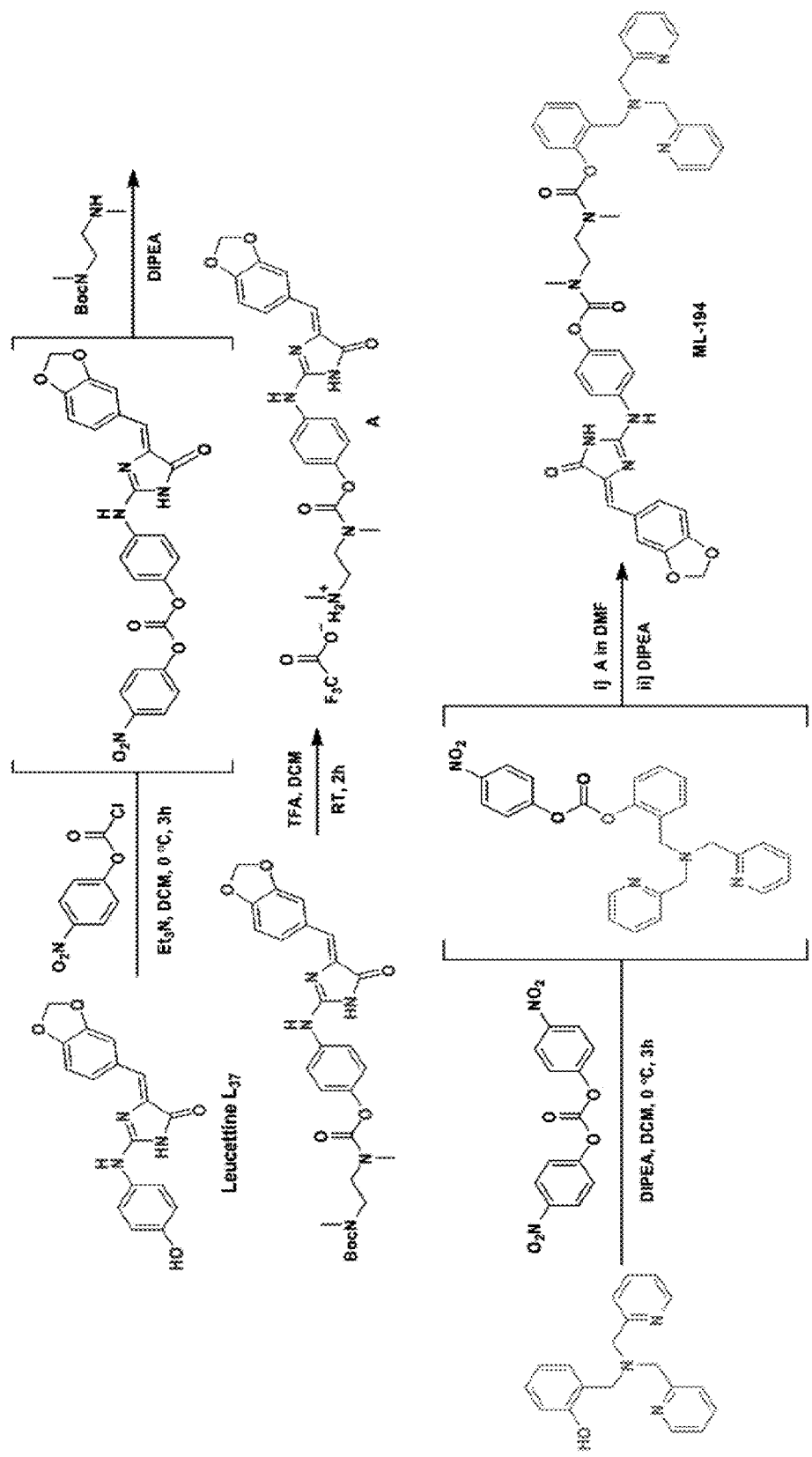
FIG. 30 shows a synthesis scheme for prodrug ML-194.

As shown in FIG. 30, prodrug ML-194 has been synthesized which comprises a cargo group (Leucettine L37), a chelating ligand, and a self-immolative linker. The self-immolative linker is covalently linked to the chelating ligand via a first carbamate group and is covalently linked to the cargo group via a second carbamate group.

As shown in FIG. 31, binding of $Zn^{2+}$ to the chelating ligand of prodrug ML-172 catalyzes cleavage of the first carbamate group between the chelating ligand and the self-immolative linker, thereby releasing the chelating ligand from the prodrug. Without protection of the chelating ligand, the self-immolative linker is chemically unstable, and the second and third carbamate groups are successively cleaved via intramolecular cyclization cascade and quinone-methide cascade, thereby releasing the cargo compound Harmine.

As also shown in FIG. 31, binding of $Zn^{2+}$ to the chelating ligand of prodrug ML-173 catalyzes cleavage of the urea group between the chelating ligand and the self-immolative linker, thereby releasing the chelating ligand from the prodrug. Without protection of the chelating ligand, the self-immolative linker is chemically unstable, and the first and second carbamate groups are successively cleaved via intramolecular cyclization cascade and quinone-methide cascade, thereby releasing the cargo compound Harmine.

Figure 32:
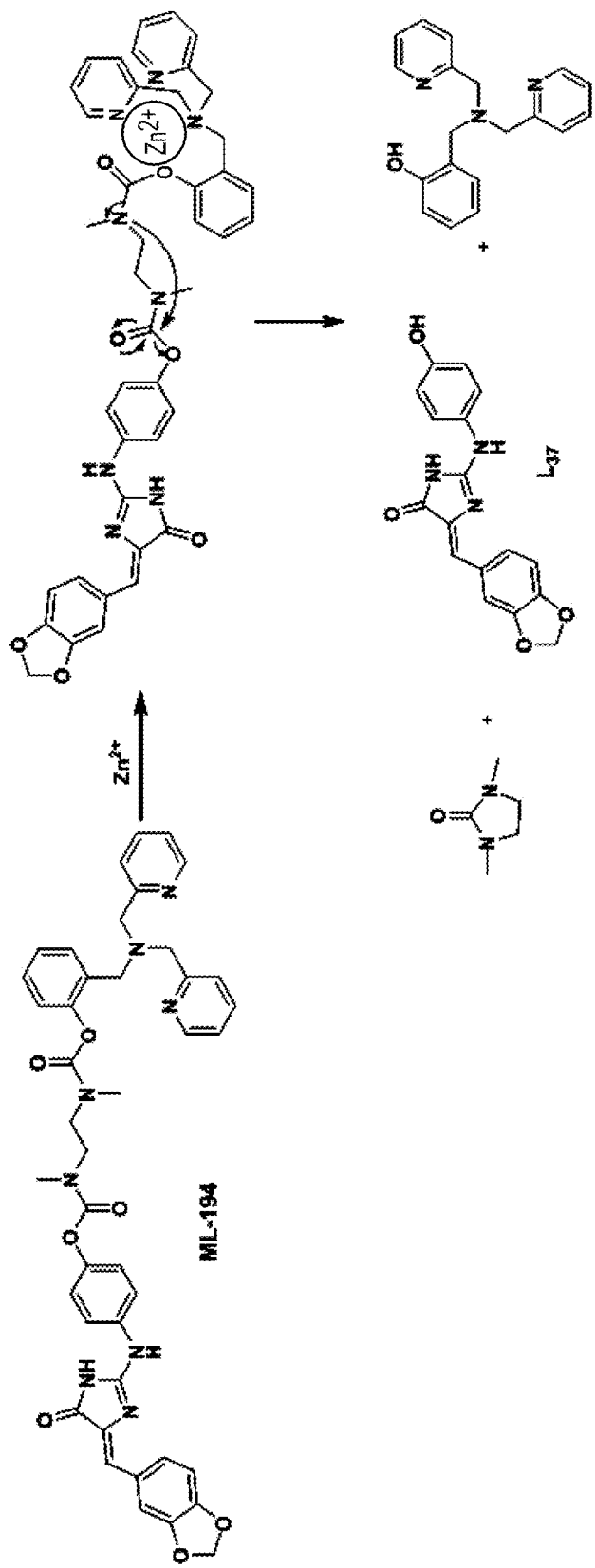
FIG. 32 shows $Zn^{2+}$-mediated release of Leucettine $L_{37}$ from prodrug ML-194.

As shown in FIG. 32, binding of $Zn^{2+}$ to the chelating ligand of prodrug ML-194 catalyzes cleavage of the first carbamate group between the chelating ligand and the self-immolative linker, thereby releasing the chelating ligand from the prodrug. Without protection of the chelating ligand, the self-immolative linker is chemically unstable, and the second carbamate group is subsequently cleaved via intramolecular cyclization cascade, thereby releasing the cargo compound Leucettine L37.

Figure 33:
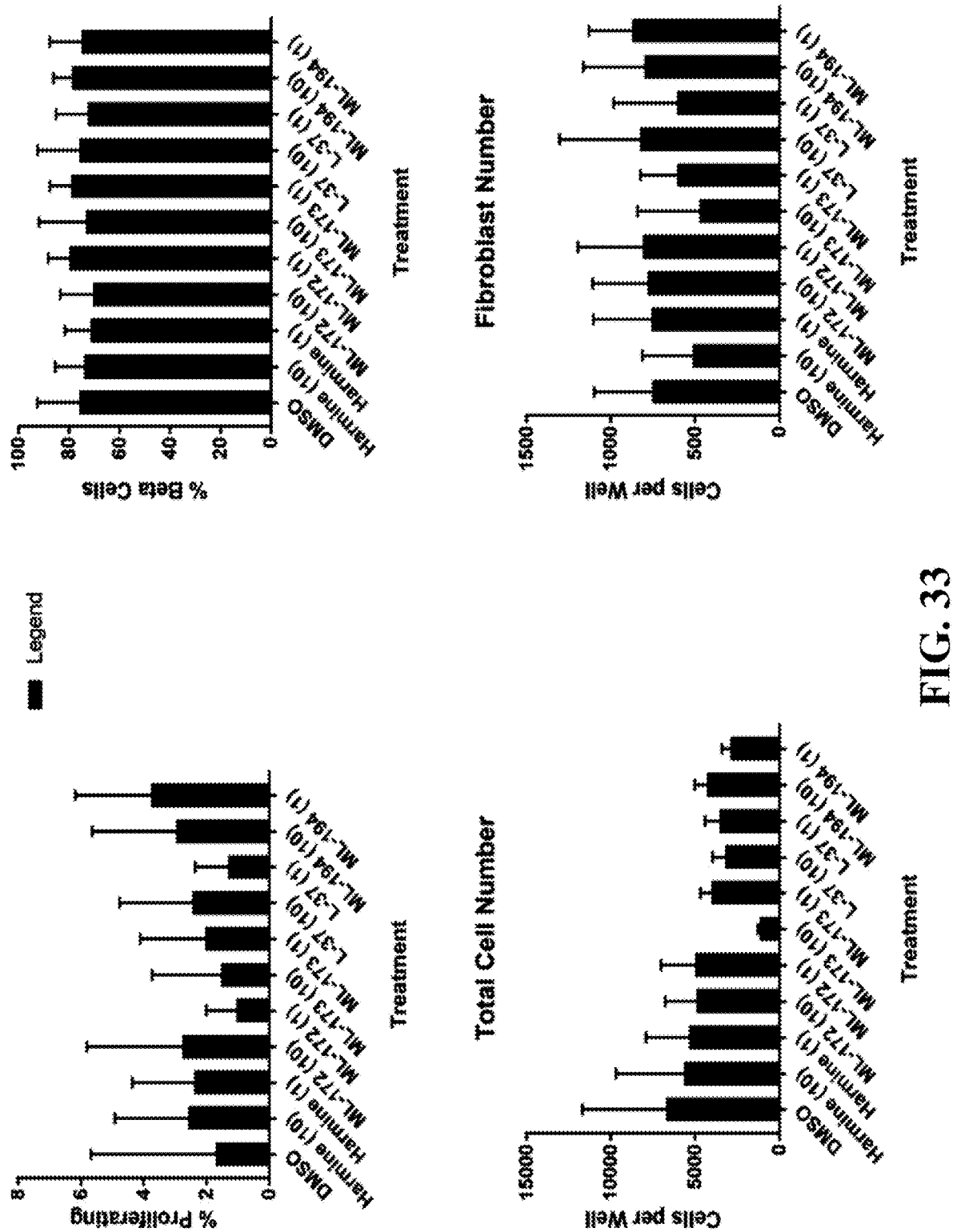
FIG. 33 shows cellular activities of prodrugs ML-172, ML-173, and ML-194. The cargo compounds (Harmine and Leucettine $L_{37}$) were each selectively delivered to beta cells and proliferated beta cells only.

Cellular activities of prodrugs ML-172, ML-173, and ML-194 are shown in FIG. 33. The cargo compounds (Harmine and Leucettine $L_{37}$) were each selectively delivered to beta cells and proliferated beta cells only.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A composition comprising a prodrug, the prodrug comprising a cargo group, a $Zn^{2+}$ chelating ligand, and a self-immolative linker interconnecting the cargo group and the chelating ligand; wherein the self-immolative linker comprises at least one cleavable bond between the $Zn^{2+}$ chelating ligand and the cargo group and the at least one cleavable bond is an ester, amide, or thioester, wherein the prodrug is represented by Formula I-A:

$$(\text{Car-H})_m\text{—S-}(L)_n \qquad \text{(I-A), wherein:}$$

L comprises a chelating ligand, the $Zn^{2+}$ chelating ligand is

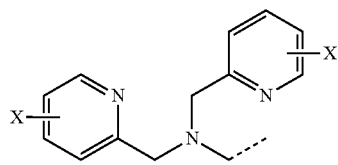

wherein X is H;

H is a heteroatom selected from O, N, and S;

Car comprises (i) a cargo group, wherein the cargo group is a diabetes therapeutic agent or a β-cells imaging agent, wherein: the diabetes therapeutic agent is selected from the group consisting of insulin analogs, pramlintide, metformin, sulphonylureas, meglitinides, thiazolidinediones, glucagon like peptide analogs, dipeptidyl peptidase 4 inhibitors, bromocriptine, diarylamide WS6, adenosine kinase inhibitor 5-iodotubercidin, adenosine receptor agonist 5'-Nethylcarboxamidoadenosine, TAK-875, gliptins, TUG891, AMG-151, MBX-2982, vorinostat, IL-1 receptor agonist anakinra, HDAC inhibitors, CMGC kinase inhibitor, DYRK1A inhibitors, a DYRK1B inhibitor, a DYRK2 inhibitor, a CLK1 inhibitor, a CLK2 inhibitor, a CLK4 inhibitor, elastase inhibitors, BRD047, BRD3308, harmine, 5-IT, sivelestat, leucettine, and GNF4877; and β-cells imaging agent is selected from the group consisting of

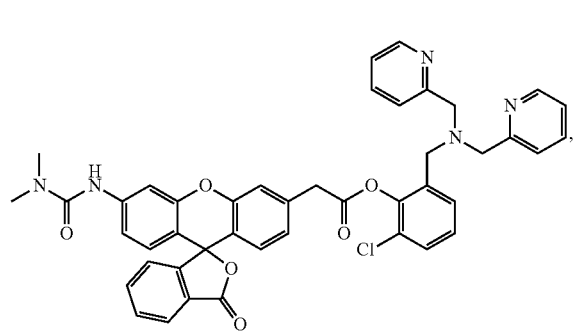

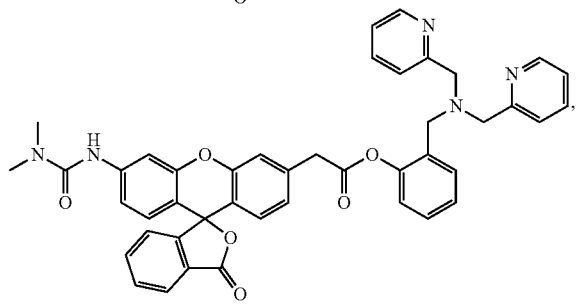

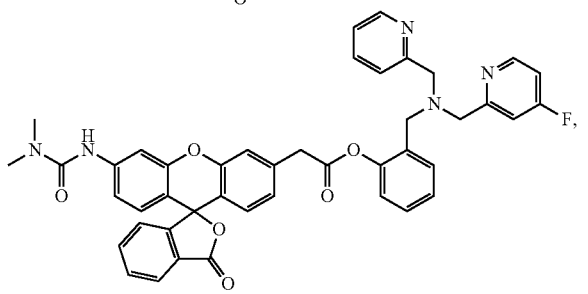

and

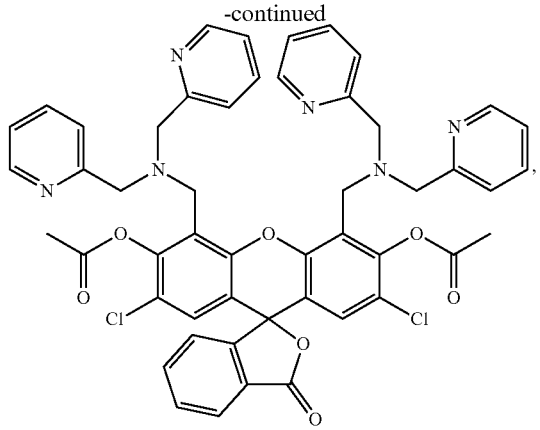

and (ii) a self-immolative linker interconnecting the cargo group and H, wherein the self-immolative linker comprises an acyl group covalently bound to H to form an ester, amide, or thioester group;

each of m and n is at least one; and a scaffold S.

2. The composition of claim 1, wherein the self-immolative linker is represented by any of Formulae II-A or II-B:

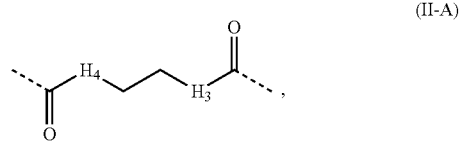

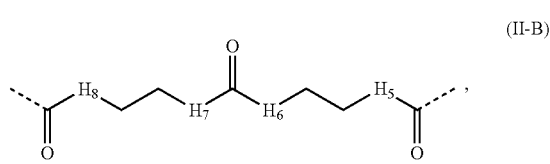

wherein $H_3$, $H_4$, $H_5$, $H_6$, $H_7$, and $H_8$ are each independently selected from O, N, and S.

3. The composition of claim 1, wherein the composition further comprises a pharmaceutically acceptable carrier.

4. The composition of claim 1, wherein the cargo group is the diabetes therapeutic agent and is selected from the group consisting of insulin analogs, pramlintide, metformin, sulphonylureas, meglitinides, thiazolidinediones, glucagon like peptide analogs, dipeptidyl peptidase 4 inhibitors, bromocriptine, diarylamide WS6, adenosine kinase inhibitor 5-iodotubercidin, adenosine receptor agonist 5'-Nethylcarboxamidoadenosine, TAK-875, gliptins, TUG891, AMG-151, MBX-2982, vorinostat, IL-1 receptor agonist anakinra, HDAC inhibitors, CMGC kinase inhibitor, DYRKIA inhibitors, a DYRK1B inhibitor, a DYRK2 inhibitor, a CLK1inhibitor, a CLK2 inhibitor, a CLK4 inhibitor, elastase inhibitors, BRD047, BRD3308, harmine, 5-IT, sivelestat, leucettine, and GNF4877.

5. The composition of claim 1, wherein the cargo group is the β-cells imaging agent and is selected from the group consisting of

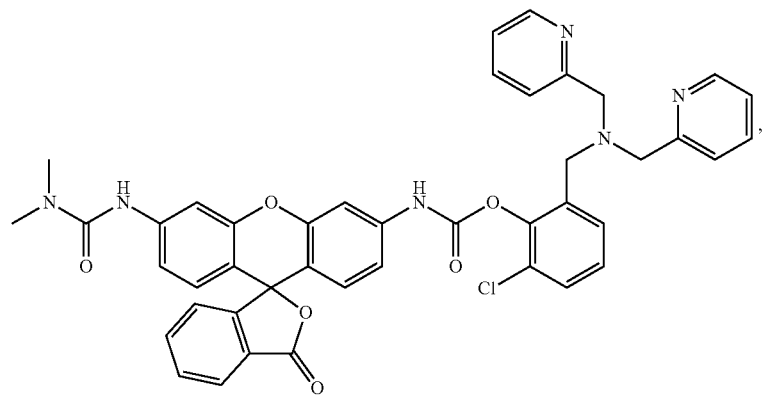
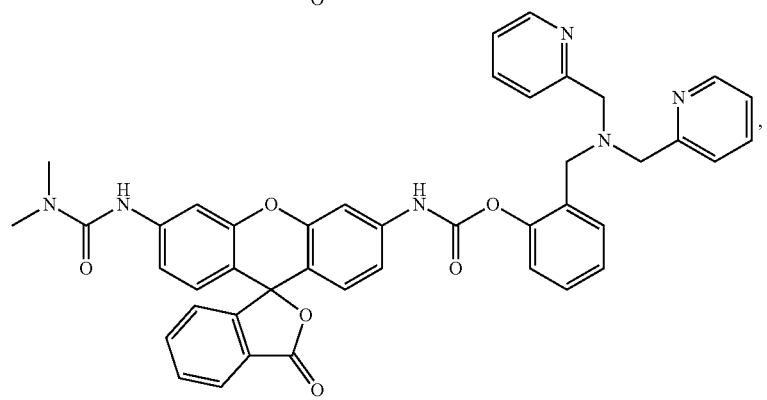
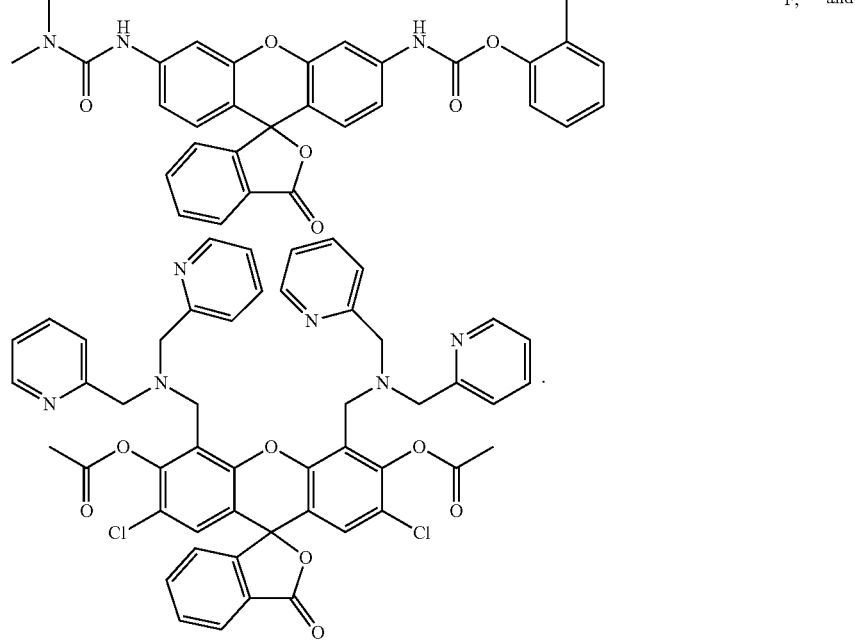
6. The composition of claim 1, wherein the self-immolative linker comprises an acyl group covalently bound to H to form the ester group.
7. The composition of claim 1, wherein the self-immolative linker comprises an acyl group covalently bound to H to form the amide group.

8. The composition of claim 1, wherein the self-immolative linker comprises an acyl group covalently bound to H to form the thioester group.

9. The composition of claim 1, wherein S comprises an substituted aromatic.

10. The composition of claim 1, wherein S comprises a heteroaromatic ring.

11. The composition of claim 1, wherein S comprises fused rings.

12. The composition of claim 2, wherein the self-immolative linker is represented by

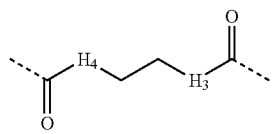
(II-A)

and $H_3$, $H_4$, are each independently selected from O, N, and S.

13. The composition of claim 2, wherein the self-immolative linker is represented by

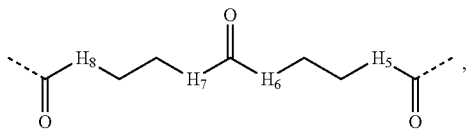
(II-B)

and $H_5$, $H_6$, $H_7$, and $H_8$ are each independently selected from O, N, and S.

14. The composition of claim 4, wherein the diabetes therapeutic agent is selected from the group consisting of 5-IT, CMGC kinase inhibitor, DYRK1A inhibitors, a DYRK1B inhibitor, a DYRK2 inhibitor, a CLK1 inhibitor, a CLK2 inhibitor, a CLK4 inhibitor, sivelestat harmine, and leucettine.

15. The composition of claim 5, wherein the cargo group is the β-cells imaging agent and is

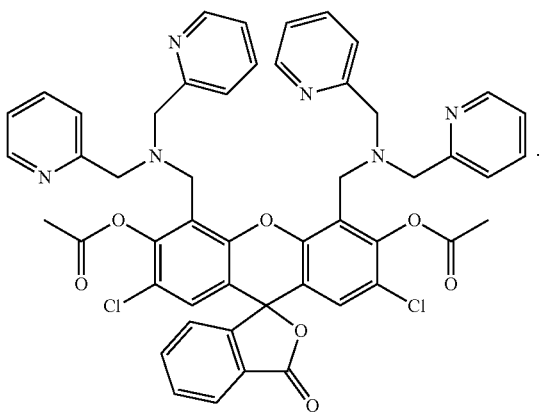 [SMILES: CC(=O)Oc1c(Cl)cc2c(c1CN(Cc1ccccn1)Cc1ccccn1)Oc1c(cc(Cl)c(OC(C)=O)c1CN(Cc1ccccn1)Cc1ccccn1)C21OC(=O)c2ccccc21]

* * * * *

UNITED STATES PATENT AND TRADEMARK OFFICE
CERTIFICATE OF CORRECTION

PATENT NO. : 12,208,140 B2
APPLICATION NO. : 16/607089
DATED : January 28, 2025
INVENTOR(S) : Amit Choudhary et al.

It is certified that error appears in the above-identified patent and that said Letters Patent is hereby corrected as shown below:

In the Specification

In Column 1, Line 37, delete "3-" and insert -- β- --.

In Column 4, Line 16, delete "His" and insert -- $H_{18}$ --.

In Column 7, Lines 15-24, delete " 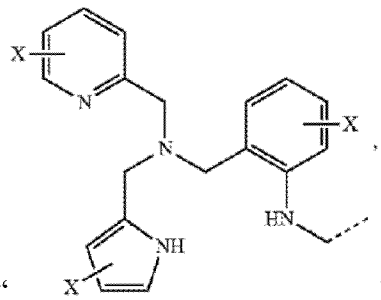 " and insert 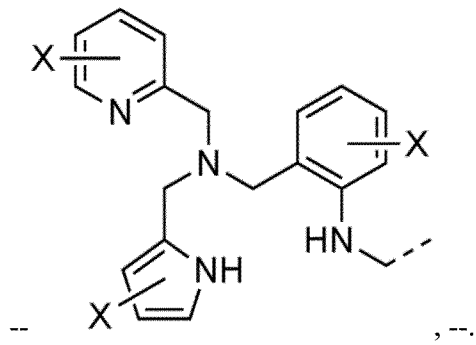 , --.

In Column 13, Line 66, delete "3-" and insert -- β- --.

In Column 15, Line 58, delete "(HNFE1B-" and insert -- (HNF1B- --.

Signed and Sealed this
Fourth Day of November, 2025

John A. Squires
*Director of the United States Patent and Trademark Office*

CERTIFICATE OF CORRECTION (continued)
U.S. Pat. No. 12,208,140 B2

In Column 21, Line 66, delete "3-" and insert -- β- --.

In Column 22, Line 4, delete "3-" and insert -- β- --.

In Column 22, Line 32, delete "3-" and insert -- β- --.

In Column 22, Line 51, delete "3-" and insert -- β- --.

In Column 22, Line 66, delete "3-" and insert -- β- --.

In Column 22, Line 67, delete "1p M" and insert -- 1 µM --.

In Column 23, Line 4, delete "3-" and insert -- β- --.

In Column 23, Line 8, delete "3-" and insert -- β- --.

In Column 23, Lines 25-26, delete "log 2" and insert -- log2 --.

In Column 23, Line 34, delete "3-" and insert -- β- --.

In Column 23, Line 41, delete "(1 g" and insert -- (1 µg --.

In Column 23, Line 46, delete "3-" and insert -- β- --.

In Column 24, Line 4, delete "R-" and insert -- β- --.

In Column 24, Line 16, delete "IPLC" and insert -- HPLC --.

In Column 24, Line 43, delete "IL-" and insert -- ML- --.

In Column 26, Line 45, delete "OH" and insert -- —OH --.

In Column 26, Line 57, delete "CH(NH$_2$)COOH" and insert -- —CH(NH$_2$)COOH --.

In Column 27, Line 65, delete "Ra" and insert -- R$_a$ --.

In Column 32, Line 64, delete "1-cells" and insert -- β-cells --.

In Column 33, Line 11, delete "Tar Get" and insert -- Target --.

In Column 35, Line 32, delete "His" and insert -- H$_{18}$ --.

In Column 37, Line 30, delete "0.6 µM," and insert -- 0.6 pM, --.

CERTIFICATE OF CORRECTION (continued)

In Column 40, Line 51, delete "3-" and insert -- β- --.

In Column 46, Line 7, delete "3-" and insert -- β- --.

In Column 46, Line 17, delete "3-" and insert -- β- --.

In Column 46, Line 24, delete "3-" and insert -- β- --.

In Column 46, Line 28, delete "3-" and insert -- β- --.

In Column 47, Line 62, delete "(3-" and insert -- β- --.

In Column 48, Line 34, delete "40HT)," and insert -- 4OHT), --.

In Column 50, Line 21, delete "3-" and insert -- β- --.

In Column 50, Line 43, delete "3-" and insert -- β- --.

In Column 63, Line 34, delete "(GGGGS) 11." and insert -- (GGGGS)11. --.

In Column 65, Line 25, delete "in a" and insert -- in Sa --.

In Column 73, Line 37, delete "Cl." and insert -- C1. --.

In Column 78, Line 38, delete "(TIN/T)" and insert -- (HMT) --.

In Column 84, Line 54, delete "3-" and insert -- β- --.

In Column 94, Line 60, delete "2'-0" and insert -- 2'-O --.

In Column 96, Line 53, delete "7, 552-564;" and insert -- 7,552-564; --.

In Column 97, Line 45, delete "CRISPR Cas," and insert -- CRISPR/Cas, --.

In Column 120, Lines 40-45, delete " 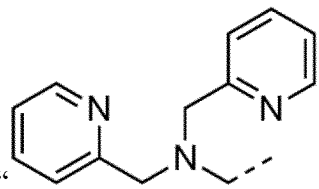 " and insert

-- 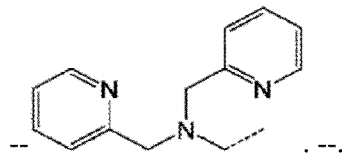 --.

CERTIFICATE OF CORRECTION (continued)
U.S. Pat. No. 12,208,140 B2

In Column 122, Line 32, delete "3-" and insert -- β- --.

In Column 123, Line 16, delete "(3-" and insert -- β- --.

In Column 123, Line 35, delete "(3-" and insert -- β- --.

In Column 126, Line 61, delete "(1×)" and insert -- (1X) --.

In Column 127, Line 51, delete "[Zn2+ ]" and insert -- [Zn2+] --.

In Column 131, Line 9, delete "p and" and insert -- β and --.

In Column 133, Line 23, delete "−8°" and insert -- −80 --.

In Column 134, Line 20, delete "PH1" and insert -- βH1 --.

In Column 134, Line 43, delete "3-" and insert -- β- --.

In Column 137, Line 37, delete "(3-" and insert -- β- --.

In Column 138, Line 15, delete "(3-" and insert -- β- --.

In Column 138, Line 50, delete "3-" and insert -- β- --.

CERTIFICATE OF CORRECTION (continued)
U.S. Pat. No. 12,208,140 B2

In the Claims

In Column 143, Lines 32-65, in Claim 1, delete " 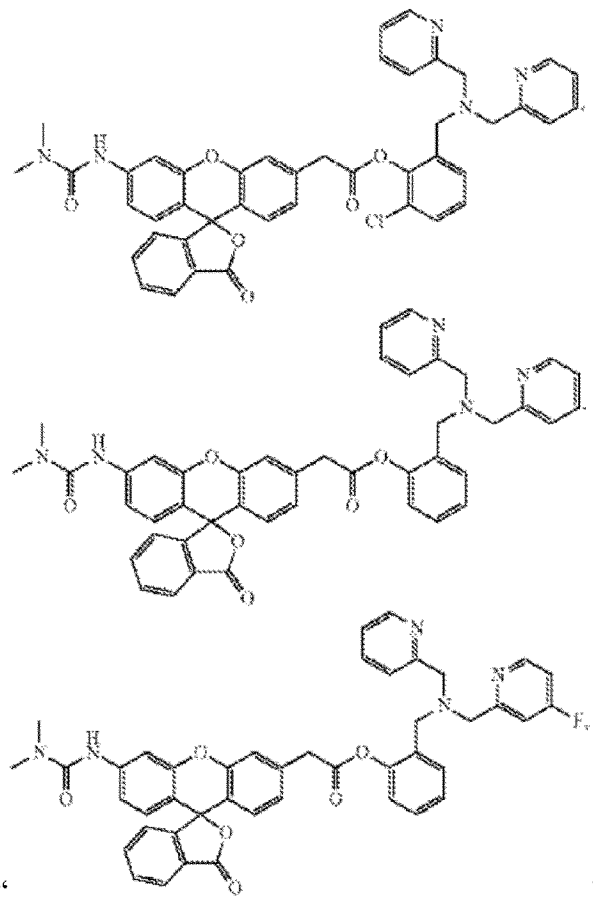 "
and insert

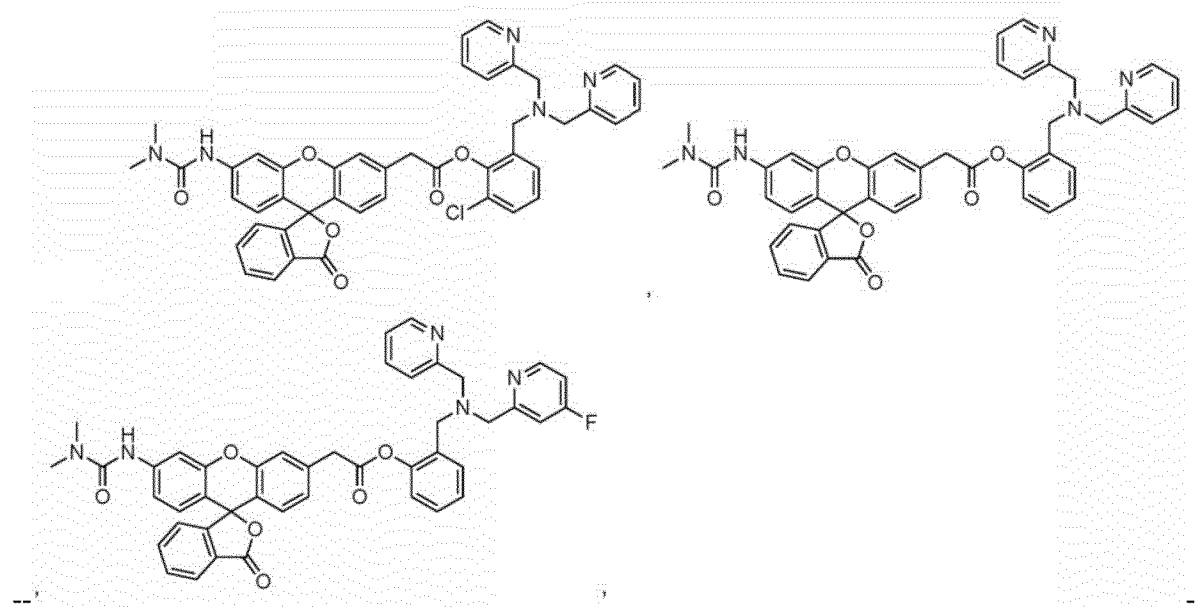

CERTIFICATE OF CORRECTION (continued)
U.S. Pat. No. 12,208,140 B2

In Column 144, Line 60, in Claim 4, delete "DYRKIA" and insert -- DYRK1A --.

In Column 144, Line 62, in Claim 4, delete "CLK1inhibitor," and insert -- CLK1 inhibitor, --.